(12) United States Patent
Schweiger et al.

(10) Patent No.: US 9,540,697 B2
(45) Date of Patent: Jan. 10, 2017

(54) PROSTATE CANCER MARKERS

(75) Inventors: Michal Schweiger, Berlin (DE); Hans Lehrach, Berlin (DE); Stefan Boerno, Berlin (DE); Thorsten Schlomm, Hamburg (DE); Holger Sueltmann, Limburgerhof (DE); Guido Sauter, Hamburg (DE)

(73) Assignee: Max-Plank-Gesellschaft Zur Foerderung Der Wissenschaften E.V., Munich (DE)

( * ) Notice: Subject to any disclaimer, the term of this patent is extended or adjusted under 35 U.S.C. 154(b) by 449 days.

(21) Appl. No.: 14/112,370

(22) PCT Filed: Apr. 19, 2012

(86) PCT No.: PCT/EP2012/057225
§ 371 (c)(1),
(2), (4) Date: Oct. 17, 2013

(87) PCT Pub. No.: WO2012/143481
PCT Pub. Date: Oct. 26, 2012

(65) Prior Publication Data
US 2014/0051082 A1    Feb. 20, 2014

(30) Foreign Application Priority Data
Apr. 19, 2011   (EP) .................... 11162979

(51) Int. Cl.
*C12Q 1/68*   (2006.01)

(52) U.S. Cl.
CPC ....... *C12Q 1/6886* (2013.01); *C12Q 2600/154* (2013.01)

(58) Field of Classification Search
None
See application file for complete search history.

(56) References Cited

U.S. PATENT DOCUMENTS

| 6,812,339 B1 | 11/2004 | Venter et al. | |
| 2010/0291044 A1* | 11/2010 | Rodriguez | G01N 33/5011 424/93.7 |
| 2013/0143210 A1* | 6/2013 | Model | C12Q 1/6886 435/6.11 |

FOREIGN PATENT DOCUMENTS

| EP | 2 213 749 | 8/2010 |
| WO | WO 2009/105533 | * 8/2009 |

OTHER PUBLICATIONS

Weber et al. 2005 Nature Genetics, vol. 37, No. 8, pp. 853-862.*
Keshet et al. 2006. Nature Genetics. vol. 38, No. 2, pp. 1249-153.*
Tokumaru et al. Clincial Cancer Research, 2004 vol. 10, No. 16, pp. 5518-5522.*
Yu et al. (Carcinogenesis vol. 26 No. 2 pp. 471-479, 2005).*
of Serre et al. (Nucleic Acids Research, 2010, vol. 38, No. 2, pp. 391-399).*
Eads et al. who teach MethyLight as a high-throughput assay to measure DNA methylation; Nucleic Acids Research, 2000, vol. 28, No. 8, e32, pp. i-viii.*
Nair et al. (Epigenetics, 6:1, 34-44, Jan. 2011).*
Weber et al., Chromosome-wide and promoter-specific analyses identify sites of differential DNA methylation in normal and transformed human cells; Nature Genetics; vol. 37, No. 8, 2005, pp. 853-862.
Keshet et al.; Evidence for an instructive mechanism of de novo methylation in cancer cells; Nature Genetics; vol. 38, No. 2, pp. 149-153, 2006.
Tokumaru et al.; Optimal use of a Panel of Methylation Markers with GSTP1 Hypermethylation in the Diagnosis of Prostate Adenocarcinoma; Clinical Cancer Research, vol. 10, No. 16, 2004, pp. 5518-5522.
Obaidul et al.; Quantitative Methylation-Specific Polymerase Chain Reaction Gene Patterns in Urine Sediment Distinguish Prostate Cancer Patients From Control Subjects; Journal of Clinical Oncology; vol. 23, No. 27, 2005, pp. 6S69-6S75.
Supplementary table for SP002485531; Sep. 20, 2005, XP055005228, Retrieved from the Internet: URL:http://www.jcojournal.org/content/23/27/6569/T4.expansion.html/, retrieved on Aug. 19, 2011, the whole document.
Jacinto et al.; Methyl-DNA Immunoprecipitation (MeDIP): Hunting down the DNA methylome; Biotechniques; 2008, vol. 44, No. 1, pp. 35-43.
Ke et al.; Global profiling of histone and DNA methylation reveals epigenetic-based regulation of gene expression during epithelial to mesenchymal transition in prostate cells; BMC Genomics; vol. 11, No. 1, 2010, p. 669.
Mathews et al.; Epigenetic regulation of CpG promoter methylation in invasive prostate cancer cells; Molecular Cancer; vol. 9, No. 1, 2010, p. 267.
Cottrell et al.; JA282616 = SEQ ID No. 57 of EP2280084, Feb. 2, 2011, pp. 1-2, XP055011564, Retrieved from the Internet: URL:http://www.ncbi.nlm.nih.gov/pubmed/, retrieved on Nov. 8, 2011, the whole document.
Egholm et al., J. Am. Chem. Soc., vol. 114, 1992, pp. 1895-1897.
"SEQ ID No. 198370 of US6812339", Nov. 2, 2004, OX055011755, Retrieved from the Internet: URL:http://www.ncbi.nlm.nih.gov/pubmed/, retrieved on Nov. 10, 2011, the whole document.

(Continued)

*Primary Examiner* — Juliet Switzer
(74) *Attorney, Agent, or Firm* — Ballard Spahr LLP

(57) ABSTRACT

The invention relates to the identification and selection of novel genomic regions (biomarker) and the identification and selection of novel genomic region combinations which are hypermethylated in subjects with prostate cancer compared to subjects without prostate cancer. Nucleic acids which selectively hybridize to the genomic regions and products thereof are also encompassed within the scope of the invention as are compositions and kits containing said nucleic acids and nucleic acids for use in diagnosing prostate cancer. Further encompassed by the invention is the use of nucleic acids which selectively hybridize to one of the genomic regions or products thereof to monitor disease regression in a patient and the efficacy of therapeutic regimens.

7 Claims, 7 Drawing Sheets

(56) References Cited

OTHER PUBLICATIONS

"Nucleic acid hybridizing to the 5' and 3' vicinity of SEQ ID No. 2 and to this sequence as such", Dec. 29, 2010, XP55039305, Retrieved from the Internet: URL:http://www.ncbi.nlm.nih.gov/pubmed/, retrieved on Sep. 26, 2012, the whole document.
"Nucleic acid hybridizing to the 5' and 3' vicinity of SEQ ID No. 19 and to this sequence as such", Apr. 5, 2011, XP55039307, Retrieved from the Internet: URL:http://www.ncbi.nlh.nih.gov/pubmed/, retriieved on Sep. 26, 2012, the whole document.
"Nucleic acid hybridizing to the 5' and 3' vicinity of SEQ ID No. 49 and to this sequence as such", Sep. 26, 2001, XP55039308, Retrieved from the Internet: URL:http://www.ncbi.nlh.nih.gov/pubmed/, retrieved on Sep. 26, 2012, the whole document.
Summerer et al., "High-Throughput DNA Sequencing Beyond the Four-Letter Code: Epigenetic Modifications Revealed by Single-Molecule Bypass Kinetics", Chem Bio Chem, vol. 11, (2010), pp. 2499-2501.
Flusberg et al., Direct detection of DNA methylation during single-molecule, real-time sequencing; Nature Methods, vol. 7, No. 6, 461-465, 2010.
Tibshirani et al., Diagnosis of multiple cancer types by shrunken centroids of gene expression; Proc. Natl. Acad. Sci., vol. 99, pp. 6567-6572, 2002.
Radpour et al.; High-throughput Hacking of the Methylation Patterns in Breast Cancer by In vitro Transcription and Thymidine-Specific Cleavage Mass Array on MALDI-TOF Silico-Chip; Molecular Cancer Research, vol. 6, 1702-1709, 2008.
Clarke et al., "Continuous base identification for single-molecule nanopore DNA sequencing", Nature Nanotechnology, vol. 4, (2009); pp. 265-270.

\* cited by examiner

SEQUENCE LISTING

<160> NUMBER OF SEQ ID NOS: 114

<210> SEQ ID NO 1
<211> LENGTH: 1449
<212> TYPE: DNA
<213> ORGANISM: Homo sapiens

<400> SEQUENCE: 1

| | | | | | | |
|---|---|---|---|---|---|---|
| cagcctcttt | cagactctcc | gctggcgttt | tcatgacacc | caaactcaga | ctcagcggat | 60 |
| cacacttaag | gcaccggctc | ctgacccta | tttttggccc | gcccgcctgg | tccccaggcc | 120 |
| tgcctggacg | cacgcgcgcc | ttccacacca | ggtgcttctc | gggacggggc | ctggcctccc | 180 |
| caccccgcaa | gaaccagacc | ctcttcagga | ctgggggggt | taccgcttcg | cctcctctac | 240 |
| ccggactcag | aagcccaac | ccaagacccg | cctagcgtcg | cttgtcagaa | cccctctgtg | 300 |
| gcacgacttt | gagcagaggg | cgagggaaag | gagggtcagc | gttcggcccc | gtcccctgcc | 360 |
| tgggctttct | ccccgcttc | cccgtccctc | ccccctcgcc | ggttcaccgc | atccccacag | 420 |
| gagtcataaa | gatcaggccc | cagcgccgga | cacaaaggcc | aagggttccc | gggagccgcg | 480 |
| ggtattcaga | gccaggagag | gggtcccggc | gcggagggtg | ctgcggccca | gcctcctggc | 540 |
| cacagagcgc | gccggccgcg | agggaggacc | aaggtcccca | accacgcccg | cgtccacccg | 600 |
| tgaatcccgg | cgctcgcagc | cccgggcgg | cgcagccgcc | accgccgccg | tcttctctgg | 660 |
| agcgcagagg | ggtgtgcttg | ggaggggcg | ggagggcact | ttcctctgtg | tcggtgaaag | 720 |
| gaagagcttc | cagctccctc | ctccgcacaa | accttcactt | cctctcttgt | tcgatcgcgt | 780 |
| cctaaaatct | gggatcggcg | acgcaaggac | agcctggttt | ggcgaagacc | cctcggacac | 840 |
| cctgcgctcc | ggactccagg | cgggtggctc | cacggtgccg | gccgggacgc | gcagctcggg | 900 |
| gggcgggacc | acgtccggga | ccccgggcc | gctgtccgag | gacggaggtc | ggtgacttga | 960 |
| accgcgtcgt | cctcagggct | gtggcgggc | ccctctccca | gccgtccagc | ccgcagcgcc | 1020 |
| cagctcagcg | cactgaggac | caaaaagggc | gggagactct | ctccggccct | aaaaggcaat | 1080 |
| tgtgctgaga | ttttaactct | aacttggggg | ttcgcccgat | tccctggagc | aacgcttctc | 1140 |
| taaaaccacg | gagcaggcca | gtgttcggaa | ctgcacaggt | agttacgaag | gaaggaaatg | 1200 |
| aagtccctcg | ttccaacagc | ttcgggtcca | gtcacaagtt | tctctctggc | gagcacgcgg | 1260 |
| ccgcctcacc | tggggtgggg | gaggcgctga | gaaagcgcag | ttctctttgg | gggaggagag | 1320 |
| atggcctctc | agaggcgtcc | ccacctgcct | ctggaacgcc | tctccctgca | ggccccctcg | 1380 |
| gttccctgca | attcgccgcc | cgctgggata | ctcccatggc | tcggaggcgc | gctcccggac | 1440 |
| cctggtgag | | | | | | 1449 |

<210> SEQ ID NO 2
<211> LENGTH: 799
<212> TYPE: DNA
<213> ORGANISM: Homo sapiens

<400> SEQUENCE: 2

| | | | | | | |
|---|---|---|---|---|---|---|
| gcgggcccaa | gtcccgctg | aggccgggag | gtgcgggcgc | ccctcagccc | cgccctaacc | 60 |
| cgtcccacca | ttgctaccgg | gtcggccccg | cagggtctga | gacccgcacc | cttccccggt | 120 |
| cccacccgtc | accaggccgc | ccgcgtagcc | aggaattctt | agccaggttc | ctgtgcgccc | 180 |
| accgtgaccc | taagagaaga | ggcggacgcc | ctggcacgtc | cttccctcct | gcttccccg | 240 |
| cccaaagcgc | tcccgttcc | cggggcgtca | ggttggctga | cagttcgggg | tccctgcgtc | 300 |
| ctgtctcctc | agctgggctt | cgaggatgtg | atcgcagagc | cggtgactac | gcactccttt | 360 |

| | |
|---|---|
| gacaaagtgt ggatctgcag ccatgccctc tttgaaatca gcaaatacgt aatgtacaag | 420 |
| ttcctgacgg tgttcctggc cattcccctg gccttcattg cgggaattct ctttgccacc | 480 |
| ctcagctgtc tgcacatctg gtgagacggg gcacaccggg tggaccggct ttctgaaaca | 540 |
| tgggcatatt ctccgccacc tgcccctac tctcctctta tcccaggccg gcgtcaggag | 600 |
| gaggaacgcg catcagttcc caagcagtag aagaactgg aaggccttga aaggcaatgc | 660 |
| gcttcctta gaataacagt ttgggcttgg agtttcaaca ggagaaagaa tgtcggtctt | 720 |
| tcctggggtg tgatttcct tgcatacata aggctgggct gagtgtggag gcgggtaccct | 780 |
| ggaagccaca cttcttacc | 799 |

<210> SEQ ID NO 3
<211> LENGTH: 949
<212> TYPE: DNA
<213> ORGANISM: Homo sapiens

<400> SEQUENCE: 3

| | |
|---|---|
| gggagccggt gagtggggga gctgggtgc gtccaggcgg tcgcaggggc tgagcaccag | 60 |
| cgggtacaag cgggactcag atccagcccc ttgggcttca gccctaccgc ctgaggagga | 120 |
| aggcgcgaag gttgagccgc cgcgtggcgc gcccgcgtta accctgcag ccgatctgct | 180 |
| cctgctcacc tgtttctccc atggtagggg gcccctgggg tccagtgggg ggacgttctc | 240 |
| caagagcact aggaagaagg cctcctccag gcccacccac agcccagac cccgggcccg | 300 |
| ctgagcgccg gcagcaggag gtcgaggaag gaggactcct tgagcctcac cgaggagcgc | 360 |
| accagtcctg ggctctgctg cgtttggggg tggaggagaa gccgcccaga cccgacttca | 420 |
| ggttgccgta gccgagagag agggaggcga acgtcgctgt cccaccttgt ttgactcgct | 480 |
| agctatgttt ctaggtgtaa cccctataat cagaagcact cgcggtctca ctctacacgc | 540 |
| tagagagttt aaaagtttg taccacgtgt agaggtccgg gtatgggtgt gtggtttggt | 600 |
| gtattttcca gtgtaaaagg caacgctttc ctaagagcta ccgtttgttt tccttgaaag | 660 |
| taggaatgag ggttaagtat ccctcatggc tgtatttctc ccgctctact taacaaaagt | 720 |
| cagtgttcgc aactaaaggc ggtcggtctt ggcaccggat tccgatgccg ccccccatctc | 780 |
| agcggaaaat gggaggaagg attaaggctg tttgatgata ggtatgaggc tgtttagggg | 840 |
| taaggatttt aacctctcag ctctctagac tgcttcagag ctaagaaatg ggcattgcgc | 900 |
| ctgcatcctt ccttctcttc catggaatgt aaggtacctg tcaccacaa | 949 |

<210> SEQ ID NO 4
<211> LENGTH: 849
<212> TYPE: DNA
<213> ORGANISM: Homo sapiens

<400> SEQUENCE: 4

| | |
|---|---|
| tccaagggt gaccatgggg gaggccagca agaatgccac agtctcaccc tgctgcctgt | 60 |
| ctgtcttgcg gagggctcag cccttttccg tgttcacgaa aaggacagcg tgcgggccgg | 120 |
| gggactcgct cctctgcagg taaggggggt gttcgcgggc acctctgctg ccacccgcga | 180 |
| ccgagcgccg gaaacagacc ccgtggagcg catcccgac ggggctgcgc gggcctctct | 240 |
| taccttcgtc tctcttgcgc ttgttggtgt cggcgctggg ggacgtgatg cccaggatgc | 300 |
| cgctgatgga gtacgacgag ccggccgaat ccgtgctcac cgaggacacc tgcgtcacgg | 360 |
| agccagtgga cactgcgcgg agaaagacgg gcggtcaggg ccgcagaggg ctgagggcgg | 420 |

| | |
|---|---|
| cggaccggct gtcaccgcac gtgaggctgg gggcggctgg gagggagcga gcgcagggtg | 480 |
| ggcaggggc gctgaggacc ctcgctctgc ggaggcggcc acacctgagc cacgagcgca | 540 |
| ggcctcgggc gggccgtgtg ccccagttct ctgcgatggg gggagaaagg gaagggtggg | 600 |
| cactgagaag gactgacccc tgcagaaagg aacacgggga cacggggaca ggaagggctt | 660 |
| tcgcttaaat tccagcctat ccatggatgc aggaagcagg ggatggagag gagaaagagg | 720 |
| ggagccgggg cccaccaaca gtcagtgctt aaaaaaaaaa aaaaaaaaa aaaaaaacct | 780 |
| gaactactcg ttaggcattt caccacctgc ctgcacaccc aacccaacct tgggtgcaaa | 840 |
| cacaactac | 849 |

<210> SEQ ID NO 5
<211> LENGTH: 949
<212> TYPE: DNA
<213> ORGANISM: Homo sapiens

<400> SEQUENCE: 5

| | |
|---|---|
| gctggatgct gggtataggt tggccgcaat gttattttg taaggctagg agaaaaacgt | 60 |
| tatttaaat atacggaatt tgctcctctc caaatccact ctccctttcg cctccctaga | 120 |
| ggttgtcagg ttcaagaagc ggcccggagt tgcaggaagg cgccggcgt cactggcccc | 180 |
| aagagctcgg aacgcgcgcg ccgcaggagt gccggctgcg gggtcgggtt gagactggcg | 240 |
| ggaccctcgg cctctgccgg ggtgcggaag gtggatgcta cgggcaaagg ggcggggctt | 300 |
| gcggttccca gatccagagg cgggttgggg acgtgagccg cgtccatgt gttctgcacc | 360 |
| ccttctcgcc cggtgcctct ctcaaggcac gttttccaaa gtgtgttgaa ttcgggaatc | 420 |
| gatcgaaaat ttcaaggcca attaaatgcc ctctgatgta gagctccgat taggcccgaa | 480 |
| aggcttcaaa cagcccctct agaccctcga gggtcttcgc cgcggtaacc ttaggcgtcc | 540 |
| cctccccgag aagtctccct gaggctttca cagagggcgg gaggggctgc gctggggcct | 600 |
| ccgttcccag tgcccctgac tggtggggag ggatggcctt agtgtctgag agcagagacc | 660 |
| agattgactc ccacttgaga ccagaaaacg aagaggaagc ggaacccgag gtggctgcgg | 720 |
| ctcccccggg acacaaccgg gagaggaagt cctggccatc tgccggcccc gcctgggggc | 780 |
| atctgctcga ggatccctgg gagccgttat cgtattcctc agaatctgcc gtgctgtccc | 840 |
| tccgccccca aaaccaacag gacacccatt ctgtgattct cttcttctcc atcgcccagt | 900 |
| tggaggctgc tggggaccag gagaaaaaaa atgccttcc cgagttctc | 949 |

<210> SEQ ID NO 6
<211> LENGTH: 2249
<212> TYPE: DNA
<213> ORGANISM: Homo sapiens

<400> SEQUENCE: 6

| | |
|---|---|
| ctctgctgtg acctttgtcc tgggaggggt gggtggggtg cgtcgccact cttggcaaga | 60 |
| gaaaattgca cggcatatcg ttcttcccag ttacctttc cagtgttgcc gttcgggcct | 120 |
| ttttgctccc tttccaaatg gaagcaggcc aatgattcag ggcgagtaga cgagagcccc | 180 |
| tctgctcact ttaccagggt cctcccgagt gtttaggtcc cgatgcgcgt agaaagtgtc | 240 |
| ttgcgagacg cggaactggt gagactttgc caccatttgg tccaggccaa tgtcggccgc | 300 |
| cagcccaaaa cgccgaaggg agacggcggt gaaacccag gcgtgcgagc tgcgtccttg | 360 |
| cccttccccc tacccaggtc aatggtctgg cctagaccac cgctctgcgg gcgaaaggag | 420 |
| tggagcagaa tcacaggcca cgctcccagt cgttcgagcc tgcccacata accccggcc | 480 |

```
cctggcgcag tcaggcccgc agcgggcgag aagagctagg gtctcggggc gactaggacc      540
actgagcacc tcccccccgc gcctcccgcc catgctctct ctcccaggcc cctggacccc      600
gggccacagc cacaggttgg ggcaccccgg tgcgcggcgc cccgcggag ctggcgagag       660 ccggagagct gaaacccaac atctgtgtgt acaatgcgct ctccgaggcc acagctgca      720 ggaacaagga gaagaaagga gagggggggc gcagatcttg tcacacgcag atgacagtct     780
gcggagggct ctttagtttc tccttttctg gaaaccccag cggccccctc ctaggccccc     840
ctctcccacc gcctggccat tgttccctgc gcccgggaca gctggagacg gcggcccgcg    900
ccactcgacg cccctcccgc cgcacacccg gctgccgcg gcgcccgctc ccggcccctc      960
cggggccaac tcctccacac ccccacctc cccaggccag gcccaggcgg cgcttccaca    1020
gtctcccctc ccctcccttg cactctggcg ctgcccctag acctgctcgg tgcagagggc   1080
cttgcctggc gcttttctct cacaaaccta gttctgtaaa acctgggggc gagccccagg   1140
gggcagggct cagaggcggg ggttgtccac agatatgagt acggtgccgt ccgctgcagg   1200
cccctgtcta aaagtggccg aaggaccccg tttcctctga ctgcaggccc aggctgagtt   1260
ccgcatttat ttttgtattt atagggcaag gccagagcgc ttcataaagc tccagggcaa    1320
agaagtggcc tcgcatcggg ccatggttcc cgcaggcctg agcgggctgc aggaggcccg   1380
gtgcggctcg gcggggggcgc gagaggcgag aaactgcggc gtcactgcg tcctctgccc    1440 atgagtgaac ccctccagta ggcggggacg gggtacatca ccttggccct ctcgtccccc    1500
ctgcccaggg caaggcccgc aaaaaccccc gcaccctggc tcggggggcgg cgcggcggcg   1560 ggcaggtcag agagaagcgg tactcgggtt ccccccagcgc ccgggatgcc ctcccaggga   1620
ccttctcggg caaagagtcg agtggtagcg gttcctgtcc ctccccgcca ccctcctccg   1680
gtgcctcggc gtccccagcc aggctccagg gcgaccccag gccggccct gggcagagac     1740 agaggagggg aggggaggtg gcgctggggg gcggggggcc ggagacggcg ggaggaggac   1800
tcgggagccg gggcgggaag aggggaagac agcggagaga agggacgggg aggggagggg    1860
gctcggagga ggggacctgc tgccctcagc ctggctggta accggcctct ccatagcaac    1920
ggccagcgcg cgcgtctgtg tgtgcgcgcg tgtctgatgt gtgtgtgccc gtggtgttcc    1980
cgggactccc cgcgggggct gggagggggat cgcagaaccc tagggtggcg acagagcaaa   2040
cccctccagg actggaggcc cgacctccgc ggtgctggga gcgccctagg gtctggctgc    2100
gccgcgctgg cgacggggta ggctcgggga acgcgcgcag ccccgggat cggccgctgg     2160 ggcattgggg catcctgccc tcgctgcccc gaccctcccg ctgcggtcgc agggccttgg    2220
ggcaccgggg agtgggcggg tcttcccag                                       2249
```

<210> SEQ ID NO 7
<211> LENGTH: 699
<212> TYPE: DNA
<213> ORGANISM: Homo sapiens

<400> SEQUENCE: 7

```
tctaactgaa tttacttttt cttgggtgcc gctttcttgg gtttggcagt ctttggcttc       60
gtcaccctag ccttggccgc cttgggtttt acagccttag ctttagcagg cttttagct       120 actttcttgg gctttacagt tttgggtttt tttggattct tggaggattt ccttgttgcc     180
gcaggctttt tagccttttt cggagtcttg acgctctttt tgctagcccc cgtggccttt      240
ttgagctttt tagatgcacc cgttgcctta gttttttgtag ccacctttga ggcgccgggc    300
```

-continued

```
ttggttttcca cggaggacgc cttcttgttg agcttgaagg aacccgaggc tccggtaccc    360
tttgtctgca ccaacgttcc cttgcttacc aggctcttaa tgcccagctt aatgcggctg    420
ttgttcttct ccacgtcgta gcctgcggcc gccagcgcct ttttaagagc tgccaacgac    480
acaccaccac gctccttaga ggaggaagca gcctgcacga tcagctctga cacggaaggg    540
ccagcgggtt ttttcttgga ggctgctgca gccttagcag gtttctttgc cttcttgcca    600
gctaaaggtt tctcaggagc agcagaagcg gcggggcgg gaggcactgt ttcagacatg     660
gtgactaaca cagcacacca aataaagtgg tataaacct                          699

<210> SEQ ID NO 8
<211> LENGTH: 899
<212> TYPE: DNA
<213> ORGANISM: Homo sapiens

<400> SEQUENCE: 8 tcatttcaa agggtcatta acattattta aatattcatg gtggaggagg ggatgagaga      60 ctgaaattc agacatctca agagtgaggg atggctggcc acccgcctaa tacagcccca    120
gtctgcggat cagctgcctc cttcccctcc gctggctttg ttagcacacg cgctctgaca    180
ccgggccacc ggctgccact acacggaggg cagcaggaag gctctggcga ccagtgagc    240 tggaagcatc tctgtccaca cctcagcctc tgaaccccat cgggggagtc ctcaaacacg    300
cggagacacc attactgcca caaagacgca cttcgcaacc agttccggga gtcgctctga    360
ccctgaggac agtcgtggtg ctaggtaagg acgaggggc tgtttccccg cctgagtggg     420
aactcagcgg ctcctggcat ttgagcgcac acaggcactc acacacttcc acatacgctc    480
atgcgcacat atgtgtacac caacacacac gtccacatgc acacacagcg acacgccacc    540
ccgctccaaa gccccgtgcg ctaacaagta tccatatacc cagacacagc gctcccctga    600
gttaggaaac actcagcttt gcccgcccca tccatccctc cgtctttccc tctctccagt    660
ctctgcattc attcatttct tcgtttgtgc atcgattccg ccgaagccac tgagaggaga    720
aggtgtgggt agatggggag gggaggggag ggaggggcgg tccgtgggcg ctgggctact    780
ggaggggaag cgaggaggcg gggaaggggc gggcccagg agcaggcggg cggggctccc     840
cgccctccag cgcgcccgga ggctaccact ccctgcagat gcgctggccc cagcccggg    899

<210> SEQ ID NO 9
<211> LENGTH: 2249
<212> TYPE: DNA
<213> ORGANISM: Homo sapiens

<400> SEQUENCE: 9
cagttacgcg cccactggct ccctgtctct ggcgcttctg ggcacggggg agctggggcg      60
gccccgcctg cgcacggcgg tgccgggatt ggggcgggc acgccgcctc cgtctcccac    120
gcgctcgctc gctcgctcgc tcccgccctc ccgcctcga gcgatctcct gcctcagcct    180
tgcaggctcc gcactgcaga tgcctgctgg cttccctgcg ctcggcggct cccgcggtgc    240
cccgtaagtc cccgtgaccc tccagcacca gccggctgtg cgctccctgc tcccacgggc    300
cggtcagccg cagacactca cccagctccg cgagctcagc cgctcagcga gtggggtagc    360
ggggaccgag acggacggta ccgtgccag agccccgggc gctctcggat gcggcaggac    420
aagctgaccg ggtctctgag gcgcggggg agatgcctga agcggcaggg cggcggcgtg    480
ggcaccatcc tgagcaatgt gctcaagaag cgcagctgca tttcccggac cgcgccccgg    540
ctgctgtgca ccctggagcc gggtgaggac cccagggctg cagatggggc gctgtaaagt    600
```

```
agcgccgggg ctgcccgcgc ttctgcctta gcctgactcc gtctaggccg gggagctctg      660
gggaaagtcc gcgtgccacc tggtgcgggg caccgcgttg gcacctgcag ggagcgattg      720
gtctggaagg gtagagggca gacggggggcc tgggtggggc agcggccacc ccaggcgcgg     780
```

```
agcgccgggg ctgcccgcgc ttctgcctta gcctgactcc gtctaggccg gggagctctg      660
gggaaagtcc gcgtgccacc tggtgcgggg caccgcgttg gcacctgcag ggagcgattg      720
gtctggaagg gtagagggca gacggggggcc tgggtggggc agcggccacc ccaggcgcgg     780
agaacccgct gcttccaccc tctccccgcg accccccacc ctgcgcctg tgtgctcggc       840 tttctccgcg tggcggggaa gtgcgggtgg ctgcccgggc cctcagaggc cgcaccacct     900
attgtgttcc aggctcgcag gaagccgac cttgcgagag gtgtgtgggg gcggagagtg       960
gcacaggttt gacactgcag gtcggaggag aagacagtg gctgcaaagg caaaatcggg      1020
tgttattttc ccaagagtcc cttcagcgtg agtgccgggg tcagctcgaa ctggagcctg     1080
taatttgtga gtgcgagtgg ggagcagcag gagatccttt tcataggtga ggtccaggaa     1140
cgagcctggt cgtgctaggc aaggccttc ccactgtcag cctgtgttta cccatccctg      1200
cttctccaga ctgcataact ccgtgtcggc tccatcaccc ggcatccctc cccgggattt     1260
taagagcctg gccctagcgc gggctcctgg gcacggaggt ttctggcaag gagtggctgc     1320
agagggagtt ggctgtactc tcactggtgc ttggcgctca cctgttccct ggagtggcac     1380
cggctgcgtt ccaggcgggt tcacggtccc cggcccccgc ccccagcgc cagcgccttg      1440 gggacctgct gtagagccgc aggagaatcg agctgcagag tcccaaaggg tgggatgcgg     1500
cactgccttt cccaacctcg tggtttctt gttgttctcc cctaggaagt gtctagttgc      1560
agaggctgta gtatttattc accatcttcc tttacctctt ttttttttct tttaaatctc     1620
cttcccacgt taaagtaag tgttttgtat ttctgaatcc ggaatagctg tgattatcag      1680
atgaaacata aaccttctct ctgcccgtat tctgttagaa gaaagaaaa gtggggtgaa      1740 agtgacctgg tttaagcttt tgcatgcagg cggcgaatca atttcagtta aatcctcttg     1800
ctcatttttg atcatgagag gatagttgtg gttttggcca actaacccct gctgggtttc     1860
actatgagaa ggcaatcggc atgatgccca gcaggtgccc cggaaaagtc agaagagcat     1920
attggtcaga catacaggga atccttgtag tgtggcaaga ataagtcagc gcgggaccga     1980
atttcctggt ctttgttatc aagcaaacgt catgattata cgctcctcca ttcagcacct     2040
cgcgtccgga cagcaaccte acttgttttc agcgtgcctt aaagcgtgcg ctgggctgga    2100
aacactcccg tggccgttgt tatcaccgtt ctatgtttgg gcaggacttc gtttaaacca    2160
cctcagagag aggcggatcc atgtggtact taatattcct tcggagaaaa aaaaaactta    2220
tctatccagg cagagtatgg ttatggccc                                      2249
```

<210> SEQ ID NO 10
<211> LENGTH: 1749
<212> TYPE: DNA
<213> ORGANISM: Homo sapiens

<400> SEQUENCE: 10

```
aactcaagtg tcactgaact tcttcccagt cagaaagaca ttcccaatcc ccttctctcc      60
ttgagggaaa tatatatata tatatacaca gttaatggta actcattgct gcctcgttag    120
aaaagatcaa agaatgaaca caacgtggta gaataagcag agcaatgttt atttgttgta    180
aataaatgag agaataagtg gaaaccagc agtttgggga ggaaaagag aagggaaag       240 aagtcagcca cagtgggaga aggggctcct tttcttcatt tcttgtcttc cccttttctct    300 ccccacccta agtctaccct tctcatcaat ttctcccctc tttcccttcc ttcgcctcac    360
cttcaatccc ttgggtggag gggctgaaca gcgtgttccc gggcggaggt gcgcgcagcc   420
```

| | |
|---|---|
| acccccaggct gctgccaggt gcccgctggg gctgccaggg cgaggaggcc tctgggctgt | 480 |
| ggagcgaaag tcagatccac cgcctactgc ggggtagggg ccgcagtggg daccgccagc | 540 |
| cctgtggtcc ctctcgcgct gactggcgta aagttgtggc cgaattcgca tctcttctgg | 600 |
| tgcttctcgc ccgccagcgc agggcccagg tgtttgaggc gaaggggctc tagctccccg | 660 |
| caagcctgga gccaggcgtc gcgcttcctc cgggcttaat ccagaccttt caacacacac | 720 |
| ctcattcggg ggaggagaaa agcacaggac cgcggagagc ccagctttga ggccaggcct | 780 |
| gaagggataa cccacacagg gaacgttttc ctatcagaga ataatggagc acaaaataat | 840 |
| tcagaaagcg aatgggcagg accacagcct gagagtcccg cgccgcgggg ccgctgcaga | 900 |
| gccggtctcc cgagcaccgc ggcaggacca tttcgttgga atgtagggcg aggccgaagc | 960 |
| ccgcccccgga cccaggccgc gaggtgcgcg ccggccgccg aggggccgcc tgtaaattac | 1020 |
| agcccgccgg gaggactcgg aaatacacaa aaggagccga aagatttaaa cagtcggagg | 1080 |
| cagaggcgtc ccgaggcggc caaagcgaaa atcaatcacg taattaaaac agggagggga | 1140 |
| cgaagcccaa ggctgggggt cccgggttcg gaggaggcgc ccaaggtgca ggccgaggct | 1200 |
| ggcgagcggc ttagggacgt ggctcgcccg ccaggaccag agcgcgcgga ggggcttcgg | 1260 |
| ggaagtttat aacacatcgc tattgattcc cgcttggcta ggaagagcag actctggtgc | 1320 |
| cctctcccag gccagaccct gaagcctccg atggccccct ctccgacttt cccgttttg | 1380 |
| tggggttgag acgcgcagtt gcagttgaag gccgctcccc agatcccact ggtgccacga | 1440 |
| ttttgccaag gcaagtttgc gaacccaaat ggcatcaaga tgctgccttt gggtttgagg | 1500 |
| ggatggaggg aggtgacacc ccagtttcag gcactaagaa atctctctcg gccttgattc | 1560 |
| ctccaaccca ggattcaaag catgcccgga aagactctga tctatgggcc gaggcttgga | 1620 |
| agggggtgtgc gaggcagacg gggttattaa agggagagct tggggctgag caaactggac | 1680 |
| cccctttgggc tggaaaggag aaagaacagc tcctggaaga gaaaaaaagg cacaccggga | 1740 |
| gctgtgttt | 1749 |

<210> SEQ ID NO 11
<211> LENGTH: 1699
<212> TYPE: DNA
<213> ORGANISM: Homo sapiens

<400> SEQUENCE: 11

| | |
|---|---|
| agtccagggg aacaggtaag cagcggggaa gcagggagtc catttcaggg acaggaattc | 60 |
| ccggatgaaa agtgaaagga gagggacggg gcccaagctg agggtttctt cctggttcct | 120 |
| cggacagctc ctggaccaag actcagggaa cattgagaca gagcgtttgt cacaggagga | 180 |
| gcggggtcag ggcgaagtcc cagagcccca ggcatggctc tcagggtctc aggcccgaa | 240 |
| ggcggtgcat gggctgggga ggtgcagcat tggggattcc ccatctccgc agagtttctc | 300 |
| ttctcccctct cccagcctgc gacggtgtcct tcttcctgga cactcacgac gcggacccag | 360 |
| ttctcactcc cactgagtgt cgggtttcta gggaagccaa tcagcgtcgc gcggccccgg | 420 |
| ttctaaagtc cccacgcacc caccgggact cggagtctcc ccagacgccg acgatgggggt | 480 |
| catggcgccc cgaaccctcc tcctgctgct ctcggggacc ctggccctgg ccgagacctg | 540 |
| ggcgggtgag tgcggggtca ggaggggaaac ggcctctgcc gtgaggagcg aaaggtccac | 600 |
| ctggctgggg cgcaggaccc ggggagccgc gccgggagga gggtcgggcg ggtctcagcc | 660 |
| cctcctcgcc cccaggctcc cactccatga ggtatttcag caccgccgtt tcctggccgg | 720 |
| gccgcgggga gcccagcttc attgccgtgg gctacgtgga cgacacgcag ttcgtgcggg | 780 |

```
tcgacagtga cgccgtgagt ctgaggatga agacgcgggc gcggtgggtg gagcaggagg    840
ggccggagta ttgggaccta cagacactgg gcgccaaggc ccaggcacag actgaccgag    900
tgaacctgcg gaccctgctc cgctactaca accagagcga ggcgggtgag tgaccccggc    960
ccggggcgca gatcacttac tccccgctcc atgcctcacg gacggccctg gtccctgag    1020
tctccgggtc caagatcgac cccgaggctg cgggacctgc agagatcctc gacccgggag   1080
agccccaggc gcctttacct ggtttcatct tcagttgagg ccaaaatctc cgcaggttgc   1140
taggggccgg ccagggctc ggtgggcggg gctgaccgcg ggaactgggc cagggtatca    1200
catcctccag ggaatgtttg gctgcgacct ggggcccgac gggcgtctcc tccgcgggta   1260
tgagcagtat gcctacgacg gcaaggatta catcgccctg aacgaggacc tgcgctcctg   1320
gaccgccgcg gataccgcgg ctcagattac ccagcgcaag tatgaggcgg ccaatgtggc   1380
tgagcaaagg agagcctacc tggagggcac ctgcatggag tggctccgca gacacctgga   1440
gaacgggaag gagacgctgc agcgcgcggg taccaggggc catggggagc ctgctcgatc   1500
tcctgtagat ctcccgggct ggcctcgcac aaggagggga agaaaatgga accaccacca   1560
gaatatcgcc ctccctcctg tcctgacgga gaggaatcct cctgggtttc cagatcctgt   1620
atcagagatt gactctgagg gcccaccctg ctcttcctgg gacaattaag ggatgaagtc   1680
tctgagggag tggagggga                                                1699

<210> SEQ ID NO 12
<211> LENGTH: 1099
<212> TYPE: DNA
<213> ORGANISM: Homo sapiens

<400> SEQUENCE: 12
gaaaaatcat ctaacagtgc aaactccaca ctaccctgta aaacacagaa gagccaccgt     60
aggagagatt tgcaggcaaa gtaaaaccac taactgcacg atccagtctt cttttaggtg    120
cctcgtctgt atttacttat ttcactggag tgaccacccg gtaacatagt agaaacatta    180
tttccatttt acagatgagg aaactgaggg acagtagatt caggacgatg cctcgagtct    240
cacccagctg gtgggcggta gggctgggat ctgaacaggc tggctggctc cggcgaacct    300
cggctcttcc ctactctgct cttatgttgc gtggaaacta ggccaggatc agggaactcc    360
tgatcttcac cctgaggaga agcaaagaga agacagccct gaggcgcccc actctggggc    420
agcgtgtgtg acccaggcct tcggaccgag aagggagaaa ggaaatacgt ccttccctat    480
cctgaagcgg agggcgttcc aggtttcgca ggtagtgctg cagccgcgca aggaccgggc    540
gaggctgcgc ccctgagccc aagtctccac tcaccggcct tcccttgccc cctcacctgc    600
acgcgggtac tttagccct gggcaagcct tgagccaagc gccagacca aacccgggaa      660
attaaacagt gtgcatggaa tgaaatgtgg tccgtggaag gtgcctgcag ctggcggtta    720
acaccggcag taagaggatc aacgcccggg ccgctggctt aaaaatggga gtgggagtgc    780
gaagtgtgcg cgctcctttt tacccattca cgttagttaa tttggatgat aagggttcgc    840
gtttaatctc tttgtgtgcg agtgaatatc ctgaaatcga caacccctga gagggcactc    900
gcggctggca gagcaacctg ggagggtgcg atcgtgtcc aatctggcgt gaagcagaaa    960
ggaaacatcg tgaggagact agaggcagga ccgagaggga cccctaggg gtgcgaggtg   1020
cagaccgagc cctcacatct cccaggccgc agcaggtggg ccgatggctt ccccgaggcc   1080
tggcacccca ggcctggct                                               1099
```

<210> SEQ ID NO 13
<211> LENGTH: 899
<212> TYPE: DNA
<213> ORGANISM: Homo sapiens

<400> SEQUENCE: 13

| | | | | | | |
|---|---|---|---|---|---|---|
| ctaaaaccgt | tcgctgggca | ctaatatgaa | atcacttaaa | aggaaacatg | ccactttcgg | 60 |
| ctaggggaca | gcatgttcgt | cattcagtgt | cctactggtt | tcttaacacg | catataatta | 120 |
| atattggtac | tcaggaaaga | gaacttcttc | tgaccttgag | cgtgcgcgct | aaataaatta | 180 |
| cctcagaacg | aaagtggtgc | gatctcaaaa | cagcatctgg | ggagaaaaga | gataaatgag | 240 |
| acttcattta | actccttgtt | cttcacctac | cgagtgactc | atgacttacc | tgggagacca | 300 |
| gggttgggaa | agcacatcgc | agactcctgg | aattcggtgg | gacatcctgg | gggagggagg | 360 |
| aggagtcctg | gggccatcgg | tctctacgtg | atttctccgc | gagaagtttg | catgaaagtt | 420 |
| ctggggagt | tggggagccc | cgaagtttcc | atgccttact | ttcttacccc | tacgctccag | 480 |
| cgaaggatgc | gtgaaggcga | ggctggcgca | gccccgact | acgctcaaat | tacccttaag | 540 |
| gctttagcaa | actgactaaa | aatttgagtt | ctttcctccc | ctccctgccc | tcggcatcgc | 600 |
| cgtggttatt | caaacctggg | agactggagg | gcggaggtga | cggcaaaaag | gcaaggggc | 660 |
| gttaaagaaa | cgcactcagc | ctggggagtg | ggcaatgatg | gggctagggg | cagccgagga | 720 |
| gaagggagcg | agccgcgctt | cactctccaa | atcggcttaa | ttgttcctgg | tagcccgcag | 780 |
| aaacccgtcg | cggcgtgtct | tacctcggct | tcttgaacga | cccgagaaga | ccgatttcat | 840 |
| cggatgcctc | cctttctgga | gcttgcggtg | ccagcagcag | aagaagacga | tggtggcga | 899 |

<210> SEQ ID NO 14
<211> LENGTH: 1099
<212> TYPE: DNA
<213> ORGANISM: Homo sapiens

<400> SEQUENCE: 14

| | | | | | | |
|---|---|---|---|---|---|---|
| cgccccgcct | gctcccacct | tcccaacctg | ccaaggtacc | tccctccctg | tgaacccacc | 60 |
| ttggccacct | agtcggcact | tctgtgcagc | agtgtcacca | agaggtggtg | gtgggaggcg | 120 |
| attcactccg | ctgaatcctc | gcaggatcct | ccctcccct | taaacatcca | tgcaaatagt | 180 |
| atcagtgttg | tggttttgca | aacccagctt | caacctagtc | ggtaacaatc | cactccccac | 240 |
| cccttttcatg | ccccgctttt | tcagcagttg | gtggccctaa | gtctttctat | gtagaaattc | 300 |
| tagggccgcc | ccagactaca | ggcaatccca | gccttcgca | aaggcttcct | gccctcatcc | 360 |
| cgtggcggcc | ggcaccttgg | ctgacctgac | cctgttttgc | ttcaggcacg | ctggggcttg | 420 |
| ccacacgtcc | cctcaccccc | gatctcactg | cctctgcgtc | tcctgtgtgg | gatgcctccc | 480 |
| cgcagctggg | tcctgggtgt | gggaactggg | ggaggaagaa | gggattcccc | ggaggttctc | 540 |
| gctacagtcg | ggtaagggaa | gcgccgggct | ccctgggagg | agagactagg | gctgggtac | 600 |
| cctggacgcc | gcggcattgg | cgaatgcctc | tgctacacac | tacatgcgcg | gaagcaacag | 660 |
| gccggagcag | atggagagag | gaggggggagg | ctcgggcctt | cggaatgcat | ggcagggaag | 720 |
| ccgctcccctt | tgtctgcgga | ggaggaggac | gcagattcct | aaggagaaac | tgtccccagg | 780 |
| cttcctcttg | aaaccatagc | ctgtaaggaa | cccatggtct | cctggagcgc | caaactccta | 840 |
| tcttttcatg | agaatcaagt | tgtcactgta | gccagcacaa | accgcttcc | cagctgacct | 900 |
| gcctttccag | gtcagagcca | ggaagggagc | ctccaggatg | gggccttggg | gggtggggag | 960 |
| tgggggtgct | gcccaaggga | gagcaaaact | gcctctcttt | gctcggtcct | tgcttaatcg | 1020 |

```
atgacccggg aagagtttct gcctccgtca gtgacaggtg gggaggggc cattgtttct    1080 ggaattctgg ctcggcttt                                                1099

<210> SEQ ID NO 15
<211> LENGTH: 2249
<212> TYPE: DNA
<213> ORGANISM: Homo sapiens

<400> SEQUENCE: 15
gggcggggcc ggggccgcgg tggcgatgca ccgggcccgt tagcgccagg agcgccaggc     60
agctgaggcg gggggcaagc cctccctcgg aggagccgcg ccccggccc cgccggtccc    120 gccgcgatgc tgttccacag tctgtcgggc cccgaggtgc acggggtcat cgacgagatg    180
gaccgcaggg ccaagagcga ggctcccgcc atcagctccg ccatcgaccg cggcgacacc    240
gagacggtag gcgcgcggct gtggggtcgg ggctgagagc tgggatgggg ccgggccagt    300
cagcgcctct gctccccgaa gtttgggag cgtccttcgt gccgcacggg actgggtgct    360
ggggatcctc ggtcagaatg caaggccggt ggctcccggt tcggggaaa cccggctgct    420 gggacgcaga agggaaacaa ggttgaaacc gaaatctcgg ccctggggt agaggagagc    480 gtttcttccg aactggaagc gaagtcccat ccgcggcccg gggcggctcc cttctcacct    540
tgcccggtgc cggggtcgac agcccgcgc tctcctccac ctctcggctc cggttgctgg    600
cggcgccgcg agcggcgcca gggaagggcg aaccagctgg gagcattggg gctccagccg    660
gcttgggccg ctcccagctt tccggcaatc ggggatcctc ctcaacccc agcgcagttt    720 cagaggccga agtcttcggg gccaacattt gtcgttgatc gcgtcccag acccttgact    780 ggtcagactt agccaggcca gggctgggag ttcaggctcc ggcctggccc tcgccgaagg    840
agactccatt tggatctcta cacctggctc cgcgggccca gccccaaata gccagttcct    900
cgcctcaggc ctccctgggg gccagacgag cagacactgc ccgaccagcg ggcccagaag    960
tgacctttag gaggccgcgg aggtggggag cacgggagaa gcttctctgc tccgggagca   1020
ggagcagcgg cgccagtgtc ctcccggcct ctgagcgctt cttcggttag accttctctg   1080
ctggtcagtt tggataggga agtatttggg ttgaacctgt ccttcaccca cggactttga   1140
gggtgtccct gcaccccact tacctcatcc ccggacccaa gagggcccca gcccgtgtgg   1200
cagaggagcc agaagttggc tgacttgtcc tggccttaac ctctggtcta aggatccagg   1260
gatcactgga gctggggccc aggaactccg ctgtctctcc aaagaggatt ctgtgtggag   1320
ggtgacttaa tggtcacctt atccccgg tggctcattt aagaagcagt ttagggaaag   1380
ctcttggagg gcttgactgg agtagctgtc ctggtcccta aacacagccc gagcattttg   1440
ggggaaagga cagggaggac tggaaggaag agaggtaagc accagagcca tttaggccag   1500
gagcccggcc tgggcccgtg gctggcgagg gctgcgcagg caggcctggg ttctgaaccg   1560
cccagaaatg gaaatgggcc ttttggggtg ggggaagcg cgccgcatgt cctggcagcc   1620
ccctccgcgt tcagggtagc caaggccaca gagggagttg tgggtgccgg tttccggcg   1680 gcggaggggc cgctggctga cgcaggcgct gctgtcttcc gcctccctcc cttcgcagac   1740
catgccgtcc atcagcagtg accgcgccgc gctgtgcgcc ggctgcgggg caagatctc   1800 ggaccgctac tacctgctgg cggtggacaa gcagtggcac atgcgctgcc tcaagtgctg   1860
cgagtgcaag ctcaacctgg agtcggagct cacctgtttc agcaaggacg gtagcatcta   1920
ctgcaaggaa gactactaca ggtagccccc ccacccaact gcccctcagg acccctcccc   1980
```

| | |
|---|---:|
| ccaatctcag gcacagtctt acagtttggc cctctccttt ccgtttagtc ccaggagagg | 2040 |
| gttcactact caggactccc ccgctccccc cccaagttct ccaagccacc acaagttggg | 2100 |
| tgataacctt ttaaagcagc aatttgggga gctcttggaa aggtctacga agtaggagaa | 2160 |
| ccagaaaaaa agcagaagct gccctcctgc tcggagctta gaccacaaaa aagcttgagt | 2220 |
| tgggatcctt gctcccctct ctctttgaa | 2249 |

<210> SEQ ID NO 16
<211> LENGTH: 1349
<212> TYPE: DNA
<213> ORGANISM: Homo sapiens

<400> SEQUENCE: 16

| | |
|---|---:|
| ctccagcccc cagccctgag ctggaaactc cgagctcctg ggtcacgcct tgaccactgc | 60 |
| agttttggag gaaactttgg ccaggtcctg ggctgaccgt ccgtttgcat cccccacttc | 120 |
| tgggatccga gcaacgggaa tcccccgggc ggcgtgggaa tgaacccat tcctccggtc | 180 |
| ccttgtggct caggcaaagt tccacgtccg aaatctggac tgggggaggg acgaggctcg | 240 |
| tcgcttccta ggggtgcgag ggaaagtttg ggttctggag agggaggggc gccctcgagc | 300 |
| gcggcggccg ggggtgagca gctcggctgc gaagcccaac aggtagaacg ttccgagaag | 360 |
| ccttccgggt aacgcgggtc tccccgccaa gccgtggctc ccctgctccc ttttacccct | 420 |
| ccttagcagc cccctgccgg gccacgttgg ctcagaaatc cattttctac gcctccgagt | 480 |
| tgcctttctc agcgtagtca cagcaataat ttgcttttct aattgcaagg aggagggagg | 540 |
| tggaaacgca tttccttcca gggaagtggg gttggtgttt ttcattttttg cctcccgcct | 600 |
| tctcctttca ctgtgtatct aacactttaa acagacgcag tcccgaattc atcaagcctg | 660 |
| cgtttgggtc gatggcagag gaataaagct gttctttcca tcaaacaggc agggctgcag | 720 |
| gctgcagatt ccttgacagc gcagggacag acggccccctt tgccccactc ggtctggagc | 780 |
| agttgttaag gcagccacac tgccaaggat atggtccgac tctaccacat gtaacctcag | 840 |
| gacgtccgag ccagccctgt taaagatggc ttttgtttgc agctgggtat ttttagttta | 900 |
| atgtcagcaa actacagcgg tgtttgtctc ctcacccaaa cctgcggttg tgaaacttat | 960 |
| aaaggaattt aaaaatggac ctggcttgca ttccggcagg caggccttgg ttgcagtggg | 1020 |
| cagggccaga cagccagggg tatctcagag tgccaagctc cagggcccac cggagaccgg | 1080 |
| gccagactca ccccagagcg ccaggggact ggtggtgtac agatacactc gggttcaaac | 1140 |
| agtttaaaca aggggccggt gatttggtct agactctaga gctgtgttca ggtttcgctg | 1200 |
| ggaccgtgaa tgccagtaat gctctgtacg aatgcccaga acacggatga gtgtcagcct | 1260 |
| tcagcaggaa tgcgcttgag cttctgtgta cctgttaatt gcccagggaa atacaattgt | 1320 |
| catggaattc tttgtgagaa ttgggaaat | 1349 |

<210> SEQ ID NO 17
<211> LENGTH: 599
<212> TYPE: DNA
<213> ORGANISM: Homo sapiens

<400> SEQUENCE: 17

| | |
|---|---:|
| gtggaggccg agccgggaa ggtgcggcgg gcggcggcgt tcaggatgag ctctccggct | 60 |
| cggacgcgtg cagtaggagg ccgccgccgc cgccgctgct ggacttgtgc ttcttcaaca | 120 |
| gctgcgtgat tttctcgtcg tccgagttgg gatccagagg cttattgtag tcgtcgtcct | 180 |
| cttcctcgtt ctccgaggcc cccttgaggc gctctgtctc cgagtcctgc ttcttcttgg | 240 |

```
ccgtggccat ctcggcagcg tgcttcttcc tccacttggt ccggcggttc tggaaccaga      300
cctgagggcg gagaaaaggg aggagagggg aggcaagggc gaggaattaa acgagcagat      360
ccaggccatg ctaccactcc cgcatctcga tggccctccc gcggcccccc gaaggcctgc      420
tgccctccct cgcagccctc ccttttctcg gccgtcaaag tcagtctccg tcgcccaag       480 ttccccctga gtaactggca ccaacaaact gactgccgtt gccatagcga tggtaacaca      540
agagtattga ggttgtcagt gagcgagttc tcaaaagtaa aacaaaact cggaaactt        599
```

<210> SEQ ID NO 18
<211> LENGTH: 1199
<212> TYPE: DNA
<213> ORGANISM: Homo sapiens

<400> SEQUENCE: 18

```
tgatctgcgt gcctcaggga gtattctatc aaatgcacag tgtgtgagaa gggatgttct      60
aaactcccag aggctgtcag cactcagctt ggagtctggc ggggctccac tctcttcttt     120
cctcccaggc ccaaagccag tctgcaaaga gcacaacggt gacgtctgag aagggagggg     180
gctggggagt gggggggcagc cggcagggag gaggggagct cctccatgcg cgtaaacaca    240
cacacacaca cacacacaca cgaacgctca ctcaagtctc caggggccag tgccagtggg    300
agatagagct cagtcccaaa gccagtgttc acaaagatca aagggcagta ggacagtagg    360
ccacaagtaa tgctctgtca ccagctaccc gcgaccctgc tcaagccccg ggccttctca    420
tccgacaaag cagcggatta gacgcggttc tctaggtcag gccctcaggt aactcaacca    480
cacaaagcaa gcacacacaa acatcagatg tcagaacctg gagaggagga gcaatgcggc    540 aggggggatgc gggacccaag cgcagaggaa aatcaccagc agaaatacgg acacaaaggg    600
gattctctgt ccccgatgat ttctgatttc ggcacaccca gcccacggc gcacccatcg     660 cgccccgcac ccccgccccg gcctcccgcc ctgccctccc cccgcagca cccaggccga     720 gtccaccgtt gctggcccct tctccagcct gccaggcttt tggagagggc cactcaccag    780
gtcaccctgc gatttccacg ggggcaggtg ggagcgggca gagcctggcg cagagaggaa    840
tgcacaggga agaggcttcc ctgtaccagt gactgggcga ccgagccggg atttgggagc    900
ggggaggagg ctggagctgg aggagaggag gggtttccac gggagtcccc tcctccccac    960
ttcctcccag gctggagtgg gagctccagg gggcggcgct tggcggggga cagcgcttct   1020
ttgtgtcgcc ggccctggtg gcttggcatt gctgtggctt agggacgcct ggagacccca   1080
tcctggcagt gtggacggct gtttcattaa agatacaaac ttctctgact ctacattagt   1140
aagggaaagg ctgagcaaat tgtgggacaa acattctgct tagtattatt cagttctta    1199
```

<210> SEQ ID NO 19
<211> LENGTH: 899
<212> TYPE: DNA
<213> ORGANISM: Homo sapiens

<400> SEQUENCE: 19

```
gtgccaagct ttggggagca gctttgaagt cagactttaa agcgcccagt tagccacgct      60
gactttccgc atcagttttg gctggtgatg agcacgcccc attgccagag cggtccacag     120
tcaggagcgg ttccatggca tttgccagtg acatgacatt ctgcaggaaa gcgtctctgt    180
gccgcgtcgt aaatgatacc ggtgtggttt accaacctt gtcttttgaa cctgcctttt     240
cagaaacgga atttgccttg agtgcgcggg cggccagtga gcctttaact tcttgtgctc    300
```

-continued

| | |
|---|---|
| agccccggcc tgccggcgcg agcacggcg gcaggaaacc attctcttct cccattggga | 360 |
| gcgcgacccg ccattcacta gcgggccttc ggggcaccct gatcagtttc ctcaggttca | 420 |
| gccaaggcct ctgtggttct gctctttctc agaaatgaat gagtaatctc tgcaccatct | 480 |
| gggatatgct aaaactttat ctccgtgcgt ggaggggtg cgattcattt acattgatgc | 540 |
| tctgattgct tttgcccgcg agaactgat aagcgattcc agcctttcag gagagcgtgt | 600 |
| cttggcgccc accgaggagc tgcaggtcgt tgcactcctg gctgtggtga agtcagtctt | 660 |
| ttcgcacttt gccattggag tgggcgctat tcaataacgt gcaccagtgc ctgcaatcac | 720 |
| ccggagattt ccactgggca gggcgaaacc agttctgtgt ggttgttctt taggcttcat | 780 |
| acttttaagc cctctaggtc acattcggat tacttcgctg attaatgtaa tcttggtgga | 840 |
| tgccagaagt tctaggtggt gacaggactg aaaagagtcc gccctccctc tccccttttt | 899 |

<210> SEQ ID NO 20
<211> LENGTH: 749
<212> TYPE: DNA
<213> ORGANISM: Homo sapiens

<400> SEQUENCE: 20

| | |
|---|---|
| ctggccctgc aggagtggga agaaatcgct tttgtctttc cgacaactga gccttccacc | 60 |
| tggggctggg agggcggaca gcaggaccgg ctcttccact ccccaccgcg gccccccgac | 120 |
| ctggtcagta gctctggcgt tcagacaaaa ggtcccctga gctgggggtg gggggcaggt | 180 |
| cgagagtagg ccggtaaatc agacttcgca gctccttaag tcaccagtcc tgcatttggg | 240 |
| tgcagagatt ccgttttaaa aattcgaagc atcgctttgg ttcgctcttt gttcgcgggc | 300 |
| gcgggttctc gctcatccat ccatccatcc atccaaccat ccatccatcc attcattctt | 360 |
| tcttgacgca ctcgctcgct ccccggtcgc tccgggcgca ttaccgcttc ttcttctgct | 420 |
| tgagggactt cctgcgtttc aggatcatct catagagctt gtccatgccc tcggtgaggc | 480 |
| cctcgccgat gatggcgcac gccggctgga cgtgataggt ggtggccggg ataagctcgt | 540 |
| gcagcgccag ctgcttctca atctctgcca ccggcagcga cttgggcagg tcctgcttgt | 600 |
| tggcgatgac cagcagcggc gtgccctggt tctcggcgaa cttggtcacc ttgtgcagct | 660 |
| ccgtcttggc ctcctccagc cggtccacgt ccaccgagtc caccacgtag atgatgccgt | 720 |
| ccgtgcagcg gctgtaggac ttccacagc | 749 |

<210> SEQ ID NO 21
<211> LENGTH: 1399
<212> TYPE: DNA
<213> ORGANISM: Homo sapiens

<400> SEQUENCE: 21

| | |
|---|---|
| ttttagtgca tctatagcca aaactgggag caatgcagtc ccgcgtacag tcgcaagata | 60 |
| cttttttgtc ttatatcttt tgacatttat tgggacctct ccgtccccat attacagtca | 120 |
| caagctacat tttattaacc gtcggtaacg ttaactgtga atggaatcgg gaaatgaaaa | 180 |
| gaaaaatgag ccccccctcca tatacctcca accatattag atctcaaggt agtcaataat | 240 |
| gagtgtttga taccaggaag cctcacttcg gaagtcacaa agagctggtt acgctcgcct | 300 |
| agaacccggc agggaaggcc gccgttctcc ccggaaaccg ccgggcgaag tgctgaggag | 360 |
| gtgcgatgag aaaccaccaa gtcagaaatc gtcagcgatg tggatgactc gggaaacttc | 420 |
| tctgtctggg tctgggagta tgaagatcta taagaacctc tctgcacaca gaaatccaag | 480 |
| agctcacacg ctacttagat gaattaagca cccaagagga tatatttaaa taccttcttg | 540 |

-continued

```
cttgtgcact cttgtcctgc ttgaatttct tttctccatg tgcatgtact acctagcaaa      600
atataaacaa tacaaaattt atttgtaact gaaggcggct ctgcctcccc tctgtctacc      660
ttgcggagac tattcaaacg ccctcgcttg cggggtttcg gagccagaag tctcgagctc      720
cgcgcctccg cgccccgcg ccgcgccctt ccacctgcac ccgttaggcg cgctgcggga      780
caacagcgca gatgcaaaca gctttctcgc aaggaaaaag ggaattgagg agaaagtttc      840
ctctctgagc cgagggaagc ggaaaaagat caaaggtcgg gggcgggtag agtgggggtg      900
gggggaaccg cgggacgccc tagctgtgtg cgtttcggga ggcctcgcag tgccattctg      960
caagagtacc tgctatctcg aaaatctttt gccaccgccg accgcagcgg gaggggggcaa    1020
ggggctctct ctgactcagc tccggatttg tgcatccccg cagtgcggca cccgcagtct    1080
tgacttcccc agtctctgac tgaacagatg ttttttgtccc tcgcggagat ttgtaaccga    1140
tgttgggaac agctagtgga cggtgctagc aacctgtatc tgttctagaa cacacctagt    1200
gggagctgcg gggtagagtg gagaggtagg aatgcagcgg gactggggca ggggacaaat    1260
caaggtgtgt gggtaaatgt gaacatatga acacacgtgt gtacgcacgt ctctaaatgt    1320
gtcattcata acatttttaaa aatggtcaag tccggccggg cgcggtggct cacgcctgta    1380
atcccagcac tttgggagg                                                  1399
```

```
<210> SEQ ID NO 22
<211> LENGTH: 924
<212> TYPE: DNA
<213> ORGANISM: Homo sapiens

<400> SEQUENCE: 22
cacaaatatt ccaaagtcct tttgtttctg tatcacttca cagggagctg cttccacctg       60
tctcctgtgc ccttggtttc tgctaatcct acattccaag aataaaagtc ttcctatgcg      120
ttcctaggca gaagccaagt ttccctgctt tgggcacgtt caaaatagaa ggtattttcc      180
gcttctcttg cttctgagca cccacgaaat caacacatcc ccaaaacacg cgttgaggga      240
gtaagggaaa gtgtcctgca cccgccaccc tcccgcgcta agagcggcag aggaccccac      300
agcttcgtac ttccccggag gagctcctgg agtaggagac ggcttctagc ctggaagaac      360
cccgggtgcg acagttgtgc caggaaactt caagagtatt ccctcggctg ggcgcacgca      420
gtacatcccc aatgctccaa tttgaacttt gactcggcca cgaccacccc actccagtct      480
cactctacgg tgctttctcc cctgttggtg ctgagggctt ttgagactac ctgccccgcg      540
ctccctaagt ccgagggacc gagggagagga cctgtcccgc tgagctggca cgacccacgc      600
agggcaggcg gcacttacgc ggcgcagtcg gtgctcctcc ctgagccgcg cgcgcaagg      660
accccagccg gttgtccttg cagcgcttcc caaatcaggc agaagtgagg cagccccacc      720
cagtcacgag gaccctgcag aactcgagcc tttaagcgct cctctaggct cacatgaccc      780
agacccacag ggcaaaaagt gcgtcgtcgt gtcccaacct cctggtccca gaaacctggc      840
cgcatcaagt cagcgcttcc catgctggaa gaagcaagca gccccagggt ggaatcttaa      900
aaattaatga gagcatcgg cggg                                              924
```

```
<210> SEQ ID NO 23
<211> LENGTH: 2749
<212> TYPE: DNA
<213> ORGANISM: Homo sapiens

<400> SEQUENCE: 23
```

```
cctgcctcta gaattttcca ccagcgctgg gggctggtaa agattctgcc cccctctgac    60
aatttaatag tcccaagtca tcatctgcgt gacactggcc atccatcttc tcccagggga   120
ggacaaagcg gggcctcccg gactccaggc ctctccctcc ccagctcttt ctattttggg   180
acagcctcac cacaatggcg tccttataaa ccataatggc gatgtttatg aaggccgcaa   240
taccagtgta tgaagacaat tttatgccta attagaaaat gatgtaactc gagagaagac   300
aaaggaaagc tgtcccccctc ccgtttctct ctcttcaatc acaccccctc cccacatttc   360
ctagggccgg accccttgtg agtgcttaag gctgaaggac tctgttttga cagtagctgg   420 gctcccgcg ccccgctggc cctggccgcg cgacaggagg ctgcaggcac gtcctgcggc   480
tccggggcga aggctaggga aggggataga gggaggtcgc tgcggggagg gggacagagg   540
caggcacaga gtcctaaaga gatttgagac tcgcgctcct gcactttcta tcccacgcgc   600
ccccatccga ggggacctca cccctgggaa gactccaata aatgcaaccc ggcgccactc   660
gattccggga taatttttaa tatatatgca ataaatgttc actttgttag attgaatgac   720
agacaataat atcggcaaat cttcatatcc atccattacc agcaaatgag ccgcacaaag   780
gacagatttg cttttgatta atttatttgc agactcgggt tgataaagca ataactattt   840
ggttaaactt gacatttggt cttcaggggg ttatcagaca aatctctgtc gcccagaaga   900
gataataaag ctgtttaaag gggattaatt attaattggc tgcaattaat ttccccccctt   960 ttctcggctg ctgccacaat tcgcatccct cacccacaaa caaaagacag aagtttgccc  1020
tcctccccac ccactgacct ggggcgacga ggggatcccc aaagccctga gtgaagacgt  1080
gatctcttgc accccggtta ttccagtgca gactatttta atgaaccctt ggcaaaacct  1140
gtccatgtct gtccccggca gcttttctgg agtcgagggt gcgattaagc atcaatctga  1200
gggtcgtgga ttcggagctg aatttctagt ctcaatattt ttggttgtaa ggacatcagc  1260
tcacacccgt tgttatgtct aaatccacac tccccaactt gttttcttgg ggcagcagtt  1320
tgggggctga gctggaacct gggtgtgaga gtatcacaag cccgccctac tgatcacgcg  1380
gagaggattc cttcttcccc tctttactcc gcgccctgcc gcggaaaccc ttcccgtggc  1440
ctcgaactgg tccccgacga ctgcggggta cgcggggccc aaagccagac tctactcccg  1500
cgcagatgcg ggaagactcc aggctgtgct tgagctgttt tactgggcct ggccgaggaa  1560
taagcgagcc tcagcatgct tgggccagag cgagaagcat cttcatgacc ctggggtgcc  1620
ccttccttta ctaataacct gtcaagactt taaagaacac atactgagac taaagcccac  1680
caagcctgcc tggccacagc gcaggctgcc tcggcctctc cgacatccac ccgcttccag  1740
ggacctgtac gctttccttg ggtgcgaact cgagtccagg accggcaggg ttctcgcctt  1800
aatctgtacc accgtcccgt aaatctgtcg ctcagcccat agccggcctt tgatctccaa  1860
gcggagcagc tggacaggtg tcgaactgca cttcccttcc cgctctgagc caccgaacaa  1920
acttggccat gcccggaaag gattcccgtg ctcagggaac ctgggcaca ggagagggtg  1980 gataggcgcg aataagcggg ctccaaaaag tggtgtggct tggcaatcct attcgttctt  2040
ggcgggcaga aaattcagtg cgaataatct ccaaataccc tggttggaga aaagataact  2100
tgtagaaaga atgtgacggg gatggccagg tcagataaca agctcgggtg ttagtgagcg  2160
taatctgacc gcagaaaagc tgatgggaaa cctgggcttc gcgccgcgtc ccgcttttcc  2220
tactttccca ttccattccc atctcccttc cctttccttc ccttctctac cttatcctcc  2280
attcccttcc cttcccttcc taggcattta aataagaaca aagattacac ccacaaaaag  2340
aaccttgcct aggagcgcgt ggaaacagca agggcgcccg agcgggagag gttccctcgg  2400
```

```
tgaggggtc cgcgcagcgg cggaccccgc accccggccc ccaacggcgc ctaggaagtt    2460
gtcactcctc tcatttaaag cctcagaaaa atgcattcat gagattgttt ctttattttt    2520
cctttctgcc cctctccgca ttctttgcct atttgcttta cggcttttca gccttgttga    2580
ggccaagaaa agaaaccagg ttcttttctc ttgcgattgg atccgtattc ccagttaggg    2640
cgccttttga tgtccccatt tagcgccttt gactggtcag ctgaatgggg ccgcctgctt    2700
ttgtcctttc ccacaagtcc cttcagaaag atccctttaa acgcccggt             2749

<210> SEQ ID NO 24
<211> LENGTH: 549
<212> TYPE: DNA
<213> ORGANISM: Homo sapiens

<400> SEQUENCE: 24
caccgctccc ggggcgcaga ccctggggac ggtgaccgcc cctcccgcgg cgcgcagcac      60
cctcacgtcc acctctggtc cgactgcggt gggagtgggg aacttgggtt tcatttaagg     120
ccccagagct cgagagaaga gtcacgggca gaccacaccc gggagaaaaa caagggcgtc     180
tgggacttcg cagacttact cgggttggaa tcagaaggca tttcttccac ccgcctgttg     240
attcagagaa cgaacgccgg acgcaaaacg tagatgggca ataccgcag tgacagaaac     300 ggcgggccca gttgctttcg gccgaggcct ggactgcgt aggggaggg ctccgcgggg     360 ctggaggtgg agtggcgggt acggctggga gaccgacggc gccgggcccc gggcctcctt    420 ccctcccctcc ctccgccgga tagggatgcc ggcacacgca cactgccccg acaaacccat    480
ctcctggggc ggcatgggcg gcactacgat tcctcaaacg cttctggtcc tggcttacct    540
aacaaaacc                                                            549

<210> SEQ ID NO 25
<211> LENGTH: 1899
<212> TYPE: DNA
<213> ORGANISM: Homo sapiens

<400> SEQUENCE: 25
atgaactcga gtcaaccccc cgaccccgg cacgcatgga acgggcgtga ccgcgcgcag      60
cctcgtctcg gagtctgccg gcgccgggaa gcttctgaag ggatgggatt cgagtctccg    120
tgcgcgctgc gggcggcggc agagggatct cgcccctccc tacaccccaa gtgtcctgag    180
ggccacgcca caccaggttg cccagcgagg gacgctggct acccatccgg ggatgggtgg    240
ggagccctgg cggggcctct ccggctttac gccctgttgc ttcgcctggc cggagaatgt    300
gaggaagggg cataaggtta ctggtgcttc ggccacaccc atctttctga gcccactgga    360
ctgggcgcag aggggggatt gccatggaaa ccacaggtgt ccggagaggg gatcttgggg    420
ctggcctcac cccttccctg cggagattgg ggaccctggg gtaggggag ccgcgcccag    480 tcggcctcct ggaggacacg ggaggaagcc ccgaaccccc gcgcctgagg ctgtttctga    540
ttggcccctg gaggccgcag acacgcagat aggcggccct gggtgtattt ttattaatat    600
tatgtccgta ctgattaata ttatttatct taaataaatt tcaccccgtgt ccaagttcac    660 cgcgcccca aaaccgagtc tggggcggca ggggaactc ctggccaacg aatccatgcc     720
tcgccctcct gtgatgaacc tggtacgcac ggttttctgg ttaattctat cgctgaaaac    780
tggtgcgggg ggcgcacttc tgagacgaa gagcatctag gagctgaatc ctccacgcgg    840
gtcgcccagg ttgatctgaa tttctgggga atggcttggc tgcccgcccg ggaccaggcc    900
```

| | |
|---|---|
| gaccctcctt gacggtggcg tagagggctg gagcctgggt actgcgaggc tcctcgcatg | 960 |
| gctgggcccg ccgcgagggg ttgcagagcg gctcagggat cgattcaagc atcgtctctc | 1020 |
| ctccctcgcc cccagacaga gctgggcgcg gggttcccct tccagatgga gcgagggtct | 1080 |
| cggggtggcc ccggaaaagg ggagcccgcg gccacggcta cgtattgcca tctcgcgagc | 1140 |
| agagatgtca cctcctgcct ttggaggaaa gggagcccgg tggggatgag cgcatttagc | 1200 |
| ccaatgctgg gaacaaagcg cactccgcgc ttctgcgatt cgctccatt ttgaaatgtg | 1260 |
| ttggcgcttt ggtggggccg ctgcggtggg caaggccggg ggcgctgtta atggaggaac | 1320 |
| ctcaggggga cggtccttcg taggaaactc tatcctggct ctgcgcgcgc tttaaggaaa | 1380 |
| tggcttccct ccaggacctc gagggatgca gcttttgcgc ggatgacggt ggggtgctga | 1440 |
| accagccggt gcgcctctgg aaatgtctgg gcacggatcc tggggccatc gacgactcct | 1500 |
| ccccattccc agcaggcggg agctcttaca ttccgagcga gtgacccctc tcaccctctg | 1560 |
| gcgctcacac acctgtaact ccaaacctcc gtctcagaat ggtccaggct ggaagggatg | 1620 |
| atgggggctc cgacagcgac tgcctagctc accctctgc gtgctcaggc tccaggctca | 1680 |
| gcaggaccaa tttgagttct atctgatccc cctcggcccc ttaactgacc catcctacag | 1740 |
| gagacaggga aatgtctttc ctaccgcggt tgattctggg gtgtcatttt gtgttttgtg | 1800 |
| atggctgctt atatttactg tataagcatt gtatttactg tataagcatt gtattataat | 1860 |
| tactgtataa gctgcttata tttactgtat aagcatctc | 1899 |

<210> SEQ ID NO 26
<211> LENGTH: 749
<212> TYPE: DNA
<213> ORGANISM: Homo sapiens

<400> SEQUENCE: 26

| | |
|---|---|
| taggagcaga acttcccagt aggtcccagg aaaccacctt ggcgctttgc tcgcgcatcc | 60 |
| cttactgtat ggaagtcggg gccttttagg gatttagatt cgtgtgtgtg tatgtgtgtg | 120 |
| tgtcgctcta caagcaaaca cgggggtaaa gaatcgggca tgagcaaagt ggattgaaac | 180 |
| tcgagtcctt ccctgagcgc gtcggtttct tcatctgtga aactgacatg acaacgtccc | 240 |
| agggtgcggc ggggcattca tgcccagcac ccagcaagca ctcagcggta agttacgtta | 300 |
| ccgggcctag gggagagcag agtacaaatc agatctcaaa tcagcgcaca aacgggaggc | 360 |
| gcttggcccg gcgcgcctgg tctgcattac aggataatgg tctctttccc aaccagcggt | 420 |
| gggggcgaga gacctggccc ctcccccacg gtttccccag ggagcagccc gtggggtgtc | 480 |
| ctgcgcagcg ctccgaggtg cctgtgacgg tgcatgggac tgcgggtcct tcccaacagc | 540 |
| aggggaggtc tggctgctgg gaacccgggc gctgccggag tggggtgggc ggggacgagg | 600 |
| tgggcgggc agggacccga accggaggt aagtcagcgg gtggaaggct ttcccctcta | 660 |
| ggaccggccg gcttctggct ttcctttga atgggttacc cggagaacag cttgtctagg | 720 |
| gaactgttgg ccctgggacc gtgaacagc | 749 |

<210> SEQ ID NO 27
<211> LENGTH: 649
<212> TYPE: DNA
<213> ORGANISM: Homo sapiens

<400> SEQUENCE: 27

| | |
|---|---|
| ccagtgggca gggccccccaa gacagaatta atgcccgtgt tctggaggga ggggatccat | 60 |
| ttctatactc ctcctcggga gtcccatcct ccctgccacc atcttgctga ggtgcaacct | 120 |

```
cgaaaatcac gccgctttcg ccgcggcctc ccatcgtgga ggctcagagt gcagctattc    180
ctgcagccgg ccttcctatt ttcagtaatc tgattagggg tcgatgttgg tgggctcggg    240
gacggcttct ccgtgaggtc gttatttagc gcgcaccggg tcgcctgagc ccggggtcgc    300
ggccaaaggg gtaatcggct cccgcagtct cagcccttcc cccggggctc ggggcaggat    360
tgactgcgca accctgcggc cctgtgctc tccgcggcct ctgcgacccc gccccgccag      420
cctctccgcc gctgggctcc accctcccgg gctctgctgt agtctgagaa ctccgtggag    480
aatgcgaacc gagcggcgaa cggaggcttc ctgcctccca ggttgtgccg agcctcagac    540
ccttctccct tccatttacc accaagtctc tagattcaag gtcaagtcaa aggagcacag    600
cccgtcttac ccctgggact cccagcgccc agcacggagc ctgggatgt                 649
```

<210> SEQ ID NO 28
<211> LENGTH: 1399
<212> TYPE: DNA
<213> ORGANISM: Homo sapiens

<400> SEQUENCE: 28

```
cttcaggtgc gggggcgctg atcctagttt tcagcaggag aataaaatat gaacgaggaa     60
gatcacagcc tgggagtggt ctccgagtcc accctaggat gtgtggagcg ggcgggagcc    120
gcttttcctc gaaagggctc ccagtccctg gtccctcgct tcccaaggct ttgtccaaac    180
aagtcacgga cccgacaagg tggtccattc tctctctttg gcctttcttt tctgcccttc    240
gaatccgaag gactggatgg agggagggg atatggcaat agtgtagaag tgtcaagatg     300
tgaaaattgc tcaactgaga acgcacgcgg gggctcgcgg cccaacagcc tgcaccacac    360
tcaggagcct gggcctgggc ctgggggtgg ggtgggggg acaggcgtcc cccccacccc    420
aaccccaccc ctatccctgc ccggctgtct aaacggacct aaatgctaac ctgctgttgc    480
cttgactcca gagacacgaa actgaagcta gccctcgccc ctctctggga tcccgcgctg    540
cgctgcgggt agctgcccgc agggaggccc aacctgccgc ggctggagca cggtttctgc    600
tagccgccgc cgtcaacttg aacttcagtg agcctaggcc ggcttccttc gcgctcacct    660
ccatccacca cctaagaagt cccctcagcg cgagcgtcgc tttatccgga ggcagctgga    720 gcccctcgg gaggcccgtc attattatta ttaattatcg tgatccttac tgcattatta    780
atgcccagga tgataaccgg catcggtatc agctttccct ggttcagtga tatcccacga    840
agttcggggc ggggaggaag tcactccagg atcagaggcc gcgtcggttc tgcttggggc    900
atgggcagag ggaggctgct ggggccaagc cccggctgga cgcgagggaa gaaactcgtc    960
ccaggacccg cacgcccata cctggctgtc ccagagctct tccctaggcc ggcaccttcg   1020
ctcttcctct tccccacccc ctagcccttt tgtctctttt tcagacggat gttttcagtc   1080
tcaagtggtt ttattttccg cacaaaaccc tgagatcaag ggcagatcac agactgtacc   1140
ggaggctcgg gttccctgg actctgtgct gttctgcgtc ccaggttgg ctaggaagga     1200 aggcctgggc cggcgaggtg acgggtctcc cgcccaggtc ggcaggacgg ggggaggtgt   1260
gtcccggtag gtccctggtg agctcacccg tggcatcggg gacccgcggg aacccaccgg   1320
gcgcccacta gagactcggg tcctaccctc ccccacacta ctccaccgaa atgatcggaa   1380
gggcgcgcta ggcctgctt                                                 1399
```

<210> SEQ ID NO 29
<211> LENGTH: 1599
<212> TYPE: DNA

<213> ORGANISM: Homo sapiens

<400> SEQUENCE: 29

```
gaaagattga gagatcaaaa acatcactca agaaagcaag aggagagaat aattgagaga      60
aacgcagaga gacagaggcc cagagaaact gaagaaagag gtagcgactc aggggggaaat    120
agagatggag actcagagag aagggagaag gcacagggag aggataggac ccgcgagaga    180
aagcctgagc gcgcgctgag acccacccag cattttcacg gtttgcttgt ggttctggtc    240
cctgagcgag gcacccacga cagcatcgcc gcgcctcctc cgccacagct tcctgccgat    300
gagactgtag aggaccgtga gacagaagac aggaaggaag aagaagatgc tggacaccca    360
caccatgacc gtgagcagtc cagagcgcac cgcaaactcg gtggggcggc actcgttggt    420
gtcccaaggg tcggtgccgt tctcgtgctc caccccgact agcacgaaga tgggcccggc    480
gctgcagaag gccacggccc agatgacgaa gatgaccagc ttcacccgcc ccttggtgac    540
caccaccttg gcccggagtg ggaagcagat ggcgaagtag cgctcgacgc tcagcgctgt    600
gatggtgagc accgtggcgt aggtgcagct ctcactgacg aattggaaga gtttgcagag    660
gaggtcgccg aagttccagg gccggtactg ccagaggcga acgaggtcca ggggcatgca    720
gaggaagatg agcagatcgg agaaggccat gctggacagg tagaggttgg tggtggtgcg    780
cagctcgcgg aagcgcgaca ccaccagcat ggtgagcagg ttgccagcga tgcccaccac    840
gaaagtgcc acgcaggtgg ctgtgacgcc cgccagcagc ggcgcgggga agagctgcag    900
cagctcgtcg cccagcgagt cgttgccggg ggaagcatcc cagtccaggt cggccagtgt    960
gaggttgaac cccggctctt cgctgggcgt cgcgttccac atgctgccgg ctcagctgaa   1020
caggctctgg gacgtgactg cgctgggagg ctggaccgag ctggctcccg aggaggtccg   1080
cttaggcgcg ggagggtgcg agggaggagc gggtgcagac gcgtagggag gatgcttgga   1140
gaagaaagag agggaggtga gaggcagaag ccgaggaaga aggtgagatg gggacaagga   1200
agagggagag agactggtgg tcagtgggtg agagagtgac ccactgcttt ctctgacacc   1260
tccccttttcc cccaccaact cccccaaagt ttctcccaac acatcctccg gccggcgccc   1320
acacgcatac ctgtcaccag ccctgcctcg catttgcgtt ctcgatccag ttccatctcg   1380
cacttcccaa agcgtcgcag cgagtgggga ccgcagggac caggcgccgc gaagcgggag   1440
cgtgaggcgc tctctccgaa gccctgggcg acgctggact agtgtgcccc ggaaggacag   1500
gtcacacccg ggggtggggg tgaagacgac ggtggcggtg gggaggacac ctttagcagc   1560
tgggacctga tttcttcctc cacaaggctg cagctggct                          1599
```

<210> SEQ ID NO 30
<211> LENGTH: 2399
<212> TYPE: DNA
<213> ORGANISM: Homo sapiens

<400> SEQUENCE: 30

```
ggaagctaag gaggcagtga agacacctcc tcagccctgg tctcccccac cagcacacca      60
cctagcacag acagcaccag ctcacggccg ccgcagtccc tgggtggcct ctacgggaat    120
cctggggcag agatgggatt acgaaaccct aaaccactcc cgctgcgcgc gaatcacgtc    180
tggcaggctg ctccagcccg cagtccacac accccgggc ctttgcgcca ccgcaccaat    240
ttgcatcccc aacgaatgcg cgctgccctg atccccgagc acgcgggtat taatgatcat    300
aaaaaactgg gcgattacaa aaagagaaag tgctaaatcc cggagctggg gcaagatttt    360
caaaaggcaa cacaccgaat ccaagtctgt actttaactt ttttaataac gattttttttt    420
```

```
tttctgggct ggaagctcgc actgaatcct ggaggaattg ctaaatcgga ttaaggttat    480
attttgcaac agactggatg gagcaataaa ggagagcgcg cggaaatggg acttcaccca    540
tcaattagat ctctattagc agccaatgca ggcttcacca caggaaatgt cacgtcccag    600
ccctagcgga ccctttcgtt ccccaccccc agctctcacc tccctgtcc ctggagttaa     660 acaactcttc tggcgcacac attggaacta acaaaccct tttgtgtgga atacggtttt     720
tgtgttttgt tttttgtttt tcttattgaa cttgttttgg aaccctgtac cacctgcctt    780
ccccaacccc agcgcagcga gctaaccccg ggacactccc accccggccg gctgaacagg    840
ttgcagcgcg acacctgcgc tgtctgctgg gtcgctcagg accgcggtgc ggggcctggt    900
gcgctgggcc ttattaatat taaaagcttt atgacagtcc tgggcagtcc gtaatgaaag    960
gtgattaaca agacaatgga caggattctg aatgctgggg caactcatct gctataatag   1020
atcagacccg cctcgggggc ccagcgtgcg aattccgccc cgggatgcga aggagttcga   1080
acgcatggag tggaaaacag gcaggcgtga tgtggccata gtgggagtca agactgcgga   1140
aatggagcga cctgcaggct agaggagaga tccacgtgcg ggatccactt tgacctcggc   1200
ttcatctctg atgctcttac tgtgttcgct tcggctttgg agtccaagat atgtgcggtc   1260
cccactacga aaccagctgc ctgcacccgg attccagagc ctaggccctt acctatggga   1320
aatcctatag ctccagatgc tggaatccga gctctgatag gaaaacgccc taatgctggc   1380
atctctcgct tagcacatag gcaagaaaat ggggcacgac cccaaatcc actcccttcc    1440 agcctccgaa aaatgcaccc aggtcttgac cctccactct tccgctcccc agcagaacga   1500
aaatttcctc aggccctaga aagcctcatt tatcattctc gtgggggctc aaatgacaac   1560
gcttcttgtc ccagcacggc tgtgaatcgg ggccccccac ttctgctccc ttatccttcc   1620
tgcgcccctc ccgctccaca tcccagccca taaggagaca aggtgcaaca gccagggaat   1680
gagcaagcag gagaagtggc cgaacggata aaggaggcac tgttgtggtt gccgcagccg   1740 ctgccccat tcagggaccg aattgaaatg gatatttccc tcctcggccc agctgaacga    1800
ggctcaatgc ctcaaagatg cagagctgcc tcggtggaca tgctctgtgg ctgatattat   1860
aattttcata atgcgctttt atgtcgcgcc agactcctcc ggtgaggagc ccgcagagct   1920
gctgaaaggg gctttgagag gcccgggcgc gcggctgctg cgagctgcgc gccccccgcc   1980
ggcctgagtg gcaccgcgtg cccctgccgg ggcgcggctc ctgcactgcg ggcgcgcagg   2040
cggcggcggg ctctgccggc gccccttatt agcatgcacc ctgggtgcgc ctggcctgct   2100
cccgctgctt ccgggcctct ctgcgcccct ccgagtctct gccatccgcc tgggtgcgag   2160
gtccctggcc ttgctcctgg tcaaactcca ttccgctcca gctcaggctt tagggaaggt   2220
caaggtgtta aaatgtgggc agaacattcc ggaagcagtc gggggctgga agtcttccga   2280
cctgagtgga ggctgctttc ccaagggtcc ggaagcaaag ggaccccttgc tgtgagggt    2340 ttgtagcgaa gcaggcatt gagtgggagc ctcatcattg caacgagtaa ggtgtacta     2399
```

<210> SEQ ID NO 31
<211> LENGTH: 749
<212> TYPE: DNA
<213> ORGANISM: Homo sapiens

<400> SEQUENCE: 31

```
ggctcctctc cctctggcca atgtggggag cctccctaaa gtgctcccct cccgcccagg     60
accaggagct gccccaaagc agcacagtcc agcaagcagg acgcctggac cctttaaaca    120
```

| | |
|---|---|
| acccgactgc tgcgccgtat tcaccgcaat aggcgggcag gagcgggacg cactgcttcc | 180 |
| agagtcccgg ccctttaagc gacccacact ccccgcgtcg cattcaccct aataggcggg | 240 |
| catacaaatg ccgttgcctg gagccgcagc ccagcgaatg ggacccacag cggcgcgccc | 300 |
| tttagttgac tctgtcttat tcgccgcaat agctgatcag gagaaatccc gctggctgcc | 360 |
| aggaaagggg cgcggagatg cggatgctcc gccccaacac cacgccttcc tctgctgacc | 420 |
| atccccaaag tcccctttaa atgacaaccc tcccccccc caccccgccc ccacaccgag | 480 |
| cgccgtattc accccaatag cacatcaatc cctccgcaac gccgggatac tgagctctcc | 540 |
| ctcccctggc cgaggaaggc ccttcccgc gaggaagcag ctgagaatgg ccagcgaga | 600 |
| gaagggacaa aggcacgggc gacagagctc cctctgtgct gtccccagc gtctggaggc | 660 |
| ccgttcccgc cttgctcaga agcacagggc acttaccaag gggccatccg tgaccagcag | 720 |
| tcagggggcat gctgtctcca agctggggt | 749 |

<210> SEQ ID NO 32
<211> LENGTH: 1024
<212> TYPE: DNA
<213> ORGANISM: Homo sapiens

<400> SEQUENCE: 32

| | |
|---|---|
| cttgggcgcg gactcgggat gcccctgct gggctgccct gggtttgcgg ctgcggcttg | 60 |
| ggcggcgcgt tggggctgcg tgtacttgtg cgcgtacacg tggctgagtg tgggggtgtt | 120 |
| aggcctccac gctcaacatc catttccgaa tctgaatcag gctccctctt tgccacctcc | 180 |
| ccccagtctc cttggtctcc cttttctctt ctcccaccgc ctctgcacac gtcccttttag | 240 |
| aaataaaaac acttattttg tgggcgggtg gggagggtgt ccagcttttcc cctgcctcct | 300 |
| cctgagtgcc cccctctgtc ccacgcggct ttcttctgaa gtctgtgcag tcgcggacgc | 360 |
| aggggggatga cgcccccgc cacccccacc actgtatcac tcttctgacg tccccgccca | 420 |
| gacttggcta gctcaccctt atcagatggg gaaactgagg caggagggga gaagagaggt | 480 |
| acggcctgga gaagcgctcc cgcccggctc gctcaccacc cccgcactcg cgcccgattt | 540 |
| agccgcaggg aggctgggaa cattgtcttt attttaagcc tccgagtgcg gcacgaacgc | 600 |
| ggctgctcgc gacaaagggc ttcttgaagc ggctgcaggc ggcgcacgtg gggctttggc | 660 |
| cccgcccccg cgcgacccc tccagttctc cctcatttct ggctggttg ggtgggtct | 720 |
| gactctcggg tctcggctcc tgctggttgt tattttttggt cgcctggtcg agaattcagt | 780 |
| cctccaggcc accaagggaa cgtggagtcg cccttgcgcg gtctcggccc agtctcggcc | 840 |
| cccttactgt gcaagaggag agtgccctga atgcgaattc agcttggcct ttttctagtt | 900 |
| gaagcggcct gagcaagcta ggccccctct ctaggtctca gtttcttcat cagtgacaag | 960 |
| aagggtagaa atacctcccc gaccaggctg tttgacgggt tagttgagct tctgcaggta | 1020 |
| aaac | 1024 |

<210> SEQ ID NO 33
<211> LENGTH: 1099
<212> TYPE: DNA
<213> ORGANISM: Homo sapiens

<400> SEQUENCE: 33

| | |
|---|---|
| gacccgcacc cttccccggt cccacccgtc accaggccgc ccgcgtagcc aggaattctt | 60 |
| agccaggttc ctgtgcgccc accgtgaccc taagagaaga ggcggacgcc ctggcacgtc | 120 |
| cttccctcct gcttcccccg cccaaagcgc tcccggttcc cggggcgtca ggttggctga | 180 |

-continued

```
cagttcgggg tccctgcgtc ctgtctcctc agctgggctt cgaggatgtg atcgcagagc    240
cggtgactac gcactccttt gacaaagtgt ggatctgcag ccatgccctc tttgaaatca    300
gcaaatacgt aatgtacaag ttcctgacgg tgttcctggc cattcccctg gccttcattg    360
cgggaattct ctttgccacc ctcagctgtc tgcacatctg gtgagacggg gcacaccggg    420
tggaccggct ttctgaaaca tgggcatatt ctccgccacc tgcccctac tctcctctta     480 tcccaggccg gcgtcaggag gaggaacgcg catcagttcc caagcagtag gaagaactgg    540
aaggccttga aaggcaatgc gcttccttta gaataacagt ttgggcttgg agtttcaaca    600
ggagaaagaa tgtcggtctt tcctggggtg tgattttcct tgcatacata aggctgggct    660
gagtgtggag gcgggtacct ggaagccaca cttcttacca caggctgctc tcggggccct    720
gttgtgactc gtacctgcgg ttctgggcag gactcttctt tctttcattg ccttttattc    780
agtcactgcc tgtgcttggg gtaaaacaaa agtgatctct gagcagaatg ccgctgacag    840
tagaattgga tgaggatgtc agacctggtt aagcagtagt gtggaggggc tgcttcaact    900
ttgcccctgg cagatggcaa ggatgggacc cagaggaaag ggaggtgtgt gcagttaagg    960
cgagggtccc ccccagtaca aacgaatgaa aactccagct gcgggataat gaatgagaag   1020
gcctccaaat tacttttca ctgatgaaac acaaatggaa gtggcatata attaaagggg    1080
aaagaaatat ggaagccca                                                 1099

<210> SEQ ID NO 34
<211> LENGTH: 749
<212> TYPE: DNA
<213> ORGANISM: Homo sapiens

<400> SEQUENCE: 34
ctagacctag tgagataata attttttttcc aaagtttaca acttatatta gaaacatgtt    60
ttttatatta taaagaaaa aaaaatgtgt ttctgttaaa ggagaggcgt ttttggttt     120 tgagtgagtc cagcgctgtg ggttttatag cctgggggga ccatggcatc cgccttcccg    180
gtgcgtgtgc cagattatat cgcatagttg ttgacaccgg ggtcccactt cctcccttct    240
gtccaccctg daccccacat gatactccag gcacaccagc caccttgtg ctttgagacc     300 gtgcgagccc ccggccagcc cagccaagca gcaacacaat agcacccctc gctgcgagcg    360
ctgggccgca cttccccctc ggatgtataa tagcaccaac cggatatttt tagatgggct    420
ttgaaaagtc gcagtgtgct gagaccgcat accagacgcg tgaggtcacc gggcctggga    480
gcagcctcta tgcatggata attggtgcac ggggtaatcg ggtaatcgca gaaccagaaa    540 gccagcctt gggcagccat ggtggtggga ggggcccctc atatcccaag gcgttccctg     600
tgttacgttc ccaagacacc aggcctggct gtgatattag aagtcactgc agagacttgt    660 ccctgggtt taaagtgagc actgtggctc tttaaggtac aaatgtacat ttctggggca    720
cctctgccac agaccaggct ttacaccaa                                       749

<210> SEQ ID NO 35
<211> LENGTH: 2749
<212> TYPE: DNA
<213> ORGANISM: Homo sapiens

<400> SEQUENCE: 35
aggaagagtt gggtgaatct tccacagccc ctaggtcctg tcttctcggc cttcgtccct    60
tggcagcttt tcaacctctc agcaggccac aggcgcacgt ggctggcagc tccccggcct   120
```

```
ccggctctga cagtccgggg gcaaccaggc ctgcagttct cgaggaaacc cccagccccc      180
cacgtctcgt tctggaccag gaacccccte cccaacaacc gcgcagcaag tggcgactct      240
gggagctgaa ctggagtgga gctcgaagtg gctgggggcgg gcaaagactc ccgcttcact     300
ctgggacaca actgggacgg cgcttcaacc tctgcctgca ggcgtgcttc tcgcgcgcac      360
cagcaagctc tctatccacc tcgcctgggc ctttgcagcg ccctgccgcc caggctccag      420
cgcctctact accctagccc cttctcaaca gcggctctg ccttcttccc cagtaccact       480
gcactgccga aaataagccc ggagactaac gcaccttgta gggaagagaa ggacatctgt      540
atctccaagc ttatccaagc aaaggcctcc agagtccctc ccatggcccg aaacacctcc     600
ctctgaccga agagcgtcct ttcttttccgc cgcctcctgg actcatccta aatagggcag      660
acccgggcta aaccagtgat ttttttttcc atgaatacga agaacccga ttgcactttg       720 cgaagtctgc gcgtattcct ttatcccgca actagcttgc tcccgggtgg agtgggcaca      780
gtggggagcg gtcagggcag ggcagggccc aacgctggcc cctcgcggag ctttccctgg      840
cgcgacctca cacggtcgct gcctctattc cgaccacgct ctgcttcgct ggctgcggct      900
ccgccaggaa tccgaggggg cgcaggccca ggctcggccc tagatgcgcg gaatcgccat     960
cagcctttgc ttacaccagc gtggccgcag ggaaactcct ttctctccct ccagtgtcac    1020
tttgcgagac aagaacagag ggctcataca aagaaggct aatttggggt ctgtagcttg     1080
gaccaggtgg aactgtgagg aggaaccacc tgtctcaccg ccccacccccc caactgcttt    1140 ttctaactcc cttgtggtc ctccacacct gtttagggcg ctgagccact ctgtctcctg     1200
gtagtgttat tttgctccaa gttttatcgc aattttgat tcactcgaca gtatttattc      1260
agctagggct ctgtgccagg gactacgcaa ggcctgaaaa ttcaaactta atctagatgc     1320
agctcctact cacacggaac ttacacattc acaataaatc acccaaataa tatgtagtta     1380
ctttctgaca gatgttactc taggatccag tgagatagag agggttgtaa tggagattcg     1440
tgtgtgggtt tttgcaccat ttcttgatct ctcagcattc caaggtcgtg agaggagtcc    1500
ttgagtggaa gtccgtccta ggtttgaacc ctggctttgc cttttttccag ctgtgcagta    1560 ccgctcttgt gggctcccgc cacacccctgg agtcactccc atcacagcca gagtaaacca    1620
gtgtgtgttt tctggcttcc ctccttgagg gtgagcccct gttttatcta tcttttgaacc    1680 ccccagtgcc tcgagaaacg ctgaggaaac acagcctccg agcacctgtt tcctgagctg     1740 taaaaatgg tcacaacctg ccctgtgtac tggcttggtt tgtgctaggg atccaaacaa     1800
ttcaggatga gatcatgtgc ctgagtttgt agatcacaaa agtcgctaat agaaggagtt     1860
attccttctg attctgtatt ttggatttag agaaactgtg actctaggcc tctgaccttc     1920
aacaagaaac acttgggccc ctcagttgct cccgcagtct cccacagcta ggcacaggct    1980
tctaagccgg gctgagctgg gctcgcgagt gccatcgagg caaccaggcg cagggagcgg     2040
aaggcaggag tgtaactggg cgctgggggg cgctgctccg caaccccaag atccgaggaa     2100
tgcctccggg ggatgatttc tctggagggg tctcgcaggg ccccctctgc gctgctttct    2160
caggcaccag aaccgaaatc ctcgggaggg accgcgggag cccggggcgt gcagacaggc     2220
ggctttcaca gacgcagcgg gaggaaggat ccctctactg ctccctttcc cgatttgacc    2280
gtctagggcc tttgagagga cttctccttt tgggaaagctt ttctcaattc gtggcctgtg   2340
ggcaggctgg ggggtggggc gccaagtcat ccgagcgcgg cttctgcttc tcccttttccc   2400 tcacaggcat gctctacgga gggtatggga ggcgagggcg cgtctatgag ggccagagtc    2460
cgcgaagaga gtccggccct taggcctttg gtgttgaaga atctgctcct ctgtcgggtc    2520
```

| | | |
|---|---|---|
| aagcccccact agaagttaac acctgtggtc tccaaacttg cctatttcc tgtcacgcag | 2580 |
| ttcaagccaa gattcaactc gtcttgaatt tttgtattta gagccctac cttctccacc | 2640 |
| gactccaggg gcgccctctg gcgggaaggg gcctggggta ggagggaacc tgagggagcg | 2700 |
| ggttacaaag cagagaacag cgggagctca gcagctccct ttgaattgc | 2749 |

<210> SEQ ID NO 36
<211> LENGTH: 799
<212> TYPE: DNA
<213> ORGANISM: Homo sapiens

<400> SEQUENCE: 36

| | |
|---|---|
| gtggaatgga aagtttccca acccaagcct ttcccaaggg gtagccattc tctgttctac | 60 |
| agtttagggc ttgcatgtgc tttttctgga gtggaaaaat acataagtta taaggaattt | 120 |
| aacagacaga aaggcgcaca gaggaattta aagtgtgggc tggggggcga ggcggtgggc | 180 |
| gggaggcgag cgggcgcagg cggaacaccg ttttccaagc taagccgccg caaataaaaa | 240 |
| ggcgtaaagg gagagaagtt ggtgctcaac gtgagccagg agcagcgtcc cggctcctcc | 300 |
| cctgctcatt ttaaaagcac ttcttgtatt gttttaaagg tgagaaatag gaaagaaaac | 360 |
| gccggcttgt gcgctcgctg cctgcctctc tggctgtctg cttttgcagg gctgctggga | 420 |
| gtttttaagc tctgtgagaa tcctgggagt tggtgatgtc agactagttg ggtcatttga | 480 |
| aggttagcag cccgggtagg gttcaccgaa agttcactcg catatattag gcaattcaat | 540 |
| ctttcattct gtgtgacaga agtagtagga agtgagctgt tcagaggcag gagggtctat | 600 |
| tctttgccaa aggggggacc agaattcccc catgcgagct gtttgaggac tgggatgccg | 660 |
| agaacgcgag cgatccgagc agggtttgtc tgggcaccgt cggggtagga tccggaacgc | 720 |
| attcggaagg cttttttgcaa gcatttactt ggaaggagaa cttgggatct ttctgggaac | 780 |
| cccccgcccc ggctggatt | 799 |

<210> SEQ ID NO 37
<211> LENGTH: 3949
<212> TYPE: DNA
<213> ORGANISM: Homo sapiens

<400> SEQUENCE: 37

| | |
|---|---|
| tcctatctca tttcactagc agttgagctg acgggtgcgt gcgagaatgc gagacctgcc | 60 |
| acgtgtacac gtgtacgcgg agtgtcgatc tgcctgcgtg tccttggatg tgcctgtcta | 120 |
| ggtgcccacc cgcgcgcgcc accacatccc caggcctctg gaacgcagct gctgtgtggc | 180 |
| ccggcccgaa gtttctggag gaggaaatcc ctccacagaa ggtttacatt atttcgctcc | 240 |
| gcgggagacc cggcttcggc agcacttagc agaagatttt ggcgggaaag gcccaagccc | 300 |
| tagctgagga ctccgggtgg agcaggggct gaggtccgag cgcagatggc gccgccgagc | 360 |
| gcctgaaata tacttgcaag gccgcagcaa tatacttgca aggccgcagc cggagcagct | 420 |
| gttccagccg atcctagctc gaaagttcct ctgttgctct gggagagggc gggggagagc | 480 |
| aggctcgaga gccaggctcc tccgaggctg gtcttgaggc acttctctag tagcttctcc | 540 |
| aaaagactga gagtgccggc gtaggtatga cagtgagggt acctcacaga cccttctcca | 600 |
| aagtctggcg ggccttgggg ttttttcgggg ccaccaggct cggtggaatt tttgaaacgc | 660 |
| tttcgaaata catagtttcc tctgtggagt gagtgcctac aacgcgcagg ccggactgat | 720 |
| cccccgttgc tgcaggttgg tgccccaagc tgcgggtgct cgggcgccaa ctaaagccag | 780 |

```
ctctgtccag acgcggaaag aaaaatgggc tgtgaaaaag caaaaggcct cgtctttgaa    840
tgaaagttaa acattaaaat ctgaccctag agttgtctaa agatcgcgga attttgaagc    900
tccggcagag cggactaaaa aacggtgcta tgagagatgg tgagaatact ctaggcatga    960
acgtgtgcgt gtgtgtttgt gtgtgtgtgt gtgtttcatt cttcccgcaa acaattttt   1020
tgtttttttc ctattcccgg tttgttatcg gcctagggcg ggagaaccac gcagcggctt   1080
ctgggcccta aggacaaaag agttaaaaca atgaggctca cccgggaaga gacgctgccc   1140
tgggcacaat agggtcgcct gcattactcc tccatacaca catctttaaa tgtgtccctg   1200
tgtgtgttcg ttagggtgct gtattacaga aaaagaaagg cctaaaaaca ccccagccc   1260
tggtcgcgcc tttcgctacc gcctgagtct ggagccgaca gctccacctc ttctgctccc   1320
tggaccgccg cgtctccacg ccacggcgcc ctttttacta aaagatcttt tctcatccta   1380
tcagcaaatc gttaagaaag cttagccat tgcggggct ccaacttaag gattccccg    1440
gcccactaaa aggctaggcc cggcctgtag cccagctccg cagaaagcca gagggtgctg   1500
ggctttcagc ttcttcctcc tagacacttg ccccacaaat atatttcgtt ttctctaatc   1560
caaatacccca tctttttctt ttttaaaaaa tgataacgta atgggaaatg accaaccgaa   1620
ctctgttaca taaagttagt tctgttagat cttccacccc accccatcc cgcgggagcg    1680
agtaaataga attcatgagc ttagctcccc aggttcacgc tctggaatgg tttcttttg    1740
cctcattccc taagttttct ctcttctgcc tcctgaatgg agctcaggct aaggagaacg   1800
gcagaaagag caaactctga tctgaatctc taattatgac cccatgtatt acccatttga   1860
acataaggcc ctagacgggc tccgtgcgat ctggggcctc ccaagagaaa acttccccgg   1920
gacaggacgt ctgccacgcg cagctaaaca acttctgttt tttccgccgt ggggaaaata   1980
aaagaacctt acaaattcta aggcgtcata accctgcaa gaacttctaa ctgtatgaag   2040
gcccacgcga gattttgaca atagataaat gagctgagga atagggtct ggccagcgaa   2100
gggaaacaca cagtagccct gggtgccttt ctggaatgcc cacgcagggg tccgcgtgga   2160
caagcacttg cattcaaata caggaaaagg cttggacggt cgaaataaat ctccttttaa   2220
ttttcttttc atcgactaat aaaaataatt ccccagcact aaactcaaat accgtaacgg   2280
gccacaaaaa cacggagaat tcataaaact ctatctctgc aggtcacccg ctaatcgcat   2340
tattattagc ctcgggagca tggaaattga actgtcactg cctaaagaga aaatgtaagc   2400
gacagctgtc cctcctctga gttggacagc tttgtggctg agatccccaa gctcctgagc   2460
cccagaccgt ctctatccca gtgcaggccg ctgcccctc ccgggcttg tcagcgtgtg    2520
aagcggggtc tactccccag ctctggctgt tcagcaggag caccttccag catggtttta   2580
gaagtccggg ctgaaaagct tctgaaaccg ctaaaccaag ttgcgagcgt tgtatgtgcg   2640
cgcgcgcaca ctcaagattc ttccgacaac agctgttccc ccgggctgtt tttgcacagt   2700
tgaaatcttg gcacttaaca caaaacgtta agttggctt ctccctcct agggttctgt    2760
taaaatacag acatgacatc cccctgctt tttacatgtt ccgtgcacat aatatacatg    2820
ggttactgta ggatctgaga cacaaatcaa tcgtacccac accctaaata cacagagatg   2880
tgggccctga agagtgaccc aaggagtaag gggtctaaca tccattcttg tttccgtaaa   2940
cgccaaagga gtagaaatat aattatgttc caccatcgaa aagttggtgg agaaaggca   3000
aggacgaggt tgaaggctaa atgagacaac tggtcattcc ccgaagactg aggtattgga   3060
ttggagaacg ccgcgccagt cctcccgagt tctcagaagc gagtcctaga tctcggctcc   3120
cgccgttgcc ttcggcccgc gcccctccca atcccaggga ccggcagccc ttcatccacg   3180
```

```
gacacccaga aagctgcgct ctccacccaa agaaaaaga aatgcaaaca aacaggactc    3240
cttgcttagg ctggcgacga aaatgcaagg ctcagtccag ccccaaaaat tggttccggt    3300
gaatttaggg aggctcaggg catttgcgcg aagaaacaga aacctatgtt ggggcaaggc    3360
agggcgtcaa tggcagggcc tagctcctca cccgcgaccg gcgactggcc cttcggcgtc    3420
ccctctccgc ccgcctcccg cggtcggctg cgacgcactc acccgggtga ggctccaggc    3480
cgtgtgccgc cgcgtcctcc gtgtctccga gtgggcccgc ggggctcagc gcctccatag    3540
acaggtccag ccccttctcc tcccagtctc gcagtttccg tttttatttt gagccgatca    3600
aggcttcaac ggagaaggca tgtgctcgcg agctcagggc gactgcagat cttctccttt    3660
cactcatttt agccgcccac acccctgcct ccgcttgccc ccgctaccga gggagcagcc    3720
ggcgccctca agtctgagc gcccaccggg cccggcccgg gagaggcgga ggcgcgtcgg    3780
acgaggctga gactgcggct cgcgggtctc tccaccctcc ccctgcgtcc tcctccgccc    3840
tcctctgccg gatccgacct gcgccccctac gctggcccag ctgctaggaa ctagcgcccc    3900
gagcgccgcc cgctcgctgc atgagcgccc gagtcctgct tcccaccca                3949

<210> SEQ ID NO 38
<211> LENGTH: 649
<212> TYPE: DNA
<213> ORGANISM: Homo sapiens

<400> SEQUENCE: 38
tgtttacact taagagtcca ggactacagc aggcctggtt ggaggggagt tactaatgtt     60
cccagactta aatccagctg gaacaccacc taaaatatgc agtaacataa gaccatcaaa    120
agcaatgtcc caggacttac aatgtttgct aagacgcaag agggtgtgac acagacgcta    180
agcgccactg gcgaggagat gaaggggtcg tcttcatctt cgccggatga tttccgccca    240
catagagggc gccagtgacg cccacacacg tgctggtgtc ccgggaagag ttcctggcaa    300
agagctcagg aacgttggat cttaatcaag gctttctccg tcggggtgga tgggttggac    360
tttaggctcc agcaagcccc gccccactcg gcgggtcggt gccgccgggt cccaggtgcc    420
cgctacttcc cagaacctcc gcctcccgct ccgggccctc gaaccagcgc ggacaccaca    480
atggaccggg cgtccgagct gctcttctac gtgaacggcc gcaaggtgag cgcccgcggg    540
cttcctctgc ccccagacct gcggccaggg ccggggcaga gaggagcccc tgccgttcgt    600
cccatccttt cgtgcccgcc gtttaaggca ctcaggcacg gactggctt                 649

<210> SEQ ID NO 39
<211> LENGTH: 1799
<212> TYPE: DNA
<213> ORGANISM: Homo sapiens

<400> SEQUENCE: 39
ccaccacggc tcccacttcg ctcagataaa atgcagagct cttaccaagg ctcacggccg     60 tccccgccc cccaccgtct gccccccatca cctctcgggc ctccggtgac ctctcgggct    120
acagcagcgc tgacgccctg ggtccctgcg cttctgttcc ctcggcctgg aatgctcttc    180
ccccgggtac ctgcacagct cgctcccctcc catccttcgg gtcttcgctc gaacgtccgc    240
tcctcggtga ggccttccct ggacaacgca tttgaaacgt aaccccaagg caagaagcca    300
ccttccaggc gcgcagccga agcccagtgc caaggaggcc ggagactcgg gtgcccgcgc    360
atcccgaaaa cagcctctga ggggtcctct gagcatcctt ccagcgtgtt tgggaggcaa    420
```

```
actcgttgac tagctcttga gaggagtggc tagaggaatc caggcgggga aggggacggt    480
ggactccagg agagtgtaat ttacaaaggc gggggcggg gacgcccagg tccgagtccc    540
aggactctgc gccggacgct cgcccgccc tttcaggtcc cctgcccggt cctcgtaccc    600
gcgcgggtcc ggagaacctc tgagcaccgg cccccagccc ccgggcgggg ctccagcggc    660
gctactcacc cggctccccc gccacctgcg gggccacctc cgcacactcc cggcgcgcag    720
gccgcggctc ctcggagttg aggtgctggg gcttggcctg cttgcgccgc gacatggcgc    780
gaggaccggg ctccccgcgc gtccctagga gtggcctact tcacacaacg aattcccgga    840
gttcggaaat tacccccctt cggcggaac gcgcatgtcc cggcaattct gctcatcagc    900
cgagcagggc gatttatcaa gagtcctgac ggctgattgg cctggagcca agaccccagg    960
agtcccgcgg acttgcggtc cgctcccggg cagcccgcgc cacctgggag ctcgttagaa   1020
atgcagactc tcgggctcta ccccagaccc gctgaatcag aatctgcatt ttaacaagat   1080
ccccaggtga ttcgcatgca cattaaagtt tgagaaaccg tgtctgcatt ttaacgagat   1140
ccccaggtga ttcgtttgcc cattaaaatt tcagaagcgc agctctcctc caactttaat   1200
gtgcgcacga gtcactgggg atctcgttaa aatgcagatt ctgactcagt gggtctgggg   1260
tggggcctga gctcctgtat ttctaacgag ctcccaggtg gcgctgtggc tgctgcgctg   1320
cacaggctgc gcttttagat tcggacttaa ttggtctggg ctgggacctg gcactggga    1380 tgttttttta aaaagccgt ctccctccct caccaccccc atcacacaca caggtcattc    1440
tgatgtgcat ccaagctgag aagcacgacc tccactcctg gttctcaacc ctgctgcata   1500
cccaaattta aattttaaat gaggagtgtc tccaactgca gggagaaatg cagattccga   1560
aagttctgga ttcaggtggc cgaggccaga aatgtgtgtt tttatatagc acgcgcccgc   1620
tcccgccccg tgactcgggc gcaccggctc ttggaccaca caggagtgct tttgggggcca   1680 acccggcgcc ggccccgccc agcaggtgac ggaggcgtgg tcctcggggg gttgagctaa    1740
ttagcgttca tgctcagact ggctgggacc tcgatgagac ccgagggaga cccctccttt   1799

<210> SEQ ID NO 40
<211> LENGTH: 1249
<212> TYPE: DNA
<213> ORGANISM: Homo sapiens

<400> SEQUENCE: 40
cccgccgccc gggcaggagt ttctccgtag cccacggaca tccgggaggc ttgtggaggg     60
caggcgggta accccactc ccaccccacc tttatccagg ggcagccaga ggagccagca    120
ggtcgggact cgctgagggg gctccacgcg gggcctccca cgcacaggta cgcgctggtc    180
ctcggggtgt cccagttttg ggagggagac acgcacagtc gctcccgtcc acactcctct    240
cgtgtcctgg ctccatgact gggagtctgg ggaaagaaga atgggtgtct gagacctacc    300
cctccgccgg tgtcgccccg ctctttctgg gcgtaggagc gggctgcctg cccctctccc    360
gcaccttcct ggtctcgggc tagaactggg gcttcccatc ggccgcgctt cccttagggg    420
cgccatctga ggtcggaagc aaagctggag gggcgtccag gccagaggac gcgggctggg    480
gcgggagcct cggcagcctg gtgggagctg gtgcccactg cagggtgcgt gtacggggct    540
gcctgcgtgt gcttggtgtg tgtcacttct gggagcgtac ccgtgtgtc cacggggtgt    600 gtatgcgccc acggaagtcc tctgtgcatg cgtgtctgtg ccataggcgt gggaacacct    660
cgtgcaccca tggtacttgc ccggagagta ggaagccagc gagggagcgg ccctgctcca    720
gggtctcttc cctgctcatc cctccagctg gcccagatta caccctactc acacccgggt    780
```

| | |
|---|---|
| cgcggcccac tttccccata gccgcagctt ccggcggctg cacacttctt agtgctcatc | 840 |
| ctgccttctc gccccaactc gttgtgccct tccctccttg gagagtgagt agaagagggg | 900 |
| atggggagga atccgtttcc atccccgcg acccctcac ctagggcgga ggcgcaagct | 960 |
| ctgctgggtg ctctccgccc ccttgatcgc cgctctcggt tttcagcacc aggatccgga | 1020 |
| cagctcccca cctggccctg aggggcctct ttccttgccc tggcctggaa cgccccgcc | 1080 |
| ctggccttta tagcttccag ctagctcag taccctatcc tagaccctct tccctgcccc | 1140 |
| caacacaaac acacatccgg ccttcccatc ccggacttct gtcgggtggc caggagcacc | 1200 |
| cagggccaga acctgcctgg gaaatctctg aaactgactg gcaggcgtc | 1249 |

<210> SEQ ID NO 41
<211> LENGTH: 3649
<212> TYPE: DNA
<213> ORGANISM: Homo sapiens

<400> SEQUENCE: 41

| | |
|---|---|
| ggtgagtttt ctcccgtcca cctatgccta cagggctaag aaacggtcgt ttttctgaat | 60 |
| cgaaatgtct gcagctggct atcctccgtc gcagctgatt ccgaaagagc agggagagga | 120 |
| actgggagga ggtgggatgg ggggtggtgg cattctcttc tacagacctc aaggttccct | 180 |
| tgattccggg gcaggcgtct ccccggcgag gatccgcagc tccgagggca agctgggcat | 240 |
| aagcaatagg aggacggcgc gctgccgagg cgtccgagcc aagcaggagc ccaggtggcc | 300 |
| ttagtctctg ggcctgatga ccggacctgt ggagtagatt ccgacgcgac tgggtcattt | 360 |
| ccagttctct agacgctcgg ggcttgggac ccctaaccga gagaatctca gggtttctgg | 420 |
| catcccgact cagtccctct aaggagacag cactacgttt agcgccagga cccggcgggt | 480 |
| gtcatgtgta gggggaaatc aaataaaaca tacgaggag cgcggcaccc agtcgaaacg | 540 |
| catgaacttt ataaccaacc cttaaacaag ctaatcaacc accactgttt ctactatcca | 600 |
| taataataaa gtcatgtcct cttaataaag aaaactaatt acttatctaa gcgcttccct | 660 |
| ttccagatta ctaacggggg ggggggggga ctacagaagt ctccggaaat tatttcggcc | 720 |
| aaacatagct gtgtagatcc tttggtacca cagtaggact tgtagcccaa actaatcagg | 780 |
| agactgctct agcccttatc agctgggttt tgggtccggc caagtagccc aactggtgaa | 840 |
| cgtgtctata tttgtaacac tcattcagtg ccggggcccc tggtcggagt aaagggctaa | 900 |
| actttacttt ttcaggcccg ctgaagtttc gtggggaaga tcaacccatt tctgctagtc | 960 |
| gtgagggaaa tgtccggagg ttaactcctt ttcccttttt ctggtcatca cttttaaaaa | 1020 |
| caaatagtag caacccaaac ccaaattttg cagcggggct gggctcctca aggtggggcc | 1080 |
| actgggcat cccgagtcgg gtcagtggga cccagaggga agcataactt gggcactaaa | 1140 |
| cagattttca agacaaaggt ctcagtacgc ctgttgatgc tagggaaaga ggggactgta | 1200 |
| tacagcgggc tggacagcgg accctctttg ggaacagcca cttacacat ttattgggaa | 1260 |
| cggcaccaat agccctgaaa attagggaac agcagggct gccaaatata tctcaatcaa | 1320 |
| aacaaagtcg accaaattat gagcagaggt ccataatct cccctttgct tttgatttca | 1380 |
| atgctgctta taagaattta gagaaatcga actgtaatat ttttttgtta aaataaacct | 1440 |
| gtgctcgttg aaatttcctt ttcactccct tatcatttcc gttgttttat tttgtgtgcg | 1500 |
| tcgaaaacca caattttag cttgtaatta tttgaattcg gaacgatca ccaaactgta | 1560 |
| gtcaatattt tcctagtcct ttttaagcga ggctccggat ggctgggatg tctttaggtt | 1620 |

-continued

```
agtagtcccg ggaggacgcg aacgccggtt caggcagaca cggaagaaag caagcgggcc    1680
gcaaagagag aaatcacaaa tgtttccccct gacttttgcc tttgtgcagt ggaccctggc   1740
ccctgccgct ctccctgcac accctgggct tggtctgcct ggggagaac cccgcgtcgt    1800 gcggctacac cgcgcgccct cctcagcctt gcggtgtgct ttctttgcag ggcatgcccc    1860
cgctcagccc ggagaagccc gccctgtgcg ccggctgcgg gggcaagatc tcggacaggt   1920
actatctgct ggctgtggac aaacagtggc atctgagatg cctgaagtgc tgtgaatgta    1980
agctggccct cgagtccgag ctcacctgct tgccaagga cggtagcatt tactgcaagg    2040
aggattacta caggtactcc cctacacccc cacttcctac gcccgagtac acctggaggg    2100
gccatctgcc tgagcccgga atcccctctc cgtcccctac cttttgcccc attccgggtg    2160
ctgttatcat ttcggagacc aggcaaaccc actgcatatg ccttcaagct gtaatctccc    2220
tgaccgacgg tgagggtggg tgggagggac attaaaaatc tagagcttta tcagcgaata    2280
ccacgcactc ccatcacttc tcagcttggc tggcggaact tggggaaatc tggggaagag    2340
taaatggacg tggtctccgt ctaccgagac ttgattgggt gtttgttttc cgcttgctac    2400
gaattgggca agttctgcgc cttgaaactg aactagtggc tcgggcagca gcaacagagt    2460
gttaggtttt cgtaggtggc aggagactct gtaaatgact atgaaaagga ataaatgcca    2520
ttgccaaaac ccaagccact cagttccggg ttccttttat cgctagttac aaccatgccc    2580
cccagattgg agaaaatcag cagcaggcgt ctttattgat tcttctcagt tatgtttctg    2640
gattgggaaa gacaggacta agtgcaggtg acctagttcc gctctcagcc caagcaagat    2700
aagttgttaa aaaaataata acctttcctt tacaaaatcg tcatcttcca ggactgtgtc    2760
cgcatgcttt cccacacccg cgcacatcca ggaataatta tatcttcttt cattcatatg    2820
ttttgtaatt gattaagtgt tttcacttgg catggcaatt taatattcta gtaccgtgag    2880
ttagctagtg ctaactagtg gtttgctttt ttaaattttt tttaatgttt taaattttca    2940 cttttgcagag aagaaaacta aggcttagtt gcccgattct tctgacttta atgtaaagat    3000
cctttgtctt ggtttatcag aaaaggtcga tgagcaaata aaattaatgc ctactctcct    3060 gtcccccctgg aaccctccca ggtcccagtc tcaggccact gcagaccaaa cccaggtgtc    3120
gcgggtggga tatggctctg ccttgcttca actagcgccc tgactcaact cttttccttcc   3180 agaaggttct ctgtgcagag atgtgcccgc tgccaccttg gcatttccgc ctcggagatg    3240
gtcatgcgcg cccgagactc tgtctaccac ctgagctgct tcacctgctc cacttgcaac    3300
aagactctga ccacgggcga ccatttcggc atgaaggaca gctggtgta ctgccgcgcc     3360 cacttcgaga ccctcttgca aggagagtat ccaccgcagc tgagctacac ggagctggcg    3420
gccaagagcg gcggcctggc cctgccttac ttcaacggta cgggcaccgt gcagaaaggg    3480
cggccccgga agcggaagag cccagcgctg ggagtggaca tcgtcaatta caactcaggt    3540
gtgcctccta tcctcacccc cggcgcagcc ccggcctccc tgaggaaaat tcgtagagct    3600
ccttccccgt ccaaagtctt gctgcaagag tgtgttttgc ccaatgcct                3649
```

<210> SEQ ID NO 42
<211> LENGTH: 3999
<212> TYPE: DNA
<213> ORGANISM: Homo sapiens

<400> SEQUENCE: 42

```
aggatccagg gatcactgga gctggggccc aggaactccg ctgtctctcc aaagaggatt    60
ctgtgtggag ggtgacttaa tggtcacctt atcccccggg tggctcattt aagaagcagt    120
```

```
ttagggaaag ctcttggagg gcttgactgg agtagctgtc ctggtccta aacacagccc      180 gagcattttg ggggaaagga caggaggac tggaaggaag agaggtaagc accagagcca       240
tttaggccag gagcccggcc tgggcccgtg gctggcgagg gctgcgcagg caggcctggg      300
ttctgaaccg cccagaaatg gaaatgggcc ttttggggtg ggggaagcg cgccgcatgt       360 cctggcagcc ccctccgcgt tcagggtagc caaggccaca gagggagttg tgggtgccgg      420
tttcccggcg gcggagggc cgctggctga cgcaggcgct gctgtcttcc gcctccctcc       480
cttcgcagac catgccgtcc atcagcagtg accgcgccgc gctgtgcgcc ggctgcgggg      540
gcaagatctc ggaccgctac tacctgctgg cggtggacaa gcagtggcac atgcgctgcc      600
tcaagtgctg cgagtgcaag ctcaacctgg agtcggagct cacctgtttc agcaaggacg      660
gtagcatcta ctgcaaggaa gactactaca ggtagccccc ccacccaact gcccctcagg      720 accctccc ccaatctcag gcacagtctt acagtttggc cctctccttt ccgtttagtc        780
ccaggagagg gttcactact caggactccc ccgctccccc ccaagttct ccaagccacc       840 acaagttggg tgataaacctt ttaaagcagc aatttgggga gctcttggaa aggtctacga    900
agtaggagaa ccagaaaaaa agcagaagct gccctcctgc tcggagctta gaccacaaaa     960
aagcttgagt tgggatcctt gctcccctct ctctttgaag tttcttgagt taatccgagg     1020
ttatagaaac aggcaccccc aaacctaggc agcccaagct ggagtgaaaac acagctggaa    1080 agagagctgt gggagtgggt gcatttccag gtctttgag aaaatgggaa tgaaaggtgg     1140
ccaagatcaa agaaccagaa tcactagtag actccaagtt ctctgtttct ccttctcccc     1200
agttttagga ttagggtcta tgtatattct ctctgtctct gtctctacgt ctgtgtctct    1260
ctctctttcc ctgtctctgt gtttcttcca aattataaaa gtcagtagga ttcccaggcg    1320
ctggtttgga gggaggagta aaggttgagg aggggtaag tggtaagtgt ctccctccac     1380
tcccaggtaa aggcttttcct agggcttgcg gagactctgg gtgaagtaga agtctctgta   1440
ggcataagtg tgttaaggga aactatttta ggacaggacc aggcctgggt caaaatctag    1500
ttctctctcc cccccatcct ccaaataaag gccgggttgt tcgtcttgag gaggggattg    1560
ccccccgcag cagcagcggc acctggagga ggaaaagggg ggtacccaac cgtgtgttcc    1620
cacagcccct ccctccatgg tccctacagg cgcttctctg tgcagcgctg cgcccgctgc   1680
cacctgggca tctcggcctc ggagatggtg atgcgcgctc gggacttggt ttatcacctc   1740
aactgcttca cgtgcaccac gtgtaacaag atgctgacca cgggcgacca cttcggcatg   1800
aaggacagcc tggtctactg ccgcttgcac ttcgaggcgc tgctgcaggg cgagtaccccc 1860 gcacacttca accatgccga cgtggcagcg gcggccgctg cagccgcggc ggccaagagc   1920
gcggggctgg gcgcagcagg ggccaaccct ctgggtcttc cctactacaa tggcgtgggc   1980
actgtgcaga aggggcggcc gaggaaacgt aagagcccgg gccccggtgc ggatctggcg   2040
gcctacaacg ctggtgagtg cgcggcgcac gaagcgcccc cataggggttg ggggaaagtg   2100 tgcggcctcg acggccggga gctggattga atctctgtgt gctgggcaaa tagcgagcct   2160
taagcaccgg acggcctcgc agaagggaca ttagccccct gggcttccag actgtgcgtc   2220
ctcggctgga gcgggaggag agggtgcagt ggtcccttgc tgctccgggt gcagggcctt   2280
gtctctgata aattgttttt ttggagatgg ctttttggtt tgggccttg ccccactttg     2340 ctaggcagga agtggcaggg atggagaaag caaggcggcg ctgacgccaa acaggttttg    2400
ggttggcgcg gctgagggcc gggaactggg gcagcgaagg aacgaggcag gcggcgagg     2460
```

| | |
|---|---|
| gtcccaagag aaagggctgg ctgtggcccg gggcgccgag ctcggcctgg agtgcggcct | 2520 |
| gacctcgtga aatgtcccaa gggcggcagg cttggggaac tcgggcttgg ggaactcagg | 2580 |
| aaagcaaagg ctgcggttcc ttttgctcgg cccgatcctc ctttaaagac aggtctcagt | 2640 |
| tttcccggac ttttcctcc gagtttcctg gcgcctgctg gggtgagggc cgtgaccctc | 2700 |
| ggaagcgagc ccccggggcg gggacgagac cggagcaggc ctggcctcgc gccggggtgg | 2760 |
| ggtggggtgg ggtgaggtgg ggggcttggt tcggatttcc ggcatctttg aaccccaggc | 2820 |
| cattcccgga gaagctctgc cccctcccgc gccctccct gctcaggaca gctgcagagg | 2880 |
| ttctgagttc cggcaaatga gccgtcaaca tctgcccgaa gtctgcaagg cccggaaagg | 2940 |
| tttatgactc tccgggcttc cgaactagag tttatgtgca attattttct ttctttcgtt | 3000 |
| tgcaacagaa ttagatttgg agattttgtg ttcttcttcc ttttcccttt agtctaatgc | 3060 |
| acaagcagaa aaaagcaaaa acaaaaacaa acccaagact gtgcagaggg tgctacggcg | 3120 |
| ggaagaagtc agttattttc atcttaaaga atctgagttg aatagagagg gaaatgaggg | 3180 |
| gcgggtgttc gctccaacga aatcgcttgg aggatcatgg ggcgtgtgtc cctgtgtgcg | 3240 |
| gaactgggag gaaaacgcag ccccagttt ggtaaatggt gaagcagcgg taggccggtc | 3300 |
| ggtgcgcgcg atttaagatt tgctgaaggc actaccacag atgtagctct ctggaacttc | 3360 |
| catccctcct ctcctaccac ccccaaaaa aagacaaaac cgagttcaga ccggctcccc | 3420 |
| caacaccaag ccgcttctat ttatcaagtg ggtcaacttc cactcggaag cacctcgcgg | 3480 |
| ggctcggctc cagggcacct ggtggctggg gagctgtatt gttttcctgg cacggaggt | 3540 |
| tcggcgccgg ttttaggatt tgtgcaaaaag agagtagaag gtacagagat ttatttctgc | 3600 |
| tttttgctgt tcagccgccg tttgccccag cgaggtgggc tggaggctga atttcaagcc | 3660 |
| ttgtttaacc tctacaagag acaccctcca ttcagccatc tcactttctc tctggcctcc | 3720 |
| ctctctcttt tttccttc cgttctctcc gtcctttctc tctatctctg tctctgtgtg | 3780 |
| tgtcgtgttt gttcccgtgc cctcctctcc gaccttggcc ggggctccta gtcctgagag | 3840 |
| aaacggcgtt cggtgcgccg gcggtggcta tgcggctggc tctttcgggg ctcccgggac | 3900 |
| taggttgggg aaagagggca tctccccggc ctctcggggc ccagcccagt cttcctagat | 3960 |
| ctggcgtccg cccttccctc ccctcccgca ctggcagga | 3999 |

<210> SEQ ID NO 43
<211> LENGTH: 1449
<212> TYPE: DNA
<213> ORGANISM: Homo sapiens

<400> SEQUENCE: 43

| | |
|---|---|
| tcccgggcag gatgggtcgg tgagttcggg gatgtagcct aagcagggcg ggggccaaac | 60 |
| ctgggaggtt gtggactgca gcgggtttca gaggagggga ggcttctgga aggaccggcg | 120 |
| cgatctccct gaacgaacat cgcggtctcc ccgaacgtcg cggtccctcc gaacgtcgcg | 180 |
| gtctccccga acatcgcggt gccccgaac atcgctgtct ccccgaacat cgcgatctcc | 240 |
| ccgaacatcg tgatctcccc agacatgccc agctgaaggc actcagttcc cctcggtggc | 300 |
| tccttttccgc cgggtccgct tcctgcggct gctgcttgcc cctcaggcca ggaggttctct | 360 |
| ggaaggaccg gtgctgtctc cccgaacatc gtggtctccc gaacatcgc ggcctctccg | 420 |
| aacatcgccc tctctccgag caacgcgatc tccccgaaca tcgcggtctc cccgaaaatc | 480 |
| gcgatctccc cgaacattgc catctcaccg aacatcgcga tctcgccgaa catgcccggc | 540 |
| tgaaggcact cagttcccct ccgcggctcc tttccgccgg gtctgattcc tgcggctgct | 600 |

```
gcttgccccg caggccagga ggcttctggt agcaccggcg cgatgccccc gaacatcgcg      660
ttctacccca acatcgcgat ccctccgaac atcgtgatcc ccccgaaca tcgccgtccc      720 cccgagtaac gcggtctccc cgaacatcgc ggtcccccg aacatcgcgg taccccgaa      780 catcgccgtc tccccgtaca ttgcgatccc ccgaaacatt gcgatctccc cgaacatcgc      840
gatctcgccg aacatgcccg gctgaaggca ctcagttccc ctccgcggct cctttcctcc      900
gggtccgctt cctgcggctg ctgcttgccc cataggccag gaggcttctg ggtggaccag      960
cgcgatctcc ccgaatatcg cggtctaccc gaacatcgcg gcctcccga acatcgcggt     1020 ctccccgaac atcgcgatcc cccagaacat cgcggcctcc ccgaacatcg cggtctcccc    1080
gaacatcgcg atccccaga acatcgcggt ctacccgaac atcgcggcct ccccgaacat     1140
cgcggtctcc ccgaacatcg cgatccccca gaacatcgcg gtctcccga acatcgctgt    1200 ctccccgaac gtgcctggct gaaggcactc agttcccctc cggggctcct ttccgccgag    1260
tccgcttcct gcagctgctg ctagcaccgc agtccagggg gagtgtcaaa gaaggctgaa    1320
aaggaattgc aggagggtgg agggaccaaa aggctacaga gggcaaggta gggcggggat    1380
ccctggtgca gacccgcagc cccactggcc ctagggaagg agaaaccaga ttcccgaacc    1440
ctagctggg                                                            1449

<210> SEQ ID NO 44
<211> LENGTH: 1099
<212> TYPE: DNA
<213> ORGANISM: Homo sapiens

<400> SEQUENCE: 44
gggttttcct gaaggtgcgt cggggccccc ggggagctgg agccgcaggc gacctccccg       60
gtgacctgtt gttcccctct ggagggccgg ccggcgctcc aggcaggccc cgttgacagc      120
ccaggaaggg agagtttcgc cgcaaagggg cttggcacac agtaggtcta aggcaccgag      180
gcaggagcgt ccccgcggc ctcgctccct gctctctggg ccccaccgct gccgcctgga      240 gtctccctc agcctcgcag agacgcgact cggttggggg aaggggacta gaaccgtcgc      300
agtcctgacc gcggccgccg ccgccgttct atctgatctc caggagcgcc ggctccagac      360
tgcctggagc gctgaaagag ttaatcagga acgcctcccc gctgtggttt tgtggtcgaa      420
accatgattg ccaggagcaa attttgtcg tgcacgaggt gtgttattaa agtcggagc      480 tacgctgctg ctgaatgaaa agttaaaagc cctctttgag ttcggctgt aaaactggcg      540 gactgggccg agaggcttga ccaaccccta acgcggcgg ccggggcggc gcggggtcc       600 tgcggctccg ccagctgctg ggagcgggca ggctgcgcag tcccagcagt gagtggccgc      660
agccaggcgg tcggcagagc tcccactgac ccaccggagg agtgaagagg gaaaacgggg      720
ctgaaaccca gatgggatca tccagctttc tcttacgtta gaacaaaaat gacagccaac      780
atttatggag cgctgactcc gcatctgaca ttgtgtcgag tgcttgataa atacacgctc      840
ttctttaaac cctcccaaca aactaatgcg ggatgggagt gtaaatgcag ttttgccgaa      900
gaggggaccc agacctggtt caggcttgcc caaggtctca cggaagcact gggatcttaa      960
ccgggtctta gccgagcagc cataggccac cccgcttcct ctgtgcttag cctctgaaaa     1020
gaagacagag gagatgtgcc aaactgttaa gagtggttat ttctgagcag aagaatgtgg     1080
atgaattcca ttcttccta                                                  1099

<210> SEQ ID NO 45
```

```
<211> LENGTH: 2849
<212> TYPE: DNA
<213> ORGANISM: Homo sapiens

<400> SEQUENCE: 45
tttatctgct ccatcctcgg ggaggaaggg gggagttgct gtgcctccag attgtataac      60
gtgagattat cctgatgaaa gctttatgat gtttgctcaa ataaaagctg cgttttgtaa     120
ataggcgcta attaagcacg ttgcgaacgc aaggagtgct caccctggcg ccgccgcccg     180
gtttccagcg cgaggactcg agggcgcgcg gttcctcttt gctaactgca ggatggagcc     240
gatcccctca ggatgtttcc cctgttctcg acaacggtaa agaccccaa atttgaaagt      300 aagggaattt tggggtggag ggaaactagg gacgtactta tccctcttc cattttcaaa      360 caaaaaactt tcagctcttg tcttcccttt aaaaatggaa tcacttcttg acaacggcag     420
accgtgcaga gcgcaccagc gcgagcgggg cttcctcgag tctccaaggc ccgggcttca     480
acttcccggg tctagacgtc agccctgaac cgccaacagc accgggttgg ggagaaggaa     540
agaagggcat tgttagttcg gtcattaaaa atcagctcac gccgaggagc tagtggttgg     600
ggagttggcc cgtgttggac gtgtgttatg tatcacttac aagcacattt aattgggaga     660
taaagataaa tcgatcttta tgaatttatc gacccgattc tttgaagctc ttttttcgcg     720
ttcttcctct ttctctcgct ctagccccaa ggccccccgg gggacgtctt aatcccagat     780
cagctcctct gccaggagtc ccgccggaga cccactgccc acccagcaga cctggaggaa     840
agaggggagg gtgtgtcctt ggcgccccgg gacgctggga aaactcgctg gtccgccgcc     900
agccctctcc tcctcctcgc ctcctccctc cctaccacca cccggacaaa gacgtctcga     960
tcgcgtttcc ccactccagg ccgcagtaat agatcgctcc ggcagcaggc ggtttgaaag    1020
gaattcatta ggacgctgcc tggattgcct ccctgactt cacgcccaga ccccgaggtg     1080
gcttaggcag tgtgagggga atgaattcc ctttgggatc catggagaag gaggtgtctg     1140
tgggatctcc aggctctatc cctccttctt cactcccaga aaagaagaaa agaaaaaaa    1200 aaatcgaagc ccagggcaaa aggctgatat ctttatgagc ataataaata ctcccctca    1260 ttatgagata gttacagtga cacagccttg ggtgccatta ccctgttttt tgaatactaa    1320
gaaacgctcc attccttcct tgatttacgt ggctacagcc ggggcccttc cggcttgcca    1380
ctgacatgcc gggggaagct gttattcatt ttacctaggc aggtttgcca tgcactttgc    1440
tatttcgccg caaaaatatt gttctaggga cttttgtcgc ctgattaccc tctgagaggc    1500
agggattcct ttgattattt tggtgattat tctacattta aagttcagca agaagattta    1560
ggtccgtcga attatagctg cacttgaaat aatttgatgg catgttattt gcatccataa    1620
attgccatag caagtattga ctgcagggggt tataatacta atcttttatt agtgagttca    1680
gataattccc atcaatatga attttatttta ctagtgcctt tttcgcaaat gcaatgcagt    1740
aatactttct catctaatgc ttagctgctt agaaaacgac tgttcgtgtc ataaaaggat    1800
ccttgtgttt cggcgtgatt aacaagatgc attcggggca cctcagctac ctgcaaagcg    1860
ttcagagcgt ggggactgcg gataataaaa gcctttagag ttttttcctcg gctcctcgga    1920 tagatttatg gacaggagcg atagatgcat ggcttatcca tcctccggat tcctacctgc    1980
ttagctcgta acagcctcaa actgcagagt cctccgtgac tcagctcggc ccagtctacg    2040
cgggaaaatc accgggcaca gatgtttgca acttggtccc ctccccctc caattaggaa    2100 aaatgaaggg cgcacccgaa gggagagctg ggtcctccaa ctccagttaa cttcgtgaac    2160
ttccctcccc tcttcccccc tagatgaaga tagctcagcc cctgggcact tcactcgaca    2220
```

```
ggtgctaggc tagtgtcagg ttcagatgat gccacttaaa acctcagaca ttccgaaaaa    2280
gtgatggtaa ttaagttggc ccctcgcttc ggggttgtcc caggctgcgc ttgcatgcag    2340
atgtatgaag gttgagggtg aaatagaaaa cgcacaagta aatgaatatt catgcagcaa    2400
acttgtgctg gcctgcccag cccagcccag cccaatccgg aggaggaagc accgcgaatg    2460
gcgcgcttcg ctgccgccgc cagagtcgag gtaacgggtg gtcgtggaga gggtacggtg    2520
tggccacccg tggtctcgga ggacgcgggg aatcctgcgg gcctcgaggg tctggcgctc    2580
ccgccagtcg cccagtccta ggcgacaggc tggtttctcg ggcaaccgag ttgtttttat    2640
ttacagggat tttgagaagc ccgatcgttt ggtcattgcc gcagctcttg ctcctggcaa    2700
tagttgggaa ataacttggg atgggtttta tttatggaag ggcaattggg attcacaccc    2760
agctaaccct gaacagtccc tcccgagccc aggacgcact acaaaggggg cgcttgtgta    2820
aaattcccca tcagacacac taatttgca                                      2849
```

<210> SEQ ID NO 46
<211> LENGTH: 1449
<212> TYPE: DNA
<213> ORGANISM: Homo sapiens

<400> SEQUENCE: 46

```
tcctatctca tttcactagc agttgagctg acgggtgcgt gcgagaatgc gagacctgcc      60
acgtgtacac gtgtacgcgg agtgtcgatc tgcctgcgtg tccttggatg tgcctgtcta     120
ggtgcccacc cgcgcgcgcc accacatccc caggcctctg gaacgcagct gctgtgtggc     180
ccggcccgaa gtttctggag gaggaaatcc ctccacagaa ggtttacatt atttcgctcc     240 gcggagacc cggcttcggc agcacttagc agaagatttt ggcgggaaag gcccaagccc      300
tagctgagga ctccgggtgg agcaggggct gaggtccgag cgcagatggc gccgccgagc     360
gcctgaaata tacttgcaag gccgcagcaa tatacttgca aggccgcagc cggagcagct     420
gttccagccg atcctagctc gaaagttcct ctgttgctct gggagagggc ggggagagc      480 aggctcgaga gccaggctcc tcgaggctg gtcttgaggc acttctctag tagcttctcc      540
aaaagactga gagtgccggc gtaggtatga cagtgagggt acctcacaga cccttctcca     600
aagtctggcg ggccttgggg ttttccgggg ccaccaggct cggtggaatt tttgaaacgc     660
tttcgaaata catagtttcc tctgtggagt gagtgcctac aacgcgcagg ccggactgat     720 ccccgttgc tgcaggttgg tgccccaagc tgcgggtgct cgggcgccaa ctaaagccag      780
ctctgtccag acgcgaaag aaaaatgggc tgtgaaaaag caaaaggcct cgtctttgaa      840
tgaaagttaa acattaaaat ctgaccctag agttgtctaa agatcgcgga attttgaagc     900
tccggcagag cggactaaaa aacggtgcta tgagagatgg tgagaatact ctaggcatga     960
acgtgtgcgt gtgtgtttgt gtgtgtgtgt gtgtttcatt cttcccgcaa acaattttt    1020 tgttttttc ctattcccgg tttgttatcg gcctagggcg ggagaaccac gcagcggctt    1080
ctgggcccta aggacaaaag agttaaaaca atgaggctca cccgggaaga gacgctgccc    1140
tgggcacaat agggtcgcct gcattactcc tccatacaca catctttaaa tgtgtccctg    1200
tgtgtgttcg ttagggtgct gtattacaga aaaagaaagg cctaaaaaca cccccagccc    1260
tggtcgcgcc tttcgctacc gcctgagtct ggagccgaca gctccacctc ttctgctccc    1320
tggaccgccg cgtctccacg ccacggcgcc ctttttacta aaagatcttt tctcatccta    1380
tcagcaaatc gttaagaaag gcttagccat tgcgggggct ccaacttaag gattccccg     1440
```

| | |
|---|---|
| gcccactaa | 1449 |

<210> SEQ ID NO 47
<211> LENGTH: 2249
<212> TYPE: DNA
<213> ORGANISM: Homo sapiens

<400> SEQUENCE: 47

| | | | | | |
|---|---|---|---|---|---|
| ttcgggccac | agcgttaagc | cacgccccc | gggcccctca | tccgttgcca | agttcgctga | 60 |
| gcgtccgcgt | ctggttgcct | ctccgcccca | cagggcatgt | tcgtgctggg | cctaccctac | 120 |
| gccatcctgc | acggcggcta | cctggggttg | tttctcatca | tcttcgccgc | cgttgtgtgc | 180 |
| tgctacaccg | gcaagatcct | catcgcgtgc | ctgtacgagg | agaatgaaga | cggcgaggtg | 240 |
| gtgcgcgtgc | gggactcgta | cgtgccata | gccaacgcct | gctgcgcccc | gcgcttccca | 300 |
| acgctgggcg | gccgagtggt | gaacgtagcg | cagatcatcg | agctggtgat | gacgtgcatc | 360 |
| ctgtacgtgg | tggtgagtgg | caacctcatg | tacaacagct | ccgggggct | gcccgtgtcg | 420 |
| cagaagtcct | ggtccattat | cgccacggcc | gtgctgctgc | cttgcgcctt | ccttaagaac | 480 |
| ctcaaggccg | tgtccaagtt | cagtctgctg | tgcactctgg | cccacttcgt | catcaatatc | 540 |
| ctggtcatag | cctactgtct | atcgcgggcg | cgcgactggg | cctgggagaa | ggtcaagttc | 600 |
| tacatcgacg | tcaagaagtt | ccccatctcc | attggcatca | tcgtgttcag | ctacacgtct | 660 |
| cagatcttcc | tgccttcgct | ggagggcaat | atgcagcagc | ccagcgagtt | ccactgcatg | 720 |
| atgaactgga | cgcacatcgc | agcctgcgtg | ctcaagggcc | tcttcgcgct | cgtcgcctac | 780 |
| ctcacctggg | ccgacgagac | caaggaggtc | atcacggata | acctgccggg | ctccatccgc | 840 |
| gccgtggtca | acatctttct | ggtggccaag | gcgctgttgt | cctatcctct | gccattcttt | 900 |
| gccgctgtcg | aggtgctgga | gaagtcgctc | ttccaggaag | cagccgcgc | ctttttcccg | 960 |
| gcctgctaca | gcggcgacgg | gcgcctgaag | tcctgggggc | tgacgctgcg | ctgcgcgctc | 1020 |
| gtcgtcttca | cgctgctcat | ggccattat | gtgccgcact | tcgcgctgct | catgggcctc | 1080 |
| accggcagcc | tcacgggcgc | cggcctctgt | ttcttgctgc | ccagcctctt | tcacctgcgc | 1140 |
| ctgctctggc | gcaagctgct | gtggcaccaa | gtcttcttcg | acgtcgccat | cttcgtcatc | 1200 |
| ggcggcatct | gcagcgtgtc | cggcttcgtg | cactccctcg | agggcctcat | cgaagcctac | 1260 |
| cgaaccaacg | cggaggacta | gggcgcaagg | gcgagccccc | gccgcgcttc | tgcgctctct | 1320 |
| cccttctccc | ctcaccccgc | cccaccagc | ccagtgcgcc | ctgccgccgc | gcttgggagg | 1380 |
| ccaagcttta | acatctctg | gttcctagtt | tctgattatt | cggggatggg | gggatggga | 1440 |
| ggggacaggg | attcacgatc | catcgcgtct | gcgtttctgt | tgtcctttct | tttccacaac | 1500 |
| accctggttt | tggggggagg | cggggtgcat | ttgcgggcag | ggttctctgt | ccttccaagt | 1560 |
| ggggccccga | cactttggtt | ccagtcatcg | agggggttgg | gaagggaggg | agaggggcg | 1620 |
| cagctcgcag | gcgtggcaac | ttgaccttgg | gggaatattt | cacatccatc | cagagctcgg | 1680 |
| aatctacagc | gtccagccat | ttccagcaag | agcgcttccc | attccggaga | cgtttcaacc | 1740 |
| ctgcagcggg | aaaggctgac | tgggaaatcc | attttgggtg | ggcaatttcc | ttcaacgaag | 1800 |
| ccggaaggcg | agaagccgcg | gcggggccag | cttgcctgcc | ggttttcagg | aatctaaact | 1860 |
| ctcatcttgt | gcaatttatc | aggtgtggaa | ctgttctact | gtgcgtgtgg | tgtgctcgtg | 1920 |
| gtgaataaga | tgaaatgtat | atcagaaaaa | aatctatctc | taatttagag | tgcggtacat | 1980 |
| aattatatcc | gcaaataaag | aagagacaaa | ggcttgcgcg | gccggtgtc | gggtttgtgt | 2040 |
| gttcgtacca | gccgggatcc | cctggcgctg | ggaggcgtgg | gaactggctc | ccgccggctg | 2100 |

```
aaaccggaga tggtgagcag ctgtggttaa agggtccggg gagggctcta gggagtacaa    2160
agattagttg gcggcgagga ggctcctcag gtgtgaggag gaagctgaag acggagagtg    2220
ctgtagcggc ccccctcagct gccaggtcg                                     2249
```

<210> SEQ ID NO 48
<211> LENGTH: 2749
<212> TYPE: DNA
<213> ORGANISM: Homo sapiens

<400> SEQUENCE: 48

```
ttgcatagag atgaattata cgggcctgct tgacacgact tttaataaat gattgaggag      60
gttattataa ggatgcactt tggtgtgtgt taacaggttc ttttagtgca tctatagcca     120
aaactgggag caatgcagtc ccgcgtacag tcgcaagata ctttttttgtc ttatatcttt    180 tgacatttat tgggacctct ccgtccccat attacagtca caagctacat tttattaacc    240
gtcggtaacg ttaactgtga atggaatcgg gaaatgaaaa gaaaaatgag ccccccctcca   300 tatacctcca accatattag atctcaaggt agtcaataat gagtgtttga taccaggaag    360
cctcacttcg gaagtcacaa agagctggtt acgctcgcct agaacccggc agggaaggcc    420
gccgttctcc ccggaaaccg ccgggcgaag tgctgaggag gtgcgatgag aaaccaccaa    480
gtcagaaatc gtcagcgatg tggatgactc gggaaacttc tctgtctggg tctgggagta    540
tgaagatcta taagaacctc tctgcacaca gaaatccaag agctcacacg ctacttagat    600
gaattaagca cccaagagga tatatttaaa taccttcttg cttgtgcact cttgtcctgc    660
ttgaatttct tttctccatg tgcatgtact acctagcaaa atataaacaa tacaaaattt    720
atttgtaact gaaggcggct ctgcctcccc tctgtctacc ttgcggagac tattcaaacg    780
ccctcgcttg cggggtttcg gagccagaag tctcgagctc cgcgcctccg cgcccccgcg    840
ccgcgccctt ccacctgcac ccgttaggcg cgctgcggga caacagcgca gatgcaaaca    900
gctttctcgc aaggaaaaag ggaattgagg agaaagtttc ctctctgagc cgagggaagc    960
ggaaaaagat caaggtcggg gggcgggtag agtgggggtg gggggaaccg cgggacgccc   1020
tagctgtgtg cgtttcggga ggcctcgcag tgccattctg caagagtacc tgctatctcg   1080 aaaatcttttt gccaccgccg accgcagcgg gaggggggcaa ggggctctct ctgactcagc 1140
tccggatttg tgcatccccg cagtgcggca cccgcagtct tgacttcccc agtctctgac  1200
tgaacagatg tttttgtccc tcgcggagat ttgtaaccga tgttgggaac agctagtgga   1260
cggtgctagc aacctgtatc tgttctagaa cacacctagt gggagctgcg gggtagagtg   1320
gagaggtagg aatgcagcgg gactgggca ggggacaaat caaggtgtgt gggtaaatgt   1380
gaacatatga acacacgtgt gtacgcacgt ctctaaatgt gtcattcata acatttttaaa   1440 aatggtcaag tccggccggg cgcggtggct cacgcctgta atcccagcac tttgggaggc    1500
cgaggcgggc ggatcacctg aggtcaggag ttcgagacca gtctgcccaa aatggcgaaa   1560 cccccttctct actaaaaaat acaaaaaaaa aattagctgg acgtggtggc tggcgcctgt    1620
aaccccagct actcaggagg ctgaggcagg agaatcactt gaacccggga ggcggaggtt   1680
gcagtcagcc gagatcgcgc cactgcactc cagcctgagc gacaagagcg aaactccgtc  1740
aaaaaaaaaa aaaaaaaaaa aaaggtccag catagctgtg gttgcctttt cggtttcaaa    1800
gtaataacca agcaaggaag agagaagacc gaaaactacc ccgcgaaaac tagcacagtg   1860
tgcctggatg tctgtgtccc gggacctcgg ggaagagggc ccgcaccggt ctgcgaattg    1920
```

| | |
|---|---|
| caaggcccgg ccttccccag cgacgctctg gtatccgctg tcccctccct gtacctccgc | 1980 |
| gacccagggg acgcccagtg caccaggccc ttccccgggg tcagcggagg cgcagggcgt | 2040 |
| tagccacatc agaggtgcaa atttaccccg ggcccagggg aaaatggcga cagcgttcgc | 2100 |
| ggctccaccc ggggcgcgtg tcagcgttgg agagcctgcc cggcctgcag agggcgtaac | 2160 |
| aggcaccgct ggggagagcc aagcacccct gcgtccagga tccgtagcgc cgagctgcag | 2220 |
| gcccgacctg caggggggcgt gcccggcatg ggaagctcag gctacgtctc cgaagcttgc | 2280 |
| gctgaaaaca ccagaggtag ggaaaacggg gagagcgtac tgtgctgggc tctaccctgg | 2340 |
| acaccccagt ttcattctct gcgaagccac gcgctggcag ggctctcggg acggcgatac | 2400 |
| ccagggatga tggtaccccct ggtctcggcg ggacctcccg ggaacttgtc ctgggggagg | 2460 |
| gagcccaact ggccacgtac tggtagcagc agtgggtgga gcgcacaaac tccgaggccc | 2520 |
| gcgtatgccc agcaccccag gctgaggctg cagggccccg acccgggtc ccaggacgg | 2580 |
| agcctgcccc cagcactagg gaactgggcc aggtatggtg accaacgtcc taaatcccaa | 2640 |
| acagacttcg ttcggccggg ctcagtaaag aatttgccga aaggtagaaa ctggaccaga | 2700 |
| gaagggaaca cagtgccggg cacatcctag ctcgcttgaa ttttctggg | 2749 |

<210> SEQ ID NO 49
<211> LENGTH: 2249
<212> TYPE: DNA
<213> ORGANISM: Homo sapiens

<400> SEQUENCE: 49

| | |
|---|---|
| tgcccgcgcc cggtccgcgc gcctccttcc cgccgccttt cggtggccct ggtttcggcg | 60 |
| cgcccgggcc cggcctgcat tacgcgccgc ctgcgccccc agccttcggt ctcttcgacg | 120 |
| acgcggccgc cgccgcggca gccctgggcc tggcgccccc cgccgcccgc ggtctcctca | 180 |
| cgccgcctgc gtccccgctg gagctgctgg aggccaagcc aaagcgcggc cgccgctctt | 240 |
| ggccccgcaa acgcaccgcc actcacacct gcagctacgc gggctgcggc aagacctaca | 300 |
| ccaagagttc gcatctgaag gcgcatctgc gcacgcacac aggtgggcgg cacgcacgag | 360 |
| ccaggagcgc aggcgggggg acgcgggagg agaggtcgga ttcccagcgc gcgcagaaa | 420 |
| atgaatttag gacctcccctt ggggcgtggc tcagggggat ctggcaggtg gtgcacgctt | 480 |
| aggactcccc aggaggcgtg gctcgggagg ttggttgggg gggcacacag gaacactccc | 540 |
| taaggaagtg tgatccgaga ggttggggtg ggggcttgca cgcttaggac gagggggggcc | 600 |
| tccggaggtt gggaagagca cttagaaaac ctcctggagg cgtggctagg gagacagtct | 660 |
| cagaaagttg gggaggggga gcaggtttag gagccgctgg gcacttggct cagaatcccc | 720 |
| ggggctgagg ctcaggtagt tggggagtag gtgcgcgttt aggaacccccg gggagatgct | 780 |
| gcgtctcagg aagttgggga gggcgctcag gcttgggact cctctgggga caaggctcag | 840 |
| gaccttgggg agggagtgtt cgctgggaaa ccttgagaga ttccgtgtct tagaatgctg | 900 |
| gagagagggt gcatgcttag gacccgtcgg ggagcgtggc tgacaacagt ggggagtgga | 960 |
| ccttgcgctc ctccgacccc ctggggtga ggatccggat tgtgggggga gttgggatg | 1020 |
| tagggcaagg atccctcagg ggcgcaacac taccgcgggg agcgcgtcaa ggccctggtt | 1080 |
| agggataggt tgcgctcgcc ggggtagcca tacgtgccct gtcctgggag gggaactgac | 1140 |
| gcttactctc gcccctccc tgcaggtgag aagccctacc actgcaactg gacggctgc | 1200 |
| ggctggaagt ttgcgcgctc agacgagctc acgcgccact accgaaagca cacgggccac | 1260 |
| cggccattcc agtgccatct gtgcgatcgt gccttctcgc gctccgatca cctggcgctg | 1320 |

```
cacatgaaac ggcacatgta gccgggacgc ccccgcccac ctgcgcgcgg ccgtggcggg    1380
tcccacgcgc cgggcgcggc cccctcccaa actgtgactg gtatttattg gacccagaga    1440
accgggccgg gcacagcgtg gctacagagg gtctccctcg atgacgacga cgacgacgcc    1500
accaccccag cccccgtctg tgactgaagg cccggtggga aaagaccacg atcctccttg    1560
acgagttttg ttttcaaaa tggtgcaata atttaagtgg catcttctct cccaccgggt     1620
ctacactaga ggatcgaggc ttgtgatgcc ttgtgagaaa taagggcctt aatttgtact    1680
gtctgcggca tttttataa tattgtatat agtgactgac aaatattgta ttactgtaca     1740
tagagagaca ggtgggcatt tttgggctac ctggttcgtt tttataagat tttgctgggt    1800
tggttttttt tttaattaaa aagttttgca tcttttaaaa aaaatcacag cactggtctg    1860
gttgcttgga actggggcct tggggcactt ggggaggagg gggagcggag agtttgatgg    1920
agggcagccc cactaaagca tcgtgtgcag tgggtcctgc gtctgccagc accgggactg    1980
ccagctgctg tgcctgcctg ccaggaacct gtgggttttt ctgtaaattt agacactgca    2040
ttttaggact gagggagggt tattttaagg ttgttctttg agccataaat tgcctctttg    2100
ccccacagct ggggaaagtg ctggtcccac tgacgtggcc tcctctacgt tgaaaaaaat    2160
aaaactactt acctcttcct ggaagcctct gaggttttag ccaaatttct ggagtgccag    2220
ctctatattt ttattttat ttttaaagg                                       2249

<210> SEQ ID NO 50
<211> LENGTH: 1199
<212> TYPE: DNA
<213> ORGANISM: Homo sapiens

<400> SEQUENCE: 50
ttggttatct gtttttttt tccccctcag ggagtcacct aagtggcaag tgcagaaagg      60
aagaagtcct ggaagaagga agtggagtgg acacttgctg aaagaaatct taactctagt    120
atcttcccag tgcagttcct attttgggtt tcaactcccc cagaggagtc cttttagtgc    180
agctcctgac tgcccgattc caccggactt ctctcagtag acagactgaa gggcagatca    240
aaggctagag cctgcgctct gccacgccct tgcttctgcc cagaagggag ccttcttctc    300
atcacctctt gaagagccac ctttgctccc aggagagcac acttagctcg tttgctgcca    360
ggccctccac acactctgca ctcttttagag ccacctgcca gttctctccc ttctgagacc   420
ctagtatttt gtggttagcg ctacgaaact gtgtccctaa ggctccttgc cagtcgccac    480
tgaagacttc tcagcctaaa gagcccttgg ccaaagtccc cacccaccgc ccctgccgcg    540
cgccattgag cccccgcgcc gcagaccttg aggtcctgct ccaggctgcg caacagctcc    600
ccgtcgattt ccccggtctg ggcgtagcgg agccttttgc gctcggcttt gcggaggcgg    660
tactgcagga tccggcagtt tttgttggct ctctccaact cgtggcgcat ttcctgcagt    720
tgacaggcat cctcctcgaa gaaagtgtcc ctcatctcgt ccatctcggt tctcagctca    780
tcgatctcgt tctgaggcgg tgacaggccg cgtgtcaaaa tcaaactcgc ttccagccct    840
tccgacacac accgtacaca ccccattcca attccaaatt ctcagcttta attgccctct    900
ctctccacga gacaggagtg acaaggagct gagtacagaa gaggaaactg ggggaaaaag    960
gcccacttta ggccctctct cgttctctta ctctacctct ctccaggaag aagtgtgaca   1020
aaccattata attagagaaa cggaggccca gatttgaatt taaatgaaaa cctcgcgtta   1080
ctgagagcag attcaaattc cggcaaggcc taggaaaccc cctccctcct ttcttgttct   1140
```

```
cctccctctt caaggctccc taacaggtta gcagcctctg atccctgccg gtacacgcc      1199
```

<210> SEQ ID NO 51
<211> LENGTH: 2249
<212> TYPE: DNA
<213> ORGANISM: Homo sapiens

<400> SEQUENCE: 51

```
caagcagata gaagaagctt aaaatagaga cagaaagcgg ttcaaatgca catcgtgcag       60
gtatgaaatc cactacatgt cccctgcaag aaggatttgg gcagggaagt gtgtggaaga      120
tggggctgca gtggtggagg gctctaagct ctgaagacct ttttaatatg gctgtgttgt      180
aatactgcag tgacaaaccc cgccagtcat tccaaaagca aaggaaacc  ccactctgca      240
gcagaacttc ccagccctgg aaacagattg tcttcctttt gcacccattt aataaccact      300
gtatttaaca cgatcagggg aattgtgcat tctcggaagg cacagtaagg aacctcggtc      360
tgcaacgacg cgattcctca gacaccaaac taaaatgcat tcattggaac tcagcctccc      420
aaagcggaag caaagccact gcaaggcgat ttacaggcaa gagcccctct gaaagagagg      480
aaaggagggg gcttggaaag caaggggaca cacctttct  gagctgttcg aaacaggctg      540
cctgcaaagt ccacccatac tgcgctgcca agggttaatt ttctcagcaa aaattggtac      600
acgcacacac acacacattc tctctctcct actgcacccc cacaacctct gccaccacca      660
catatttgaa tctttttaat cttaaattcc cagaaattcc ctgatcagcc ctatcttttc      720
ggaacagctc ccccgcccc  gccccacacc ccacctgggc tggattccca cctcatcatc      780
agtgaaagct cagagagccg gcataatta  ttttcctaca aggttatgcc taattggtca      840
ctaatctaat tgatcaatca tctcattttt caaagcagca tcaaagagcc aagctgagag      900
ggcagaaaga aagcatgcgt ccggatggcg ggagggttaa aattacagtc tttgggtaag      960
accctggcc agcttgcctg gtttctagat acataagtgg acagaaaaga aatgaagaga     1020
acgcggactg agcgaggaaa tgctcaagac cacaggactg aacccccgg  aagtctcgac     1080
gctgcccagc cagccagagt ccagtcgtcg acgcggatga agttgtttcc ccgggacagg     1140
aagggttaaa tggctgcgcg tcaactcggc ctcgactggg gtgtcaggga gcaagagccg     1200
cttgtctcgg gggattccgc ttgggggtt  cccaggggtc gccctggcgc tccggccaca     1260
acttgggcgc tctgtgcgg  cggccctcgc ctgcgccttt gcgcgccacc caaaactttg     1320
cgcacactgc agccgccgcc ttcccgctct tcgcggtgag acgcgcgccg ccaagtgccg     1380
caggcagccc tccacagccg ccgcggcagc cgctgcctgg cttctggctc cagacttttc     1440
ccccactgcc tccagttccc acccaggagg ctccctcgcg gccgcgagag ctcggcgccc     1500
gacccacagt aggcagtgcg ggcacagtgt tgcagaccac cacctcgcca ggtccgggca     1560
gcgcccacta gacggacagg cgcccgcggc cgcccctacc ccggcgcgcc cacctcgagc     1620
ctctcacgcc gcggcgggcg ggcgcaacat attctcctac ctccagccgc cgaggaccac     1680
actctccgct cagccctctc gactcatcct ccggctgcag tagagggcga gcgggctccg     1740
cttttgttcc ctggggctgg caggtccgtg tggggccagg gcgcgcggga gacgccgcgg     1800
agctgggtat cccggagagg ggatgctcac tcctagcggc tccgctggca gcagtagtgg     1860
cggtggcagc agaggcagcg gtagcaacag cagcagtagc agcagcagca gcagtagaga     1920
tagtgccggc tctctgcagg ccacatcttt cataccttat acatcactac cgcattcccc     1980
cgaataggg  agccctcag  catttcgcca cctagcgcgg aatgctgctg caggaagagg     2040
tggcgcggcc tgaccgacct ggcctgaatg tgagctctga gggggaagga cctcagcacc     2100
```

-continued

| | |
|---|---|
| cactcgcaga ctcccttctc cgctacggtc acagtgaggt ctacaacttg cagccattct | 2160 |
| gcagtcttca gtttgcagtt ctcagtgtct gctcccctgg gaagtatgga cttcaggtta | 2220 |
| agcaaaagtg atttactggg gagagccct | 2249 |

<210> SEQ ID NO 52
<211> LENGTH: 2999
<212> TYPE: DNA
<213> ORGANISM: Homo sapiens

<400> SEQUENCE: 52

| | |
|---|---|
| tgtcggggat gccaaggtct gagtcttta tgatattcgg ggtgccccga tctcaccctg | 60 |
| ggagcctcct cgctcctgcc tgctcctggt tacccagtgc gcggctctgg cccggtgacc | 120 |
| cgctactgtc tctccatgcg ctgccgcttc acaaaggcgc atctctaggt cggtggtcag | 180 |
| gttctgcccg gacgctgcaa ctggctccgg gacttgtgtc cttggtgagc ctagcggagt | 240 |
| gctgggtgcg tcgcctgcgt gctcctcttt tggagaaagg agggagggaa cggccttgtg | 300 |
| agacgactcc aggagcgacc agcgacctcc acaagtccca agtcttccca gcgcacaggg | 360 |
| aaactgtcac ttacagggaa actgtcgctt cagtggcaag aaggttgaaa aagcccctcc | 420 |
| tgtgcctccc tggtggtctg gtggctagaa tttagcgctt tcaccgccgc agctcgggtt | 480 |
| ggattaccag tcagggaatt gttttgcact gactgccttc ccgcaggaat cttccttac | 540 |
| gcccgctgta agcgggcctt ctccaagggc cagacgcaga acagtctccg cagcgaggtg | 600 |
| caaaccctgg cgaaggaggg caactcctgg tgggccacct ctcatgacac agcgctctta | 660 |
| tttatctccg tgtctgtcat tcgcacaagc ggctttagag agcgactgag cgtctcgctc | 720 |
| aggtgtacac cgctgtgcag agatgccagc cctcctggaa ctgcacccaa gaagcccacc | 780 |
| gtctttgccg cctctgccgt cccggaggcg ccgatcgggc tgagctgcga ataactaaga | 840 |
| gagaggccaa gcaagtcgt ggcgtttgtg cgtgccacaa attatcagct gacaggggac | 900 |
| ggtcagtgga gcctcctcac ctccgttcgc gggtaacgtg cttcttaggc cttcagaaga | 960 |
| agcgactgga ggcgatgccc gcgaggttgg aagtggggtg agcggcgggt gaggccctcc | 1020 |
| aggaccgctc gtttgtagac tgagcggtaa agggaggcga tgtttgctga cccaacaaag | 1080 |
| acagcacgtg gagcaggcac aaatggaaaa ctgtggccgg tgaacagaag gcaggtgtga | 1140 |
| aaatcactag gtcgtcaaag cgatggtacc gcagtcaaat cccgcaatgt ctgtctacac | 1200 |
| tctaccaagc aattgcgcac gtttcccctt ttccattcag tattcccaag aggggttcgg | 1260 |
| aggaaccccg cgtccactgt aagctcaggg gggagccgga gccagggagg tgaagtgcac | 1320 |
| agactggaca gaggcggcgg gcagaaccgc gggggtgaga gggcgcggtg gctgcggagc | 1380 |
| gggagccgct gttgaaagga ggcctgggtt gtcctgtggg tgactgttgg tggaatcttt | 1440 |
| cgcggaaagc gttttggaag aatggcgcga cgagcgagca gagggaagg tggtgaccct | 1500 |
| gagcgctcgg ctaggggaga ggaggctgtg ctgtttctcc tcttcccta cctggcgggg | 1560 |
| dacagaccgt ggtcaggaag ggggttctcc ctggttgagg ctagtccacc gcactctggc | 1620 |
| tgcgctcacc cctgcgattt ccccacacgc ggggccctag tctgcggtgg tgttcgtgct | 1680 |
| acccccgggc tgggttcgcg cacgctcctg acctgccttg gctcacggcc aacgcggata | 1740 |
| tcgccgccag agaccttcg ccgccctccc agggctcctg agggcgcttc cttggtgttc | 1800 |
| tcactgaagc tctcgaacag acagatgtga gctctctgtc ttttacacgc tgaatttggc | 1860 |
| tattggcaaa aaagccctga cccagagctt gggtctcctt ccgacctgca cacgactccc | 1920 |

```
cgactcccgc ctccaagcgc ggctcttggc tcgctggcgg gcagcgtcca cagagtgtgg    1980
aaccgccgca gccgcagctc ccgcccgctg gcgggcagac actagcagga gaaaggacac    2040
aaggcctgcg tggtgggaaa gcatgggaga cctcgctttc ccaccggacg agaaggtctc    2100
cctgcagtct ttggacacca gatggatgga ggcacccctt ctaggaacaa gcggctgct    2160 cctgaggcct ggcttcgcac agtggctcct gggtcccgcg cgccctctcc cttcccgcgg    2220
tagcaagagc tgctttacac atctcagccg gcttcctctt tctccccagc tgtccttggg    2280
acagcaaggc ccccagcccg taggaaagac ctagcctcct ctccagcact tgtagaggga    2340
gtcggatgca cgtctcttaa ccacaggaag acagagaccc tgaggcggga gcttcccttg    2400
ctgcttctct tggcacagcg ggtccagggg gctggttcag gcccaggac tcctcgctcc     2460 tcctggaggg cctgggtcgc gtggcctagg agctggccac atgggcatct ccagcactgc    2520
tcctcaggga acgggaggca ttatcctgca ggacccactc ttacccatga gagacaccgg    2580
gaaatgctcc tgcggaagct ggagctctgc gcgcttgacc acttcggggt gaagcttccg    2640
tccgcccatc cttccttcga ggggccttgg ggagaggaga aatgctccag gacgatgccc    2700
tttgcagtgt ctcaaccgag accagaggaa aggagggtgc gtcttcctgg aagaaggtgg    2760
ccgaaggcct gcggtcgccg ggaggcttgc ggagcaggag cgccctctct ccgcccgagc    2820
tatccggtgg cttcctgcat cccacctggc ggactcctct tcctctctct ccttctactc    2880
cggctcttct atcctggtgt tccctgaatg cctatcttcc gtctgtgcca cggaacttct    2940
cacacccgct acaagttact catttccttg gttgttctga actttaaata aggtaatgt     2999
```

<210> SEQ ID NO 53
<211> LENGTH: 1249
<212> TYPE: DNA
<213> ORGANISM: Homo sapiens

<400> SEQUENCE: 53

```
ggtgcctcag ggcacgaagg ttctacctag ggaatcctta cctctgtctc caaaggaggt      60
cctggctagg gggtctctag gttccccaaa acttgtttct gcaaagacct ggcctgggt     120 ttccagggtc tcctccctct ctggggaagg agtcttggtg gggatctcgt ggtccccagc    180
ccccagggcc cctactcacc gtgggtcatc gctgtactgc actgtggcaa agcgcacacc    240
ctgtgcactg gctgctccag agaaaggcag caccagccct tcgagaaagc tgcggacctc    300
gcggaaattg ctgcggccaa tggatgagga gccatccagt aagaacacaa tgtcagcggc    360
gtaaaggcgc gtgcaggtca ctggggcggg caggagagat cagggcctct tctgggaggc    420
caaccacccg cctacccgca cggtggcctc actgggactt gggatggtgg ggagagtagg    480
cctcatctta tgcaaaccag ggccgaatcg gcctgagcct gagggccttg gagggagttg    540
agctcggtgg gtcccagagc agactcccgc ggagggttgg gggtgtgcgg gggagggaga    600
gtcgccagca cgggtgtgga cttgggactg aggtcagcct ctaggggccg gcgtggattg    660
gcataaggca ggggaccccg cacgcatcca gggagccaga atttgggtag gaacaggata    720
ggaggcggtt tagggaaccc agcaccgatc gcggagggtt cggggagtcc cagaattagg    780
aggaatccgc ggggcgtcgt ggagttggct gggttgtggg cgggggtgt tgggatgaa     840 ggccgagtgg agcggagggt ggcacggtgc agtgccccgg gccgggtcct cccttgcggt    900
gcccacctct ctccctgtgc tgggctcgca ctcggggcgc ctctgccagg atcccggcgc    960
agagcgcgga caccagaagc cgcagcgtca tcctaggcag taaaagccgt cagctaggac   1020
ccccgcctct gtcccttgct ccccgtggc cttggcaggt ccgagcccag cgccctcca    1080
```

```
gcccgagtcc tggtcttgcc tgcgcgtccg cccgctcccg ccgccgccgc tgcagtctct   1140
cgggcagagc agagaaaagt ccctgatctc gggggggcgga gcggcaggcg ggaacccagg   1200
cacccgccct cacccatatc cctgagaggt cgccgccccc cccacccct               1249
```

<210> SEQ ID NO 54
<211> LENGTH: 1149
<212> TYPE: DNA
<213> ORGANISM: Homo sapiens

<400> SEQUENCE: 54

```
tgacaccaga agattcaggg gcgcttgttt tccctctcca agctaaaagg gggtgggtgt     60
cctggcctcc tggcccacca gtggtcccac aacacctctg cccacagcag ggctggcgct    120
tatttggagt aagcgctcct ctggacaagg gagccaggtc atccactggt tggtaatggg    180
gcgagaggac tcggatcttc ttagtatacc aagcagggct ctctgacagg gatgttgggg    240
ggctctgacg gctgggaggg cggtcaaata aaaacctcat cccggtgttt tccctactag    300
ttttttcacgg ggaaaaggag tttgtgcaca tctgacaatt tcccacgcat gccctgcaga    360
ggccggcgag atgcggagtc cgcggctgca gggtagatcc cctcctctgc ccagctctgg    420
gccgagccct tggccaggtg gggaccggcg cggatatgcc tccgctgggc ctgcaggcgg    480
cgagacttac ttgggtagcg atagtagaat tcgttctcca tgtcgctcaa gttcttgtgc    540
gtcctctctg accaccagtg ggcgtcggcc tcgaagtcgt agcgcacgaa caccccgaag    600
agaatcacca taatcacctg caggagcagg caggtgagcg gcagccgcca gcggaggttg    660
gtgttccagg ccatgctgca ggggtgcctg gccgggctgg cagcgggcgg ttcggacgct    720
cggaggccgg cggggctttt gagacccggg caggggggcg gggcggccac gtggggcacg    780
gagcagctga ctcgggcacc gcccgcgcgc tcgcccaact ggcaggggcc caacccaagc    840
cgagggcccc aaaagattcc ccgcgtcggg ctggggggaca gcggcaggag cagaggctaa    900
ggcagtgggc aggaggatca gggtgccccca aattctgtgt gtcccgttga tactggggcc    960
tttctccttt tgttctgctg aacagagaaa cacgggggatc attggcctcc cagtgagatc   1020
agaaggaatt cccagaccta agtcatcatc atcaacatca tcatcatctg ccatcatcat   1080
ctgcatcatc atctgtcctt tcttttttctg attatgaaat tcatacaggg cacatgagaa   1140
acaaggaat                                                           1149
```

<210> SEQ ID NO 55
<211> LENGTH: 1399
<212> TYPE: DNA
<213> ORGANISM: Homo sapiens

<400> SEQUENCE: 55

```
gcgctggtcc ctccgggcgg cgggcactgc agcggtaacg cacggttcct gccggttgtg     60
gctcggggga ctgagggccg ggagtggggg cttctgtgaa gccagaagag aagtctgcag    120
cagagtggtg atgaggggcg ctgacacctc accccccaacg ccgacgtctc caaacgcgat    180
accctctgcg gggtgagaat gcgggcccgc ccggctcctc ccgtgaggcc agggcctcct    240
gttctcctag acaccccaag gagccaactc ctccgcagaa gttccccgct tctgctctta    300
tttccaagct tcgcgctttc tacaaactcc ctgttgcctt gactttgatt tccagccgtg    360
gtgagggtca gagtgaaccc cggcgcgctc cccgacggca tccccgcaca ccaggatagg    420
agaaattgga gggcctgggg cctcgggctc cgcagtcgtc ggaggaagaa cccaccgcgg    480
```

```
ggtccgcaag ggaaagtgaa gaggcccggg attttttccaa agcgctggcc aggaccccga        540
aggaagggga ggagtcacct gaagccgggg aaggcccctt gggtgctctg ccttggatcc        600
ttatgttcac tgactttcgc gaagcccccc tggaggggg caaatccgcg ctgtttcccc        660
caacttaact tcacgcggcc cattctccga atcgcgtgcg ccaaggccgg cgtcggggc        720 gcactgtgat ggcgctttgc tcttcccagg cgaagacaaa tatctcgacc cgatgtcccc        780
atgcatgcgg gtgcacaggt tctgagaaaa tcacgcagaa ggcggctgcg atccacggcc        840
cgggctgggc tacacctgct tggaggtcgc tggtgtgtgc gtgcgcgcgt gcgcagccta        900
actccttcca gccccgggtg gtgaaattag tttccaatac tagtacccttt caagtttcca        960 tttattttga ctgtacccgt ctgaaagcag atttcattta cgctagcaag actggaagcc       1020
acaaataaag aaaagaaac ggattcattg aatctcagta tctcagtagc gtttaataga       1080
ttcccttggc taaattcaga gccctgtttg aattcactca cgcaggagtt gttttgtttt       1140
ttttgttggt agaggtgccg gtttcccatc cccacggctt atttacaatt atgggtgttg       1200
ttatttttaa aggattcaca aggtgactaa ctctctgtta tctgttgaat ggaaggagtg       1260
ttacatatgc aagaccgaat ggggcaggcc gagcccccgc cctatgctat tctacaatcc       1320
agatgggatt cgtgattaga aaataaaatt ggccaaagct gtctcggaat ccttttccca       1380
cttctaattt catcagcac                                                    1399

<210> SEQ ID NO 56
<211> LENGTH: 1399
<212> TYPE: DNA
<213> ORGANISM: Homo sapiens

<400> SEQUENCE: 56
agcttaaaag tgattttata aaccacgctg tgaaaaccta ctgacgatca gtccctgtc          60 caaacacttt tcctcccact cctttgggaa catacaggga tggtgcattt taattacatt        120
aaaaccagca agaaactctt gttttattct gatgtaaatc agtcacctaa tgctgagaag        180
gactgaagtg gctcatatgg tcgttctgtg ttttgtagaa tacgtagggg actcctgaaa        240
tgtgtgggat gtaggtaggg gcgggagcga ctctgtgggg agagaaggga gaaaagatt        300 gagagaagga aagagaagtg tatttgcaag gcaggctgac aatttctcaa ttaatttggg        360
gcagagacag aaagactccg agtttctagc ttcttttcta tacctcagat aaaaaactga        420
agacagcctt attctaacaa ctcaatttaa aaagagcccc cctgcgtacg tccccgcacc        480
cctttcgccc cagcggccgc tcacaaagcg ccacccgcgc tcgggcgcc cgcagaagcc        540 ggagccagtt ctcagccctg atcgccgcca gccgcccagg cttcggggaa ggagggaggg        600
gagaataatg cgcccctctt tcaataaacg ccactgccaa ccactccaac agacacactt        660
tcggtccccc gccagagctc cggtgcccc gagtgaccgc tttctgcgat cgcgtccgcc        720
gggaccccgt ccctctttcc ccttcagtct tcagggaggg ggaggcgctc cgcattagcg        780
gggcagttca gcaaccccga ccccacccgc gtggctccag gcccaggggt ccgttcactt        840
ccccgtccgg tttgggggac gccaattcgc ctaagaaaac cctggcagaa gagcgcggac        900
ccttcactac aaacctcacg tcagggttac agccacattt aggaacctct tcggaaaagc        960
tgagaaatca ctgttttgca aaaagccttc tgtactgtga tggggctttg tggtgagagg       1020
aacctctgag aagcctcgtg cggcttgagt ttagagtcac gccctgccca gcgacattct       1080
cccgcgcacg ggagaacctg cacttccggt ctccaaccct cgcggccgt gactcttccc       1140 ctcccccgcg ccgggccctg catttccggc ccccttgctc tcctgcactt ccgcccagtc       1200
```

| | |
|---|---|
| acatggatga tggatagcgt tgggagctgt tttctctatc ttccaggtgg ctgctgggat | 1260 |
| cctaaacttg tttctttaat ttctcttta aaattgaatg tcctttagtt ttttcactt | 1320 |
| ccttaaattt gagggtcgag aaagctagag gtggagacaa aaggctcatt gaagacaaat | 1380 |
| cttttttggc ttttcagat | 1399 |

<210> SEQ ID NO 57
<211> LENGTH: 1199
<212> TYPE: DNA
<213> ORGANISM: Homo sapiens

<400> SEQUENCE: 57

| | |
|---|---|
| ggtctgggtc agatcccagc ccaggcccag aagttccagc tctccaccct ccgcctcgcc | 60 |
| cgcagggctc gcgcttccac agttctcgcc gagagcgcta tgggacagtg ttcaagacgc | 120 |
| acctgctggg caggccagtg atccgcgtga gcggcgcgga aacgtgcgc accatcctgc | 180 |
| tgggcgagca ccgcctggtg cgcagccagt ggccgcagag tgcgcacatc ctgctgggct | 240 |
| cgcacacact gctaggtgcg gtcggcgagc cgcaccggcg gcggcgcaag gtgagtggaa | 300 |
| acgggaatgg accgtagata cgtcggatcc gcggtccccg gcatctgcca tgggccaggc | 360 |
| cggggccccg gtgttggata cactgtgaac ccgaccaagg tccctggtaa ctagcgggtg | 420 |
| gccttgggcg gtccgttac cttcagcttc ggttataaa gttaggactg cgctaaaaga | 480 |
| ttctttcatc tcccatcttc cgtggctgtg atagcagaag cgctggagac tcagacctag | 540 |
| aaagggccca gggaagactt cttagaggag atggcagctg gagcctggat ggttgggagg | 600 |
| gactgtgtgc atcagagcag aactggggga aatggcgaaa gcaaaagcca ggaagtttag | 660 |
| gtctgggccg cttggaagag ggagaaagga ccggaactgg ccttctggct actccggaat | 720 |
| cgccaagcag atgaggccag accgccgcca gcgctgatca cgcgcgctcc acaggtcct | 780 |
| ggcgcgcgtg ttcagccgcg ccgcgctgga gcgctacgtg ccgcgcctgc aggggggcgct | 840 |
| gcggcatgag gtgcgctcct ggtgcgcggc gggcgggccg gtctcagtct acgacgcctc | 900 |
| caaagcgctc accttccgca tggccgcgcg catcctgctg gggttgcggc tggacgaggc | 960 |
| gcagtgcgcc acgctggccc ggaccttcga gcagctcgtg gagaacctct tctcactgcc | 1020 |
| tctggacgtt cccttcagtg gcctacgcaa ggtacggccg ccccggctcc agaccttcct | 1080 |
| ccgaggctcc gcggcgcggg cgggcctccc agacccagac gggacgccct cggcgcaccc | 1140 |
| cgcgcgtccg tcacctctgc tgggaacggc ggcagggccc gggggtggga ggcgttgtg | 1199 |

<210> SEQ ID NO 58
<211> LENGTH: 2349
<212> TYPE: DNA
<213> ORGANISM: Homo sapiens

<400> SEQUENCE: 58

| | |
|---|---|
| ggaacagact gcttgaaggg cgatgcacag ggaacatcga agatctgtgc ctctcccttg | 60 |
| agactctggg catgccaagt cgaggaagga cagtaataaa tgcatggaca cccgtgaatt | 120 |
| ccgagaagca ttggctgcaa tttgggcctc gggccctccc agatcccagt tcctcaacct | 180 |
| gggcgcttta cctggacccg gacctctggt aggttgacct tgccggccag ctcctcgcgg | 240 |
| ctgtacacgt ccgggtagtg ggacttctcg aacgcgcgct ccagctcatg cagctggtac | 300 |
| gtggtgaaag tcgtgcggtt ccgccgatgc ttttttcttgg gctgttcctc ctctgacagt | 360 |
| ttcgcttcgc cggtggctgg cccgacgggc agccctgggc tcggccgtgc ctccccgggc | 420 |

```
tccttggggc agtagggtcg aggggctggg gcgacgaggc ccgggagggt cagatgcact    480
ccccaaaaca cccttgggcc gaccccgcct cgctgtgggc actggccagc ccgcctgcgg    540
gctccgagat ggcccgggga ggtccgtggt gagggcggcg atgggtccta agctttctct    600
gaatgcaaat tggaagctcc cgccatagac ggtccccaac cccgcgccca gttgccttaa    660
taaaagttaa ggaaggggcg ctctcgtctg gccaactcct aagctcgggc gcccgaacgg    720
cctcgcacag ccagggggtgc gcactcacct tcgtactcgg gggcgggcgc cggggctggc    780
ggcggggagg gctcggagcc ttcctcgggc gccttggggc aggcgggccg cgcgcccagc    840
ctcctatccc gctccttcgc gccccggcg ccccgctccg ccgggaaggt gccgaggatc    900
ccgtcgtcct tggtaaaccc caggatggcc tcgatgctgt gaagtcgcga ggtgctcccg    960
cccgggctgc ggagcaggtg gccggcaagc gagaagctcc cgtcggccat ggctggcgcg    1020
cagcccggca ggtgcatggg gagcgccggg aggcgggagg gcgctttgga gacggagagg    1080
agaggctcga agccgggtct tcccgagtgc ggcggtgcaa cccgacgggt cccgacccta    1140
ggtcaagctc cgcggggcgaa gcccgcccgg gctgcgcacg ctgggggtgg ccgagcgctc    1200
agcccgctgc cgccttagtc ccagaagtcg gaagttcggg ctcggggtag ctggggctct    1260
cggcgctaaa ggcggggagc caactggccc tcggctcctc ccctctcgcc ctggacccag    1320 cccttctct cggcccctcc ctccacagag gggcgtgtcc tcacccggcc cagccacagg    1380
gtcctctagt ggccacccct gggcggcac taggaatatt cccttccac ctcttgatcc    1440 gttttaagct ttacaaacac actccgggga tccgcggcgg gatgcctgat gggctcggga    1500
acctggtcgc ggcgcacccc tagtcctgcc tcagtgggc cgacgccctt gggctcatct    1560
ctccccttgc gtttgtctcc ctctacttcg ggcttaccct ctcacttcag actaccccct    1620
gggggtcacc tccctccttg gacgcaccc tcccagctt cagactcgcc cctctagccc    1680
cctctggctc acctccgcgg ggccgccacc ctggcctgtg ccccctggaa gcgccgagac    1740
ccagccgaag gcttcccagc cccgcactcg tgcagtttg aatttcccct cgctggctcc    1800 ctttttcggga cccactcctt tcttggctgg gttgtacgaa gtcccggacc tcgcgtttag    1860
tttgtccgtc tatatctgtt gtaactcctc ccagtcccct cggacttgag cgccggcagc    1920
ctccctcctt ccccgcagcg cccaccccag ggccatttat gtccgcaagt ccggtgacct    1980
ctagcgcccg atcgcccagc aggagactgg gagcccgag tcggatgtgc tgccgggctc    2040
aggtcccgca ggagacccac ctggagttcc tcgctcccgc cccttgtcct gcggggaggg    2100
cgggctcctt tactgatgag cagcggtgtc gcactcccgc ctccctccaa cactccgggc    2160
caaggagatg gcccagagct ggctggggaa ggaccttctc ccggggaaga ggcctctcgc    2220
ctccccgagg gttcaggagt aattggcttg cagttctttc tcctttggac ccctcgagg    2280 cttccgtggc ccacagtgac tgatcggcca cttggaaaga tgattggata gggtgagtgt    2340
gtttcacct                                                          2349
```

<210> SEQ ID NO 59
<211> LENGTH: 1149
<212> TYPE: DNA
<213> ORGANISM: Homo sapiens

<400> SEQUENCE: 59

```
agcgcccggc ggctggtttc cattagggca gttccggcgc cgacttcgct ggggacgggg     60
aaggtgaccc ccctactcgg atcccccagg tcctaaaggt agcaggattt ccagaacgct    120
ccagggctct ctcaggagcc tagggagaag ggcaaggaag gggcgtcttt ggcgagctag    180
```

```
cccgcaatgg gacgaccagt actgcacgct ctgctctatc cagactccaa aagaaaaccc      240
catcgtgggg tgtcccaggc cgttgggtcg tttatacca  gagtggccta accagagaaa      300
tccgttcttt tccctcaaaa cttgtaaagc agctggcgcc tcagcttaag gagcgtggcc      360
cttccttagc aggtggtgga gagaggggca gtggaggagc gttaggacga gatttggggt      420
catccagccg gagagaggga ggccgaaagg agagacgttt tcaggaggtg gaggcttcag      480
catttggatg cctgcgaggc gggagaggcc ggggagcctg tcttgtgctg agaggctggg      540
tagactgttt tgtcccctac aggctgatca ccagttcctc ttaggaaccg gtgaacctca      600 ggggggcccat tgcacatcca ggtgtgaaac tgcggtgtgg cctccaggtg aggacagact      660
cggtatagtg gggatcttgg gcaggccctg cggctgcagc ccttggggaa ggtgaatgtg      720
aggaccatgg aggctgggag ggtttatccg gagaagtgcc agaggaaacc caaactttct      780
gggcagaggg gccaaggaga accaggcatc gactcttttg gaaactaaga ggggaggggt      840
ttgaaagcag tttgggagct ggggacagat cgtaggttgg gcgagcttgc ctggtcgtgg      900
gccagaggaa agaaccacca ggagaaaagc ttaactttca aggaggtcac ccaggattcc      960
tgagcaaggt ggcacccatg cactctggtt cctctcctct gcagccaaca caagccatca     1020
gccccatgct cagctcccag caggcagagc gttcagaagc gccagcgcca tcatcttggg     1080
agcctgcagt ccacacaccg ctgaccttac ctacttcctc tttccaggtt gatagatttt     1140
ttgttcttg                                                            1149

<210> SEQ ID NO 60
<211> LENGTH: 3749
<212> TYPE: DNA
<213> ORGANISM: Homo sapiens

<400> SEQUENCE: 60
caggtagggg tgggtctcct gaactccttt ctcaaacact gatgtgttgg atacagcatg       60
ctctgggcag ccagagagca aagacaagag atctcagagt acagaaagaa aacgtggtta      120
ttgggagaaa gggctaagag actgagggcc ctagggagtg gaagacccag agcagtggga      180
gtttggccag attgactcgg gcagaggacg gagggaccct gggttcagcg tgaaggtggg      240
agaaattagt gggaagccgt ggtgtttgtc gctttaagta gttaatattt tcccaaatgt      300
taatccaatt tgaggttatt aggcaaagtg ccgagaaagg ttgcacatca gagttattcc      360
agtaaatctc cgtgctctgg atgtggggaa agatatatac attggccctc cacccactga      420
gtccgcagct gccccaccc  ctccactatt agagaagaag gtgaacggct ttgagtttcc      480
ctctccaagg caggaggtgg ttttctctct gagcgtctcc tcccctctct ttaattcact      540
ttcccggact ggagcctcag ccttgacttt tcctcctgca ctcccaagc  ccccaccatc      600 gcccccagca tctcttcgtc aaagacaaat aaagcctagc ctcctgcctg ggttgaccgg      660
ttctccggtg gaggggaaga gagagagaga gagtgagaac gaacgagaac gctggcgaag      720
aggaatgcgc tgcaaacccg ggtgaacaga tgtgcatggt gccctcaccc agccccggca      780
tggcctagac aaccgctgct cagccctgcg cccgtgaaat tacattattt tctccccggc      840
ccaatcatcg ttttacagga aaaaaaaatt aaataaatat aaattgctgc tttgcaagat      900
caaagtgccg atttctggtg catctggagg agtggggaga tggggaggaa agagagggggg     960 agagtggcgc agccgtggtt gcccaacttc aaagggttct caacagtgca ttttgccatt     1020
gtattttaac atctcttccc caccagtttg gcagggtgcg cagcggagaa gcgtgtagct     1080
```

```
tcagagttca gagcttgtgg agaaaccttg ctttgaccat ctctgagcgc ccccacggga    1140
ctcagaaccc tgaggctctt ctagagacac caacttgcgg tggtggggtg ggggtgggga    1200
ggcgtggtga ggaagagtgg ggtgggggct gatctggatc tgtagagtca ccaaatacac    1260
caataaaccg caaagaagcc accaagtagc catgcccta ctcaagctca aagctagaag     1320
gctagctgaa ggctccttgt caattttccc tgcgctcagg ctagctgttc caccggaagg    1380
actgggggag attcagatta tttgggagac ctggatcagt attaggtttt cagaggttag    1440
cggggtacag aggttagcgg gtttcttgat ggtggaattg tttatttgtg acccggccac    1500
ctgggcgact acgtaggcct ggtacaggag gcaggagttg cctctgtccc cactgcgctt    1560
tccttaatcg aagagcgggt agatgccggc caagcaaagt gctcgaaagt gtagctggga    1620
cgcccacgcc ggaagcctgg agaggcaagt tgcgagttcg cagggcttgg gagttttttg    1680
cggcggaaga agctgaatct aggggctgag tccccgggaa gggatggccg cctcttagct    1740
ttcgccagga gattatcttg gagcccagcg gccgagattg agagctcttt ctgcggaacc    1800
tgcctccgga gtcagatgag caaggggacc gccacgtcct caccgagctc ccagcggcct    1860
ttggggcggg tccggggaca agccggagga ctaggcttct cccagagcgc ggctgtcttt    1920 cccgaaaga cccaagtgcg cgatgtcagc ccgcctgcac ttcatctgag ttgtccttat     1980
gtggccattt ctgttcaaa tttcagattt tctactaaa aaaggatggg ttaaaacagc      2040
tgagagcgcg cctgctcttt cccgccctgg gttctacatc tctctagccg cccaccagac    2100
tgcatctcca atctgggagc tatcctcacc ttgggagggt ggggcaacaa tgttattctc    2160
gtttcccgat aaggaaacca acgtccctac aacttgacgt taaatggtcc caggttcctg    2220
agcctcaaat ctaggactat tacctaggtc acctaaaaat ttttgttctt tccactcccc    2280
cgagggtgat tctgttagcc tcgcaggcc ttctcccacc cgtcatttga agtcatcgac      2340
cccggggcag ccccaacagt tctgtgcggg cctgcgcgca ccgccctcac cttgcgcgcc    2400
aggcatctca cctcagccgg gcaggtcag aggtgacagg cgcggcagcc gcggttcgtc     2460
cggccgaggg gcaggaggag gctggccgcc gccttctgct gcccgcaggc tgagggggca    2520 ggggagggg aacagggctg ggaaactgcc gtcagcgggt cccggccccg cctcccgaac     2580
gcaacgtcca ggaaacctca gaactttcta ttgtctgaga agcttcactg aacaaattgt    2640
ccctaaaact ttagagctgc gaagagcgga tcagggcagg ttctagtgtg gccctgtgcc    2700
ccggagcctg cctgccataa agtgtgaccg gaagccccc ccccccgcc cactgtcaga      2760 accactgagg agagaagagc gcggcgcctt agtgccgccc tgcgtcgtgg tcgggaagcc    2820
gagcaagcgg tgtggacgcc ccaggagcag ggggatccag gcctaaactc atgggttccg    2880
aatgggcaag ggagcagaat caagcatcgg tgggcgctta tagaaagcgc gtctgtcttg    2940 gaacacctt accagggtac ccaaccccag cgccaggttt cctggccttg caaggagagg     3000
ttgaatttgt caggattccc cactctagaa ggtggctcgt ggtggtgaag cttcacctt     3060 cctggtctgc acagaagtca gtcagtctct ctctctctct ctctctctct ctctgtgtgt    3120
ctctctctct ctctcacaca cacacacaca cacacacaca cacacacaca cacacagaa    3180 gcacccttaa cctcacccgg cgcgcttgtg ggtagattcc cgagagggtc agggaatctc    3240 ttattttct cacagccttg ggtgagaaac cggctacctc ctctcaggaa acacccggat     3300
gtgggtgtgg accagaggac tcactggaac actgactcac cacctaatct tgcacaagtc    3360
tcttaattac agaaaccaca ttcctatttt gtccaactgg ggtgattggg gcagcctaaa    3420
gtttcctggg aatggtccac tatgtgcttg ggtgcccact tagagtacat ctgacacgtg    3480
```

```
tgcacatctg tatttgaatc cgaccacctg agccccgcta acaccagcgc acagacctac    3540
actgtctttc tgtccctccg gctactttcc ctgcttgctg tttctgctgg gtgattaacg    3600
accccaaata gtgtaaggaa ttcgacttct caagctcagc attttcaatt ccttaatttg    3660
tccctgggtg accgttagca attgtggctg tagatcacat ggggcggacc aggtagaatg    3720
agcagctgat tcaacactgt tgagttggg                                      3749

<210> SEQ ID NO 61
<211> LENGTH: 1999
<212> TYPE: DNA
<213> ORGANISM: Homo sapiens

<400> SEQUENCE: 61
ccaaccccac ccctgagatt ccagtggagg cggggatgg ggggatccct aacttgcagg       60
aagaatttgg cgagcgagaa aggtcccct cccgcaggct cttctgaagc ggaggatccc      120
gggacgagaa atgctgcccg gggggcttaa ggtagccgac gatctccttg ctacatcctg     180
tgtccacgtg gcagccgagg agggggtgtg ggggccgcct gttaagtgcg acagcatcac     240
tgctctatcc ccaccacggc tcccacttcg ctcagataaa atgcagagct cttaccaagg     300
ctcacggccg tccccgccc ccaccgtct gccccatca cctctcgggc tccggtgac         360 ctctcgggct acagcagcgc tgacgccctg ggtcctgcg cttctgttcc ctcggcctgg      420
aatgctcttc ccccgggtac ctgcacagct cgctccctcc catccttcgg gtcttcgctc    480
gaacgtccgc tcctcggtga ggccttccct ggacaacgca tttgaaacgt aaccccaagg    540
caagaagcca ccttccaggc gcgcagccga agcccagtgc caaggaggcc ggagactcgg    600
gtgcccgcgc atcccgaaaa cagcctctga ggggtcctct gagcatcctt ccagcgtgtt   660
tgggaggcaa actcgttgac tagctcttga gaggagtggc tagaggaatc caggcgggga   720
aggggacggt ggactccagg agagtgtaat ttacaaaggc gggggcggg gacgcccagg    780 tccgagtccc aggactctgc gccggacgct tcgcccgccc tttcaggtcc cctgcccggt   840
cctcgtaccc gcgcgggtcc ggagaacctc tgagcaccgg ccccagccc ccggggcgggg  900 ctccagcggc gctactcacc cggctccccc gccacctgcg gggccacctc cgcacactcc   960
cggcgcgcag gccgcggctc ctcggagttg aggtgctggg gcttggcctg cttgcgccgc  1020
gacatggcgc gaggaccggg ctccccgcgc gtccctagga gtggcctact tcacacaacg  1080
aattcccgga gttcggaaat tacccccctt cggccggaac gcgcatgtcc cggcaattct  1140
gctcatcagc cgagcagggc gatttatcaa gagtcctgac ggctgattgg cctggagcca  1200 agacccagg agtcccgcgg acttgcggtc cgctcccggg cagcccgcgc cacctgggag   1260
ctcgttagaa atgcagactc tcgggctcta cccagaccc gctgaatcag aatctgcatt   1320
ttaacaagat ccccaggtga ttcgcatgca cattaaagtt tgagaaaccg tgtctgcatt   1380
ttaacgagat ccccaggtga ttcgtttgcc cattaaaatt tcagaagcgc agctctcctc   1440
caactttaat gtgcgcacga gtcactgggg atctcgttaa aatgcagatt ctgactcagt   1500
gggtctgggg tggggcctga gctcctgtat ttctaacgag ctcccaggtg gcgctgtggc   1560
tgctgcgctg cacaggctgc gcttttagat tcggacttaa ttggtctggg ctgggacctg   1620
ggcactggga tgtttttta aaaaagccgt ctccctccct caccaccccc atcacacaca   1680
caggtcattc tgatgtgcat ccaagctgag aagcacgacc tccactcctg gttctcaacc   1740
ctgctgcata cccaaattta aatttttaaat gaggagtgtc tccaactgca gggagaaatg  1800
```

```
cagattccga aagttctgga ttcaggtggc cgaggccaga aatgtgtgtt tttatatagc    1860
acgcgcccgc tcccgccccg tgactcgggc gcaccggctc ttggaccaca caggagtgct    1920
tttggggcca acccggcgcc ggccccgccc agcaggtgac ggaggcgtgg tcctcggggg    1980
gttgagctaa ttagcgttc                                                 1999

<210> SEQ ID NO 62
<211> LENGTH: 599
<212> TYPE: DNA
<213> ORGANISM: Homo sapiens

<400> SEQUENCE: 62
catgcccgcc tttgaagctg aggcgctctt tagttaacaa actacaagtc ccagcaggga      60
ccgggacgcg ggtgggagag cgcctgtgg ccccgaggcg tgccgcgagt tgtagtccct     120
cctgcccgct gtgttcgctt ttgagctctc cgatgggatg cggcgcttcg gaatttcggg     180
ctttgatccc tgtcccgccc ttggccacag gcacctgccg gcctgaaggc ccccgcggtg     240
ggggtaccct gcgcccctcc gcgggaaggt ggactacagt tatcggcagg ctgtgcggcg     300
ccaaagccac ggtgacccag acccgaggtt tttccgggcg tcgcagtttc ccgagactcc     360
gtggcggcgt ttgtcttctt tttcttagtc agatcccgta cttttgtgga gggtagagga     420
ggctttgacc gccgcggccc cggggctgg tgggaaatgg agttccaaat gagaaaatag     480
aattccccac ttctctttcc cacaggtgcc agggaaacgg agtcatcgac caagaaggt     540 cgtgggagat gaggtcccag ggtaaacagc gggtcccgcc actatgtcac cctttcctg     599

<210> SEQ ID NO 63
<211> LENGTH: 1899
<212> TYPE: DNA
<213> ORGANISM: Homo sapiens

<400> SEQUENCE: 63
aagaaacttg cccaaggtca aggagaagtg gaggcgtggg gaggaaacaa agtcacctga      60
caccagagcc catgcctcca aactccaagt ctgggactcc tgattaaatt ccgtctctgt     120
ctgcactttg ggaagattct ttcctctcct aggcaagtgc ccgcggggcc tgagctctcg     180
atagcggggc cccaggagcc acgttgtggg gtctgctatc cggcctccct ctgcacgcgc     240
gaccgtccac ttgagcgcag tggctggagc tgggactcca cgcagccccc tgagcgctca     300
cgtcgacccc tccaatcaca agaggccctc gtgccaggcc cccagatttg ccaatcagg     360 gaagaccttt ccctgtcaca gaatgggtc gaggggccca ggaaacaggt agtccccagt     420
cacaaatcat cgcgtcgcct tcgctggtcc ctttctctta tcgagcctca gttttctctt     480
ccataagccg ggccagcagt gcccacccca caggttggcg ccagctccgt aagggcccta     540
ccaccgcggc cggccagatc ctcggcgggc cagtcctggc gctgcggtca tttagcctga     600 tgaccctgg ccaggttcag cctcaattgc tccaaagaac tccggacccg taccccgagc     660
ccggcgtccc agcggcgaag ttgatgggcc ccgcaggagc ccttgcggtg agaaccgagt     720
cctggagccc ctggagcccc ggagccccc ggagctgcag ccggggcagc ctcctttccg     780
ccgggagtcc agcgctctcg agagcccaga aactcaccgc gcgcaggagt tggtgcgggc     840
gtcccgggca ggttagactt ctgtgagccg cagccccgaa actgaggttg gtgcagaccc     900
gtcctgggag ccaggaggtg ggacctgtcc ccgccagtcc gcgagctctg ttaaggcca     960 gagcccgtga gggagggggc gcgggcggg cggagagtca gccgagtggg ggcggcgctc    1020
accggtggtg ggactatggc gggagcgcag cgcacccttct ccgggcgggt ctataaatgc    1080
```

```
catgtaaaag ccaaccccgc aggggcctgc gctctttccc gcttaggtca agaagactta    1140
ctgtggaccc ttggagaatt cccagggctt tgaaaagtcc caagcaccca gcagggctgg    1200
cagttctgag cgctggcaag gctaagtggg tcagaggaga ccctcgccaa gccggtgact    1260
cactcactcg ctcaccctct ctcactcttg atgggccaag tacctgccat gtgctacgga    1320
cacagcagag cgaaaggaga cgctgccctc cgggaatttg cagccgcttg cagaggcggc    1380
cccttagcag ctgcgcatcc gggtggatag cggcgcttct gcccgcccag tgcctacccg    1440
cctctccgag agaaaaacag cccctggttt tctctctgca attccccttc tccactctct    1500
cccttctact cagtcctggt gccgcagacc cctcctcctg gttcccagag atcctggcca    1560
gcccggtctc aggcaaggcc atgtagaatg ccgggagtga taattgcgta ttgtttcatg    1620
actgcaagcc tgtgtccagg tggctccttc tcctggaaca cccttcccac cacacctgcg    1680
gccgcactgc tccgtgccct gctaagcctc acttcttttg aggcgaccct ctcgctaagt    1740
cccgaccacc tggccctctc tctgctcagt gcctgaacac atcaggcttg ctgcagcccc    1800
tgcctttacc tctctacttg tagtgttctt tcagagcctg ctcccatatg gtatcacata    1860
tcagatatct gatgcagagc cttagagagg ctgttccag                           1899
```

<210> SEQ ID NO 64
<211> LENGTH: 2599
<212> TYPE: DNA
<213> ORGANISM: Homo sapiens

<400> SEQUENCE: 64

```
tcccaatcga cccccgcaga tctggcaccc tagaagcccc tgtaaaatga gggtggtgct      60
tagcctatgc tcccaccaaa cctaacccctt gcacttgaag accgttaaca ccttgtcttg    120
ggctcgagca aaagaagggg gtgaggcagt ggaagcgggg cccgggaaat ctatagtttc    180
cccaccccca gctcctgccg agccgggagg ggccaagggt gacggcaagg atacgaaccc    240
ttcaatatgc ccgactcccg ggcagggcct gctgaagccg tagatgtcgc agccagatgg    300
atcgggaagc aagattccca ccccaggtgg ataactggac gagtctcagg gcctcggggc    360
ccctctcccc atgcagccag ggatgggcac ggtgagcgag aacccggaca gcggagataa    420
tgagcacgtc acagagccca acgggccaaa aggggtgat agctccacat taaccccctcc   480 ccgtcctact agcattcccc cgcccatcta ggtcgcctcg agcctccctg gctgtctctg    540
cacccgcgcc ctacctggtc ctcagaccca tgcgatgctg ggcaacccgg gccgggtgtg    600
cccaggaccg caaagcggga agcgcaggcc ttgcggactg cgagtggccc ccgcggcctg    660
ctgctcccct ttataacgcg cgccccgccc ccgcgctcc gggcgccccg ccctggccca    720
ttcacctgct gtcgagaacc agacaccgcg cagcagaaag ctagccgctg ggccgcgagg    780
tccggccgtc ggagcgggcg gggctggggc gccgccgaga cagatccgat ttccaccttt    840 tcttaaaatgc gctgctgaaa gtcgagaagg ccccggccgg ggagctcgcg tcgcttcctc    900 cccccctcagc tcccctcgca ccctgagtcc cccagcccca ctccgggagg ggccgcgaaa    960
ctgcacccgc aagggcctca tacatatttt aaggagcagg ccaggcaggt aaccggagct   1020
ggactcggac ggtgagggg cggccccgg ggacctgata ccctggatcc cttacggctc    1080
agggctcagg cggggaaga ggtggctcag gacgacctgg ggtcctcact ttgctggcct    1140
gtccagcgca tcctaagccc gcgtgtatcc taccccctcc ttctgcagat ccaatgtccg    1200
tctggcaatt gccccattcc ctctcgctgg agagatccct tccgcctcgc cacaggcgtc    1260
```

```
ccacgctgcc cggagtcgtg cgccccggga cgggtagttt tgggttcctc gacgcttggc    1320
caggtttagg aaagacccgc tgtcttcctt gctgccccca cctaggagac tcggcgcctt    1380
gcgctccgtc cttttaatg tgtcgcggc ttgtccctct ggcttgctcc ctcctagtcc     1440
ctaccccaca cggctccctt cgccagctcc atgacaatcc cactcgtgct gaagaccttg    1500
ggcaaagaag taaccatcgg tcttcccctc ccttcccatt cctccggcgg caggactagg    1560
gggaaaggtg cccgggatac aagcccctca cgcagaccca ctgatgcggc cgtggttctg    1620
ccattggccc ctctccgaat ggtgaggttc tcctgctaac cctggcccca tggcataact    1680
agtataaccc cagtgagagg aacccagagt tccagtcctc ccctgctcca gtccctctgt    1740
gatctcgatc tcgagggatt cacttcacct ctctaagcct cagtttccca tttgcaaaat    1800
gggcagaatg actcgcacct ctggggatga agaaaatgca catgtgagca cgtgggtact    1860
tggcgacccg agatctctg caaactgcag gcccagcgag atggcctcag cacgccctgc     1920
accctcgtcc gcgcgactgc cgccgggtgc ccgccccagc cgctgtgtcc ctggtgcttc    1980
ctccgccagg gccacgtgcc ggggaagcca agcgggagt ctttcgatct tggcccagcc     2040
cttagccctc ggtcctttgc tctagcatct agattctcgt gggtcaacaa agtcactgga    2100
aacccaacga acttcccgac attttcgaa accgtatgc gtgtgcttct gtgcgttttt      2160
cctctgatcg aggtagggcc ctgtagggtt ctgtttggac gggaggctgg agtggttcct    2220
tcccggctgc ggggtcggag gatgcagaga ttcgaaagaa ggagaaacac agagactgtc    2280
aaatgaaagg agattctgtc ttcggaatcg acccagctct ttaaaagaat gaggaaaaca    2340
tggggtcttt atatatcctg gaaagtcgcc taggcgttca gtgaaaaacg caaaaggcac    2400
gtggattcct atttgtgtaa aaatataaat ggggcagggg gttaaacatc aggttttttc    2460
tgcacgaaag gtctcagcgc agagggttgg agatttttct tttcattgta tgtctttcgg    2520
gactgttcga agccaatgtg tgttgcttac catattcttg cattgaattt tcaattaaaa    2580
aaagaaactg caggaattg                                                2599
```

<210> SEQ ID NO 65
<211> LENGTH: 2199
<212> TYPE: DNA
<213> ORGANISM: Homo sapiens

<400> SEQUENCE: 65

```
attgccctcc ctgcgggtag cgtggagccc ccactcctcg gtgcaaccca accccggagc     60
cacaaaggcg cgcccctag gcggaaaag tacactttcc tcctcacccg ctgttcctct      120
ggggtgctgg gagggcaggc aaggcaggct gagtagagga gaaacccacg tggcggggga    180
cggagtgagc ggggctcgag ctgcctcgtg ccttcgcagc acccgcccac cgagccttct    240
ttcccgggca caggcctgcg ccgacccgac cctgctcgag agcccgcgct agagtcgggg    300
aggatctgcg cagagaccgc agcatcaccc aaatcggcgc cggccccggg aggatctcaa    360
taaagaactc gagcgtccca gacccgtatc tcctttcgct gcccaacccc gcagcctggg    420
cttcgaaggc gacccgccca ccatcctgcc cttcccagaa cctgagaccg tctgggggc     480 ggaagccaaa tgaaccccta ttgggcacct ctgtgatgcc aggagcgaac tggtgagccc    540
agcgccctgg gaagagggcc gagggcgggg cggtggtgcc gggacctctg aggtcctggg    600
gatttgggga cccttggggt ccacatgcac ctggctgacc tggctgaaag ccgctgtctc    660
ggagcccccc acagcatttt gttccccctcc cgctggcccg ggggcccac cttcccacgg    720 gttcccacgc tgctgtgact gccctgcctc tacgacaaaa gccaacgggt cttcagtact    780
```

```
tttattaaaa aatagtcacg cagacagtgc cctggtggct ctgccccgca tcccaactct    840
ggggtggggg aaaggggtca acgttttcgc agccccaaac cgggccatca cttgcccacc    900
gagtcgaata tgatgcggtt ctgctcggcg cgctcccgct ggctctgcgt ccgcgccagc    960
tccagcaggg tccgcagcag gtgaaaggtg aggtcaatgg acagagaagg gttgtcccgc   1020
cgcggccgct cgcctgccgt cccgagtccc aatcggccgg ccccgcgcg gcgcgggaag   1080 cgctccgcca gcagcaagag gagcgcgcgg gccccgccac cctggttccg tgccccgggg   1140
ctccagcgca gactcgggtc ctggaccccg gccgcctcgg ggctcctctg gctgctccca   1200
gggcacagct gtaccaggag cagcagcgcg ccagcagcg ctgcgcgtcc cgcctgcctc   1260
atggtgccgc cggccctgga cacacagggg cagcgcaggg tgaggtgcgc ctgggacagc   1320
tgcaggccgc cgctcccctc cccgcgctcg cccggcgacc cctccggccg ccgcccaatg   1380
cccgcagcct gccctccagc cccagccact gcgccagtgc tgttccatcc cttccaccca   1440
gcctccctcc ccggaggagc gtggtggctg agctgagcgg agtcctggtg caggggagg   1500 ctgggcggac gctctgagcc actcacaggt tgtcggcgag cgtctgtacg gtccaagatt   1560
gagctccagt ctctgtccct cggggcaggc tgaagacgcc ttggggaaca cagggtctgt   1620
cccggggctg tcgccagcct tatatagtgc caggacagct ccgactgacg tcagcgaaga   1680
acatgcactg attgtagaag caatgacagc cacagcttcg agtctgacgg ctggcgggcc   1740
cccggagggg cgcacctccc tacaccagcc ttcgtgcccc tggggctagc gctggaagca   1800
gcactggacg caggaaagcg agaagccggc tggggcgtaa agactgctct gggacccacg   1860
ggagtccctc gccccgctta aacagccag caatgactag ggccgtcccc agaccagact   1920
agtccgggtc gcgtgttctg acacacgaaa gggaggcggg accgtgaggc tgtccatggt   1980
gctgaccccg tcctctgcct ctagaagtgg ccagaaatgt gagaacgctg tgccgctgga   2040
acccactgcc tccctgcagc tatcagttct gcaaatgcag gcatcaggag tccaccgctg   2100
gcactcagcc aacacagtgg gacccactga gaggcagtct gccacaacca aagtctccca   2160
gcattcttat cttttccag ccccaggatc caaattgta                          2199
```

<210> SEQ ID NO 66
<211> LENGTH: 1099
<212> TYPE: DNA
<213> ORGANISM: Homo sapiens

<400> SEQUENCE: 66

```
gctcctcatt cttcatttat aaagtgagaa ggctgaagag gttactcttt aaggcttccc     60
tctaacctcg tggtctgtga ttataatctg aagtgaggaa ggcccaggaa agggtcccta    120
ggacgccggc gagcgtctgt gacccaccac tgtccagaaa tgtcggtaag cgctgaaccc    180
aaggatacac agcccgaagc aaacgcggaa ggtatgggcc ttacagcctg gaattgctgc    240
agagactggg agccaaaccc tcatcctaat gtcccaacgc actttgggga gggagagctt    300
cccgcggatc cgcctgggtt tgggaggacc ggggtccact ctgcaccggc cagggcctga    360
ggggcccagc agctgaata cagcaatctc ccgcccacct gctcgcagcg tacagagcac     420
aacatcgctc acctgcggcc cccagggcca aagagaact ccctcctacg agcgaaggc     480 aagaggcctc gaacccttt gggacccgga accatcaaa agtgacccac aaaggccgga     540 agcgccacg gggggtctaa gaaccagccc gcgcgggcg cacttccgcg gccgctctag     600
gaagggagcg aaagggggctt tcaactcggt agtgtttccg cgcgtctacg tgagaggaag   660
```

| | |
|---|---|
| gttgatggct tcaggcccg ctggtaaatg gaacgggttt atcttctcct cttctttacc | 720 |
| cagccattgt ccacacttcc cccgacccga tgggtggtcg aggcttgtag aactgatctt | 780 |
| aagacaggga aatcccttgc gtctccattc actttgggat tctgtgtctc tgaggttaga | 840 |
| gatgcctcaa agggatgttc tccgggggac cttcccaaat ccgcgcttag cggtggcgaa | 900 |
| gggacttctt ccacacagac ttctcaaggg ccagccggct ggtttctgcc ggctctttcg | 960 |
| ccatccacga ttcttttgat gttctctttt atgtgctgat gtatgattat atgtcagaaa | 1020 |
| acccggttca atggaaaaac tataaaaaaa ggataattta gtaaaatagc aagatataaa | 1080 |
| gttaacacac taaaatcaa | 1099 |

<210> SEQ ID NO 67
<211> LENGTH: 2199
<212> TYPE: DNA
<213> ORGANISM: Homo sapiens

<400> SEQUENCE: 67

| | |
|---|---|
| tccatcccct tttgaagaac agtaggtgga gctatttaag atataaaaac gaaatatcct | 60 |
| ttctgggagt tcaagattgt gcagtaattg gttaggactc tgagcgccgc tgttcaccaa | 120 |
| tcggggagag aaaagcggag atcctgctcg ccttgcacgc gcctgaagca caaagcagat | 180 |
| agctaggaat gaaccatccc tgggagtatg tggaaacaac ggaggagctc tgacttccca | 240 |
| actgtcccat tctatgggcg aaggaactgc tcctgacttc agtggttaag ggcagaattg | 300 |
| aaaataattc tggaggaaga taagaatgat tcctgcgcga ctgcaccggg actacaaagg | 360 |
| gcttgtcctg ctgggaatcc tcctggggac tctgtgggag accggatgca cccagatacg | 420 |
| ctattcagtt ccggaagagc tggagaaagg ctctagggtg ggcgacatct ccagggacct | 480 |
| ggggctggag ccccgggagc tcgcggagcg cggagtccgc atcatcccca gaggtaggac | 540 |
| gcagcttttc gccctgaatc cgcgcagcgg cagcttggtc acggcgggca ggatagaccg | 600 |
| ggaggagctc tgtatggggg ccatcaagtg tcaattaaat ctagacattc tgatggagga | 660 |
| taaagtgaaa atatatggag tagaagtaga agtaagggac attaacgaca atgcgcctta | 720 |
| ctttcgtgaa agtgaattag aaataaaaat tagtgaaaat gcagccactg agatgcggtt | 780 |
| ccctctaccc cacgcctggg atccggatat cgggaagaac tctctgcaga gctacgagct | 840 |
| cagcccgaac actcacttct ccctcatcgt gcaaaatgga gccgacggta gtaagtaccc | 900 |
| cgaattggtg ctgaaacgcg ccctggaccg cgaagaaaag gctgctcacc acctggtcct | 960 |
| tacggcctcc gacgggggcg acccggtgcg cacaggcacc gcgcgcatcc gcgtgatggt | 1020 |
| tctggatgcg aacgacaacg caccagcgtt tgctcagccc gagtaccgcg cgagcgttcc | 1080 |
| ggagaatctg gccttgggca cgcagctgct tgtagtcaac gctaccgacc tgacgaagg | 1140 |
| agtcaatgcg gaagtgaggt attccttccg gtatgtggac gacaaggcgg cccaagtttt | 1200 |
| caaactagat tgtaattcag ggacaatatc aacataggg gagttggacc acgaggagtc | 1260 |
| aggattctac cagatggaag tgcaagcaat ggataatgca ggatattctg cgcgagccaa | 1320 |
| agtcctgatc actgttctgg acgtgaacga caatgcccca gaagtggtcc tcacctctct | 1380 |
| cgccagctcg gttcccgaaa actctcccag agggacatta attgcccttt taaatgtaaa | 1440 |
| tgaccaagat tctgaggaaa acggacaggt gatctgtttc atccaaggaa atctgcccct | 1500 |
| taaattagaa aaatcttacg gaaattacta gtttagtc acagacatag tcttggatag | 1560 |
| ggaacaggtt cctagctaca acatcacagt gaccgccact gaccggggaa ccccgccct | 1620 |
| atccacggaa actcatatct cgctgaacgt ggcagacacc aacgacaacc gccggtctt | 1680 |

```
ccctcaggcc tcctattccg cttatatccc agagaacaat cccagaggag tttccctcgt    1740
ctctgtgacc gcccacgacc ccgactgtga agagaacgcc cagatcactt attccctggc    1800
tgagaacacc atccaagggg caagcctatc gtcctacgtg tccatcaact ccgacactgg    1860
ggtactgtat gcgctgagct ccttcgacta cgagcagttc cgagacttgc aagtgaaagt    1920
gatggcgcgg gacaacgggc acccgcccct cagcagcaac gtgtcgttga gcctgttcgt    1980
gctggaccag aacgacaatg cgcccgagat cctgtacccc gccctcccca cggacggttc    2040
cactggcgtg gagctggctc cccgctccgc agagcccggc tacctggtga ccaaggtggt    2100
ggcggtggac agagactccg gccagaacgc ctggctgtcc taccgtctgc tcaaggccag    2160
cgagccggga ctcttctcgg tgggtctgca cacgggcga                          2199

<210> SEQ ID NO 68
<211> LENGTH: 1449
<212> TYPE: DNA
<213> ORGANISM: Homo sapiens

<400> SEQUENCE: 68
atctttgaca aagtaattaa ggccgtagtg actggctaat tcagaccgaa tggctgcgcg      60
gtgatggatg cggatttacg gcctccttgg ctgcggcgcg ctgggcctga ttatcactat     120
aaacaggcgt ccgcggaggg cggggcgga ggcccgcgtc tagaggacgt gcggctggtc     180
ttcttcttct tcttcttctt tttttttgtt tttgttttt aatactgcgg ttccatcctc     240
tgcgcttcgt aggcgctgac acacacccat acgcacgacc tgctgcccca gggcctggct     300
tcctgcctcc gcatgctctc tcccgcccct gaagcccaac cttcaagccc tgctgatgcc     360
cgcccctccg tcccagcgtt ggcctcatag cgaaccctct taggcctctc cgttccagac     420
cctccctcca ttctccacgt agccccctccc ttctagaatc ttgcggctga aagtggggc     480 aggcggggag cccgaatagc gcctcagcca aaccccgcag ccgttcctgc gcgtcacccg     540
cctctgcaga gcctgacgcg cggcagtctc cacgccggaa cccaagtgct cactgggccg     600
gggagggcca gcgggcgaaa tatcaggcct gggggctgag cggggcgct gggcgtcact     660 caggcccagg gccgcagctg ggggaagtga aaggccggc aggattctgc ccactctgcg     720
cagttctccc ttcctcccgg ggcagccaag tctgtgcgcc ctggaacgtc cgggcgccgc     780
gtagactctc cattcgcacc tggcccttg cgggggctgc tcaaatgcaa attgggaaac     840
tggccagaac cttccaaagt cgtgactgtc cctcggggaa gtcggccggg gaaccgcaga     900
gggaggccta caccgatctt tgggcccgcc tcgtggtacc gctccggccg atcgctctct     960
gagcccgagc ctgcctgcca ggcctgcctt ctacagttct cgcattcgtc ttgagccctc    1020
tcggaaactg gggactgttt aggcagaaac actcgtaggt cccttggcg tcccccaaga    1080 tgccaagagc ctgcggggtg cttctcagcg ccagccggaa cttgagcagg cacccctgcg    1140
gaattctcag tcccacccac tcagacgacc ctcctccagc cagagtccac cacagcccac    1200
cctaccctct taaccctcgt tcccgacctc tccctacgag cgggcccgg ggagagagcg    1260 actgacccta gcgacagccc ggcgggaggt ggttgggatc ttctccaggg ttcaaaagcg    1320
actttctgag ccccaatttc ctcagctttg caattggtat agtttctgaa aggccattgc    1380
taaatctaac cgagataatt catggatatc ccttgcacaa tggttgagta ttgagatctc    1440
aatagacgt                                                           1449

<210> SEQ ID NO 69
```

```
<211> LENGTH: 899
<212> TYPE: DNA
<213> ORGANISM: Homo sapiens

<400> SEQUENCE: 69
tcaagtgtgt aaatgttcta agaaagggtc ctgaatatttt tatgaatatt tgtcataaaa      60
cagaaataat aaccactgtg cagagctatt agaattaata tttatgctgc ccgccatgaa     120
atattcatgg ggacagagaa aggggggccg taagacaaga attaatttac actgggctcg     180
gtttacccgc tggcttgatg tttaaagacg gttgacaagc ctccatatga atccgccagt     240
cacttcccgc agtctgcgga gtggaggggg tggagacggg tccgggctgc tgacagctca     300
cagattgagt ttctgacagc ccttaaaaaa cctaaacggc ccccacctat ttccccttct     360
tccattgccc aaagcgctct gttctgccac cgttcatccg atctcccctt ccatctgctg     420
aaattaacga attaatgagc gagatacgct ttacggtggg gccttatgaa tgtttacagg     480
cgattaaatt ataatgcggg gcggctgtat aattcatgaa ccaattaaag gaagtgttag     540
ttgatttgat gggatgagga cgtacaaaat gcatttaact aatggggaac cgcgggctgc     600
ccagggccgg ctccctctct cggattacgc ggctaattgc tcgactttac ggggctgtca     660
cagatagcca tgcatatttc attgttctca aatacttcaa ttgtgtgcgt ccgtgtcgcg     720
gctgtaatgt ggagaaggcg ggccaaactt gggtgtagtt acagtacccg agctgggccc     780
cggcagaaac ctgagctcca gagtcgggtg tctgggccat taggtgatta aaaaggctca     840
gcatgcgatc gccttttgtt ttactatgtt ctcttcggga cactaattcc ggatgctga      899

<210> SEQ ID NO 70
<211> LENGTH: 2499
<212> TYPE: DNA
<213> ORGANISM: Homo sapiens

<400> SEQUENCE: 70
ttgttttgta acattataaa gaatgaggaa aacttgtgca ttggaaaata aatttgttta      60
aagggtctcg aattaattaa tttatttcac ctgggaaatc gcacttattt ttcaactggg     120
aaggcaaacg gctgaccttc aagttactaa catctacagg acttgaaaag agaagggagt     180
ctgtaacctc atcagaaaag actgaaacag tcagatactg ttccccaaat attacagatt     240
tcctgtctta taggattcta agcaaataac cagaatatca ctccggggta caccttcctg     300
tataagcaat gccctggact agaccctcct aacagctgct ctccaagtct ccgcagccaa     360
ttccttcctt aatttgcctt cactttgaga aagaaaaaag aaaacaaaat cccccccattc     420
cccgttccca atctattaca tttcaaagga ggagaaagaa ctggaaaacc ccgtttcctt     480
tgagaaacgc gtccgcggca gctactgagg gtctgcccca cctttagctt caggttgaca     540
actgccttca gcgcgttctc agctcagctg gccctatggg tcccctaaaa tcgcccgagc     600
gtccgccctg tctgacctgc ccccctgccg cggcgcacat ttcagctttt cagcttcacg     660
gtggagctcg cagtaattga gtcgcgaggg ttatttttcc tggcctcacc tcgcggtcct     720
gagcctgcag ggagctttcg gaaagacatc gcccctcccc ctgagtccc cggcagcttc     780
tgaacgctgc gcgggtctcc gccccgcggg aaccaggatt gcgatccgtt cctcggcggc     840
tagaggttga ggccggaggc tgacaccacc agggacccaa cggagggttt attctgccca     900
gcttcacatc tggggtcaa atcgcattaa agccaaacca ccaacggggc agggagcagg     960
tggttaacta cacaaaataa agttacagaa aaaacctcgt tttgcaggcg agtgacttag    1020
tttccctctg tagctttgcc gtcataaaaa gcaagtccct cccctctcct gagctggaag    1080
```

```
gcggggaaag gttatcagcg gctccagatg gacgcccgta ggcagggtca gtttaggaag    1140
accggcaggc aggcgtatta ggcgcgcggg ctcccatcct catggctatg ggaagcaagt    1200
ttccctcatc ccttcttgga aggtaagagc tttgacatct ggaagtgtca gaaatgagcc    1260
ttttgccata aatcatcctg aaaagcattc aaatcagaca agcgtctaga gaccctttag    1320
acactccacc cccaaaatcc tagatcaaag tgcagttcct ggaaccataa acacctatta    1380
tatgcaaaat cctacttatc tggaggatgc caaaactgag agtaaagtaa ggggtaaggg    1440
gcacttttcg ctgtaaattt cctatacaaa tctcaaaatt tttcttagca ttgtcaacta    1500
ccttcttgga gacaggctac agcgcttcta aacccaatac gcttttctgg agtcctcgga    1560
acagctggcc ggggctttta gcacacggga cgggaccttc gcctttgcct gtttttttttt   1620 cgaccaggag aagcaggtgc gagagtctgg ggcttaggag gtggaaggcg gggaaagaga    1680
atccactagg tcctcgtgta gagaacaaca gtcgctcctt agatattact ccaggacgga    1740
aacctgattg caaaccgctg ttccttcgaa acttgcaaaa cccggaacag aaaactcccg    1800
cccagccaat tttagctctc gctgaactct cccgcctgcg ttacgtttgc acagcaactc    1860
tttgtaaatg tccgagtcct ctcggaggaa agatcgttag ggcgacgaga acattaagag    1920
gggacctgga gggcagatat cctcgatccc aagagagcaa ctttgtcgcc tcagaaaaca    1980
cgccaacttc cctcctgctc tttccttggt caactcagaa tcaaccgatt gtattgaaat    2040
ctcctgaaat cccgaacagg gattggccca gtcggcttct gaaaccgagg ccggggaatg    2100
gcaggaatgg ggggcagaga ggatcggaaa gaagagtcct tcccccacag acattcccag    2160
ctgggacacg agctcgctcg cagcgcgttt atggaaagag ggggcgctgg gaaccgcgct    2220
ggcggcgagc agactccagg gtcgagatta ttcgacacgt gtcttttatt cctcacaatc    2280
catttcttac gggtgattta tgaacgaatc tctttgatca gggacggttt tatctgtcca    2340
ctgctacaga tgacagatgc ggctgctaaa atgcctggtc cccgctgcct aaaaggttgc    2400 tcccccccctt cccaaatgct gttgcttttt ctctggcggt ccccaccccc tgcttcttcg    2460
ttctccttcc ctaccccaa ccccgtttgc tgtcttagt                          2499
```

<210> SEQ ID NO 71
<211> LENGTH: 549
<212> TYPE: DNA
<213> ORGANISM: Homo sapiens

<400> SEQUENCE: 71

```
cccatttctg cacctacagc ctcacacctt cttcccggga cacagcactg ccaggagccc      60
atcctggttc agttcagtac ccaggaggaa tccctcgggc cgactcccag gactttgttt     120
cttggacttc accaccgccg cctccccagc acagctcccg cagcccgcac ccgcccacag     180
ggtctccgcg accctagagc ttagggaaga attgccgagg ggcggggggt ccctcatgcg     240
catggaaggg acgtacgccc caggcctcca ccttcctcct gaccccgggg attcttggac     300
gtcgattctc cgtctcgtag gggcgagggc cctgggttcg cagtcagacg cgggcccctc     360
tcaaatctag tggcctggtt ttattgagtg ggggaaggca catatttttcc aagattaact    420 gccccgcaac agggaatttc gcaggatttc agtattttcg actccccagg tgacgccaag    480
agggtgggtt ccactgtgca cggtggggaa actgaggctc ggaggggaca aggaaggtac    540
tcgaggtca                                                           549
```

<210> SEQ ID NO 72

```
<211> LENGTH: 999
<212> TYPE: DNA
<213> ORGANISM: Homo sapiens

<400> SEQUENCE: 72
ctccagccgt tcagcttgtc cggagtcggc atcctgggcc gcaccctcgg cttcgaatcc      60
agccctgac gccctccgca ccgcggttcc tgcctccggg cgccgagggc gggggcgcc       120
tggagagaaa tccagctccg gctctgagcg tctccagtca ggcgaggcgg ataaatcctt     180
cgcaaaaccc tcttggaaat tgccgccgct tcctgagcca tcagtcccag cgggtacgtt    240
atcgagtagc acaaacagtt ggattttttcc ctcaagaacc gagtctggac gcggagatgg    300
agccaagtgt ggctgcattt tcggacccgg aaatccgttg ggcactgaag gacttttcga    360
accctgtagc gctgttgctt cgcggtccat cgtcgccgct gcagacggat gcgctccccg    420
gcggctctac gccctccagt cccggccagg cctctgggct gggagccgag ccgtctcggg    480
ccctccggcg ccgcgttttc tagagaaccg ggtctcagcg atgctcattt cagcccgtc    540
ttaatgcaac aaacgaaacc ccacacgaac gaaaaggaac atgtctgcgc tctctgcgca    600
gcgcttgggc ggcgcggtcc cggcgcgcgg ggaagcggcg tctccgctaa ccgaggcgct    660
ggaagggggaa aagcgaatgc ggaatcgtcc aggactccga aggtcgggggc cgctcgcgag   720
caccgaaggg gaggagccga cgaagaccag gagtgggccg catttcggta ctgtttccc    780
gagatcagga actttccggg tctaggagca acgcctggag ggggctgtag agacccagcc   840
ccccgggacc cgcaactaca atgggccgga gcttctaagg tcgcctttgt tctggcagga    900
ggacggggaa tgaggttatc tccgccgcct gtcctgcctc tccctctcct agccctaggg    960
ccctccgccc agccgtccgg ccctgagccc ctggccggc                           999

<210> SEQ ID NO 73
<211> LENGTH: 899
<212> TYPE: DNA
<213> ORGANISM: Homo sapiens

<400> SEQUENCE: 73
cgcagccgag ctggtggtgg cggggtttcc ctccggggct agggctgagg gaggagaaga      60
ggcggactg gctccttccg ttctcggcca ccctccccgc cactccttga ggctgctcca     120
tgctaacagg agactgtttc tcggagcgca gcgcaaagac agtggatttg gagtggcctc     180
cctagaatcc ccccaaaagc atcttggcac aagttgtaga taaaaatagc tcatgataac    240
attgtgggaa agggaggagc gagactcgcg caaggcgagg caagggtacc actggatctg    300
caaaggagga ggaagaggga ggatgcaacc cttggcccaa gagagcgccc tgagtgtgcg    360
aggaatcgct ggctcccagg ggagggaaag agatggaaga cctatagcgc ctataactgc    420
agagttatag acctataact gcagagccca gcacacccca tcccgcgccg gcacccggct    480
ttggctccag cttcttcttc ccatcatccg cctacgttct gggtctgtcc tccgcttcct    540
gggacaggct ggggctagaa ggaggagcag cgcgccgtcc gcccccctggc tggtagagcg    600
cacctggaga ggtcaagctc gcgaataag accttcctg ggagctgggg tctaggcgtt    660
ccaaccgcgg gttcgcaccc cgccatccct cacctccatc cgctgccact acccaagggc    720
ccggaaatag aaaaccacga agggggaaaa aaatcagtaa aaagtaacaa gaaaaaaatc    780
aagaccctca tgtaattggc attagggatg agaggtttat tgtcagggct gtcacctcaa    840
tctctctctt tgggagatgc ctatctccaa ccaaatgcaa aggcaaaccc gaccaaggc    899
```

<210> SEQ ID NO 74
<211> LENGTH: 1049
<212> TYPE: DNA
<213> ORGANISM: Homo sapiens

<400> SEQUENCE: 74

```
gctcctcatt cttcatttat aaagtgagaa ggctgaagag gttactcttt aaggcttccc      60
tctaacctcg tggtctgtga ttataatctg aagtgaggaa ggcccaggaa agggtcccta     120
ggacgccggc gagcgtctgt gacccaccac tgtccagaaa tgtcggtaag cgctgaaccc     180
aaggatacac agcccgaagc aaacgcggaa ggtatgggcc ttacagcctg gaattgctgc     240
agagactggg agccaaaccc tcatcctaat gtcccaacgc actttgggga gggagagctt     300
cccgcggatc cgcctgggtt tgggaggacc ggggtccact ctgcaccggc cagggcctga     360
ggggcccagc agctggaata cagcaatctc ccgcccacct gctcgcagcg tacagagcac     420
aacatcgctc acctgcggcc cccagggcca gaagagaact ccctcctacg gagcgaaggc     480
aagaggcctc gaaccctttt gggacccgga acccatcaaa agtgacccac aaaggccgga     540
agcggccacg gggggtctaa gaaccagccc gcgcggggcg cacttccgcg gccgctctag     600
gaagggagcg aaaggggctt tcaactcggt agtgtttccg cgcgtctacg tgagaggaag     660
gttgatggct ttcaggcccg ctggtaaatg gaacgggttt atcttctcct cttctttacc     720
cagccattgt ccacacttcc cccgacccga tgggtggtcg aggcttgtag aactgatctt     780
aagacaggga aatcccttgc gtctccattc actttgggat tctgtgtctc tgaggttaga     840
gatgcctcaa agggatgttc tccggggac cttcccaaat ccgcgcttag cggtggcgaa     900
gggacttctt ccacacagac ttctcaaggg ccagccggct ggtttctgcc ggctctttcg     960
ccatccacga ttcttttgat gttctctttt atgtgctgat gtatgattat atgtcagaaa    1020
acccggttca atggaaaaac tataaaaaa                                      1049
```

<210> SEQ ID NO 75
<211> LENGTH: 2299
<212> TYPE: DNA
<213> ORGANISM: Homo sapiens

<400> SEQUENCE: 75

```
ggtttcgcgg gtcccactgg aaggggaatc aattaggagc agatgggtgt gtgtgagaaa      60
gagaattttc cttctcccat agccacaact ctagttacta cgcaatgggc ttttttgtttt    120
gttttgtttt ttcacattta cgctcacgga cgtgaagcgt ccccaacact ctcgagcagc     180
ctccctctcc gcgcgcactg acgctttctc cggctgcacc ctctggcacg ctgcaccctc     240
tggcacgctg cacccctcccg cacatctggc ccttgcccgc cggagtttct ccctagctc     300
aggcccatg gggtagcgcg ggagagtctg ggcgaagtcg gcgggcgccga gacgggcggg    360
ccttggggca ggaggaagga attggagttt cctcttttc tgaacgaagg cgaggaatct     420
gcctgggatt ccgcctacgg ggccacaaag gaagccatgg ccccacgatt ctaccacaac     480
atttctgacg ctgggaaagg agtgggggat gcggcctcag accttggaac gctaaagagg     540
gagccagggc tagctcgggg gttgggggga ctccggtttc caaggcctac tgagggctgc     600
tggcctaggg gaggagaggc agcctggcag gcctcccaga gagggggca cagagaaaga     660
aagaggcagg caaagagaga aactgaaaca caaccagttt cagaggtgga gagggatagg     720
gaccccgctc aaggaaaaaa aaggagaaaa acaggcagcc tgcagaagtc ttatttatgt     780
ataataaaga aaaagcaatg gatgactgaa accaccattt tcttttcaaa caaattcctt     840
```

```
taattcagag agaaccaagt gggtggggag gagagaaaac gagagataag acacaaagcc    900
taaaagagaa atattcaggc cgtttgaaat gcagggggata agggaaagac gaaagacgga    960
aagatacaca gagtcaagaa aaggcggccc agagcaggtc agcagccgct gctggaagag   1020
gcccttgcag gcttcgcatg gcttcatcga tcgcctacaa attgcttctg aaggccccag   1080
ggactcccat taggtctgtc caccttagag acagacgttt gatctcagtt gacagggtgg   1140
aggggcggca gtaaatggaa taagtgagtc atcgcctccc tgaactgcct cagaggaagc   1200
cagtgggtcc agcaggagcc ccggtagggc acagggctcc acacagaagg cccaagtcct   1260
agaagacatt cgcagagaga gggaggaaag agacgtcccg cagagcagat cgtacccgct   1320
ggtccttgcc tctctgccct ggacttgtgg gtagggtgag ggccctctgg cttggaatgg   1380
cacctggtct ccctcaggge cggggagggg gaggcgagat gccatcctac cccggctgcc   1440
ccttgtgagg cctccggggt gtgggcgctg cgcgtggatg cgagtcccag ctgtttgggc   1500
ctcgcagact ttcccatcgc tcctcctctg ggatacctgg ctccatccg ctttggggtt   1560
tccagtcttt gttggagtca ggactctcaa agaagggaa cgcgttatag ggcccaaac    1620
tggatttggg gactgcaaag gcgagcagcg ctcgttcagt ttatctcctg gaacgcacc    1680
aggagttggg cacacgcggg agctgggtcg gtgctcctgg caggtaacgg cttgttcccg   1740
gtgcagacgg cagactgcgg aggaacggga ggccgagagg cagcaagcga accgcatcct   1800
cctgcagttg cagcaggagg ccttccagaa gagcctggca cagccgctgc ccgctgaccc   1860
tctgtgcgtg cacaactcgt cgctcttcgc cctgcagaat ctgcagccgt ggtctgacga   1920
ctcgaccaaa atcactagcg tcacgtcggt ggcgtcggcc tgcgagtgag cctgcccatt   1980
ctgccctgtg ggaccccagg cccactcagg ggtcactgag gcctgagacc caggactcct   2040
ccccacccctc ctggcctcag actgcaccca ggaggggaac actgccctcg cacggccccg   2100
aagggccccc acatttgtgc cgacactgtt ctcccttcgg tggaagagct caagggacaa   2160
ggacacgcgc ccccctccca gaggcgtccc gcacctgtct gaactgttaa gaaatctgtt   2220
tttgtttatt tcattttatt ttaattttta acgtgggatt cagagaaagg caagggaggt   2280
aagggaggag gagcttctg                                                2299
```

<210> SEQ ID NO 76
<211> LENGTH: 2199
<212> TYPE: DNA
<213> ORGANISM: Homo sapiens

<400> SEQUENCE: 76

```
aaaaggtcct cttttgcgct ttgaagtcag tccccgcttt ccctgacccc agcaatcaat     60
gatgtagttt ctgtcagtca ctatacaggt aagttttacc tgttctagaa attcaccttg    120
atggcgccgc ataggatgca ctcttttcat cactcagcat aatgttttg agattatcca    180
tgctatctca tgttttgtaa tgtgtcccat tttattgctg ggtagttcgg gtagttggag    240
tagatcgcag cgcattctgc tgacaggtca gactgcggtt ccgacctgcg ggcctcggtg    300
aatatgcgca agggcacctg ggcgcgggca gagccgttcc catccacaaa ataagcatgt    360
tatgtctaca accgaagggg gtcacagagc cccaaaggcc ctgctttcat cgcaaagaac    420
tgagcccgtc ggcatacagt ttctacctgg ctctatgagg tgagaacaca ttccccgcca    480
gcacagaaat cctataaact cctgtggggc agcggttaga agcagaggct gttaaaggta    540
actctagagg ctgcggaaaa acacgaagat tttcacagag cgtgagaacc caggagactg    600
gagaccacgg gccaatctct gctaaaagca gccccacgta gaaaggaaag cgctctgggg    660
```

```
ccatcgcgct agttagctta tgttaaacaa tctcacctcg gctgacctta taatttctcc    720
ggcggcaagg acaacaacca acgcgttact ttctatttca tagcctccta actacaagga    780
aaaacacttc ggatgccgtc caggatataa cacgatagac tgcatgcagt ctatctttcc    840
acactgcaaa aaaaaaaaaa acgggggaaa agagcgaacg cagtctccca ctaccacaaa    900
ttatgcagtc gagcttccca catttgggga agttgcacga attagcttcg ccctgcgaaa    960
accaccttcg taaacacgat ttttcttctg ctaggtaaat gtgagtctgc acgcttccgc   1020
cccggcacag cctcatacgc ctcacccttt acacgcacgg tcacttgccc cgcgcaccct   1080
cgaggcctcc tagccctgat acacagctag gactctcagg tccgaccagc ggtcctggac   1140
tccctcccac agcacgggaa ctccttcgtg gcgaagccgc cggtgacgaa gcagcagccc   1200
ctgcgctgcc tcatctacat agaagtcgcc ctatccctga tgtcactgac agcgccttcc   1260
ccgtcccagt cagcttttcc atcccaccct ccgccactca gccgaacaac atgctgccac   1320
agcctgcggg agaagtgacg tttgcctctc cttctttttc ctcccttccg cgccgctggt   1380
ctcccccaag gaagagggtt ttgatttttg ttttgttttg tttttttgttt tgaaccggag   1440
tctcgccctg tcgcccaggc tggagtgcag tagcacgatc tccgctcact acaacctccc   1500
ttcccgggtt gagacggttt ttctgcctca ggcttccgag tagctgagat tacagcccgg   1560
ctaatttttg tatttttagt agagacgggg tttcaccact ttggccaagc tgatctcgaa   1620
ctcctgacct caggtgatcc gcccgccccg gcctccgcaa gtgctgggat tacaggcgtg   1680
agccaccacg cccggccaga aacgggttct tagcctgtgt tgctgaggac ctctttggcg   1740
ggcagctgga gcctgtgcac ccttcttcaa ataatggctt ttaatacact gactagaacg   1800
tttgggatta caaagaaac cagttctttt cacatcgtta ttcttgtgat gtagcattct   1860
acttgaaatt ggaagccgtt caatatcaga gagaaaccat atctatgaaa ctagagaggt   1920
tgctcagatg actgcaaacc agccatcctt agttgtttta ccactagtag tgttataaag   1980
atggttgtcc aatttcgtga atcttgtagg gttttttgcaa atacagcaat gtacaaaaat   2040
atgctgcctc agcagagcac actggacact caggcatcat gctggagttt gtcatctctt   2100
ccacagcctt ctctagacct tagcacttac ctcatgttag cacttcatat tgtgcaaaga   2160
cagaaacaaa gtcacccaaa tttggcaaaa aatatttgg                          2199
```

<210> SEQ ID NO 77
<211> LENGTH: 2999
<212> TYPE: DNA
<213> ORGANISM: Homo sapiens

<400> SEQUENCE: 77

```
gccagccacg ggcgtcttgc cacgcgagtg cccctagaca gcaacacacc cactggaaac     60
gcacgtgaac aaagctctcg cccccgggag ccgctgcctg cggtttccta gtcgatccca    120
gcttctctag ggagtgtcag gcgcacacag ggttaagtta gttccctccc tggtaggagg    180
gagaggagga ggagggaaa agcagcatac tgtctcaggc tgggtacctt gtagttagtt    240
gtacgttcga aacctgtcgc cgtcacttgc gcgtttggca ttatccattg tcaccgcgga    300
ggaacgagcg ctcgagatat catcagtgcc cgcaaatctc cgcgcaagg cgctgagcta    360
ctcctttccg aggtgcgcct ctggtcctcc gtccctggtg cccagcagcg gcgaggcggc    420
atctccgctc ccgccgccgt gtccaccgag ccctgggatc agggtggcag ttctcaacga    480
tgggcaggag ggacctcggc ggcgacccct aaaacaatac catgccccgg gatccccgct    540
```

-continued

```
gctgccgcgc cagcgtcttc cctttccacc tccctgaccc tgtcggattc ggatgagccc    600
attgcaagga gaagacgcag ccgtcaggta aaaggggctg cgttgccagg tgaagtttcc    660
agtaaccggc cgagctgctg ctacgctggc accacgctgt ctcttcgggg attttttttt    720
ttttgaaaga gctggggggtg gtcatcttaa gtgggggtgct ctaggctttg tctttcacct    780
ggagagaaaa taggcagctt agctctctct cgactttggg gacatctgtc tgctggtcga    840
atccacctcc tctacggagc atcatgactg agttctgggt caaaacgcaa attttcttgc    900
ctggtagatg catcgatgct aaattggggt tctcagtgcc cctaaccttg tcagagttca    960
gtctcctact tccctagatt gaatctctta actttcacca gtaacaaccc tctcccctcc   1020
acaagctgtt gttaatgtca ccagcgttat tatcaggctg ttgtatctaa agacaccaac   1080
ctactacctg cccgtaatct gggatctatt agcagttaaa cagatgcggt ggatactaat   1140 tcctttcct tccagttggt gggggcgggt ggggcttttt ccaaaaccaa gtcccttcca   1200
gccctgcttg tcctcttcgg gctggcgggc actgagctgg ggccatcacg cctttctaga   1260
gcgcctgcgg aggtggcgaa ggcttggaga gcatacgagg cggaatccgg atcgagtgag   1320
ttccttgagc cgcttgcgtg ggacgcaggg agagggcgaa taacgccctc aggcgctgaa   1380
tgcaggggca aggagccagc gagggtggct ggagcaggcc ttgccagctg ttaccaagtc   1440
tctccacagg cttgggggct tggggcctcc tggaaagatc cctccgccgc gctgaccagt   1500
acggggctcg ctcccgcact ttgaaggctg ccgcggtctt tcgtcattta taatcaagcc   1560
caagatcaag gttgcaagct gaggtcgggg tactgacaac gggaatgaag ccataggga   1620 agaggataac tgggacgggc tggacccata cttgatacccc gggaaactcc tagagcgtgt   1680
ggtgctcctg ccagcggcag ttactggtgg agctgaggcc accgctactg tcgtcgttgg   1740
cgctttgctt ctggaacctc ccagcaagat ggcactcact gtctgttccc ttccgattag   1800 caccccccagc cgcgctccct cctccccggg atacgtatta gtcacatact gtggggagaa   1860
gatgggctat gtaaatgtaa gtcaacgcgc tttcccagcc acctttgcat aatgcaacag   1920
gaacagcgac ccgcgcgcac gaaccgggta gtgtgcgcgt gtgtgtgctc gcgtgtgtga   1980
gcgcgtgtgc cagcgtgcgt ctccgcgcgg gcgtgcgtct gggtggatcc ttgcgtggct   2040
tgggaggcaa atcgggcgtt tctccaagtc gtcttaacat gatttaggct ctcaaatacg   2100
tgaaagcggt agacacaaca gggatgcgaa ggaaataaaa aacaattggg gaagtggtgc   2160
caagtcactc aggctttgaa ctgaggacga gtagtgcggt cgcgcctggg gcgcgtccgg   2220
aaatcatcct cagcctgtgg cggccactgc cccacttaaa ctcttctgcg gggagagttg   2280
agcggatccc tgggggggttg gtcctgggct agttttaaac tctccggttg catctcgcgt   2340
ggccccaccg acggcgcgtc tcggcgtagc tcttggcgcg ggctcgttct ccctcttctg   2400
ttcagattca gcctcaccgg acttgttaca acatgacagc aacttactgg aggcaggaag   2460
agcagcacga aataagatga gaaaaccaaa aacatctcct ccttcctaaa tagagacgtg   2520
cacctagctt tttttacttg tttgtttgtt tttacatta ccctttaacc tttggaaaga   2580
gactgcgaag tggaaacgtt gcctgtacag aaatcaggct tcttagctgt caagactgtt   2640
tcctaatctt taggctgaat ctttctttgt ccgctgcaat ctatgggaa atttaacaac   2700 gctcttgcca gaagcagcca ggttgaagga agaaagtggg ggtgtttaaa ttaatcctat   2760
taaattttgg attactcccc cagttaaagt catttaaggt ggtccaggat gagggaacta   2820
gtgatggggt gaggagtggg gggcacatca ccaaggttgc ctgcatttga ataacgcca   2880 ttttggttga gaggtttgct gtattttacc ctctaatctc acatttcgat catttctcag   2940
```

| | | |
|---|---|---|
| tgtctaagta atagatcctc cctcttggca gtacaccatt aagcaggtat ggggaattc | 2999 | |

<210> SEQ ID NO 78
<211> LENGTH: 1399
<212> TYPE: DNA
<213> ORGANISM: Homo sapiens

<400> SEQUENCE: 78

| | |
|---|---|
| gaggaaaaga ggggtcttac tcaagtcagg gccggacaga actccaaaac ttacgaggac | 60 |
| agctatccaa cactgcctca cagacccttg ggcgctgccc cctctttgcc cctgtcctcc | 120 |
| tgcggtgcga gaaacccgac cactctgctt ctacccgaac cccaggacgc aacagtaaaa | 180 |
| tcaaggcccg tcgttgaact cccaggtctg cgcatccctc cctcctggct ccctggggtc | 240 |
| ttggccccag caggtccagt acccatcccc agagggaccc actaccctgg gcgtcccagg | 300 |
| gtgccaggca cgatggcctg caatgggggc tgcaatttaa ccgaggcgag ttaaattcct | 360 |
| tttgccggtg cctggctgcg aggacaaacg tccgtacttt cgttcgggag ccacgggcag | 420 |
| tccagggct tgggttagaa gcaacggctc tcttccaggg gctgtgatcc gggtcggcca | 480 |
| gggagagcga ggccccgggg tcctctgtga ggtccccagc gaagagacgc agctggggaa | 540 |
| ggcgccgccc ccgggccccc tgcgccaccc taaccgggcc tctccttagc aaagttgaca | 600 |
| aattcttgag agtgtcagcc cagggctgcg cgtgagggcg ctgggaccgg ggaggaaaga | 660 |
| gcacctgccg cgctcagccc gactttgaat ttgtttgttg ttaccgtttt tgttttttcct | 720 |
| cccagtttcc ataaacgctt agtatttcga ggcactttgc aggtgttggc gcaggtgatg | 780 |
| atgggcctcg ttggactctg cctcccacgc atccttttgt tttctgcgcg ccagcctgtc | 840 |
| tgactgtgtc ctgcggggac cccgagacag tccggggtca gggcgtagag actcatgctt | 900 |
| gccacttgac ccatccgcaa cccggggacc ccctagcccg tcgcggagct ggagtttggg | 960 |
| cttccggctc ccagctctcc gccctggata caggaagagg gcgggagagg tcgcgcaccc | 1020 |
| gcgccgctcg gcggggatcg ctcacagggg ctccggggcc accgcgagcg cggactgcgg | 1080 |
| ctgctggcgg gctccttcgt cgtccaacgc accccatcct ctcccgcccc gcagtgtccc | 1140 |
| agggaaggct tcactgaaaa cagacgctcg acggaaaact gactctgcag gcccgagctt | 1200 |
| tcggagtttg atttctgtgg gccccttaaa cgggcactgg gtacaggaga ggccccaact | 1260 |
| ctctgcaggg acgggaggg aagggcactc actctcccgc aagttttcct agaggcgagc | 1320 |
| tgaagatgca ggccacctcc ctcccgcacg gcccctccct tggcctagtt ctgtccaaag | 1380 |
| acacttccca gccctcgag | 1399 |

<210> SEQ ID NO 79
<211> LENGTH: 1649
<212> TYPE: DNA
<213> ORGANISM: Homo sapiens

<400> SEQUENCE: 79

| | |
|---|---|
| ggcgacccct aaaacaatac catgccccgg gatccccgct gctgccgcgc cagcgtcttc | 60 |
| cctttccacc tccctgaccc tgtcggattc ggatgagccc attgcaagga gaagacgcag | 120 |
| ccgtcaggta aaagggctg cgttgccagg tgaagtttcc agtaaccggc cgagctgctg | 180 |
| ctacgctggc accacgctgt ctcttcgggg gatttttttt ttttgaaaga gctgggggtg | 240 |
| gtcatcttaa gtggggtgct ctaggctttg tctttcacct ggagagaaaa taggcagctt | 300 |
| agctctctct cgactttggg gacatctgtc tgctggtcga atccacctcc tctacggagc | 360 |

```
atcatgactg agttctgggt caaaacgcaa attttcttgc ctggtagatg catcgatgct    420
aaattggggt tctcagtgcc cctaaccttg tcagagttca gtctcctact tccctagatt    480
gaatctctta actttcacca gtaacaaccc tctcccctcc acaagctgtt gttaatgtca    540
ccagcgttat tatcaggctg ttgtatctaa agacaccaac ctactacctg cccgtaatct    600
gggatctatt agcagttaaa cagatgcggt ggatactaat tccttttcct tccagttggt    660
gggggcgggt ggggcttttt ccaaaaccaa gtcccttcca gccctgcttg tcctcttcgg    720
gctggcgggc actgagctgg ggccatcacg cctttctaga gcgcctgcgg aggtggcgaa    780
ggcttggaga gcatacgagg cggaatccgg atcgagtgag ttccttgagc cgcttgcgtg    840
ggacgcaggg agagggcgaa taacgccctc aggcgctgaa tgcaggggca aggagccagc    900
gagggtggct ggagcaggcc ttgccagctg ttaccaagtc tctccacagg cttgggggct    960
tggggcctcc tggaaagatc cctccgccgc gctgaccagt acgggctcg ctcccgcact    1020 ttgaaggctg ccgcggtctt tcgtcattta taatcaagcc caagatcaag gttgcaagct    1080
gaggtcgggg tactgacaac gggaatgaag ccataggggga agaggataac tgggacgggc    1140
tggacccata cttgataccc gggaaactcc tagagcgtgt ggtgctcctg ccagcggcag    1200
ttactggtgg agctgaggcc accgctactg tcgtcgttgg cgctttgctt ctggaacctc    1260
ccagcaagat ggcactcact gtctgttccc ttccgattag caccccagc cgcgctccct    1320 cctcccggg atacgtatta gtcacatact gtggggagaa gatgggctat gtaaatgtaa    1380
gtcaacgcgc tttcccagcc accttttgcat aatgcaacag gaacagcgac ccgcgcgcac    1440
gaaccgggta gtgtgcgcgt gtgtgtgctc gcgtgtgtga gcgcgtgtgc cagcgtgcgt    1500
ctccgcgcgg gcgtgcgtct gggtggatcc ttgcgtggct tgggaggcaa atcgggcgtt    1560
tctccaagtc gtcttaacat gatttaggct ctcaaatacg tgaaagcggt agacacaaca    1620
gggatgcgaa ggaaataaaa aacaattgg                                       1649

<210> SEQ ID NO 80
<211> LENGTH: 2299
<212> TYPE: DNA
<213> ORGANISM: Homo sapiens

<400> SEQUENCE: 80
acactgagat gtagcctcta gaatcagagt ctgggaagcc agtacccct gggctgagcc       60 tatccaagag gaggccaagg cagagtgggc acagaacctg cattcaaagg ctccagtcca    120
cgctggaggg ggaacagaag aaaagcccca gtagctgacc cattcttcct gacaccacaa    180
actgaatacc tcccgacctc caacgcagac ctcgtccctg agaagcgggg gattttcatt    240
aagtagccca gcaatttgg tcaaaaagta agagttctat gatatcaagt ttgagatttg     300
gatgatcgtt tcctcaaact tatttaaact atctgtctgc acagacagaa ctcaagtccc    360
cctattccaa cacatatcct tctccatgcc caaatatggg gagcccacag gcagggaga    420 gcctggtgcc agcctggagg aggcaggtgg aaagccttag cgggctgccg tttctcctct    480
gcactctcct ggctcaccag gctggatgcc aggccctcct tgcagcgaag cgctgccttt    540
tcagttgaaa agtctcgatc cctaacggct caattaaccg gattattgtt tcctacagag    600
agaaatcacc ttgcattcag ctgaaccccg tcactgcaaa cgccacgcac aatgaaactc    660
caccataaaa gaaacagag aaaaaaggga gtaggttggg ggaaagcccc agtctgagcc    720
gccaattttg gggaagtggt ctagctggtt atataatcgc tttagaggga aaggaggg      780 gagcattgag cttgttcgat taagtgttttt ctgtgcagtc aaagccgaac gaaagtgtct    840
```

```
gggataaaga aactacctgt gccaggtcta tccttcgacc tcaggagctg ggccccggt      900
gtaattctgt cccgactgtg gggtgtaaac acacgatgcc acgcaggtgt agcaggagcc      960
atcgttagcg ggcaatgtaa tgacaacgga acgcagacct gggcaatgcg cgctgcgccc     1020
aaggggcaag cgagtggcag ggtcgcttat tctcccagtg ctcggcgctc gcagacccgg     1080
agccttccgc ccagcgccct gtgtaggtag cgagtgtcgg gagaaatcat cactacgaat     1140
tcgtttccat ataggggcaa cgccaggcgg ggcacaatga tctgtccttg aggacaaaga     1200
gtgattccgg agagagcagg tttttgtccc tccacgcagg tttctctccc cagaccccag     1260
ccttcggctt cctcccttcc tgtcacggac gcagccggag aaactggggc ccagacgcgg     1320
agctcactcc gccagaaacc ctgggtccct tcccctacgc tggcaggctg ggtccggttc     1380
catcgtcgcg gctccgttta tccctccagg gagcgcgggc agagcgccga gcgcggcgca     1440
gggactggag ttctcgccag cttcgggttc tttctccccg gagctgcccg ggggtctcg      1500
gcctcgggcg ctcccgccgc cgtcctgttc ccctcagggt tcatgtcctg ttcccggggc     1560
cccagaggtc ccgtctgaga gcggcccccg cgagcttggg tgtcgcggaa ccaccgctgt     1620
cggaagccga ggttacacaa acgccacggg caggagcggg agggcaccgg cggcggctgc     1680
gaggccgggc cctgacatgc cgctgtgtcc gcagtgaagg aggagggcga ccgcgagatc     1740
tccagctcca gggacagtcc cccggtgcgc ctgaaaaagc cacgcaaggc gcgcacggcc     1800
ttcaccgacc atcagctggc gcagctggag cgcagcttcg agcggcagaa gtacctgagc     1860
gtgcaggacc gcatggagct cgccgcctcg ctcaacctca ccgacacgca ggtcaagacc     1920
tggtaccaga accgcaggtg aggcctggct gcggggggtag aggcagaaag ggaacttccc     1980
ctttcctcac agctcctgga ggggaccagg agtctacagg ttggtgctaa gggagggccc     2040
cagagcctcc cccattctgt aaaagtggga aactgagtcc ctaaggggac aaggccttgc     2100
ccaaagtccc cacagcgagg gacagagatg agactagact tggtgtccag cgtccagtca     2160
gccctccccc ggatgggtgg acagacacat aggccactga aaatccaagt cctgccccag     2220
ctcagccgga gtgggggggag gtctgcctgg agcccccacc tgagccagcg tgggtcttgg     2280
aagccccagg cccttggag                                                  2299

<210> SEQ ID NO 81
<211> LENGTH: 1349
<212> TYPE: DNA
<213> ORGANISM: Homo sapiens

<400> SEQUENCE: 81
agagccctga agctacaacc cggacaatcc cagccttccc ggcttcctca gcaatcaaac       60
aaatgagaaa aaaaaatccc cttgcaagta gaggcagctg cactctggat acagtgctca      120
attgcaggga ccttccgagg ccctgccacg acatactcta attggggtgc agccagagtt      180
gcaggaagct ggcgaggaaa gcggtgcacc tgtgagcata aagcgaaaaa catagacaag      240
cacagggtga gggtgtaggg ggtgaaacgc cttcacggtg ttaacaacaa gctgcagggt      300
ataaagcaat aaaactgcca cgtctacctg ctggtattga ggacattaca aacagtctcg      360
gcgcgcagcc cgcgtgtacc gagagcgcac taggggtggga agtgggaagg tggggtggga      420
aatcttctct tttcctgaca ttcccttctg tcccccaccc ccacatctc ccccttactt      480
agcccacctt tctttttcca tgaagctttt ctgttgttgt tttaattcat tgccgatttg      540
taaacgtgta gatcgtgtta ctggttcgcg tgttaaagtg cacctcttgt taaaggtgg      600
```

| | |
|---|---|
| ggaacagggc acgccactta aaaatgaatt cagagttact gaaccggctc cccagactca | 660 |
| agaacttaag cgcaacgggc tgggaaaagg aggggagag gagcgcaaac gccgctgacc | 720 |
| tgggaactcg gaggaaactc gcgggcagcg agcttcaggt cttctgatac attgaaggaa | 780 |
| agaaagaaag acagaaaaag aaaaaaacaa actgtcctgg agatagctag acatccaggg | 840 |
| ctgggagctg gaaaatcaa ttggcataag ccgctgccgg cgggcttcgc gcaacgtaaa | 900 |
| aaataaagtc caagctgctc catctgcagc caccctttc tggagttaaa ggggcaagcg | 960 |
| gcacctttc tctatttctc agtttccttc ggtcctgtaa cttatggagt ccagaagaag | 1020 |
| taggatatac agaagtcctc agtagttttc ccaaagggag acactgtctc cttcccgcaa | 1080 |
| cctccagaca ctgcagtaca gggttgttag atattagata gtacgtttct ccgtgtgggc | 1140 |
| aaaggctcgc ggcttaggtc tctaagcaga tcgaaagtcg gggtccagac cgagaggatc | 1200 |
| ttcaggtctc gtccacccaa tctcaagcct ctggaagggc gggctgccgg cgacctcctc | 1260 |
| cagtcccggg acccgaaccc cgggaccctg gacgccggtg cgggcgggcc tgccctcctc | 1320 |
| tgtgcctggc ccccagtctg gccctcccta | 1349 |

<210> SEQ ID NO 82
<211> LENGTH: 1699
<212> TYPE: DNA
<213> ORGANISM: Homo sapiens

<400> SEQUENCE: 82

| | |
|---|---|
| ttatcttgga aggtgttgta tcaatgtctc gatgtctgtt tgaaaaaata caattagaag | 60 |
| atttttatgt gattgggatt gaaggaaag ggtggggttt ggggggatgg aggggacgaa | 120 |
| ggaacatgaa agactggagg acggaaagaa gtggggagc gtgttccctg ggagtcaggg | 180 |
| agaaccttgc ctccctccct gtcagctaga caactcctgc ccacacatct cctttgtgtg | 240 |
| gcacgagaag ctggtgaacc tgcctattcc caatccagcg ctgggtcccc ttgaggatct | 300 |
| tgcgtcctcc tctccgagtt attaaggatg caggacgtgt ttcggattcg acgtggaaag | 360 |
| agggagggaa gcacattagc attaaggtaa tcatggcacc ctggctcgtg gactattaga | 420 |
| ttggctacca gtggtctcta atcttactgt ttgcagagtc aagaatgggg gcggggttg | 480 |
| ggggactgta tagattgcct tttaaaatag tgtgacttca taataacgga gatggctgaa | 540 |
| agattgcttc cttacactac ttctcggcca tcagggctga ataaaggacc cgcctccgcc | 600 |
| ctctactccg gctcttctct ggctgtctct tccccatcaa gtcataaagc gagcgggttg | 660 |
| ggcgagaggg cacagctcga ggcagagaag agacggggtc actttcacaa ctcccaggaa | 720 |
| tcggcttcag aaaggaacca tctgcgactc ccacgttcct ttcgaagttc tccttcaaaa | 780 |
| ggaattacaa aaaaaaaaa aaaaaaaaa gcgatggggg tggggatcgg taagacacag | 840 |
| gggtcctccc cctgctcttt tcaattactt tcccaatact ctttcaacac atcgaattta | 900 |
| cctgcagtgg taactgggtc agcaggtaaa tagatttgta tctgtatatg tcgaaatgtg | 960 |
| gctctcctgg tggatgaaaa gcaatttttt gtgagcatat tctaacctag gcgaaatttc | 1020 |
| taagcacaat agagattttt atagcgtggg cgagaagagt gcattccagc gaaagcagga | 1080 |
| cacgtgatcc ctccaacggg tgagatacag tattaggaac tcgatttct ttgttccagc | 1140 |
| ctgagcctat gagatgttca gcatcctggt tgcttaagtc ctcctataga aggaaaataa | 1200 |
| taataataat aataataaag ttgatcggag gcgaaataga gggaaaataa gcacaggtag | 1260 |
| acatgcgtga acgtttgaa agcttcgcct ctgcctttt ttaccgccca cccttcaccc | 1320 |
| ccaccccttg ctccagccag cccctatt taaaatgagg catttcctct gggagacggt | 1380 |

```
ggaaaagttc tccagcccct gcacacgtgg gttctccagc acttcagaac ctgctgtgat    1440
tcgcaacaga ttacaccacc ttcccagtcc aagtgtcacg cctccgtcca ggcttccttg    1500
aattggcttc caggaaggac tctaagggaa ctaccacgag gtgttttttg tttgtttgtt    1560
gttttttgtt tgtttgtttt tacaaaagac agtaaagcaa tgaagtcttt acttttttaga   1620 aatcattgat tgcacagggg gaaaaatgag caaataggga tgtaggaatg attttatgtt    1680
tccttaagag tcatatggc                                                  1699
```

<210> SEQ ID NO 83
<211> LENGTH: 1649
<212> TYPE: DNA
<213> ORGANISM: Homo sapiens

<400> SEQUENCE: 83

```
gtggcggacc cggcagtggc acccaggctg tgcgcgcggg tgtgtggggt tccgaggcgc     60
agggcgaccg ccggctccgg ctccccgagg aagggggcaca ggcgctgccc gcggtcactc   120
gggccaggtg agggcagggg acgcgcgggg gccggaggag gaggcctggt ctgcgggcgg   180
caggagggac ccggggccag ccgaggctgt tcccagggag gcagacacct gctgtcgccg    240
ggaccctcga cacgctccgc acgcgcggga gcggaaccgg gcctgctttg gaggcctccc    300
ttggcgcgct tggatttact caaaggtcaa agaaaaatgt caaggagagc gattgcctgg    360
agagctcctg gctctcctcc cgggtccccg ctgggtccca ggagtccccg gaggggaagc    420
aaggagcccc agtgccctgg agtcctgtct ccaccaacct cgcccggctc cctgctgcct    480
aggcccgcgc tgtcccagca gaggaggggt gggagccgcc ccaggcccac ctccccgcgc    540
cggtccacaa ggaggcccct cctgcaacct gggagaggcc ggggggaggcc cggagggcga   600 ccgcgcgggg ccgcgggacc tggacagccg gggagtcgtg accgcgggca gcgccggggc   660
tgagggcgag gagggtctta ctgcaggaa gggcggacg ctggacagag ggaccgactg     720
gggtccaccg gcctgacaca gaagtcgctg gatcccaggg cccggctggg aaacccgctt    780
cctacccgcc cgcgggcgcc gcagaagaaa ccgaagaaag aggtcttccc tccacgccca    840
ggacggtttc aagtgtccca cccagcgctg agcaggaggg tgatgcggag ggaaaaactg    900
ttggctgcaa gtcaggtctt aggaatcccg gaagaaacga agatttaaag aattttttc    960 taagtgattg agttccaata actttacaat gacttgactc ccttttttgtg gagttaaaaa   1020 aaatcttcaa actcctgcta gccatggcct ttaagagaaa gaaatgagtt taaaagtgag    1080
tttgaggcac agtcttgacc caggtgtggc tttggtggtc ctcagcgcca tctcccccat    1140
gggcaccgac cccccaaggc tgcaccacgg cgggtggacc ccaaagagag cccagactaa    1200
ttagaggcat cttatcagtc ttgacttgaa attgaaagaa aattatgttt aaatatttat    1260
gactttgaca tttacagtca ggcgttttttg aaaagcggaa caccccttc tgtacagcgg    1320 cagctcaatg actgaaagtt tggaacagag aagaagtgag gaggaggagg agggagaagg    1380
aggcctggta acacagcggc aggggtgcgt cccgggtggg ggagatgcac agataggcac    1440
acttcagtgc tgagttctca gaggcaggaa tagtataatt taaaaaaata atcaggaatg    1500
attaagttaa ttttatccca ggttagatct atcttgagaa taagatgaag tacaatatcg    1560
catatttctt cctctcaacc gtctgcacct gcaactcctc aaatttagaa tagacagtat    1620
tgcaaaagtt gtgattcaaa ataagtgta                                      1649
```

<210> SEQ ID NO 84

<211> LENGTH: 1949
<212> TYPE: DNA
<213> ORGANISM: Homo sapiens

<400> SEQUENCE: 84

| | | | | | | |
|---|---|---|---|---|---|---|
| actcattgct | gcctcgttag | aaaagatcaa | agaatgaaca | caacgtggta | gaataagcag | 60 |
| agcaatgttt | atttgttgta | aataaatgag | agaataagtg | gaaaaccagc | agtttgggga | 120 |
| ggaaaaagag | aaagggaaag | aagtcagcca | cagtgggaga | aggggctcct | tttcttcatt | 180 |
| tcttgtcttc | ccctttctct | ccccacccta | agtctaccct | tctcatcaat | ttctcccctc | 240 |
| tttcccttcc | ttcgcctcac | cttcaatccc | ttgggtggag | gggctgaaca | gcgtgttccc | 300 |
| gggcggaggt | gcgcgcagcc | accccaggct | gctgccaggt | gcccgctggg | gctgccaggg | 360 |
| cgaggaggcc | tctgggctgt | ggagcgaaag | tcagatccac | cgcctactgc | ggggtagggg | 420 |
| ccgcagtggg | gaccgccagc | cctgtggtcc | ctctcgcgct | gactggcgta | aagttgtggc | 480 |
| cgaattcgca | tctcttctgg | tgcttctcgc | ccgccagcgc | agggcccagg | tgtttgaggc | 540 |
| gaagggctc | tagctccccg | caagcctgga | gccaggcgtc | gcgcttcctc | cgggcttaat | 600 |
| ccagaccttt | caacacacac | ctcattcggg | ggaggagaaa | agcacaggac | cgcggagagc | 660 |
| ccagctttga | ggccaggcct | gaagggataa | cccacacagg | gaacgttttc | ctatcagaga | 720 |
| ataatggagc | acaaaataat | tcagaaagcg | aatgggcagg | accacagcct | gagagtcccg | 780 |
| cgccgcgggg | ccgctgcaga | gccggtctcc | cgagcaccgc | ggcaggacca | tttcgttgga | 840 |
| atgtagggcg | aggccgaagc | ccgccccgga | cccaggccgc | gaggtgcgcg | ccggccgccg | 900 |
| aggggccgcc | tgtaaattac | agcccgccgg | gaggactcgg | aaatacacaa | aaggagccga | 960 |
| aagatttaaa | cagtcggagg | cagaggcgtc | ccgaggcggc | caaagcggaa | atcaatcacg | 1020 |
| taattaaaac | agggaggga | cgaagcccaa | ggctgggggt | cccgggttcg | gaggaggcgg | 1080 |
| ccaaggtgca | ggccgaggct | ggcgagcggc | ttagggacgt | ggctcgcccg | ccaggaccag | 1140 |
| agcgcgcgga | ggggcttcgg | ggaagtttat | aacacatcgc | tattgattcc | cgcttggcta | 1200 |
| ggaagagcag | actctggtgc | cctctcccag | gccagaccct | gaagcctccg | atggcccctt | 1260 |
| ctccgacttt | cccgtttttg | tggggttgag | acgcgcagtt | gcagttgaag | gccgctcccc | 1320 |
| agatcccact | ggtgccacga | ttttgccaag | gcaagtttgc | gaacccaaat | ggcatcaaga | 1380 |
| tgctgccttt | gggtttgagg | ggatggaggg | aggtgacacc | ccagtttcag | gcactaagaa | 1440 |
| atctctctcg | gccttgattc | ctccaaccca | ggattcaaag | catgcccgga | aagactctga | 1500 |
| tctatgggcc | gaggcttgga | aggggtgtgc | gaggcagacg | gggttattaa | agggagagct | 1560 |
| tggggctgag | caaactggac | cccttttgggc | tggaaaggag | aaagaacagc | tcctggaaga | 1620 |
| gaaaaaagg | cacaccggga | gctgtgtttt | gtgaggggaa | gatcttatta | ttgaggttaa | 1680 |
| tcatggtaat | gatctggtat | ggctgggtca | gcccaggaga | ccgcgctctc | caaagttctt | 1740 |
| tctcacagag | gtttctctgg | gggagtcaag | ggttccccaa | cttcactatg | gttggggaaa | 1800 |
| ataaaataaa | gacctccaat | cctctcctct | gccttttcct | ctccctccct | taaaaactcc | 1860 |
| agaaaaaggg | aaaccttata | aaatctccat | caccccactt | attttttcctt | ggctctctcc | 1920 |
| agtttactaa | aatgcacggt | ctttgggaa | | | | 1949 |

<210> SEQ ID NO 85
<211> LENGTH: 1399
<212> TYPE: DNA
<213> ORGANISM: Homo sapiens

<400> SEQUENCE: 85

```
atgaaaatga cttccagaaa aggaagaata tgaaccccag accgaagggg aaaagatagt    60
taatagtatt atctaacctg gttggtattt gtaatgaatg gtgattttaa ttagtcatta   120
gccataatga tgtttattta cagtataact cctgaatgct acttaaataa accaggattc   180
aaactgcaag ccagccaggc cgttcattat ttaaaacgtt ttaatcgggg cttccgggta   240
gaaggtggag cggcagggtg taattgggtt gatgggtggg acctgtcttg accatcggag   300
ttttataatc gagggccagg agggcccggg ttgctctcct ggttatgtat gtacttgtac   360
ataaccacct aaagaatggt gaaataaatg ttcttggaaa ttcctacccg gactggctag   420
tccttgcgga agcagcgtcc gggccctcgg gtaacgtttg aagagctggc agcgtctcag   480
gctgctgcgt ggcgaagggg cggaccgggg gacgggggg tgggccctta ggggctgggg    540
cgggacttcc ctgggcactg agtcaaagct tgagggagt gttcgctccc gcattttcga    600
ttccactctc ttccgtttct gtcgctgcag tcgtccgcgg gtaaggccct ccctagaccc   660
tttataccta ctttaccttt cggaggtcaa gacacctcct gttgccgcct cctcgcccaa   720
cacacaggcg ccccccgcac gggtaccaag cttgactaac ggcctctagg ggtgtgtggt   780
gggacttgaa atcctccctt aatgaagtca caccttctcc gtccgcttcc acccggtcgg   840
cccatggcag agccccatg tagcccagga atcggcttgg cccttcgggg aggtcagcgt    900
ccttactgtc cccactctcc agtgcggcac attcgttccc ctaggactcc ggccggttgc   960
cggccccagg cggtgcttct ccccaccacc gcccagctca gctcagccca gcccagccca  1020
ctctgccctt agaggccctt ctccccaaag acgcactcca gaagtctcgc cctcgtgcgg  1080
ctgaggagcc tgggatccca gacctgaaca aggtgagcat ccctatattt tagcccagaa  1140
agatctgtgt ggctcacttg ccggcctcgt tctgtcacac agagtccaga tttagccttg  1200
agttttccta gtgaaagaca gaccctggta tcactatgac cctcctcagg ctttcttacc  1260
ccgcctcaga aagcagtgag gtgtctgctt ctcccaggg cttctttaga taggggtctt   1320
aaccacacct gtgaccagtc tggcctcctc tctccttgat tcaaagaatc tcttttctgc  1380
cctatccaac ttccttccc                                               1399

<210> SEQ ID NO 86
<211> LENGTH: 1349
<212> TYPE: DNA
<213> ORGANISM: Homo sapiens

<400> SEQUENCE: 86
cctacacact atgttgctgg tttcctagtc ttcagcaaga aagtgtagga gagaagcaaa    60
aaacgtcctg ttcaacccct gctcctggat gtggcaagga agaggagtta cccggcttga   120
aacaaaagaa atcctaagtc tgacacacaa tgtcatgttt aaattcccct ttctccaaaa   180
tgtaaaataa atctgcttcc atcttctaaa atactatggg actaaacatc cttttgttat   240
gctaaggaaa agccagtatt cgcgttgatt tagaagaggg atgttctggt tatagaacga   300
tgctgtgtct cagaaacact taaatactat taagctagaa atagaaggga aaataatgct   360
tccccgcatc tcccctcaag tgtagtcctc ttttttttagc ctgatttccg acgaaatgtc   420
tgaatgccta cagttatttg gccatcctga aaagtgcaac ttatcctgac gtctcgaggg   480
acggaaaagt taccgaagtc caaggaatga gtcactttgc tcaaatttga tgagtaatat   540
caggtgtcat gaaacccagt ttcgaaggag aggggagggg cgtcagatc tgcagacgga    600
agcaggccgc tccggattgg atggcgagac ctcgattttc ctaaaattgc gtcatttaga   660
```

```
acccaattgg gtccagatgt tatgggcatc gacgagttac cgtctcggaa actctcaatc      720
acgcaagcga aaggagagga ggcggctaat taaatattga gcagaaagtc gcgtggggag      780
aatgtcacgt gggtctggag gctcaaggag gctgggataa ataccgcaag gcactgagca      840
ggcgaaagag cgcgctcgga cctccttccc ggcggcagct accgagagtg cggagcgacc      900
agcgtgcgct cggaggaacc agagaaactc agcaccccgc gggactgtcc gtcgcagtaa      960
gtgcccgcgc ggtgctggcc gcggctgccc gggtcacccc gccccgcatc tgtccgaggt     1020
ggccgcgctg ggggcgccgc tgcggcgagg acagtgggg agactggctt cccaaacgcc      1080 aacgccctc tttgtcttcc acctgcagag tttcctggtt tgaaggtgtg ggttggtggg      1140 ttaggggct gggggagttg ggattcaggg agaagagggt tggagaatct ttgggacgcg      1200
attctctcgc ctaaccggta caggtgagac ttcagtcctt atgtttttga tcttggttca     1260
tccgttgtgg ggcagaaaat tctgttgctt taactcttgg ataaccaccc ctaatagata     1320
cattatttct ctctttggtg tcttctcct                                       1349

<210> SEQ ID NO 87
<211> LENGTH: 799
<212> TYPE: DNA
<213> ORGANISM: Homo sapiens

<400> SEQUENCE: 87
cttgagagcc gggtaagggc ttcttatcca tccttcgtct caagcatcaa ttaaaaaaaa       60
ttgcaactac agacgcgggc gaaagcgggg agcctgcaga cctgatccgg cacctctctt      120
gcatgggacc caaagcaggg tgggcggttc gccgaagagg gccaaggacg aacctcaaac      180
tgatggtggt tttgactaac cctcctgggc acttgactcg gccacagcgg cccctcccg      240 gcgggcgttt gtcatgtgtc cagacatgtg cgcgcgcgct gcgggcttcg tcgacggaac      300
acacccgctg cagcggctct gggaacgcgg cttgtctcc caaaacctct ccgagagcgc      360
aaggagcggg aagggctttc tcgcattcta tctcccagaa agaagtgcct gtacctgcgg      420
ggcagctcgg gagtcccaga aaactcaacc ccaagctccc ccctcgcaag gtccgcctgg      480
agctagcaga gccaagggca ggagcggggc cgactccttc ccgccgcgat tcctcgggac      540
ttactgtggt tgcagtaaag ggtgataacc agtgacagga gaaggacccc acaagtcccg      600
gccaagggcg cccagatgta gatatcacag gcgaagtcca gccccctcgt gtgcactgac      660
gacaccaaag acgccgacat ttaggagagg gcccgggacc tcccaaccgc ccaccgtcc      720 cgggaacgtc tctccgcctc agatctcggt ttcccaccac ttggacagcc cttgactcta      780
cctacagtat cagggctgt                                                  799

<210> SEQ ID NO 88
<211> LENGTH: 2249
<212> TYPE: DNA
<213> ORGANISM: Homo sapiens

<400> SEQUENCE: 88
tcctccttgc cccagctcct tggagataat tgtcagaaaa tagcaggccg ggctgaatgg       60
ggagtggaaa cagaagccag cagtagaaga gatcctctgc tctggggctg gggcaggag      120 ggtcagtggg tagcagggga aggcgagact tctgaactct gcttttgcca accacttcct     180
gtctctcttc agcgggggct caaccccag acctccagaa atgacgtcag aatcatttgc      240
atcccgctgc tctacctgc ctggtccagc tgggaccctg cctcgccggc cgcatggcca      300
gagggttggg tgagtgtgta tggggaagag gggctggact ctggtatcct tggatggggg      360
```

```
gcactccagg ctctccagcc tcctcggctc agcctgggcc cctccccatc aacatccac      420 tccagtcctc attcaacttc ctcttcctgc gaaagagggg cgctgccccg tgacctacac      480
agactgagac acgatcgcca tgaatggaga cctctggaaa agctcaggag ccgaggccca      540
cggggcccag cagaggcctg aggggagacc ctgggcgggg gctgaatcac tgcctcccga      600
cagtccccca atgcccgggc tttggagggg agccgggagc ttcccatctc cttttgcagg      660
ggagggttgt cagtctggcg ggatgtgcac tgggggcact ccaacctctg ctagctaacc      720
ccacatcacc acccaccccc gcctcccagc accaccacca ccacacacac aaaaaaattg      780
gatacatttt gaataaagcg attcggttcc ttatccgggg actgggttgc tccgtgtgat      840
tggccggagg agtcacatgg tgaaagtaac tttacagggt cgctagctag taggagggct      900
ttatggagca gaaaaacgac aaagcgagaa aaattatttt ccactccaga aattaatgat      960
catgagctcg tatttgatgg actctaacta catcgatccg aaatttcctc catgcgaaga     1020
atattcgcaa aatagctaca tccctgaaca cagtccggaa tattacgcc ggaccaggga      1080 atcgggattc cagcatcacc accaggagct gtacccacca ccgcctccgc gccctagcta     1140
ccctgagcgc cagtatagct gcaccagtct ccaggggccc ggcaattcgc gaggccacgg     1200
gccggcccag gcgggccacc accaccccga gaaatcacag tcgctctgcg agccggcgcc     1260
tctctcaggc gcctccgcct cccgtcccc agccccgcca gcctgcagcc agccagcccc      1320
cgaccatccc tccagcgccg ccagcaagca acccatagtc tacccatgga tgaaaaaaat     1380
tcacgttagc acgggtaggc aactttgctt tttgctcccc cctcccctcc cttcttccct     1440
agcgctcccc accctcctcg gccccctctg gccccgtcc tcctttctct ccttcccct       1500 ctctctccag gagcgactct gggttagcac aattgaactg gatttacgag cgagaatggg     1560
taattacatc ccccataaat tttatggctt agctactctg ggcagtccga gccatgtgct     1620
acgatctgtt atgtatgtgt gaaaactatg ctcgctttct aagggcgcat aaataattca     1680
gtgtcgttac aatgaggatt cccctcttat tacactacaa agtcttcagc ttccttcaac     1740
ttctttataa cccatttaag cttgatgact ttatttccac cactccctcc tcctgtttct     1800
cagagctgag gatggggtga gggtggggg cgggagcct gctgcctctg aaccccacta       1860
tttgcttttc ccctccccc agtgaacccc aattataacg gaggggaacc caagcgctcg      1920
aggacagcct atcccggca gcaagtcctg gaattagaga aagagtttca ttacaaccgc      1980
tacctgaccc gaaggagaag gatcgagatc gcccactcgc tgtgcctctc tgagaggcag     2040
atcaaaatct ggttccaaaa ccgtcgcatg aaatggaaga aggaccaccg actcccaac      2100 accaaagtca ggtcagcacc cccggccggc gctgcgccca gcacccttc ggcagctacc      2160 ccgggtactt ctgaagacca ctcccagagc gccacgccgc cggagcagca acgggcagag     2220
gacattacca ggttataaaa cataactca                                       2249
```

<210> SEQ ID NO 89
<211> LENGTH: 499
<212> TYPE: DNA
<213> ORGANISM: Homo sapiens

<400> SEQUENCE: 89

```
gtttctgctt agctgatagc cttgggctct gcgcttgaag ccctaatcag gagtgtaaac       60
tctgctatat ttcaatttgg agaagcgctc ttccgctaag aggcccctgg cactgcgata     120
aataaaacgc ctatttactc tattgccaca cttagacatc taatgcactt actaccagcc     180
```

-continued

| | |
|---|---|
| ccctaatcat agcctacagt taaaaccgcc tataaatcac tccgttctca tcctgcacat | 240 |
| tagtgaagcc attttcccca aaccccacaa tgagcactgt ttccttttct tgttagtcaa | 300 |
| aagccagatg attttattta ggttaaagac gagttcacag atggtaaatc gcgtggagag | 360 |
| aaatgagctg gagagttaca ccgagtcaac gcgggacacg gctcccggcc cgggccgggc | 420 |
| caggggtggg aggcggttcc ctaccgcagg cggcgggact cccatgcgcc gagggaccca | 480 |
| agtctccact ccacccaca | 499 |

<210> SEQ ID NO 90
<211> LENGTH: 1949
<212> TYPE: DNA
<213> ORGANISM: Homo sapiens

<400> SEQUENCE: 90

| | |
|---|---|
| gatgaaagca aagtcacgca aagcagaaca atgagacaga agaacttagg aagggaacct | 60 |
| tgaaatacgg ctttctgcta tgagaatatt gattaagaaa tgtccgtgca tatgaagaaa | 120 |
| gcttcttcca caaatgagcc atgccaactc actcggtcat tttgggagga cacaagtcat | 180 |
| cattcgtcat aatgattctg aaaactgctc tcacactacc ttattaaggc ctgtatttcc | 240 |
| catctagagg aagtgttggg cttcacact gatatgacta taaacttagc agaaattctt | 300 |
| ctcactataa aacccacgcg agctattgaa gaattcttca agtcatacat ttgttctcag | 360 |
| tgactgagtg gtaacactaa ttatattgca aaatggctgt tcctaaatta ttttagcctt | 420 |
| taaaaaaatc caaggccttc ctgaactggg ctctgacaca aactgccccc acctcttccc | 480 |
| tcctcagcga gtgttctaga gggggccaaa cgaagatgcg tgtgattagg aagctaggcc | 540 |
| atcagtgtgc acaagtttgg gtgaccgagt ctgcaggtgg cagctacgag ttatggtgga | 600 |
| caagctttat gccaaggata ttagagacag aaacagacca aagcttcgaa ggcgcccatc | 660 |
| cccacacacg gggatcgcct gtcacatcac atcaaccttg cttgtctcag agggaagacc | 720 |
| attgaaaagt taaagggaa aagagttcag ggataaagac gttaaaccaa aggggggtcc | 780 |
| ctgaatctcg gtgacggggg atgggcacca ggctaggtct cggcgagtcc gtgaacccgt | 840 |
| gcatgtacat actgcttagg agctgattca cagctttact aaggctccgt ggagccccta | 900 |
| aacgttaaat gatgctgatt cgagaagaaa acgcaccagc ggcactgtgt ctggcttggg | 960 |
| cagcctcacc aggtgcagga gatcaagctt tccagttcca atcctctccc gagctccttg | 1020 |
| cgtagggtca aggatgccct ctcttctagg agcggattaa cagggcaaag tgggaaaaag | 1080 |
| agcgaaagaa atgtagagat gccaccttgg tgggcaaatc tgagatgcct cccgcggaaa | 1140 |
| gagacgcaac ttccagaccc gctccagttc tccacttggg cgggaagctt tgcgctccca | 1200 |
| gctggaagac gcctcccaag cgctcgctgc gcccttcaag caagatccta gcaaccagag | 1260 |
| cttcagggtg ggggtggggg cgggggacg ctgaccggct cccacctgct tgctcctaga | 1320 |
| aagatcctag ctcagattaa agggatgaag cgctaaggtc gacttgtcca gaaaagagct | 1380 |
| cacggtgagt tcaccacccc ctataccaat tcatcgagtg gcctcctccg catcagcaga | 1440 |
| gcaccccgg ggattctgtc agacatgaac cccgaaactg gaagcggccg ctgcctctct | 1500 |
| ccagccacac atccttactt cggagtgccc cttccaactt cgggttgcac gccgacctca | 1560 |
| gcacaggcac tctccccggc gccccagaga gccgggatga ggggagctgc accgagctga | 1620 |
| gttaactcgg taccagccga gaggcagcgg ctgcccacga cacagcacct aaatacaggg | 1680 |
| tccaaatcca ccccaccc atcctctcgc ccctccttat cccttccaac ccttcttact | 1740 |
| cgactagagc cggcatccaa gtcggaccgg cgcgtccgga actaggtact gatcgccgca | 1800 |

```
ccggagcccg aggacgctca ccgtgccgcc tccccgcggg agcccgggga gcggcccatc    1860
acctctgcag cctcgccagg agaagaaaag ttcccacgtc tctaccagga gaagcccgaa    1920
gctcctgcgg gagaagcctg aagctgctg                                     1949
```

<210> SEQ ID NO 91
<211> LENGTH: 749
<212> TYPE: DNA
<213> ORGANISM: Homo sapiens

<400> SEQUENCE: 91

```
ctaggcccat gcccggcccc ccttactgcc tgccctcctc cctcaccacc ccaccccacc     60
cccccagtgc tcggcctcgt ttcgtcaccg gatcccctgg aatgggggac gcgggcgcga    120
aatacgaacc cagccaccgg cagctccctc cccacgtgcg ctcggcccgc agcgcagagg    180
gcggcccggg gtggggcgc ctcacctttg ccctccatgg cgtgcacgaa gtcccctgg     240 tacagctggc tgcgaagctt ctcctccagg ctgaagccgc ggacgctgac gatctcctcc    300
acgtccgaca agtcctcgtt ctcgtcgtat cgctggcggt caatcgggcg ctgcgaggac    360
ccaaaccaga gagcccggga cattattgtg ggggctggag gtcgcctctc aacctgggcc    420
cagcactaac aggtgcagca gccgagcgcc ccctgcaccc caccattgca acccaagcaa    480
ctttgcgcaa ttgccaaaga tgctgaaaag caggacaagg agaggggccc gcaccccgag    540
ggtccagctg cgctctacgc ggggtactcc cctccggtgt cttcggaagc actgaaggga    600
catctgggga ccctcccctg ccccccgccc ccgaaatgtg ctgggcttcg cccactcggc    660
cgggagcctg gttatgtaac ccgcgaaggg ggctccggac acgggctggc ggggcaaatg    720
taggccccag gaggagccgc tgcggcgcc                                     749
```

<210> SEQ ID NO 92
<211> LENGTH: 1349
<212> TYPE: DNA
<213> ORGANISM: Homo sapiens

<400> SEQUENCE: 92

```
tgcgccttga gcaccccagt tctccatcta gcgatagccg cgggtccccg cgcatgcaag     60
cagaagggcc gtggagcgag aggctgggaa ggtgcttcaa gccaggggtg catgctttct    120
cccacggacg cggggagatg gcctcgcttt gtaccccat atccctactc ccgctgtggt    180
cggctgcaca gtgttggccc atttccgcac tcagccaggg aagctcagcg cctcacgtcc    240
ccggggccat ccctagagtt tcctttaccg cagactcgtt cccaagaccc tggcgagtct    300
cacctcggtc accgttctcc ccgagagcga gtccgaagtc tctggggccc cggtccagtt    360
cgcacactca cctccgactc ccgctccgga accacggccg ccggctaccc caccccccgc    420
ccccatcccc agtggatgga agaagaccc aagcggggcg tcgcgggcca ccactcagac    480
taaaaagttt gggttggacg ggcaccggca ccaccacgct ctcccccgcag ttcctctggc    540 ccccagccgc tgtccgggcc cgcaccacct gctgaggggc cagggaggcg gcgcagatgg    600
ctagggtaag gggggcgcag agcgaacccg tccactcctc actgtacacc cccagtacag    660
tggaaggagt gcgctcagcc ccgcgcctgg tcagcagatg cctctctcgc tccgggatga    720
ggacccagct actcaccgtg caccggctc ccgctcctgc tcccgcccta gtcaccgctg    780
ccgccgccct tcccttagct cgccagaccc tggctcgtga attatttatg acccggcttc    840
tgggaccacc gcgacggctt tcggagagcc cgcctcccac tgccggccgc ggaggggctc    900
```

```
aggcggcgct gcggccggac cctcggacgt ggcgggaggc aggagaaagg cccgggtgcc       960 cgggggggacc cgttgcggct tcctctgtcc cggacgggga cctaggtatg ggccgccgt      1020 aatggaaagg attccttaaa catactcacc gcggcgggag agctgagagc atggccaggt      1080
gccgcgtggg gatctgcctc agtcacttaa agatcgcgaa acccgagccc tggacgcact      1140
ctgattggac cggctgagct gcttcgccac gtagccctgg ggcgcccacc agcacctgga      1200
cagcatccat ttcctgtaga ggtgcctgct caacccctg cactcccttc ttgcaacgct       1260
tgcgcctctt ttccccccgc agagtccctt acttagaatg cagctaccct cctaaaaact      1320
ctcctgtctc atcccggccg cattagacc                                        1349

<210> SEQ ID NO 93
<211> LENGTH: 1999
<212> TYPE: DNA
<213> ORGANISM: Homo sapiens

<400> SEQUENCE: 93
cagcctctgc cccctcctca gctggggccc ctgccctctg attatctgca gcctcttccc       60
tctgattatc tgcagcctct gcccccctggt cagctggggc ccctgccctc tgattacctg     120
cagccccttc ccgctggtca gctatggcct cttccctttg actatctgca gcctctcccc      180
cctgatcagc ctcgatgtct gcccccctgac ctgtgggtgc tgtctgctcc ttcctgcggc    240
gccgaaagga ggcccagttg atcttgggcc tccatcgcct aggggaagcc tggggcacac     300
aaacatctcc cgcgtttccc aagcgatccc ccgggctggt gccctctggc gccgatgata      360
cccctgcgct ctccactgcg gtggaggcca gccgggcctc gcccaccccg gggcccgccc     420
tcggcgccca acccttcacc ctccgcttca gcttccccca ggacacctgg ctgacatact      480
cccgccacct gtccgctttg acagctgag gccccaggtt gtcctcaaac atgggcactg      540
gcaggttgac gcggcggcgg gcaggcggcg cgctgggctg cttctcctgt cgccggagga     600
aggcctcgac cagttcctca tcatcctcac tctccaggtc gcttcccagg aacttgctgc      660
ccaggtagct gacgggcatt tgcgcacct tcttgccccg ccgcgggccc tggcggctct      720
tgtctctgga ggtctcgaag tcgctgaact cgctgtcgct ggcgttgctg ctgtcgtacg      780
tgcccacgac cagccggggc ggaggagtca ccatctgctg cactctcctc ctcactcggg      840
gctccttggg cttttggggg ggctgggcg ggtgcgggt gctcttctcc atgatgcggg       900
ccacgtcctc cagggtgcgg ccctcttctt ccaggaactg ggtcagccgc tcccgaaatt      960
ctgcttcctt ggtggcgggc ttagagatga ctctccagac gccccagcc agcctgacct      1020 cccgggggat gagcaaatag tcgacgtcct ccccgatctg cagcatcccc accgtggagt     1080
cctcctcctt gcggaacacc ttgccgatct tcttaaatgt ccccacgggc tttagggctt      1140
ccacgaggac gtccaaatcc acatctttgc agacatcggg gacgctccaa agaatgaggc     1200
agtcggggga cggcaggaag ccccagggga accagccccc cacgtggctt ttctcgagag     1260
tctttaagat ctccagggtg atatctgggg tgaggggca atgagcccca acaaactact      1320
gtagccctta gtcttgaggg agggactgga tggggggagt ccagcaacg ctgaccggag      1380 agtctcacct cccctagccag ggacgagcca aacgcctcca atctcttcgc ctgcaacaag    1440
tacagtcttg accaagtccg gctcccccac caaggacttg ggggaatcaa tttccaggat     1500
gcctacgtga gccggggcg aggtcagtcc caaggctcaa ggcccactcc aagctggaaa      1560
cgtggtgtcc cagctccaag ttgggcgcg cgggctgcca gcgactcttc ctgccccagg    1620
ccccagggac gcggctggaa cttgggacag gacttcgcag acaaagacgg tccagtcgaa    1680
```

```
gctattcaat atggccgagg cgctgggagg ccccagcccg ggcctccagt agggtccccc    1740
gcccccaggc aggccgccac ccagctccag gctgaccttg acgcgccgca gcctgccagc    1800
ccgcgcgctt agagctctgc accgtggagc gcgcgggcag gaagttcctc ctcgccctcc    1860
gccagaatga ggcccacctt cccccgtctc atcttacact cccagactct ggaagactga    1920
caggggggct gtccactccc ttcggggcgg cctccttccc ctcccccaca ggggtgtggc    1980
cgcgccccgg gcctagctg                                                 1999

<210> SEQ ID NO 94
<211> LENGTH: 1849
<212> TYPE: DNA
<213> ORGANISM: Homo sapiens

<400> SEQUENCE: 94
actatctcat gcacccaggc acaactttc cagatttaaa gaaaagaaa aagaaataa        60 aagaaaaaaa cctctgtctc tacacctcca ttcccaggga gagctccctc tctggcacca    120
agctccctgg ggtgagtttt cttttgaag agtccagggg aacaggtaag cagcggggaa     180
gcagggagtc catttcaggg acaggaattc ccggatgaaa agtgaaagga gagggacggg    240
gcccaagctg agggtttctt cctggtttct cggacagctc ctggaccaag actcagggaa    300
cattgagaca gagcgtttgt cacaggagga gcggggtcag ggcgaagtcc cagagcccca    360
ggcatggctc tcagggtctc aggccccgaa ggcggtgcat gggctgggga ggtgcagcat    420
tggggattcc ccatctccgc agagtttctc ttctccctct cccagcctgc gacgggtcct    480
tcttcctgga cactcacgac gcggacccag ttctcactcc cactgagtgt cgggtttcta    540
gggaagccaa tcagcgtcgc gcggcccgg ttctaaagtc cccacgcacc caccgggact    600
cggagtctcc ccagacgccg acgatggggt catggcgccc cgaaccctcc tcctgctgct    660
ctcggggacc ctggccctgg ccgagacctg ggcgggtgag tgcggggtca ggagggaaac    720
ggcctctgcc gtgaggagcg aaaggtccac ctggctgggg cgcaggaccc ggggagccgc    780
gccgggagga gggtcgggcg ggtctcagcc cctcctcgcc cccaggctcc cactccatga    840
ggtatttcag caccgccgtt cctggccgg gccgcgggga gcccagcttc attgccgtgg    900
gctacgtgga cgacacgcag ttcgtgcggg tcgacagtga cgccgtgagt ctgaggatga    960
agacgcgggc gcggtgggtg gagcaggagg ggccggagta ttgggaccta cagacactgg    1020
gcgccaaggc ccaggcacag actgaccgag tgaacctgcg gaccctgctc cgctactaca    1080
accagagcga ggcgggtgag tgaccccggc cggggcgca gatcacttac tccccgctcc     1140
atgcctcacg gacggccctg gtccctgag tctccgggtc caagatcgac cccgaggctg     1200
cgggacctgc agagatcctc gacccggag agccccaggc gcctttacct ggtttcatct    1260
tcagttgagg ccaaaatctc cgcaggttgc taggggccgg gccagggctc ggtgggcggg    1320
gctgaccgcg ggaactgggc cagggtatca catcctccag ggaatgtttg ctgcgacct    1380 ggggcccgac gggcgtctcc tccgcgggta tgagcagtat gcctacgacg gcaaggatta    1440
catcgccctg aacgaggacc tgcgctcctg gaccgccgcg gataccgcgg ctcagattac    1500
ccagcgcaag tatgaggcgg ccaatgtggc tgagcaaagg agagcctacc tggagggcac    1560
ctgcatggag tggctccgca gacacctgga gaacgggaag gagacgctgc agcgcgcggg    1620
taccaggggc catggggagc ctgctcgatc tcctgtagat ctcccgggct ggcctcgcac    1680
aaggagggga agaaaatgga accaccacca gaatatcgcc ctccctcctg tcctgacgga    1740
```

| gaggaatcct | cctgggtttc | cagatcctgt | atcagagatt | gactctgagg | gcccaccctg | 1800 |
| ctcttcctgg | gacaattaag | ggatgaagtc | tctgagggag | tggagggga | | 1849 |

<210> SEQ ID NO 95
<211> LENGTH: 1749
<212> TYPE: DNA
<213> ORGANISM: Homo sapiens

<400> SEQUENCE: 95

| aagggcaaga | gaacttcaga | cctaacctaa | aattatactt | tgtacttctc | aagccttttc | 60 |
| tccacgcacg | ctgcctcagt | tccctttcca | gttccttctc | ctgatggaca | gcggggacct | 120 |
| ctgctacgga | gctggctccc | tgtccttggt | gatgggctcc | tgggaacggc | ggggcacacc | 180 |
| cccaggggttg | ggagggtttt | cagcttttga | gtgccggatc | tgcgcccgct | gcctattcaa | 240 |
| gactccacca | gaaaggcaca | gtctacaacg | tggggacgc | tagctaggaa | acaggcgtcc | 300 |
| gtgaaacccg | catctgattc | tccgaatggc | ctttgtcgcc | tccctggacc | ctcacctccg | 360 |
| cccatgcgcg | ctcgtcacag | tggggcgcca | ctctgccacc | tcttaatcgg | cttcctcctg | 420 |
| gaaggaggaa | caaaagcctg | ttttgttccc | tgtcttctcc | ctccacaact | gatctctcct | 480 |
| ccctctatc | ccgccctgct | ggagatgggc | gtcgtcctct | ctaggcggga | atggaacggc | 540 |
| gagaaaggga | tgacagaagg | ttgtggggaa | aaaacctttt | aattccctct | ttccttttct | 600 |
| gaatactctc | tgattttgct | gtgtgagaca | atatccttgg | ccaccaccga | tatggaaaac | 660 |
| taagtcgctc | gcgacggaaa | gcgatcccca | tgccctgac | ttttgaaagg | agaagcattt | 720 |
| agtagtaaag | gttcgcagc | caactagccc | tgtcccgaac | tgccttcttc | taagtgcatg | 780 |
| tctaaaaccc | agcgagatac | acttggaagc | ggacttcact | gtgtgtctct | tggtgactcc | 840 |
| ccaaaccggc | gacgccggtc | ccaacactca | tttacactgt | ctggcacaca | cactcgcgct | 900 |
| ttgtgagcaa | ctgcactttt | accatcatgg | gcagccaaag | gacgacttt | gtaagcgcta | 960 |
| ggatcaaagc | gaagcgcttc | tgcgctacgc | tcacggtgaa | gctcctggtg | ccatagagag | 1020 |
| tcccccggtt | ctcacgcctg | caggcttcag | ccccagcggc | agcgggcgca | cccggtccga | 1080 |
| acacggtgtc | ggagctcgga | gagcatcccc | cagagcgccg | cagactcggg | cctggagcat | 1140 |
| cctctgggga | caggaaaacc | actctccccg | cagtaggagg | ggtcccagga | attgaagctc | 1200 |
| cacgggaaat | ttcctggtag | ttggagtgga | gtctcggcgg | ctcctccgaa | cacagcaatc | 1260 |
| ggtgagtgag | tgggactgag | aggcccacga | ggagtccgaa | ggccaaagcg | tacacgatag | 1320 |
| agaggaatag | tacgtaggag | ctggagcagt | ccaccaggca | gccccagggc | gtgcgcacga | 1380 |
| aggcgcccca | gccgcacagc | gggagcgccg | agagcagcag | actggctgcc | cacacggtca | 1440 |
| gcaccacgcc | gagcacctgg | cccgatcttc | tggaggctgt | ctggctcccc | acacctctgt | 1500 |
| gcatcgtata | aaagttgtaa | gagactagga | gagtcgcctt | caagttgcta | gagaggccct | 1560 |
| ggcataaata | cattaaggca | gaggtggtgc | acagaaattg | gaagtaaccg | ggacctcgt | 1620 |
| ttggccactg | caaaaacatg | aagatggtca | ccgacaggac | gctcatgaga | tcatccacag | 1680 |
| accaggaagc | cacaagcatg | gacacaacag | ttctgttctg | cattttcagc | agggaaatta | 1740 |
| gtgaataaa | | | | | | 1749 |

<210> SEQ ID NO 96
<211> LENGTH: 1699
<212> TYPE: DNA
<213> ORGANISM: Homo sapiens

<400> SEQUENCE: 96

```
catgtacatt cccgtagagt agataccagg cccactgggg atcttgtttt gtaaacgcgc      60
cagccaggga caggaagttg tgatcaaaag gcagctggaa ggtctgggtc agatcccagc     120
ccaggcccag aagttccagc tctccaccct ccgcctcgcc cgcagggctc gcgcttccac     180
agttctcgcc gagagcgcta tgggacagtg ttcaagacgc acctgctggg caggccagtg     240
atccgcgtga gcggcgcgga gaacgtgcgc accatcctgc tgggcgagca ccgcctggtg     300
cgcagccagt ggccgcagag tgcgcacatc ctgctgggct cgcacacact gctaggtgcg     360
gtcggcgagc cgcaccggcg gcggcgcaag gtgagtggaa acgggaatgg accgtagata     420
cgtcggatcc gcggtccccg gcatctgcca tgggccaggc cggggccccg tgttggata     480 cactgtgaac ccgaccaagg tccctggtaa ctagcgggtg gccttgggcg gtccgttac     540 cttcagcttc ggtttataaa gttaggactg cgctaaaaga ttctttcatc tcccatcttc     600
cgtggctgtg atagcagaag cgctggagac tcagacctag aaaggggcca gggaagactt     660
cttagaggag atggcagctg gagcctggat ggttgggagg actgtgtgc atcagagcag     720 aactggggga atggcgaaa gcaaaagcca ggaagtttag gtctgggccg cttggaagag     780
ggagaaagga ccggaactgg ccttctggct actccggaat cgccaagcag atgaggccag     840
accgccgcca gcgctgatca cgcgcgctcc cacaggtcct ggcgcgcgtg ttcagccgcg     900
ccgcgctgga gcgctacgtg ccgcgcctgc aggggcgct gcggcatgag gtgcgctcct     960
ggtgcgcggc gggcgggccg gtctcagtct acgacgcctc caaagcgctc accttccgca    1020
tggccgcgcg catcctgctg gggttgcggc tggacgaggc gcagtgcgcc acgctggccc    1080
ggaccttcga gcagctcgtg gagaacctct tctcactgcc tctggacgtt cccttcagtg    1140
gcctacgcaa ggtacggccg ccccggctcc agaccttcct ccgaggctcc gcggcgcggg    1200
cgggcctccc agacccagac gggacgccct cggcgcaccc cgcgcgtccg tcacctctgc    1260
tgggaacggc ggcagggccc gggggtggga ggcgttgtgg cggtggcgtg gcggtgggct    1320
ctgggcctgg cctctgtgct ggttcgctgg tgtgacctgg ggctggccac acgacctccg    1380
tgggacgcgc ctgccgcgac cgcgctccagc ctgagcaagc gcgggccgcc agagtttggg    1440
gtctcggtgg caggcgtcct gccagtcggt cggactcctt cccacagcgg cgcccctggg    1500
gccggcctcc atcacctctt cggaagccca gatggctgcg gaaccgagga gagcgtgagg    1560
gctgcagatg agccccggtc cagcccagcg ccagccccgg acccaggggt gtgggcgtca    1620
gctccaccag ccctggaccc gctaggtttc gggatcagag aactgctgct tctccagact    1680
tcagaacaat gggcaggac                                                 1699

<210> SEQ ID NO 97
<211> LENGTH: 1099
<212> TYPE: DNA
<213> ORGANISM: Homo sapiens

<400> SEQUENCE: 97
acagctagag gccccccccc cacttgatta attatttgct ttgagtatga acagctagaa      60
ttcatagaac cctttccctc tttctttcct gtaagctgca gaggtgtctc agccatccaa     120
tctggcatca actgaccaca cgccatcagg atgcctcct ccctcacctt taaatcccat     180
ctggctctgg ggatcaatcc catctggctc ctctccccac ctccacccec gcaccctggg     240 tgtcttcacc actttcatct cccgtgtcag cccgcacgaa aatagcggcg gtaatgcttg     300
taagctcaga cagcaggggc cagcaataag gtttgagggt actggggcgc tcactgcctt     360
```

| | |
|---|---:|
| aggctccgtc cctgtcagcc cgaaattaac ccctaaagca ctaaagtccg gcagggcccg | 420 |
| cgcgctcttc ccacaccgaa atggcggggt gacggtttcc aaatacccag aaaggaagtg | 480 |
| gaacctgcgg tgaggcccca gaggtgaccc gccttgtccc gggcaggatg ggcgccatcc | 540 |
| tgcagcccag ccctacatcc gctctccctc tggagtcttt acagttattt cccagcccaa | 600 |
| agcggggatt gggtttcggc ccccgctcct gggctataaa taccacccccc tacatgcacc | 660 |
| tctctcccct cccccaacc tggcctcggc ccgcgcagtg ctcagcgcca gctgtctctg | 720 |
| cccatccgcg cacccgggct tcggctggag agggccagct cgcttcagga ggccgaaccc | 780 |
| cgttcccacc aaccctctca gctcagacgc ggggtgctga gtcacgggggg ggggtggtt | 840 |
| ctgtggatag ttggaatgca tacacagagg aaaggggat gcggcaccag gtaacctgac | 900 |
| cccttccacc ttctagcgcc aagcacgtgc tcggtcagtg ctgaggacca gggactgggg | 960 |
| atgtaagagg gcagccaaac ccgtcttctt ttgcccgcgg aaaggacggg gcgcgggccc | 1020 |
| gcgtgactct catacagagt cgggacacaa atgctcgtaa ggcaggagca gagtgccagg | 1080 |
| aagggttcct ctctgttac | 1099 |

<210> SEQ ID NO 98
<211> LENGTH: 749
<212> TYPE: DNA
<213> ORGANISM: Homo sapiens

<400> SEQUENCE: 98

| | |
|---|---:|
| ttgacccttc cataatttgt ctccaccacg ccccaaaagg cccatgctcc tattccctgg | 60 |
| cccttctttc agtctcccac ttttgtggcc ctccagtgca tgggtatgta aaatagttt | 120 |
| ttctcttgtt aatctgtctt atgacaattt aatctgtggc ccagctaaag aacctagaag | 180 |
| cgtaggggga agccatatct ccctccccca cctttgaatc ttctttacac cacactctcc | 240 |
| cgggtcatct ggaccctcct tgaactggag ccacgggagc gcaaggcctc ccaagtcagg | 300 |
| gcccgaattc cgcgtggtgc caaacggcag ctggctccct gaatgcccac cctgaaccct | 360 |
| ggtaaaaaat aaaaaaaaca caacaaaat ccctccaac ccggagaaaa caagtccgcc | 420 |
| tctgttctac ctagcagcgc cgtggccagt ccccgccgcc cattctctct tcttccgggc | 480 |
| ctcgccacac caacactgca ggacccgtgt cctcgtccct tctccgtagc agaggatgaa | 540 |
| aagaacgggg tttctccatg tcgcagtggc ccagggaact cagaggtgga gcgcgggggc | 600 |
| agcgtgctcg gttgaacttg cctgttcggt ccacaaatgc cgagcaagcg ccaataactc | 660 |
| ttggcttccc caaagaggc gacgcccaca ccaaagcggg ggcgaggagc gcaagccgct | 720 |
| gccgcctccc cgggccgagg ccccccgccc | 749 |

<210> SEQ ID NO 99
<211> LENGTH: 899
<212> TYPE: DNA
<213> ORGANISM: Homo sapiens

<400> SEQUENCE: 99

| | |
|---|---:|
| ttctcgccgg agcaggtggc cagcgtctgt gagacgctgg aggagacggg cgacatcgag | 60 |
| cggctgggcc gcttcctctg gtcgctgccc gtggccccg ggcgtgcga ggccatcaac | 120 |
| aaacacgagt cgatcctgcg cgcgcgcgcc gtggtcgcct ccacacgggg caacttccgc | 180 |
| gacctctacc acatccttga gaaccacaag ttcaccaagg agtctcacgg caagctgcag | 240 |
| gccatgtggc tcgaggcgca ctaccaggag gccgagaagc tgcgcggccg ccactcggc | 300 |
| ccggtggaca gtaccgcgt gcgcaagaag ttcccgctgc cacgcaccat ctgggacggc | 360 |

```
gagcagaaga cgcattgctt caaggagcgg actcggagcc tgttgcggga gtggtaccta    420
caggacccct accccaaccc cagcaagaaa cgcgaactgg cgcaggccac cggcctcact    480
cccacacaag taggcaactg gtttaagaac cggcggcagc gcgaccgcgc cgcggcggcc    540
aagaacaggt tagtggcggg gcccgcggcc tggctacagc ctcagaggcc tgggaagggg    600
agaggggttg agatggggct agcggagcgg ccgctgagag ccagggaagc cgtgactcct    660
ggccagtcgg agaaagtttc cgcttgtccg ggacgcgcgg aagaggggc cgggctggct    720 gtgggtgtat tgattgcttt gaccaagagg ggctttcgtc agggcagaga gtgtgtgctt    780
gcgacccgag tacccgcagc ccctgggaga cttagccctg cgctgcaccc gtgcctgcct    840
cctcagccct gccgccagct cggcgatcct ctggagccta gagacaggga gggaaggaa    899
```

```
<210> SEQ ID NO 100
<211> LENGTH: 799
<212> TYPE: DNA
<213> ORGANISM: Homo sapiens

<400> SEQUENCE: 100
cactgagctc ctgagctgcc aagggacacc tgcatggagg tgccaggcca tgcgctggag     60
acagcccgta agtgagaaaa actcgcttcc ctccagcctc actgtgccca ggccgctctg    120
tgccctgcgg caagctggtg gggggcgggg ggagggcttg ttagtaaatg acccagaagc    180
gccccacccc acaccccacc acaaggactt gtccgggccg gccgggcta gatgccgaga    240 tgtaattcac cagatttgtg aaaagacgag aaatctgctc tcattttgaa gcgcagcccc    300
gccggcatcc aggaggccga atataaacct cttccggagg gcagggacat cttgcaccgt    360
cgccctccaa atctggccct ctaggggtgtg aagggcgcg gcaggggtgc agggaaaaac    420
acacagcccg tagccatctg tttggctctg acgagtcccc agactcgagc ctccagtcag    480
ctcggactcc agaccagggc tccgcgaggg gtggtgcgac tctaacccca cggtcgccac    540
agcagctgga gaattcggcc aaacctgact ctttctccag gggcgagggc tccgccagac    600
cgcgtggaca aggaaccggc cccgccgcgc tttcctggac tgcggaggcg gcctgagtgg    660
tggtgtcccc gtccctggca gagagggggct gtctcttgat tcctgagctt cagggccaca    720
tgtctcaggc gggttgagcc tcgatgatgt ctgccgtggg gttcgcttgt ggacgatccc    780
ttcctgggac cccagacccc                                                 799
```

```
<210> SEQ ID NO 101
<211> LENGTH: 2749
<212> TYPE: DNA
<213> ORGANISM: Homo sapiens

<400> SEQUENCE: 101
cacagcctgg ttcacaatca gctttccccc ctgttgaata tgcagcccca ggagtcacct     60
tttctaaaaa agtcagaaga ataggccagt ccccttctct taaggagag tttaaggacg    120 acatcaactc ggcggggttt tggaagcatt ggccctaaac cctgcccaac gattttaaaa    180
agaaaattac aggcctccca gtgttcccgg gaatatgcaa atgccagggc gcaggcctcc    240
caaatcagac cgcgaaggct cggggctgcg agccgaatgc ccgccgagct gcctgggaac    300
gggaaccgcg cacccgggaa cgccaggcgt ttctcttcat ccaggaacgg cgcggagagc    360
ctccggctgg ggagctaaac cgctggggac tccgcggctg ctgcctgagt cgctgtccgc    420
tgcccgcatc ccttccgccc tgggcctctg cacggtctgc ggttttctgt gcgcacttgg    480
```

| | |
|---|---:|
| tcttcagtac tagcacccaa ttacgtctgg gttttcttc tttacagagc tgggtttcgg | 540 |
| tggccaccag cttttctggt gtttagtgac tctgagtttg gaggtggcct accaggcaaa | 600 |
| cggggattca gggcatttag gaaacgtctt ccgcgcttaa tcccagaagt ggttgcgtgt | 660 |
| ccgtacgatc ccaagttcct cccggagcct cttctttgct gcgtctcggg ccctccagca | 720 |
| ggcgaagcct cttagacgcg ctggggaaac ttccggcgtg ttcggggctc agggtttctt | 780 |
| ctcaggcatg gattgggggcg cagaagttgc gcgaggcagc gcctaaggtc ccgaggtgct | 840 |
| gagactgtgc tggcgtttgc cacctgcccc tggctaggcc gtttctgggc cccaagaaac | 900 |
| gcctaccttg gcacttaggg accagaagcc tctggatgtc tagcaacagg ggtcacggga | 960 |
| tcactgcgtg gggtctctgt aagcagtccc ctgaggcagt gcaaaaccgg aaacctgctc | 1020 |
| tgtgcgggc cgaatcagtt catgggattt ggagtcagg agagacgtct ttctcctccc | 1080 |
| agctcctaca ctccgggtac caaggcccga aatgccgttc ccccagcccg ggtgcggggt | 1140 |
| ctgcagcaag gcctcctgat ttgcaaaccc ctccgggctg cttattcctg gtgccatgcg | 1200 |
| cagcccttgg gacctagaag attgtggggg agggaaggtc gcacgtgcgg ttttggcacc | 1260 |
| gaccgtgcct cctagtccac ctgtccccca cagctagctg ccaactcgga cggaagcgcg | 1320 |
| gaacagcgca atgcaaaccg cccaaagtga aggaatgta attgcgctcc catgacagag | 1380 |
| ccagacgcgg atgcagttta ggaagggcgc cgcctaccgg cccctgggag ccatgcgatt | 1440 |
| cgaagggagg gggacctaga ggagaccccc gctatccccc cacccaccgt ggggccttag | 1500 |
| ctttgaactc cggcccggac aaacttaaac tgcttcgcca cccaacgcg ccacagccct | 1560 |
| ggacctaaga cccagttagc attgggaatt tggggagcag ggcccacgac tagaacaaag | 1620 |
| ttaaccctac cggttcccgc cacggcttcg gcacatttca aaaaaccagg cgcaggcaat | 1680 |
| tgagaaatac gctgccggct gaaacagcct gcgggtgggg gctgcagccg tgcgcgcccg | 1740 |
| gcagttcccg tcccgcatca ggtgtacgca cttccactcc tgcgggccct tccacgctcc | 1800 |
| aactctggac cccgcgcagt tttaatctgc ggtttgggaa atggggggtgc taccgtgcaa | 1860 |
| ccgcgccctg aaagaccgtt ttggtcttaa gagcttttgg cctgtggggt ggacatctgt | 1920 |
| agaaaaagga aaaacaaaac aaaagtaacc tcccattgcg tcgaaccctc ctattccgaa | 1980 |
| aagaacttta atgaggttgg cttggcaagg cctgcggtgc ttacctcggc ttcgccctac | 2040 |
| cccgccagaa gccctcatag gttgtatcca ctggtctccc ccaggtgcag ggttattagg | 2100 |
| ggaaagggg gcgcgccctc gggctggatc tttgtttccc tcgtcgcccg gtcatcaaac | 2160 |
| aggagggaaa tcgggcccga ctgggacctt gctgcccgcc ttccccttaa actggctaaa | 2220 |
| gcttcaggac tgtccctaga cccaccccgc gggtcttcct ttgtgtccag ggcatagccg | 2280 |
| atctcctttt cgttttcacg agaactgcga cttgggcctc gggcactagg cgagcccagg | 2340 |
| ttgtggccta acagcagatc gcctcgggag cttggctgca gctctgcccg cacctccagc | 2400 |
| gctgggcggc ctctcgggggc cagtggggat ctctggcctc gtgtaggcca cgggcccag | 2460 |
| ccctgggtcc ccaaggccgc tcgccgggca gcgctcgttt ccggcaccgg gacgagccca | 2520 |
| gcgcgctcag acaccacttt cccggtgaaa tctgcttta tttgctccga gcaaacctcg | 2580 |
| ggctctcagc gctcccgcct gatggatgca aatgtaaatg tgcacttatt taattggatc | 2640 |
| aggccccaag ataaaagaga taaacggctc cccgcttgct aacttatttt cctaggcatg | 2700 |
| cagcgccgcg tggaggggaa gctaatgaag gagcagcgcg gtgctgggc | 2749 |

<210> SEQ ID NO 102
<211> LENGTH: 1249

```
<212> TYPE: DNA
<213> ORGANISM: Homo sapiens

<400> SEQUENCE: 102
tgcagggctg tctgccacga aaacaatgcc cagagctctc tcctcccctc atcaatagac        60
caaagtgtgt acatcccag  ggagcacaca ggaaagatag cagaaaagag catttggaat       120
aaataatgta caatctagct attatactcc ttgggtggtg atggagaggt tgaattttta       180
gcaagaggaa agagggaaca aagcctaaca aacattgagg ttaaaacatg aagtcatctg       240
catttacact ttgcttcagg ccgcggcagt aatgaatact cagagccggc tttctgttta       300
atgtttgatg caaagtcacc ggggagtcat tctccttcac tttcaatttc aggggtcctg       360
aaaccctgcg tttctctgcg gtaataaccc gtgctttccg ttcccggggc gggcgcgctc       420
tgactgatca gcgcagatgg aggctgtgcg gacttggact tggacggttt tcctccagcc       480
cacctcctgg gcacccgcca tctcagggct gtttcctgaa acccagctc  ttgcctggat       540
gacatgtttt ccaggcgagt gactcatcag aacagccaac agcttagaaa gtccctctgc       600
ccccagctgc tggggggag  gagcccacga tgcagatgag ctggtcacag ctaatcacag       660
cctcctcccc tcagatctgc actccagcac tccagccctg cttctccagg cagcttgatc       720
gcaggctgtg ggaagtgcta atccagacac cttcccggtc ccctcccacc ttctgctgtc       780
gtgtgctgcc aaacctcaca gggctggctg ctgccgccga agcccaccac catggcctct       840
cgtgtgtacg taggacccac tttcccactt gtctttagct gggaatccca aattagagct       900
gcaagtgtgt gttgattta  ccgtagaaaa tgcagccagt tttaatcaac agataaatgt       960
tcattagaga ataccgttgt tctgctgttt aaaaggttgc cgtgcaggcc gggtgcaatg      1020
gctcacgcct gtaatcccag cactttggga ggccacggca ggcagatcac ctgaggtcag      1080
gagttcgaga cccgcctgac caacatggtg aaaccccgtc tctactaaaa atacaaaaat      1140
tagccaggcg tgtggcacat tcctgtaatc ccagctactc aggagaccga ggcaggagaa      1200
tcacttgaac ccgggaggcg gaggttgcag tgagccaaga tcgcaccac                  1249

<210> SEQ ID NO 103
<211> LENGTH: 749
<212> TYPE: DNA
<213> ORGANISM: Homo sapiens

<400> SEQUENCE: 103
ggaaaagaca ggcggctcct gcagggcagc tctcctgggt ccagaattct ccctacaggt        60
ctccccagat caagccaagg aaatgggcgc caagtaacca gagactgctg gagtcattgc       120
cagtggtccc gtgaatcaca gccagcctca agacctcaat ttcttcaccc ggccatgtaa       180
gcagagcgga caactctgag ggcgtggctg gcgggggttc ttggggcagc ccggcgccac       240
tgccggcatc tacgcaccct gaacgcgccc gatctggtct catctcggaa gctaagcagg       300
gtcgggcctg gttagtactt ggatgggaga tcgcctggaa ataccgggtg ctgtaggttt       360
ttggcttccc gctccctctc tctttccccc ttttgtcgcc gcgcttttca accgccccct       420
aactctgctc ccccttttac tccgtcgcag cccgggacct cctggtgggg gtccgccact       480
gcagcaccag gcgccactgc cataccaccc tgaacgcgcc cgatctcgtc tgatctcgga       540
agctaagatg tggccgcatt taggaccca  ccggcttggc tgtgcctctc ccagcccct       600
ggcggagcgg actaaccta  gcatttcatt gattcacaat aacgccaccc caccccgact       660
gactattttg agccccattt gccaatctgt agtggatctt tactgttttg gagtagtaaa       720
```
ttcaatacac ctttatgggt ctattttg                                     749

<210> SEQ ID NO 104
<211> LENGTH: 799
<212> TYPE: DNA
<213> ORGANISM: Homo sapiens

<400> SEQUENCE: 104
accagcctga gtttgagtgc ttgccgtagc agaaactatc cttaccacag gtgggaagga     60
aaggaccagt ttctagcagt gtcgggccac tcctctttcg aacatcccta agggaggcat    120
tcacaaaagc tgtcccaagc agctggaaga aaacagcttc cgagatgacc aggaggactg    180
ggcggcgccg agcccagaac gctcctggcg cagcaccgtt ggcgttggcc gattgctgct    240
ggtgggggc gggggtgcag gccccagtct ctatgcaaat cagggatcag aagatcggaa    300
tttccaccaa tcagcgggaa gcctcggccc tgtaactgct aatgggagac agcagcgcca    360
cgccacaggc ttttccctg gtttcggag gggtgggag ccaggtgggg ctcccgccca    420
gacccttcc cgaggtccgc cctctccgcc ttttctctaa attcctcttt tgagtgccct    480
cccttccggt tgagaggcgg gggttggccc gtagttgtac actcagtcac cctgcactgt    540
ggaggcgggg gcctcccttg tggactgatt tgcgtgggat ttggttgttt tattaagaga    600
tttaaaaaat tcagatgact tactagtatg actgttttgt catatttgct tccaggttaa    660
taaatgacaa aaatgaaatt cccttttgttt ttcattatca tctccccact gtttctcatg    720
gttgcaaatt agtttggtga ggtcttttca ttttaacatg aaagaatata atgcctgcag    780
gggcttgttt ccttttcat                                                 799

<210> SEQ ID NO 105
<211> LENGTH: 1699
<212> TYPE: DNA
<213> ORGANISM: Homo sapiens

<400> SEQUENCE: 105
tgcccaggtc cccagtgcgc cccctagtgg ccatagcctg gttaaagttc cccagtgcct     60
ccttgtgcat agaccttctt ctcccacccc cttctgcccc tgggtccccg gccatccagc    120
ggggctgcca gagaaccccca gacctgccct tacagtagtg tagcgccccc tccctctttc    180
ggctggtgta aatagccag tagtgtagtg cggtgtgctt ttacgtgatg gcgggtgggc    240
agcgggcggc gggctccgcg cagccgtctg tccttgatct gcccgcggcg gcccgtgttg    300
tgttttgtgc tgtgtccacg cgctaaggcg accccctccc ccgtactgac ttctcctata    360
agcgcttctc ttcgcatagt cacgtagctc ccaccccacc ctcttcctgt gtctcacgca    420
agttttatac tctaatatttt atatggcttt ttttcttcga caaaaaaata ataaaacgtt    480
tcttctgaaa agctgaacgt ttctgtataa gcgatggaag ctcctggcat gtgtgcatga    540
agtgatgagc tgaggtgggt gctggaagaa gggcggaatc gggaggccac tttgtgtcat    600
tgcgcgtcta gatgtttccg aattgcgtgt gtgtgtgtga ctgtgcaata tggttgtgta    660
tgcttgcaat gccgttgtgc ctatgagaca gtgtgcgatt gtgtgcctat ggatctgtgt    720
accgtgtgcc attgtgtgat cggtccgctg tgggggtggg gatctgagtg cggcgtgtca    780
gtgtgcagtg gagtgtgcag tctaagcttg cggctgtctc caggcagaag aggagacccc    840
ggcgcgggcg ggggcgggtt ggcgccgggc aaacgccttg ggtagagggg agaggacgtt    900
tcgttagttc ccgccccttc ctgactaaaa ttgcctaccc gaagcgcccc ggagggcttc    960
acgggaggag ggtagactct cctttgcccc cgcaccccca ccccgctgc ctaggggttt   1020

```
tgggaaagcc gcgggagtgg gagggaatgc gggaggtgat tcttccaaag ccaagtctgc    1080
agctcgagcc tcagtttccc catctggaat tcgccttccc gctgacatct ccgtagcgaa    1140
gcctaagaaa ttggagggct catcctcttc ttgcgggggt caaggggact gaaaggacgt    1200
gcaggaaatg agatccatcg cagactcagc tccoctccct ccttcctgtc ggtgcttttc    1260
cactcactcg cctgctctcc catctccccg cccctccgc ctgcctcctc gaagcactgt    1320
gggattccga ggttgctgca gccagagaag ctgcagaaaa acacggagct gggggtgaag    1380
ggggacttaa aaggggaact acccggaagg acccaagaac acaaagacag agccactgcg    1440
gttatctggc tggtcagcaa gggtatgcgg cttcctccgc gctgcggagg ctcccagagc    1500
caggtcaccc attctgccag ctcaagtctg ttgtcatggg aaccaaacct tccaacttaa    1560
gaatctgggg gcgactttct agcgtgggag aagggtggt gtgcacggtt gctgagatgg    1620
aagcagggtt ttgttactca gagccaggct gcggaggggc ggggtgccgg gcgcctgggt    1680
tctattccag gcacagcag                                                1699

<210> SEQ ID NO 106
<211> LENGTH: 1349
<212> TYPE: DNA
<213> ORGANISM: Homo sapiens

<400> SEQUENCE: 106
tacatagaca ttgtcctgtg tcctttctgc agtttgacag atgtaaggag gcctcaaatt      60
tctaattaaa atgaaaattc gtgggaggat aaaactaact tgccttccct ggacaattcc     120
gccactagac ggcgttccgt ggagtttttgt ctgccacata aaaaagcgag gactgaattt    180
cctttgtgtt tctttcccct cctcacatct aagaactaag taagaggaca aaagtacaag     240
acacggtgca tgtgtggcga gtgaagtgga gcagtgcatt cgtgtcatca cccacccgac     300
cccggctgcg ctcctccgac cccgccgcct actcccgccg aggaggagga gcacgtgcgg    360
tcggtggggc gcagggccgg ggagccaggg gggtgccggg gctcgaggcc gcggggccgc     420
gggggccgcg ctctgctctc cgcccaggct gggccactgg agcgcgggag ccctggagcc     480
cggcgctgcc cggcgctacc cgccgccctc gggacagtca ccgtgagcaa aagagtcggt    540
gtcatgtgcg taaacgaagc tcttaggagc cgaggataga tttcacagga acgtagtgcc    600
ttgttctgaa agacgcgctt tggttgatat taggaagtat ttttaaaaaa ttggggaggt    660
cgtttccctt gcagctccgc caccatctgc tgcgtggact gagtcagcgt gaggtaaatt    720
tgcagcttcg cgctcctctc ggaggcattg tgctgtcttg tccctttaaa acatgatcat    780
ttctcctcgc ttccaagaag tcttgggtgt ctggtgaaat gacactgtca gtgcgtctga    840
gaggctgagg ctgttcaaag gaaatcagag gctggatttg gcaggccctt tgggaatcaa    900
agttcgcgtc tcctgttaga agagagttgc cttttctctc ctgagggcag gggtcagggg     960
atagcctgag aggaacggcg attcctctcc gtaaactcag atttcctcag tttttaacag    1020
tgtattttca aaagaggac gaaagaagaa gacgagcgtg cggctagcac tgtattctgg    1080
ctcgtgtctt cccgccactc gcaatccgcg ccatcttaac taactttcaa tgtccctcgg    1140
ggctgagcgt gccggcggcg ggtgctgctc gggctgggaa atgctgcggc ctgggttctc    1200
aaccttccgg gtggacgccg cccgtcgggg tagacagagg cgggaacaaa gcgcgttgcg    1260
gcggcgggag gcaggccggt cttgcccca caggctaggc tgcagcttgg ccctggtgca    1320
cccgagccca gagcagcggg gacgggcgt                                       1349
```

<210> SEQ ID NO 107
<211> LENGTH: 1099
<212> TYPE: DNA
<213> ORGANISM: Homo sapiens

<400> SEQUENCE: 107

| | | | | | |
|---|---|---|---|---|---|
| acccgcggcc | tgcaggccat | atttcgcgtc | ctccaaatca | gctgcctagg | gcgggccgtg | 60 |
| acccgaggga | attggagaga | aaagtccaaa | cgctgggcga | gaggcggggt | agggcgccct | 120 |
| ttggaaaccg | ccctgggttt | tgttactccg | gggcccccgg | agcttcggca | cagctacctg | 180 |
| ggtctggcag | gcgcagaggt | gccgtatgca | aatggttcac | tattaggcga | gaaagaaata | 240 |
| cttcaaatgg | ccctttgtaa | ccttctatag | aaaatcgagg | tactctgcat | gacaaagcac | 300 |
| aattaagctt | tctattcagg | agttctgcag | ctggtagccc | attgggaaag | tgggaggaaa | 360 |
| cgcgaatata | ttaatagtgt | ggcgaaagtt | ttttgtgtgc | gtgtccttt | ctaggtcggg | 420 |
| ggtggggagg | ggcggtgggt | ggacgcagag | ggaggaaggc | tcagccttgg | atccttgcca | 480 |
| cctgaacaac | gtcgcctctg | cccacgtgga | aagcctcgct | tgtctggcag | ccggggttct | 540 |
| gaatggttgc | cgcgacccct | gcgctcccag | cagggccaag | aggacctcgc | gggcaccagc | 600 |
| gtccgggcgg | gaagggacgt | gtgcccaagc | ctcgcctcct | ggccctcagt | gggctgggac | 660 |
| gcccttgatc | accggcgcag | gaaagaggct | ccccagcccg | tgagcttcgt | ccgggcgcca | 720 |
| gggcagggat | ggctggtggt | gtgcactgga | gagcacgacg | tgacgctgc | gtgggaaaga | 780 |
| gacgtgggaa | gggcatagcc | ggattatcca | ctcagctcca | attttctcca | agcgccactc | 840 |
| accccacagt | tgaggttcgc | ttcccgattg | ttcatttgta | gagtctaaag | ggaagaaaa | 900 |
| ttttgcctct | gaataaataa | agggcccta | aaaacaactc | tgctgattat | cctgcgtttt | 960 |
| ccatctggat | ccatttcgcc | ctcttctgcc | ctgctgggtg | ccctcggaca | ctgacctttg | 1020 |
| tggacagtat | tagttccttt | atcaactgcg | tcactggcag | gcgcttgcct | ctggcttcca | 1080 |
| tttgcatttg | gtgaataag | | | | | 1099 |

<210> SEQ ID NO 108
<211> LENGTH: 1349
<212> TYPE: DNA
<213> ORGANISM: Homo sapiens

<400> SEQUENCE: 108

| | | | | | |
|---|---|---|---|---|---|
| cagcgtgaga | ctacgtcata | aaataaaata | aaataacaca | aaataaaata | aaataaaata | 60 |
| aaataaaata | aaataaaata | aaataaaata | aaataaaaaa | ataaaataaa | ataaaataaa | 120 |
| ataaagcaat | ttcctttcct | ctaagcggcc | tccacccctc | tcccctgccc | tgtgaagcgg | 180 |
| gtgtgcaagc | tccgggatcg | cagcggtctt | agggaatttc | ccccgcgat | gtccggcgc | 240 |
| gccagttcgc | tgcgcacact | tcgctgcggt | cctcttcctg | ctgtctgttt | actccctagg | 300 |
| ccccgctggg | gacctgggaa | agagggaaag | gcttccccgg | ccagctgcgc | ggcgactccg | 360 |
| gggactccag | ggcgccctc | tgcggccgac | gcccggggtg | cagcggccgc | cggggctggg | 420 |
| gccggcggga | gtccgcggga | ccctccagaa | gagcggccgg | cgccgtgact | cagcactggg | 480 |
| gcggagcggg | gcgggaccac | ccttataagg | ctcggaggcc | gcgaggcctt | cgctggagtt | 540 |
| tcgccgccgc | agtcttcgcc | accagtgagt | acgcgcggcc | cgcgtccccg | gggatggggc | 600 |
| tcagagctcc | cagcatgggg | ccaacccgca | gcatcaggcc | cgggctcccg | gcagggctcc | 660 |
| tcgcccacct | cgagacccgg | gacggggcc | tagggaccc | aggacgtccc | cagtgccgtt | 720 |
| agcggctttc | aggggccccg | gagcgcctcg | gggagggatg | ggaccccggg | ggcggggagg | 780 |

```
gggggcagac tgcgctcacc gcgccttggc atcctccccc gggctccagc aaacttttct    840
ttgttcgctg cagtgccgcc ctacaccgtg gtctatttcc cagttcgagg taggagcatg    900
tgtctggcag ggaagggagg caggggctgg ggctgcagcc cacagcccct cgcccacccg    960
gagagatccg aaccccctta tccctccgtc gtgtggcttt taccccgggc ctccttcctg   1020
ttccccgcct ctcccgccat gctgctcccc cgccccagtg ttgtgtgaaa tcttcggagg   1080
aacctgtttc cctgttccct ccctgcactc ctgaccccct cccgggttgc tgcgaggcgg   1140
agtcggcccg gtccccacat ctcgtacttc tccctccccg caggccgctg cgcggccctg   1200
cgcatgctgc tggcagatca gggccagagc tggaaggagg aggtggtgac cgtgagacg    1260 tggcaggagg gctcactcaa agcctcctgc gtaagtgacc atgcccgggc aaggggaggg   1320
ggtgctgggc cttagggggc tgtgactag                                    1349
```

<210> SEQ ID NO 109
<211> LENGTH: 1149
<212> TYPE: DNA
<213> ORGANISM: Homo sapiens

<400> SEQUENCE: 109

```
tcccagctgc aggcttgtaa tcccagctgc tggggaggct gaggcaggag aatcgcttga     60
acccgggagt cggaggttgc agtgaccega gatcgcgtca ttgcactcca gcctgggcga    120
taagagcgaa actccgtctc aaagaaaaaa aaactaacat aaatgccgtc cctcctttgt    180
tcagaactct ccgtggcttc tagcatcctc acaatgacag tacaacccta ggagtaactc    240
cgcctcatat tcttcgttcc ctgcagaaaa cagctttccg aattctcctg gctcagtcgc    300
gcctcaacct ttgcacgcgc cggttcctcc gcctgtcacg ctctcccaca cctcgtcaca    360
cgcagtgtca aaaaagggc cccacccacg aacgcctcag tgtccccgac cctgggcagc    420
ggggactcga gcaggcgccc ctcactgatg gctttagaac gtgggtgggg aaggtgtgt    480 gaggacggga agacgccgca ctcacctgag ttggcgtcct cagagtggcc gctgccatca    540
gactctgcgg gtagagctgg gccgggagcg acgggcgaca ttggtaggga cccggggaca    600
gcggtcccta tcccaggcct gacgtgggtc ccccagggcg gctcgccaa ggcttagacg    660 cctttcgtgca ggagggacga cgactcccct cacgccttcg tggccccaac tcggcgctct    720
gctatctctg atccggtgaa cacacctcag agaagctaaa atggccgcca cgaagaggcc    780
cccccaaaag tcccgtcctt tctttttgtg actctcaagg aaagtcggtt ttctgagctc    840
ttactggctt agtagcgtgg cgttcaacgc agagcattct aggtaatgta gttttcatag    900
atcccgaggt gggtgccggg gacccttgc accaacctct tggagtaaaa gcgaagctcc    960
agggcgctgg gcgatgagaa atggcttatc caagtcctag ggcagtggag ggacttcgcc   1020
ctttcttaaa tgggtcgtaa tcagacagca tattagaggt gccatctgca actgatcacc   1080
caagtgtttg gggaatatta tttcaaactt cataaagttc agcaggctcc cagaggctaa   1140
aattattat                                                          1149
```

<210> SEQ ID NO 110
<211> LENGTH: 999
<212> TYPE: DNA
<213> ORGANISM: Homo sapiens

<400> SEQUENCE: 110

```
gggctccctg cagccggacg cgggcaacgc gagctggaac gggaccgagg cgccgggggg     60
cggcgcccgg gccacccctt actccctgca ggtgacgctg acgctggtgt gcctggccgg    120
```

```
cctgctcatg ctgctcaccg tgttcggcaa cgtgctcgtc atcatcgccg tgttcacgag    180
ccgcgcgctc aaggcgcccc aaaacctctt cctggtgtct ctggcctcgg ccgacatcct    240
ggtggccacg ctcgtcatcc ctttctcgct ggccaacgag gtcatgggct actggtactt    300
cggcaaggct tggtgcgaga tctacctggc gctcgacgtg ctcttctgca cgtcgtccat    360
cgtgcacctg tgcgccatca gcctggaccg ctactggtcc atcacacagg ccatcgagta    420
caacctgaag cgcacgccgc gccgcatcaa ggccatcatc atcaccgtgt gggtcatctc    480
ggccgtcatc tccttcccgc cgctcatctc catcgagaag aagggcggcg gcggcggccc    540
gcagccggcc gagccgcgct gcgagatcaa cgaccagaag tggtacgtca tctcgtcgtg    600
catcggctcc ttcttcgctc cctgcctcat catgatcctg gtctacgtgc gcatctacca    660
gatcgccaag cgtcgcaccc gcgtgccacc cagccgccgg ggtccggacg ccgtcgccgc    720
gccgccgggg ggcaccgagc gcaggcccaa cggtctgggc cccgagcgca gcgcgggccc    780 gggggggcgca gaggccgaac cgctgcccac ccagctcaac ggcgcccctg gcgagcccgc    840
gccggccggg ccgcgcgaca ccgacgcgct ggacctggag gagagctcgt cttccgacca    900
cgccgagcgg cctccagggc cccgcagacc cgagcgcggt ccccggggca aaggcaaggc    960
ccgagcgagc caggtgaagc cgggcgacag cctgccgcg                           999
```

<210> SEQ ID NO 111
<211> LENGTH: 41
<212> TYPE: DNA
<213> ORGANISM: Artificial Sequence
<220> FEATURE:
<223> OTHER INFORMATION: Primer, multiplex_PCR_primer 1

<400> SEQUENCE: 111
ccactacgcc tccgctttcc tctctatggg cagtcggtga t                         41

<210> SEQ ID NO 112
<211> LENGTH: 21
<212> TYPE: DNA
<213> ORGANISM: Artificial Sequence
<220> FEATURE:
<223> OTHER INFORMATION: primer, multiplex_PCR_primer 2

<400> SEQUENCE: 112
ctgccccggg ttcctcattc t                                               21

<210> SEQ ID NO 113
<211> LENGTH: 27
<212> TYPE: DNA
<213> ORGANISM: Artificial Sequence
<220> FEATURE:
<223> OTHER INFORMATION: primer, Quant_PCR_primer 1

<400> SEQUENCE: 113
ccactacgcc tccgctttcc tctctat                                         27

<210> SEQ ID NO 114
<211> LENGTH: 21
<212> TYPE: DNA
<213> ORGANISM: Artificial Sequence
<220> FEATURE:
<223> OTHER INFORMATION: primer, Quant_PCR_primer 2

<400> SEQUENCE: 114
ctgccccggg ttcctcattc t                                               21

PROSTATE CANCER MARKERS

This application is a National Stage of PCT/EP2012/057225, filed Apr. 19, 2012 which claims priority to European Application No. 11162979.6, filed Apr. 19, 2011, the disclosures of which are incorporated herein by reference in their entirety.

FIELD OF THE INVENTION

The present invention is in the field of biology and chemistry. In particular, the invention is in the field of molecular biology. More particular, the invention relates to the analysis of the methylation status of genomic regions. Most particularly, the invention is in the field of diagnosing prostate cancer.

The instant application contains a Sequence Listing which has been submitted in ASCII format via EFS-Web and is hereby incorporated by reference in its entirety. Said ASCII copy, created on Oct. 16, 2013, is named 0117_0002US1_Sequence_Listing.txt and is 234682 bytes in size.

BACKGROUND

Reversible methylation of cytosines is a major epigenetic modification in multicellular organisms and is found in many human diseases including cancer. Cancer epigenomes are found to be globally hypomethylated with promoter-specific hypermethylations. Furthermore, cytosine methylation results in transcriptional repression, which, in the case of tumour suppressor genes, apoptotic genes, DNA repair genes and factors controlling cell cycle check points leads to tumour progression.

Prostate cancer (PC) is the third most common cause of male cancer deaths in developed countries. Diagnosed at an early stage PC is a curable disease. Therapies reach from watchful waiting to radical prostatectomy, hormone or radiation therapy. Nevertheless, because of its yet mostly unpredictable outcome patients are often treated without clear benefit.

Prostate specific antigen (PSA) is used as a biomarker to screen men for potential tumour development. However, low specificity and sensitivity leads to wrong diagnoses. In particular, elevated PSA can also result from an inflammation or precedent transrectal ultrasound, i.e. disclosure within the state of the art lacks an unequivocal diagnosis of PC.

It is therefore clear that there has been and remains today a long standing need for an accurate and reliable test to diagnose PC.

Recent years have brought a marked extension of our understanding of the somatic basis of prostate cancer. With one to three mutations per megabase the mutation frequency is similar to that observed in acute myeloid leukemia and breast cancer and lies within the lower range of cancer. Based on the frequency and the fact that primarily a diverse array of genes is affected the main genomic alterations appear to be genomic rearrangements and changes in the epigenetic structure of the DNA.

Michael Weber et al. (Nature Genetics, Vol. 37, No. 8, Aug. 1, 2005, pages 853-862) disclose DNA methylation markers for colorectal cancer. For the analyses colorectal cancer cell lines and tissues, and a prostate cancer cell line were used, but no primary prostate cancer tissues. In addition, experiments are based on arrays which narrow down the possibility to detect new DMRs.

Ilana Keshet et al (Nature Genetics, Vol. 38, No. 2, Feb. 1, 2006, pages 149-153) disclose methylation of GSTP1 and CDKN2A in Caco2 and PC3 cell lines (has been shown before) by PCR analyses. Furthermore, they compare methylation information obtained by MeDIP array (10.000 promoter elements) analyses of PC3, Caco2, normal lymphoblasts, normal colon tissue and six colon tumors. Again, no primary prostate cancer tissues have been used, and experiments are restricted to array regions.

Tokumaru (Clinical Cancer Research, Vol. 10, No. 16, Aug. 15, 2004, pages 5518-5522) disclose the usability of combinations of the methylation values of four genes obtained by qPCR to help in tumour classification of needle biopsies: Combinations of RARRES1, APC, RARB2, and GSTP1 methylation were used to classify 72 prostate samples (56 cancer, only 16 normal) with 100% specificity and 97% sensitivity. RARB2 as well as GSTP1 are listed in our patent application (SEQ ID NO: 36 and 108).

Hoque Mohammad Obaidul et al (Journal of clinical oncology, American Society of Clinical Onoclogy, Vol. 23, No. 27, Sep. 20, 2005, pages 6569-6575) disclose the usability of the methylation values of CDKN2A, p14$^{ARF}$, MGMT, and GSTP1 as markers for qMSP based PCa detection in urinary sediment in 52 PCa cases and 91 age matched controls without precedent PCa history with a sensitivity of 87% and a specificity of 100%. Only GSTP1 may overlap with the regions listed below.

Jacinto Filipe V et al (Biotechniques, January 2008, Vol. 44, No. 1) review MeDIP experiments Ke Xi-Song et al (BMC Genomics, Biomed Central, London, Vol. 11, No, 1, Nov. 25, 2010) performed array profiling (17.000 RefSeq genes −5.5 kb-+2.5 kb) of histone modifications (chromatin IP) and DNA methylation (MeDIP) in EP156T, EPT1 and EPT2 cells and correlated the results to gene expression profiles (Agilent 44 k chip) and disclose histone modifications with correlating gene expression changes during epithelial to mesenchymal transition (EMT). Here only cell lines are used, no DNA methylation PCa markers are named.

Matheys Lesley A et al (Molecular Cancer, Biomed Central, London, GB, Vol. 9, No. 1, October 2010) disclose hypomethylation in BMX and SOX1 in the invasive subpopulations of LNCaP and DU145 cells causing overexpression of said genes and name alterations in the STAT3 pathway as key features of invasiveness. Using MeDIP array analyses they found 869 genes hypermethylated in invasive LNCaP (1015 in invasive DU145) and 44 genes hypomethylated in invasive LNCaP and DU145 cells. They compared subpopulations of prostate cancer cell lines and did not include prostate tissue specimens to validate the significance of their findings in clinical samples.

U.S. Pat. No. 6,812,339 disclose single nucleotide polymorphisms (SNPs) in genes that have been identified as being involved in pathologies associated with human disease. The diseases/pathologies that each gene is known in the art to be associated with is specifically indicated in Table 1 therein. The US patent does not relate to methylation patterns at all and uses a different approach. A nucleic acid disclosed therein shares some similarity with SEQ ID NO. 1 herein.

Aberrant DNA methylation plays an important role in prostate cancer development and seems to be one of the earliest events in tumourigenesis. The most prominent differentially methylated gene in prostate cancer is glutathione S-transferase pi 1 (GSTP1).

Other genes with changes in promoter methylation include multidrug resistance protein 1 (MDR1), O-6-methylguanine-DNA methyltransferase (MGMT), Ras association domain family member 1 (RASSF1), retinoic acid receptor beta (RARB), adenomatous polyposis coli (APC), androgen receptor (AR), cyclin-dependent kinase inhibitor 2A (CDKN2A), E-cadherin (CDH1) and CD44, but show inconsistent methylation levels in different studies.

Even though the relevance of DNA methylations for normal cell homeostasis is undeniable, little is known about the genomic distribution in normal and diseased states. Accordingly, there is a need in the state of the art of studying genome-wide aberrant DNA methylation that can be associated with high confidence to PC and identifying biomarkers for PC diagnosis based on the epigenetic cancer information.

SUMMARY OF THE INVENTION

The invention encompasses the identification and selection of novel genomic regions (biomarkers) and the identification and selection of novel genomic region pairs which are hypermethylated in subjects with prostate cancer compared to subjects without prostate cancer so as to provide a simple and reliable test for prostate cancer. Nucleic acids which selectively hybridize to the genomic regions and products thereof are also encompassed within the scope of the invention as are compositions and kits containing said nucleic acids and nucleic acids for use in diagnosing prostate cancer. Further encompassed by the invention is the use of nucleic acids each thereof selectively hybridizing to one of the genomic regions or products thereof to monitor disease regression in a patient and the efficacy of therapeutic regimens.

For the first time the inventors have identified genomic regions by genome-wide approaches based on high throughput sequencing (methylated DNA immunoprecipitation, MeDIP-Seq), having cytosines that are hypermethylated in PC (Table 1) and thus, by quantifying the methylation status of specific genomic regions, permit the accurate and reliable diagnosis of prostate cancer (PC). Notably, the regions are not always in promoter regions or genes.

TABLE 1

Hypermethylated genomic regions in prostate cancer positive samples.
Column 1: Number according to Sequence ID; Column 2: locus in genome determined by the chromosome number and start and stop position of the sequence; Column 3: length of sequence; Column 4: associated or nearby gene; Column 5: minimal distance to the nearest transcription start site in base pairs.

| SEQ ID NO | Locus | length | Gene in the proximity |
|---|---|---|---|
| 1 | chr7: 157481151-157482600 | 1450 | PTPRN2 |
| 2 | chr7: 116140001-116140800 | 800 | AC073130.3\|CAV2 |
| 3 | chr14: 31344301-31345250 | 950 | COCH |
| 4 | chr9: 37002401-37003250 | 850 | WASF2 |
| 5 | chr8: 70946751-70947700 | 950 | AP006222.2 |
| 6 | chr7: 157484001-157486250 | 2250 | AP006222.2 |
| 7 | chr6: 26017301-26018000 | 700 | HIST1H1A\|HIST1H1PS2 |
| 8 | chr9: 112810101-112811000 | 900 | AKAP2 |
| 9 | chr12: 65218251-65220500 | 2250 | TBC1D30 |
| 10 | chr12: 54440251-54442000 | 1750 | AC114498.2 |
| 11 | chr6: 29973901-29975600 | 1700 | HLA-J\|PPP1R11\|HCG4P3 |
| 12 | chr4: 185936801-185937900 | 1100 | CR1 |
| 13 | chr6: 56818401-56819300 | 900 | BEND6\|DST |
| 14 | chr11: 58940301-58941400 | 1100 | DTX4 |
| 15 | chr9: 126774501-126776750 | 2250 | AC006450.3\|LHX2 |
| 16 | chr12: 104852001-104853350 | 1350 | CHST11 |
| 17 | chr4: 85414401-85415000 | 600 | DENND1B |

TABLE 1-continued

Hypermethylated genomic regions in prostate cancer positive samples.
Column 1: Number according to Sequence ID; Column 2: locus in genome determined by the chromosome number and start and stop position of the sequence; Column 3: length of sequence; Column 4: associated or nearby gene; Column 5: minimal distance to the nearest transcription start site in base pairs.

| SEQ ID NO | Locus | length | Gene in the proximity |
|---|---|---|---|
| 18 | chr7: 143579051-143580250 | 1200 | FAM115A |
| 19 | chr3: 170745901-170746800 | 900 | SLC2A2 |
| 20 | chr2: 235404251-235405000 | 750 | ARL4C |
| 21 | chr4: 85402101-85403500 | 1400 | DENND1B |
| 22 | chr7: 29185426-29186350 | 925 | CPVL\|CHN2 |
| 23 | chr4: 41880751-41883500 | 2750 | AL358857.1 |
| 24 | chr3: 138154101-138154650 | 550 | ESYT3 |
| 25 | chr17: 43973501-43975400 | 1900 | AL449063.1 |
| 26 | chr1: 15480801-15481550 | 750 | TMEM51 |
| 27 | chr1: 203598351-203599000 | 650 | ATP2B4 |
| 28 | chr13: 100640801-100642200 | 1400 | FAM87B |
| 29 | chr3: 172165201-172166800 | 1600 | GHSR |
| 30 | chr4: 41867301-41869700 | 2400 | ATP2B4 |
| 31 | chr11: 3181451-3182200 | 750 | FAM87B |
| 32 | chr11: 62690651-62691675 | 1025 | CHRM1 |
| 33 | chr7: 116140101-116141200 | 3100 | AC073130.3\|CAV2 |
| 34 | chr19: 17246001-17246750 | 750 | AL449063.1 |
| 35 | chr14: 36991501-36994250 | 2750 | AL132857.1 |
| 36 | chr3: 25469201-25470000 | 800 | AC098477.3\|RARB |
| 37 | chr1: 119526751-119530700 | 3950 | TBX15 |
| 38 | chr2: 201450351-201451000 | 650 | AOX1\|AC080164.1 |
| 39 | chr20: 50721001-50722800 | 1800 | ZFP64 |
| 40 | chr7: 127807851-127809100 | 1250 | AL928711.1 |
| 41 | chr1: 197887251-197890900 | 3650 | LHX9 |
| 42 | chr9: 126775751-126779750 | 4000 | LHX2 |
| 43 | chr6: 150285251-150286700 | 1450 | ULBP1 |
| 44 | chr1: 24648501-24649600 | 1100 | AL590683.2\|GRHL3 |
| 45 | chr2: 237077751-237080600 | 2850 | AC019068.1 |
| 46 | chr1: 119526751-119528200 | 1450 | AL449063.1 |
| 47 | chr20: 37356001-37358250 | 2250 | NTRK1 |
| 48 | chr4: 85402001-85404750 | 2750 | DENND1B |
| 49 | chr19: 16436501-16438750 | 2250 | KLF2 |
| 50 | chr6: 127835401-127836600 | 1200 | AL096711.2 |
| 51 | chr1: 58714251-58716500 | 2250 | DAB1 |
| 52 | chr1: 146549751-146552750 | 3000 | U1\|AL596177.3 |
| 53 | chr3: 148631601-48632850 | 1250 | COL7A1 |
| 54 | chr15: 90039101-90040250 | 1150 | RHCG |
| 55 | chr20: 20345251-20346650 | 1400 | TMEM51 |
| 56 | chr14: 29253901-29255300 | 1400 | TNFRSF9 |
| 57 | chr10: 94821701-94822900 | 1200 | AL358613.1\|CYP26C1 |
| 58 | chr18: 56939401-56941750 | 2350 | RAX |
| 59 | chr7: 151107751-151108900 | 1150 | AC005996.2\|WDR86 |
| 60 | chr1: 119541501-119545250 | 3750 | AL139420.1\|AL139420.2 |
| 61 | chr20: 50720751-50722750 | 2000 | ZFP64 |
| 62 | chr19: 48983501-48984100 | 600 | AL449063.1 |
| 63 | chr3: 125898501-125900400 | 1900 | ALDH1L1 |
| 64 | chr7: 129421101-129423700 | 2600 | AP006222.2 |
| 65 | chr2: 27529501-27531700 | 2200 | UCN\|TRIM54 |
| 66 | chr6: 28367001-28368100 | 1100 | ZSCAN12 |
| 67 | chr5: 140810001-140812200 | 2200 | PCDHGA12 |
| 68 | chr11: 20618151-20619600 | 1450 | SLC6A5 |
| 69 | chr9: 135620101-135621000 | 900 | C9orf98 |
| 70 | chr7: 19145401-19147900 | 2500 | AL590683.1 |
| 71 | chr7: 45613251-45613800 | 550 | ADCY1 |
| 72 | chr2: 73147201-73148200 | 1000 | AL449063.1 |
| 73 | chr4: 11428951-11429850 | 900 | HS3ST1 |
| 74 | chr6: 28367001-28368050 | 1050 | ZSCAN12 |
| 75 | chr10: 102894701-102897000 | 2300 | C1orf212 |
| 76 | chr1: 146555301-146557500 | 2200 | RP11-325P15.2\|U1 |
| 77 | chr14: 85996251-85999250 | 3000 | AL049775.1\|FLRT2 |
| 78 | chr6: 137809001-137810400 | 1400 | AP006222.2 |
| 79 | chr14: 85996751-85998400 | 1650 | AL049775.1\|FLRT2 |
| 80 | chr9: 135461001-135463300 | 2300 | AL117337.4 |
| 81 | chr7: 96632101-96633450 | 1350 | DLX6AS |
| 82 | chr1: 70034801-70036500 | 1700 | LRRC7 |
| 83 | chr7: 157478101-157479750 | 1650 | AP006222.2 |
| 84 | chr12: 54440351-54442300 | 1950 | AC114498.2 |
| 85 | chr17: 41363301-41364700 | 1400 | TMEM106A |

TABLE 1-continued

Hypermethylated genomic regions in prostate cancer positive samples.
Column 1: Number according to Sequence ID; Column 2: locus in
genome determined by the chromosome number and start and stop
position of the sequence; Column 3: length of sequence; Column
4: associated or nearby gene; Column 5: minimal distance to the
nearest transcription start site in base pairs.

| SEQ ID NO | Locus | length | Gene in the proximity |
|---|---|---|---|
| 86 | chr7: 97360551-97361900 | 1350 | TAC1 |
| 87 | chr2: 87015901-87016700 | 800 | CD8A |
| 88 | chr12: 54446751-54449000 | 2250 | HOXC4 |
| 89 | chr5: 77268001-77268500 | 500 | USH2A |
| 90 | chr3: 68979651-68981600 | 1950 | FAM19A4 |
| 91 | chr12: 122016501-122017250 | 750 | KDM2B |
| 92 | chr4: 16084551-16085900 | 1350 | PROM1 |
| 93 | chr19: 46915001-46917000 | 2000 | CCDC8 |
| 94 | chr6: 29973751-29975600 | 1850 | HLA-J\|PPP1R11\|HCG4P3 |
| 95 | chr3: 154145501-154147250 | 1750 | GPR149 |
| 96 | chr10: 94821601-94823300 | 1700 | CYP26C1 |
| 97 | chr2: 220117251-220118350 | 1100 | TUBA4B\|TUBA1 |
| 98 | chr7: 32981501-32982250 | 750 | RP9P\|AC018648.1 |
| 99 | chr2: 45169501-45170400 | 900 | AC012354.4\|SIX3 |
| 100 | chr10: 102905501-102906300 | 800 | C1orf212 |
| 101 | chr16: 54970051-54972800 | 2750 | AL449063.1 |
| 102 | chr17: 78806501-78807750 | 1250 | AL121999.1 |
| 103 | chr7: 128337251-128338000 | 750 | 5S_rRNA\|AC018638.7 |
| 104 | chr3: 129024351-129025150 | 800 | AL390856.3 |
| 105 | chr5: 140892051-140893750 | 1700 | AC092765.3 |
| 106 | chr2: 162283301-162284650 | 1350 | AL449063.1 |
| 107 | chr4: 54975401-54976500 | 1100 | AL391845.2 |
| 108 | chr11: 67350751-67352100 | 1350 | GSTP1 |
| 109 | chr19: 158219801-58220950 | 1150 | ZNF154 |
| 110 | chr10: 112837801-112838800 | 1000 | ADRA2A |

The present invention contemplates a method for diagnosis of prostate cancer, comprising the steps of analyzing in a sample of a subject the DNA methylation status of the genomic regions of at least one genomic region pair selected from the group of Table 2, wherein, if at least one genomic region pair is hypermethylated, the sample is designated as prostate cancer positive.

TABLE 2

Genomic region pairs for the diagnosis of prostate cancer. A genomic
region pair (grp; Column 1) is determined by a combination of genomic
region 1 (Column 2) and genomic region 2 (Column 3).

| Genomic region pair (grp) | Genomic region 1 [SEQ ID NO.] | Genomic region 2 [SEQ ID NO.] |
|---|---|---|
| grp 1 | 29 | 86 |
| grp 2 | 8 | 13 |
| grp 3 | 8 | 27 |
| grp 4 | 8 | 39 |
| grp 5 | 8 | 86 |
| grp 6 | 6 | 95 |
| grp 7 | 3 | 31 |
| grp 8 | 19 | 62 |
| grp 9 | 6 | 7 |
| grp 10 | 8 | 90 |
| grp 11 | 7 | 62 |
| grp 12 | 8 | 22 |
| grp 13 | 23 | 95 |
| grp 14 | 8 | 12 |
| grp 15 | 8 | 50 |
| grp 16 | 8 | 95 |
| grp 17 | 31 | 98 |
| grp 18 | 3 | 8 |
| grp 19 | 8 | 9 |
| grp 20 | 6 | 86 |
| grp 21 | 14 | 95 |
| grp 22 | 8 | 47 |
| grp 23 | 16 | 23 |
| grp 24 | 21 | 98 |
| grp 25 | 22 | 95 |
| grp 26 | 6 | 16 |
| grp 27 | 12 | 19 |
| grp 28 | 13 | 19 |
| grp 29 | 16 | 41 |
| grp 30 | 27 | 44 |
| grp 31 | 31 | 95 |
| grp 32 | 46 | 62 |
| grp 33 | 55 | 86 |
| grp 34 | 62 | 86 |
| grp 35 | 4 | 8 |
| grp 36 | 7 | 98 |
| grp 37 | 8 | 19 |
| grp 38 | 8 | 43 |
| grp 39 | 19 | 65 |
| grp 40 | 22 | 86 |
| grp 41 | 27 | 31 |
| grp 42 | 95 | 98 |
| grp 43 | 8 | 30 |
| grp 44 | 8 | 33 |
| grp 45 | 8 | 108 |
| grp 46 | 9 | 59 |
| grp 47 | 20 | 95 |
| grp 48 | 26 | 47 |
| grp 49 | 31 | 33 |
| grp 50 | 42 | 95 |
| grp 51 | 60 | 97 |
| grp 52 | 88 | 95 |
| grp 53 | 6 | 57 |
| grp 54 | 8 | 21 |
| grp 55 | 8 | 45 |
| grp 56 | 8 | 46 |
| grp 57 | 20 | 86 |
| grp 58 | 47 | 62 |
| grp 59 | 12 | 21 |
| grp 60 | 19 | 37 |
| grp 61 | 27 | 101 |
| grp 62 | 29 | 95 |
| grp 63 | 31 | 37 |
| grp 64 | 46 | 59 |
| grp 65 | 55 | 95 |
| grp 66 | 59 | 95 |
| grp 67 | 3 | 47 |
| grp 68 | 6 | 98 |
| grp 69 | 8 | 65 |
| grp 70 | 9 | 98 |
| grp 71 | 13 | 95 |
| grp 72 | 23 | 86 |
| grp 73 | 25 | 95 |
| grp 74 | 31 | 57 |
| grp 75 | 33 | 95 |
| grp 76 | 62 | 98 |
| grp 77 | 4 | 95 |
| grp 78 | 8 | 68 |
| grp 79 | 12 | 16 |
| grp 80 | 14 | 98 |
| grp 81 | 19 | 86 |
| grp 82 | 20 | 46 |
| grp 83 | 22 | 29 |
| grp 84 | 31 | 32 |
| grp 85 | 31 | 86 |
| grp 86 | 46 | 104 |
| grp 87 | 62 | 69 |
| grp 88 | 69 | 98 |
| grp 89 | 76 | 89 |
| grp 90 | 7 | 8 |
| grp 91 | 7 | 20 |
| grp 92 | 8 | 16 |
| grp 93 | 8 | 17 |
| grp 94 | 8 | 20 |
| grp 95 | 8 | 100 |

TABLE 2-continued

Genomic region pairs for the diagnosis of prostate cancer. A genomic region pair (grp; Column 1) is determined by a combination of genomic region 1 (Column 2) and genomic region 2 (Column 3).

| Genomic region pair (grp) | Genomic region 1 [SEQ ID NO.] | Genomic region 2 [SEQ ID NO.] |
|---|---|---|
| grp 96 | 8 | 106 |
| grp 97 | 12 | 97 |
| grp 98 | 16 | 19 |
| grp 99 | 16 | 45 |
| grp 100 | 19 | 27 |

The invention also relates to a nucleic acid molecule that hybridizes under stringent conditions in the vicinity of one of the genomic regions according to SEQ ID NO. 1 to SEQ ID NO. 110, wherein said vicinity is any position having a distance of up to 500 nt from the 3' or 5' end of said genomic region, wherein said vicinity includes the genomic region itself.

The invention further relates to the use of nucleic acids for the diagnosis of prostate cancer.

The present invention also comprises the use of an antibody for the diagnosis of prostate cancer.

Another subject of the present invention is a composition and a kit comprising one or more of said nucleic acids and/or antibody for the diagnosis of prostate cancer.

The following detailed description of the invention refers, in part, to the accompanying drawings and does not limit the invention.

DEFINITIONS

The following definitions are provided for specific terms which are used in the following.

The articles "a" and "an" are used herein to refer to one or to more than one (i.e. to at least one) of the grammatical object of the article. By way of example, "an element" means one element or more than one element. In contrast, "one" is used to refer to a single element.

As used herein, the term "amplified", when applied to a nucleic acid sequence, refers to a process whereby one or more copies of a particular nucleic acid sequence is generated from a nucleic acid template sequence, preferably by the method of polymerase chain reaction. Other methods of amplification include, but are not limited to, ligase chain reaction (LCR), polynucleotide-specific based amplification (NSBA), or any other method known in the art.

As used herein, the term "biomarker" refers to (a) a genomic region that is differentially methylated, particularly hypermethylated, or (b) a gene that is differentially expressed, wherein the status (hypo-/hypermethylation and/ or up-/downregulated expression) of said biomarker can be used for diagnosing PC or a stage of PC as compared with those not having PC. Within the context of the invention, a genomic region or parts thereof or fragment thereof are used as a biomarker for PC. Within this context "parts of a genomic region" or a "fragment of a biomarker" means a portion of the genomic region or a portion of a biomarker comprising 1 or more CpG positions.

As used herein, the term "composition" refers to any mixture. It can be a solution, a suspension, liquid, powder, a paste, aqueous, non-aqueous or any combination thereof.

The term "CpG position" as used herein refers to a region of DNA where a cytosine nucleotide is located next to a guanine nucleotide in the linear sequence of bases along its length. "CpG" is shorthand for "C-phosphate-G", that is, cytosine and guanine separated by a phosphate, which links the two nucleosides together in DNA. Cytosines in CpG dinucleotides can be methylated to form 5-methylcytosine. This methylation of cytosines of CpG positions is a major epigenetic modification in multicellular organisms and is found in many human diseases including prostate cancer.

As used herein, the term "diagnosis" refers to the identification of the disease (PC) at any stage of its development, and also includes the determination of predisposition of a subject to develop the disease. In a preferred embodiment of the invention, diagnosis of PC occurs prior to the manifestation of symptoms. Subjects with a higher risk of developing the disease are of particular concern. The diagnostic method of the invention also allows confirmation of PC in a subject suspected of having PC.

As used herein, the term "differential expression" refers to a difference in the level of expression of the RNA and/or protein products of one or more biomarkers, as measured by the amount or level of RNA or protein. In reference to RNA, it can include difference in the level of expression of mRNA, and/or one or more spliced variants of mRNA and/or the level of expression of small RNA (miRNA) of the biomarker in one sample as compared with the level of expression of the same one or more biomarkers of the invention as measured by the amount or level of RNA, including mRNA, spliced variants of mRNA or miRNA in a second sample or with regard to a threshold value. "Differentially expressed" or "differential expression" can also include a measurement of the protein, or one or more protein variants encoded by the inventive biomarker in a sample as compared with the amount or level of protein expression, including one or more protein variants of the biomarker in another sample or with regard to an threshold value. Differential expression can be determined, e.g. by array hybridization, next generation sequencing, RT-PCR or an immunoassay and as would be understood by a person skilled in the art.

As used herein, the term "differential methylation" or "aberrant methylation" refers to a difference in the level of DNA/cytosine methylation in a prostate cancer (PC) positive sample as compared with the level of DNA methylation in a PC negative sample. The "DNA methylation status" is interchangeable with the term "DNA methylation level" and can be assessed by determining the ratio of methylated and non-methylated DNA of a genomic region or a portion thereof and is quoted in percentage. For example, the methylation status of a sample is 60% if 60% of the analyzed genomic region of said sample is methylated and 40% of the analyzed genomic region of said sample is unmethylated.

The methylation status can be classified as increased ("hypermethylated"), decreased ("hypomethylated") or normal as compared to a benign sample. The term "hypermethylated" is used herein to refer to a methylation status of at least more than 10% methylation in the tumour in comparison to the maximal possible methylation value in the normal, most preferably above 15%, 20%, 25% or 30% of the maximum values. For comparison, a hypomethylated sample has a methylation status of less than 10%, most preferably below 15%, 20%, 25% or 30% of the minimal methylation value in the normal.

The percentage values can be estimated from bisulphite mass spectrometry data (Epityper). Being obvious to the skilled person, the measurement error of the method (ca 5%) and the error coming from preparation of the sample must be considered. Particularly, the aforementioned values assume a sample which is not contaminated with other DNA (e.g. micro dissected sample) than those coming from prostate cells. As would be understood to the skilled person the values must be recalculated for contaminated samples (e.g. macro dissected samples). If desired, other methods can be used, such as the methods described in the following for analyzing the methylation status. However, the skilled person readily knows that the absolute values as well as the measurement error can differ for different methods and he knows how to compensate for this.

The term, "analyzing the methylation status" or "measuring the methylation", as used herein, relates to the means and methods useful for assessing and quantifying the methylation status. Useful methods are bisulphite-based methods, such as bisulphite-based mass spectrometry, bisulphite-based sequencing methods or enrichment methods such as MeDIP-Sequencing methods. Likewise, DNA methylation can also be analyzed directly via single-molecule real-time sequencing, single-molecule bypass kinetics and single-molecule nanopore sequencing.

As used herein, the term "genomic region" refers to a sector of the genomic DNA of any chromosome that can be subject to differential methylation, in particular to a DNA hypermethylation, within said sector and may be used as a biomarker for the diagnosis of PC according to the invention. For example, each sequence listed in Table 1 and Table 2 with the corresponding SEQ ID No. 1 to 110 is a genomic region according to the invention. A genomic region can comprise the full sequence or parts thereof provided that at least one CpG position is comprised by said part. Preferably, said part comprises between 1-15 CpG positions. In another embodiment, the genomic region can comprise at least 1, 2, 3, 4, 5, 6, 7, 8, 9, 10, 11, 12, 13, 14, or 15 CpG positions.

A combination of two genomic regions selected from Table 1 is named "genomic region pair" with some examples are given in Table 2. Genomic regions that occur in the vicinity of genes may be associated with the names of those genes for descriptive purpose. This may not mean, that the genomic region comprises all or a part of that gene or functional elements of it. In case of doubt, solely the locus and/or the sequence shall be used.

As used herein, the term "in the vicinity of a genomic region" refers to a position outside or within said genomic region. As would be understood to a person skilled in the art the position may have a distance up to 500 nucleotides (nt), 400 nt, 300 nt, 200 nt, 100 nt, 50 nt, 20 nt or 10 nt from the 5' or 3' end of the genomic region. Alternatively, the position is located at the 5' or 3' end of said genomic region, or, the position is within said genomic region.

The term "genomic region specific primers" as used herein refers to a primer pair hybridizing to a flanking sequence of a target sequence to be amplified. Such a sequence starts and ends in the vicinity of a genomic region. In one embodiment, the target sequence to be amplified comprises the whole genomic region and its complementary strand. In a preferred embodiment, the target sequence comprises 1, 2, 3, 4, 5, 6, 7, 8, 9, 10, 11, 12, 13, 14, 15 or even more CpG positions of the genomic region and the complementary strand thereof. In general, the hybridization position of each primer of the primer pair can be at any position in the vicinity of a genomic region provided that the target sequence to be amplified comprises at least one CpG position of said genomic region. As would be obvious to the skilled person, the sequence of the primer depends on the hybridization position and on the method for analyzing the methylation status, e.g. if a bisulphite based method is applied, part of the sequence of the hybridization position may be converted by said bisulphite. Therefore, in one embodiment, the primers may be adapted accordingly to still enable or disable hybridization (e.g. in methylation specific PCR).

The term "genomic region specific probe" as used herein refers to a probe that selectively hybridizes to a genomic region. In one embodiment a genomic region specific probe can be a probe labelled, for example with a fluorophore and a quencher, such as a TaqMan® probe or a Molecular Beacons probes. In a preferred embodiment, the probe can hybridize to a position of the genomic region that can be subject to hypermethylation according to the inventive method. Hereby, the probe hybridizes to positions with either a methylated CpG or a unmethylated CpG in order to detect methylated or unmethylated CpGs. In a preferred embodiment, two probes are used, e.g. in a methylight (qPCR assay) assay. The first probe hybridizes only to positions with a methylated CpG, the second probe hybridizes only to positions with a unmethylated CpG, wherein the probes are differently labelled and, thus, allow for discrimination between unmethylated and methylated sites in the same sample.

As used herein, the terms "hybridizing to" and "hybridization" are interchangeable used with the term "specific for" and refer to the sequence specific non-covalent binding interactions with a complementary nucleic acid, for example, interactions between a target nucleic acid sequence and a target specific nucleic acid primer or probe. In a preferred embodiment a nucleic acid, which hybridizes is one which hybridizes with a selectivity of greater than 70%, greater than 80%, greater than 90% and most preferably of 100% (i.e. cross hybridization with other DNA species preferably occurs at less than 30%, less than 20%, less than 10%). As would be understood to a person skilled in the art, a nucleic acid, which "hybridizes" to the DNA product of a genomic region of the invention can be determined taking into account the length and composition.

As used herein, "isolated" when used in reference to a nucleic acid means that a naturally occurring sequence has been removed from its normal cellular (e.g. chromosomal) environment or is synthesised in a non-natural environment (e.g. artificially synthesised). Thus, an "isolated" sequence may be in a cell-free solution or placed in a different cellular environment.

As used herein, a "kit" is a packaged combination optionally including instructions for use of the combination and/or other reactions and components for such use.

As used herein, "nucleic acid(s)" or "nucleic acid molecule" generally refers to any ribonucleic acid or deoxyribonucleic acid, which may be unmodified or modified DNA. "Nucleic acids" include, without limitation, single- and double-stranded nucleic acids. As used herein, the term "nucleic acid(s)" also includes DNA as described above that contain one or more modified bases. Thus, DNA with backbones modified for stability or for other reasons are "nucleic acids". The term "nucleic acids" as it is used herein embraces such chemically, enzymatically or metabolically modified forms of nucleic acids, as well as the chemical forms of DNA characteristic of viruses and cells, including for example, simple and complex cells.

The term "primer", as used herein, refers to an nucleic acid, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the nucleic acid primer typically contains 15-25 or more nucleotides, although it may contain fewer nucleotides. The factors involved in determining the appropriate length of primer are readily known to one of ordinary skill in the art. In general, the design and selection of primers embodied by the instant invention is according to methods that are standard and well known in the art, see Dieffenbach, C. W., Lowe, T. M. J., Dveksler, G. S. (1995) General Concepts for PCR Primer Design. In: PCR Primer, A Laboratory Manual (Eds. Dieffenbach, C. W, and Dveksler, G. S.) Cold Spring Harbor Laboratory Press, New York, 133-155; Innis, M. A., and Gelfand, D. H. (1990) Optimization of PCRs. In: PCR protocols, A Guide to Methods and Applications (Eds. Innis, M. A., Gelfand, D. H., Sninsky, J. J, and White, T. J.) Academic Press, San Diego, 3-12; Sharrocks, A. D. (1994) The design of primers for PCR. In: PCR Technology, Current Innovations (Eds. Griffin, H. G., and Griffin, A. M, Ed.) CRC Press, London, 5-11.

As used herein, the term "probe" means nucleic acid and analogs thereof and refers to a range of chemical species that recognise polynucleotide target sequences through hydrogen bonding interactions with the nucleotide bases of the target sequences. The probe or the target sequences may be single- or double-stranded DNA. A probe is at least 8 nucleotides in length and less than the length of a complete polynucleotide target sequence. A probe may be 10, 20, 30, 50, 75, 100, 150, 200, 250, 400, 500 and up to 2000 nucleotides in length. Probes can include nucleic acids modified so as to have a tag which is detectable by fluorescence, chemiluminescence and the like ("labelled probe"). The labelled probe can also be modified so as to have both a detectable tag and a quencher molecule, for example Taqman® and Molecular Beacon® probes. The nucleic acid and analogs thereof may be DNA, or analogs of DNA, commonly referred to as antisense oligomers or antisense nucleic acid. Such DNA analogs comprise but are not limited to 2-'O-alkyl sugar modifications, methylphosphonate, phosphorothiate, phosphorodithioate, formacetal, 3'-thioformacetal, sulfone, sulfamate, and nitroxide backbone modifications, and analogs wherein the base moieties have been modified. In addition, analogs of oligomers may be polymers in which the sugar moiety has been modified or replaced by another suitable moiety, resulting in polymers which include, but are not limited to, morpholino analogs and peptide nucleic acid (PNA) analogs (Egholm, et al. Peptide Nucleic Acids (PNA)-Oligonucleotide Analogues with an Achiral Peptide Backbone, (1992)).

The term "sample" or "biological sample" is used herein to refer to prostate tissue, blood, urine, semen, prostatic secretions or isolated prostate cells originating from a subject, preferably to prostate tissue, prostatic secretions or isolated prostate cells, most preferably to prostate tissue.

As used herein, the term "DNA sequencing" or "sequencing" refers to the process of determining the nucleotide order of a given DNA fragment. As known to those skilled in the art, sequencing techniques comprise sanger sequencing and next-generation sequencing, such as 454 pyrosequencing, Illumina (Solexa) sequencing and SOLiD sequencing.

The term "bisulphite sequencing" refers to a method well-known to the person skilled in the art comprising the steps of (a) treating the DNA of interest with bisulphite, thereby converting non-methylated cytosines to uracils and leaving methylated cytosines unaffected and (b) sequencing the treated DNA, wherein the existence of a methylated cytosine is revealed by the detection of a non-converted cytosine and the absence of a methylated cytosine is revealed by the detection of a thymine.

As used herein, the terms "subject" and "patient" are used interchangeably to refer to an animal (e.g., a mammal, a fish, an amphibian, a reptile, a bird and an insect). In a specific embodiment, a subject is a mammal (e.g., a non-human mammal and a human). In another embodiment, a subject is a primate (e.g., a chimpanzee and a human). In another embodiment, a subject is a human. In another embodiment, the subject is a male human with or without prostate cancer.

DETAILED DESCRIPTION OF THE INVENTION

The practice of the present invention employs in part conventional techniques of molecular biology, microbiology and recombinant DNA techniques, which are within the skill of the art. Such techniques are explained fully in the literature. See, e.g., Sambrook, Fritsch & Maniatis, 1989, Molecular Cloning: A Laboratory Manual, Second Edition; Oligonucleotide Synthesis (M. J. Gait, ed., 1984); Nucleic Acid Hybridization (B. D. Harnes & S. J. Higgins, eds., 1984); A Practical Guide to Molecular Cloning (B. Perbal, 1984); and a series, Methods in Enzymology (Academic Press, Inc.); Short Protocols In Molecular Biology, (Ausubel et al., ed., 1995). All patents, patent applications, and publications mentioned herein, both supra and infra, are hereby incorporated by reference in their entireties.

The invention as disclosed herein identifies genomic regions that are useful in diagnosing prostate cancer (PC). By definition, the identified genomic regions are biomarkers for PC. In order to use these genomic regions (as biomarkers), the invention teaches the analysis of the DNA methylation status of said genomic regions. The invention further encompasses genomic region specific nucleic acids. The invention further contemplates the use of said genomic region specific nucleic acids to analyze the methylation status of a genomic region, either directly or indirectly by methods known to the skilled person and explained herein. The invention further discloses a composition and kit comprising said nucleic acids for the diagnosis of PC.

To address the need in the art for a more reliable diagnosis of prostate cancer (PC), the peculiarities of the DNA methylation status across the whole genome of PC positive samples were examined in comparison to PC negative samples. The inventors found genomic regions, that are subject to an aberrant methylation status. Tumour associations were found stronger for hypermethylated than for hypomethylated genomic regions. Therefore, the invention teaches the analysis of those genomic regions that are differentially methylated in samples from patients having prostate cancer. Superior to current diagnostic methods, the invention discloses genomic regions, wherein most astonishingly a combination of two genomic regions (genomic region pair) is able to diagnose prostate cancer with a reliability of 100%. If both genomic regions of a genomic region pair are hypermethylated, the sample can be designated as prostate cancer positive.

Accordingly, the invention relates to a method for diagnosis of prostate cancer, comprising the steps of analyzing in a sample of a subject the DNA methylation status of the genomic regions of at least one genomic region pair selected from the group of Table 2, wherein, if at least one genomic region pair is hypermethylated, the sample is designated as prostate cancer positive.

In one embodiment of the present invention is a method for diagnosis of prostate cancer, comprising the steps of obtaining a biological sample of a subject suspected of having prostate cancer; measuring in said biological sample the DNA methylation status of at least one genomic region pair comprising a first biomarker and a second biomarker selected from the group consisting of:

1. SEQ ID NO. 29 and SEQ ID NO. 86;
2. SEQ ID NO. 8 and SEQ ID NO. 13;
3. SEQ ID NO. 8 and SEQ ID NO. 27;
4. SEQ ID NO. 8 and SEQ ID NO. 39;
5. SEQ ID NO. 8 and SEQ ID NO. 86;
6. SEQ ID NO. 6 and SEQ ID NO. 95;
7. SEQ ID NO. 3 and SEQ ID NO. 31;
8. SEQ ID NO. 19 and SEQ ID NO. 62;
9. SEQ ID NO. 6 and SEQ ID NO. 7;
10. SEQ ID NO. 8 and SEQ ID NO. 90;
11. SEQ ID NO. 7 and SEQ ID NO. 62;
12. SEQ ID NO. 8 and SEQ ID NO. 22;
13. SEQ ID NO. 23 and SEQ ID NO. 95;
14. SEQ ID NO. 8 and SEQ ID NO. 12;
15. SEQ ID NO. 8 and SEQ ID NO. 50;
16. SEQ ID NO. 8 and SEQ ID NO, 95;
17. SEQ ID NO. 31 and SEQ ID NO. 98;
18. SEQ ID NO. 3 and SEQ ID NO. 8;
19. SEQ ID NO. 8 and SEQ ID NO. 9;
20. SEQ ID NO. 6 and SEQ ID NO. 86;
21. SEQ ID NO. 14 and SEQ ID NO. 95;
22. SEQ ID NO. 8 and SEQ ID NO. 47;
23. SEQ ID NO. 16 and SEQ ID NO. 23;
24. SEQ ID NO. 21 and SEQ ID NO. 98;
25. SEQ ID NO. 22 and SEQ ID NO, 95;
26. SEQ ID NO. 6 and SEQ ID NO. 16;
27. SEQ ID NO. 12 and SEQ ID NO. 19;
28. SEQ ID NO. 13 and SEQ ID NO, 19;
29. SEQ ID NO. 16 and SEQ ID NO. 41;
30. SEQ ID NO. 27 and SEQ ID NO. 44;
31. SEQ ID NO. 31 and SEQ ID NO, 95;
32. SEQ ID NO. 46 and SEQ ID NO. 62;
33. SEQ ID NO. 55 and SEQ ID NO. 86;
34. SEQ ID NO. 62 and SEQ ID NO. 86;
35. SEQ ID NO, 4 and SEQ ID NO. 8;
36. SEQ ID NO. 7 and SEQ ID NO. 98;
37. SEQ ID NO. 8 and SEQ ID NO. 19;
38. SEQ ID NO. 8 and SEQ ID NO. 43;
39. SEQ ID NO. 19 and SEQ ID NO. 65;
40. SEQ ID NO. 22 and SEQ ID NO. 86;
41. SEQ ID NO. 27 and SEQ ID NO. 31;
42. SEQ ID NO. 95 and SEQ ID NO. 98;
43. SEQ ID NO. 8 and SEQ ID NO. 30;
44. SEQ ID NO. 8 and SEQ ID NO. 33;
45. SEQ ID NO. 8 and SEQ ID NO. 108;
46. SEQ ID NO. 9 and SEQ ID NO. 59;
47. SEQ ID NO. 20 and SEQ ID NO. 95;
48. SEQ ID NO. 26 and SEQ ID NO. 47;
49. SEQ ID NO. 31 and SEQ ID NO. 33;
50. SEQ ID NO. 42 and SEQ ID NO. 95;
51. SEQ ID NO. 60 and SEQ ID NO. 97;
52. SEQ ID NO. 88 and SEQ ID NO. 95;
53. SEQ ID NO. 6 and SEQ ID NO. 57;
54. SEQ ID NO. 8 and SEQ ID NO. 21;
55. SEQ ID NO. 8 and SEQ ID NO. 45;
56. SEQ ID NO. 8 and SEQ ID NO. 46;
57. SEQ ID NO. 20 and SEQ ID NO. 86;
58. SEQ ID NO. 47 and SEQ ID NO. 62;
59. SEQ ID NO. 12 and SEQ ID NO. 21;
60. SEQ ID NO. 19 and SEQ ID NO. 37;
61. SEQ ID NO. 27 and SEQ ID NO. 101;
62. SEQ ID NO. 29 and SEQ ID NO. 95;
63. SEQ ID NO. 31 and SEQ ID NO, 37;
64. SEQ ID NO. 46 and SEQ ID NO. 59;
65. SEQ ID NO. 55 and SEQ ID NO. 95;
66. SEQ ID NO. 59 and SEQ ID NO. 95;
67. SEQ ID NO. 3 and SEQ ID NO. 47;
68. SEQ ID NO. 6 and SEQ ID NO. 98;
69. SEQ ID NO. 8 and SEQ ID NO. 65;
70. SEQ ID NO. 9 and SEQ ID NO. 98;
71. SEQ ID NO. 13 and SEQ ID NO. 95;
72. SEQ ID NO. 23 and SEQ ID NO. 86;
73. SEQ ID NO. 25 and SEQ ID NO. 95;
74. SEQ ID NO. 31 and SEQ ID NO. 57;
75. SEQ ID NO. 33 and SEQ ID NO. 95;
76. SEQ ID NO. 62 and SEQ ID NO. 98;
77. SEQ ID NO. 4 and SEQ ID NO. 95;
78. SEQ ID NO. 8 and SEQ ID NO. 68;
79. SEQ ID NO. 12 and SEQ ID NO. 16;
80. SEQ ID NO. 14 and SEQ ID NO. 98.
81. SEQ ID NO. 19 and SEQ ID NO. 86;
82. SEQ ID NO. 20 and SEQ ID NO. 46;
83. SEQ ID NO. 22 and SEQ ID NO. 29;
84. SEQ ID NO. 31 and SEQ ID NO. 32;
85. SEQ ID NO. 31 and SEQ ID NO. 86.
86. SEQ ID NO. 46 and SEQ ID NO. 104;
87. SEQ ID NO. 62 and SEQ ID NO. 69;
88. SEQ ID NO. 69 and SEQ ID NO. 98;
89. SEQ ID NO. 76 and SEQ ID NO. 89;
90. SEQ ID NO. 7 and SEQ ID NO. 8;
91. SEQ ID NO. 7 and SEQ ID NO. 20;
92. SEQ ID NO. 8 and SEQ ID NO. 16;
93. SEQ ID NO. 8 and SEQ ID NO. 17;
94. SEQ ID NO. 8 and SEQ ID NO. 20;
95. SEQ ID NO. 8 and SEQ ID NO. 100;
96. SEQ ID NO. 8 and SEQ ID NO. 106;
97. SEQ ID NO. 12 and SEQ ID NO. 97;
98. SEQ ID NO. 16 and SEQ ID NO. 19;
99. SEQ ID NO. 16 and SEQ ID NO. 45; and
100. SEQ ID NO. 19 and SEQ ID NO. 27;

determining the presence of hypermethylation of each of said biomarkers in the biological sample; and correlating the presence of hypermethylation of both of said biomarkers in said at least one genomic region pair with a positive indication of prostate cancer in said subject. In another embodiment, the genomic region pair is selected from the group of: SEQ ID NO. 29 and SEQ ID NO. 86; SEQ ID NO. 8 and SEQ ID NO. 13; SEQ ID NO. 8 and SEQ ID NO. 27; SEQ ID NO. 8 and SEQ ID NO. 39; and SEQ ID NO. 8 and SEQ ID NO. 86. In yet another embodiment, the genomic region pair is SEQ ID NO. 29 and SEQ ID NO. 86.

In another embodiment of the inventive method, the methylation status of only one genomic region selected from Table 1 is analyzed.

The method is particularly useful for early diagnosis of PC. The method is useful for further diagnosing patients having an identified prostate mass or symptoms associated with prostate cancer, e.g. abnormally high levels of PSA. The method of the present invention can further be of particular use with patients having an enhanced risk of developing prostate cancer (e.g., patients having a familial history of prostate cancer and patients identified as having a mutant oncogene). The method of the present invention may further be of particular use in monitoring the efficacy of treatment of a prostate cancer patient (e.g. the efficacy of chemotherapy).

In one embodiment of the method, the sample comprises cells obtained from a patient. The cells may be found in a prostate tissue sample collected, for example, by a prostate tissue biopsy or histology section, or a bone marrow biopsy if metastatic spreading has occurred. In another embodiment, the patient sample is a prostate-associated body fluid. Such fluids include, for example, blood fluids, lymph, urine, prostatic fluid and semen. From the samples cellular or cell free DNA is isolated using standard molecular biological technologies and then forwarded to the analysis method.

In order to analyze the methylation status of a genomic region, conventional technologies can be used.

Either the DNA of interest may be enriched, for example by methylated DNA immunoprecipitation (MeDIP) followed by real time PCR analyses, array technology, or next generation sequencing. Alternatively, the methylation status of the DNA can be analyzed directly or after bisulphite treatment.

In one embodiment, bisulphite-based approaches are used to preserve the methylation information. Therefore, the DNA is treated with bisulphite, thereby converting non-methylated cytosine residues into uracil while methylated cytosines are left unaffected. This selective conversion makes the methylation easily detectable and classical methods reveal the existence or absence of DNA (cytosine) methylation of the DNA of interest. The DNA of interest may be amplified before the detection if necessary. Such detection can be done by mass spectrometry or, the DNA of interest is sequenced. Suitable sequencing methods are direct sequencing and pyrosequencing. In another embodiment of the invention the DNA of interest is detected by a genomic region specific probe that is selective for that sequence in which a cytosine was either converted or not converted. Other techniques that can be applied after bisulphite treatment are for example methylation-sensitive single-strand conformation analysis (MS-SSCA), high resolution melting analysis (HRM), methylation-sensitive single-nucleotide primer extension (MS-SnuPE), methylation specific PCR (MSP) and base-specific cleavage.

In an alternative embodiment the methylation status of the DNA is analyzed without bisulphite treatment, such as by methylation specific enzymes or by the use of a genomic region specific probe or by an antibody, that is selective for that sequence in which a cytosine is either methylated or non-methylated.

In a further alternative, the DNA methylation status can be analyzed via single-molecule real-time sequencing, single-molecule bypass kinetics and single-molecule nanopore sequencing. These techniques, which are within the skill of the art, are fully explained in: Flusberg et al. Direct detection of DNA methylation during single-molecule, real-time sequencing. Nature methods 7(6): 461-467. 2010; Summerer. High-Throughput DNA Sequencing Beyond the Four-Letter Code: Epigenetic Modifications Revealed by Single-Molecule Bypass Kinetics. Chem Bio Chem 11: 2499-2501. 2010; Clarke et al. Continuous base identification for single-molecule nanopore DNA sequencing. Nature Nanotechnology 4: 265-270. 2009; Wallace et al. Identification of epigenetic DNA modifications with a protein nanopore. Chemical Communication 46:8195-8197, which are hereby incorporated by reference in their entireties.

To translate the raw data generated by the detection assay (e.g. a nucleotide sequence) into data of predictive value for a clinician, a computer-based analysis program can be used.

The profile data may be prepared in a format suitable for interpretation by a treating clinician. For example, rather than providing raw nucleotide sequence data or methylation status, the prepared format may represent a diagnosis or risk assessment (e.g. likelihood of cancer being present or the subtype of cancer) for the subject, along with recommendations for particular treatment options.

In one embodiment of the present invention, a computing device comprising a client or server component may be utilized. FIG. 4 is an exemplary diagram of a client/server component, which may include a bus 210, a processor 220, a main memory 230, a read only memory (ROM) 240, a storage device 250, an input device 260, an output device 270, and a communication interface 280. Bus 210 may include a path that permits communication among the elements of the client/server component.

Processor 220 may include a conventional processor or microprocessor, or another type of processing logic that interprets and executes instructions. Main memory 230 may include a random access memory (RAM) or another type of dynamic storage device that stores information and instructions for execution by processor 220. ROM 240 may include a conventional ROM device or another type of static storage device that stores static information and instructions for use by processor 220. Storage device 250 may include a magnetic and/or optical recording medium and its corresponding drive.

Input device 260 may include a conventional mechanism that permits an operator to input information to the client/server component, such as a keyboard, a mouse, a pen, voice recognition and/or biometric mechanisms, etc. Output device 270 may include a conventional mechanism that outputs information to the operator, including a display, a printer, a speaker, etc. Communication interface 280 may include any transceiver-like mechanism that enables the client/server component to communicate with other devices and/or systems. For example, communication interface 280 may include mechanisms for communicating with another device or system via a network.

As will be described in detail below, the client/server component, consistent with the principles of the invention, may perform certain measurement determinations of methylation, calculations of methylation status, and/or correlation operations relating to the diagnosis of prostate cancer. It may further optionally output the presentation of status results as a result of the processing operations conducted. The client/server component may perform these operations in response to processor 220 executing software instructions contained in a computer-readable medium, such as memory 230. A computer-readable medium may be defined as a physical or logical memory device and/or carrier wave.

The software instructions may be read into memory 230 from another computer-readable medium, such as data storage device 250, or from another device via communication interface 280. The software instructions contained in memory 230 may cause processor 220 to perform processes that will be described later. Alternatively, hardwired circuitry may be used in place of or in combination with software instructions to implement processes consistent with the principles of the invention. Thus, implementations consistent with the principles of the invention are not limited to any specific combination of hardware circuitry and software.

FIG. 5 is a flowchart of exemplary processing of methylation status for pairs of biomarkers present in biological samples according to an implementation consistent with the principles of the present invention. Processing may begin with quantifying the methylation 510 and non-methylation 520 of the DNA of a biological sample for a first and second biomarker constituting a genomic region pair of Table 2. The processor may then quantify the methylation status 530, as described above, as the ratio of methylated DNA to non-methylated of the biological sample for the first and second biomarkers. The methylation status may then be evaluated either via a computing device 540 or by human analysis to determine if both the first and second biomarkers of the genomic region pair meet or exceed a predetermined methylation threshold. If the threshold is met or exceeded, then the computing device may then, optionally, present a status result indicating a positive diagnosis of prostate cancer 550. Alternatively, if the threshold is not met, then the computing device may, optionally, present a status result indicating that the threshold is not satisfied 560. It is noted that the output displaying results may differ depending on the desired presentation of results. For example, the output may be quantitative in nature, e.g., displaying the measurement values of each of the biomarkers in relation to the predetermined methylation threshold value. The output may be qualitative, e.g., the display of a color or notation indicating a positive result for prostate cancer, or a negative results for prostate cancer, as the case may be. Notably, this process may be repeated multiple times using different genomic region pairs, as set forth in Table 2. The computing device may alternatively be programmed to permit the analysis of more than one genomic region pair at one time.

In some embodiments, the results are used in a clinical setting to determine a further diagnostic (e.g., additional further screening (e.g., PSA or other markers) or diagnostic biopsy) course of action. In other embodiments, the results are used to determine a treatment course of action (e.g., choice of therapies or watchful waiting).

Table 2 shows examples of genomic region pairs most preferably to be analyzed regarding their methylation status. In one embodiment any genomic region pair can be analyzed.

In a preferred embodiment, the genomic region pair is selected from the group of:

| Genomic region pair (grp) | Genomic region 1 [SEQ ID NO.] | Genomic region 2 [SEQ ID NO.] |
| --- | --- | --- |
| grp 1 | 29 | 86 |
| grp 2 | 8 | 13 |
| grp 3 | 8 | 27 |
| grp 4 | 8 | 39 |
| grp 5 | 8 | 86 |

Table 3 shows examples of genomic region pairs most preferably to be analyzed regarding their methylation status. In one embodiment any genomic region pair can be analyzed.

| Genomic region pairs | Genomic region 1 [SEQ ID NO.] | Genomic region 2 [SEQ ID NO.] |
| --- | --- | --- |
| grp 101 | 1 | 59 |
| grp 102 | 1 | 9 |
| grp 103 | 1 | 6 |
| grp 104 | 1 | 29 |
| grp 104 | 1 | 10 |
| grp 105 | 1 | 50 |
| grp 106 | 1 | 56 |
| grp 107 | 1 | 12 |
| grp 108 | 1 | 8 |
| grp 109 | 1 | 16 |
| grp 110 | 1 | 86 |
| grp 111 | 1 | 21 |
| grp 112 | 1 | 23 |
| grp 113 | 1 | 45 |
| grp 114 | 1 | 58 |
| grp 115 | 1 | 83 |

In a more preferred embodiment, the genomic region pair is SEQ ID NO. 29 and SEQ ID NO. 86.

Significantly, the inventors found that a minimum of one genomic region pair is sufficient to accurately discriminate between malignant and benign tissues. The extension with additional sites even increases the discriminatory potential of the marker set. Thus, in another embodiment, the invention relates to a method, wherein the methylation status of a further genomic region and/or a further biomarker is analyzed.

In one embodiment of the invention, a known prostate cancer biomarker is additionally analyzed. Such PC biomarkers can be a gene, e.g. encoding for GSTP1, multidrug resistance protein 1 (MDR1), O-6-methylguanine-DNA methyltransferase (MGMT), Ras association domain family member 1 (RASSF1), retinoic acid receptor beta (RARB), adenomatous polyposis coli (APC), androgen receptor (AR), cyclin-dependent kinase inhibitor 2A (CDKN2A), E-cadherin (CDH1) and/or CD44. Such biomarkers can also be based on gene expression, e.g. of said encoding genes. In a preferred embodiment, the concentration or activity of prostate specific antigen (PSA) is determined by means of an immunoassay. The analysis of the biomarkers within this context can be the analysis of the methylation status, the analysis of the gene expression (mRNA), or the analysis of the amount or concentration or activity of protein.

In another embodiment a further genomic region and/or a further genomic region pair according to the invention is analyzed.

The inventors surprisingly found that the methylation status within a genomic region according to the invention is almost constant, leading to a uniform distribution of either hyper- or hypomethylated CpG positions within said genomic region. In one embodiment of the invention, all CpG positions of a genomic region are analyzed. In a specific embodiment, CpG positions in the vicinity of the genomic region may be analyzed. In an alternative embodiment, a subset of CpG positions of a genomic region is analyzed. Ideally, 1, 2, 3, 4, 5, 6, 7, 8, 9, 10 GpG positions of a genomic region are analyzed. Therefore, a preferred embodiment of the invention relates to a method, wherein analyzing the methylation status of a genomic region means analyzing the methylation status of at least one CpG position per genomic region.

In a preferred embodiment the invention relates to a method, wherein the methylation status is analyzed by non-methylation-specific PCR based methods followed by sequencing, methylation-based methods such as methylation sensitive PCR, EpiTyper and Methylight assays or enrichment-based methods such as MeDIP-Seq. In an alternative embodiment of the present invention, the DNA methylation is assessed by methylation-specific restriction analysis.

In a preferred embodiment of the invention Epityper® and Methylight® assays may be used for the analysis of the methylation status.

The invention also relates to a nucleic acid molecule that hybridizes under stringent conditions in the vicinity of one of the genomic regions according to SEQ ID NO. 1 to SEQ ID NO. 110, wherein said vicinity relates to a position as defined above.

In one embodiment said nucleic acid is 15 to 100 nt in length. In a preferred embodiment said nucleic acid is 15 to 50 nt, in a more preferred embodiment 15 to 40 nt in length.

In another embodiment said nucleic acid is a primer. The inventive primers being specific for a genomic region can be used for the analysis methods of the DNA methylation status. Accordingly, they are used for amplification of a sequence comprising the genomic region or parts thereof in the inventive method for the diagnosis of PC. Within the context of the invention, the primers selectively hybridizes in the vicinity of the genomic region as defined above.

Primers may be prepared using any suitable method, such as, for example, the phosphotriester and phosphodiester methods or automated embodiments thereof. In one such automated embodiment diethylophosphoramidites are used as starting materials and may be synthesized as described by Beaucage et al., Tetrahedron Letters, 22:1859-1862 (1981), which is hereby incorporated by reference. One method for synthesizing oligonucleotides on a modified solid support is described in U.S. Pat. No. 4,458,006, which is hereby incorporated by reference. It is also possible to use a primer which has been isolated from a biological source (such as a restriction endonuclease digest).

The methylation status of a genomic region may be detected indirectly (e.g. by bisulphite sequencing) or directly by using a genomic region specific probe, e.g. in a methylight assay. Thus, the present invention also relates to said nucleic acid being a probe. In a preferred embodiment of the present invention the probe is labelled.

Said probes can also be used in techniques such as quantitative real-time PCR (qRT-PCR), using for example SYBR®Green, or using TaqMan® or Molecular Beacon techniques, where the nucleic acids are used in the form of genomic region specific probes, such as a TaqMan labelled probe or a Molecular Beacon labelled probe. Within the context of the invention, the probe selectively hybridizes to the genomic region as defined above. Additionally, in qRT-PCR methods a probe can also hybridize to a position in the vicinity of a genomic region.

Current methods for the analysis of the methylation status require a bisulphite treatment a priori, thereby converting non-methylated cytosines to uracils. To ensure the hybridization of the genomic region specific nucleic acid of the invention to the bisulphite treated DNA, the nucleotide sequence of the nucleic acid may be adapted. For example, if it is desired to design nucleic acids being specific for a sequence, wherein a cytosine is found to be differentially methylated, that genomic region specific nucleic acid may have two sequences: the first bearing an adenine, the second bearing an guanine at that position which is complementary to the cytosine nucleotide in the sequence of the genomic region. The two forms can be used in an assay to analyze the methylation status of a genomic region such that they are capable of discriminating between methylated and non-methylated cytosines. Depending on the analysis method and the sort of nucleic acid (primer/probe), only one form or both forms of the genomic region specific nucleic acid can be used within the assay. Thus, in an alternative embodiment of the present invention the nucleic acid hybridizes under stringent conditions in said vicinity of one of the genomic regions after a bisulphite treatment.

The present invention also relates to the use of genomic region specific nucleic acids for the diagnosis of prostate cancer.

The present invention also comprises the use of an antibody that is specific for a genomic region for the diagnosis of prostate cancer.

Such antibody may preferably bind to methylated nucleotides. In another embodiment the antibody preferably binds to non-methylated nucleotides. The antibody can be labelled and/or used in an assay that allows the detection of the bound antibody, e.g. ELISA.

The nucleic acid or antibody for performing the method according to the invention is advantageously formulated in a stable composition. Accordingly, the present invention relates to a composition for the diagnosis of prostate cancer comprising said nucleic acid or antibody.

The composition may also include other substances, such as stabilizers.

The invention also encompasses a kit for the diagnosis of prostate cancer comprising the inventive nucleic acid or antibody as described above.

The kit may comprise a container for a first set of genomic region specific primers. In a preferred embodiment, the kit may comprise a container for a second set of genomic region specific primers. In a further embodiment, the kit may also comprise a container for a third set of genomic region specific primers. In a further embodiment, the kit may also comprise a container for a forth set of genomic region specific primers, and so forth.

The kit may also comprise a container for bisulphite, which may be used for a bisulphite treatment of the genomic region of interest.

The kit may also comprise genomic region specific probes.

The kit may comprise containers of substances for performing an amplification reaction, such as containers comprising dNTPs (each of the four deoxynucleotides dATP, dCTP, dGTP, and dTTP), buffers and DNA polymerase.

The kit may also comprise nucleic acid template(s) for a positive control and/or negative control reaction. In one embodiment, a polymerase is used to amplify a nucleic acid template in PCR reaction. Other methods of amplification include, but are not limited to, ligase chain reaction (LCR), or any other method known in the art.

The kit may also comprise containers of substances for performing a sequencing reaction, for example pyrosequencing, such as DNA polymerase, ATP sulfurylase, luciferase, apyrase, the four deoxynucleotide triphosphates (dNTPs) and the substrates adenosine 5' phosphosulfate (APS) and luciferin.

FIGURE CAPTIONS

FIG. 1: Overview of the MeDIP-Seq technology and validation experiments. (A) Schematics of the MeDIP-Seq protocol. Genomic DNA is sheared to a size of 100-200 bp, end repaired and sequencing adapters carrying a distinct barcode are ligated. After denaturation the libraries are incubated with antibodies targeting 5-methylcytosine coupled to magnetic beads. The enriched libraries are amplified and analysed on a SOLiD3+ NGS system using 35 bp fragment sequencing chemistry. (B) Coverage plots of uniquely mapped reads for eight samples (four normal and four tumour) for the CAV2 promoter region (left) and the GSTP1 promoter region (right). Top lane: location of the CpG-island, second lane with CAV2 and GSTP1 labels: coding regions, dark grey: normal, light grey: tumour samples. (C) Bisulphite conversion and mass spectrometry analyses were used for the validation of the MeDIP-Seq results. Left: hypomethylated, promoter associated region in the KLK4-gene (chr19:51411401-51412100), right: hypermethylated intronic region in the PTPRN2-gene (chr7: 157360901-157361600). Top 3 samples are derived from tumour DNA, sample 4 to 6 from normal tissues. Line 7: Completely methylated control DNA, line 8: water control. Dark grey circles: no methylation, light grey circles: 100% methylation, white circles mark CpG dinucleotides not accessible for analysis or failed in analysis.

FIG. 2: Separation of normal (dark grey) and tumour (light grey) samples based on DMRs. (A) Principal component analyses were performed by using the rpm-values of either all bins (upper left corner) or restrictions to either chromosome 8 (bottom row) or the promoter regions (right column) were applied. (B) PAM analyses enabled a selection of seven marker regions used for unsupervised cluster analyses.

FIG. 3: Differential methylations are due to alterations in tumour cells. Bisulphite analyses of microdissected tumour material. Normal and tumour tissue materials were prepared with macrodissections (light grey bars) or laser captured microdissections (dark grey bars) and bisulphite-MS analyses were performed for 35 differentially methylated regions. Correlation analyses between microdissected and macrodissected samples (A) and unsupervised cluster analyses (B) are shown.

EXAMPLES

Figure 1:
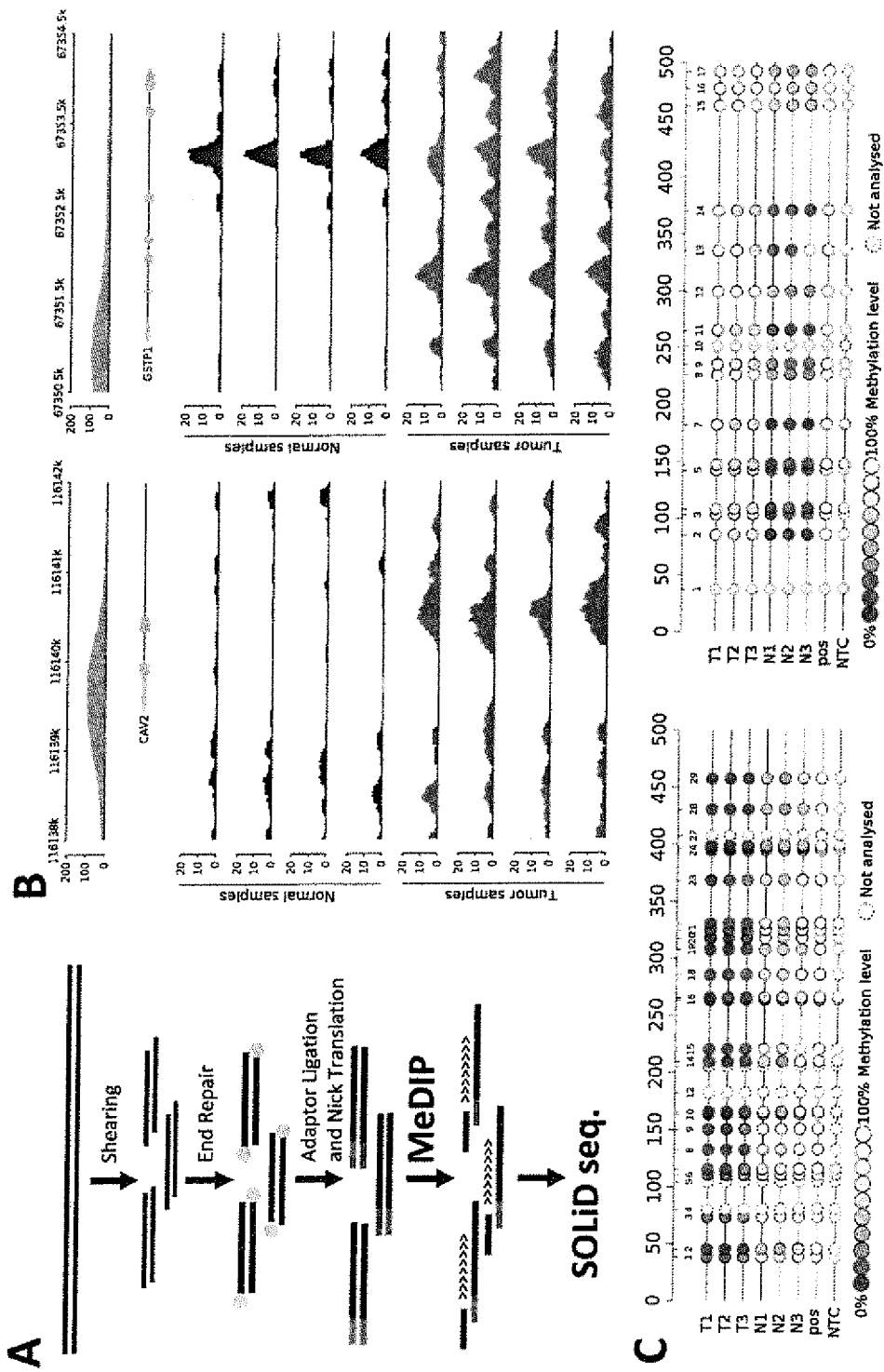

Aberrant cytosine methylation is among the earliest and most frequent events in the development of prostate cancer. Herein, an immunocapturing approach followed by next generation sequencing was used to generate genome-wide methylation profiles of 51 prostate tumour and 53 normal prostate tissues. Machine-learning techniques identified several sets of differentially methylated genomic regions which enabled a correct classification (100%) of tumour and normal samples.

It should be noted, that gene names are merely used to constrict the localization of the identified genomic regions. This means that the genomic region must not necessarily form a part of the gene, but lies in the vicinity of that gene. Genomic locations are given in Hg19 annotation.

Experimental Procedure

Prostate tissue samples were obtained from the University Medical Center Hamburg Eppendorf. Approval for the study was obtained from the local ethics committee and all patients agreed to provide additional tissue sampling for scientific purposes. Tissue samples from 51 prostate cancer and 53 normal prostate tissues were included. None of the patients had been treated with neo-adjuvant radio-, cytotoxic- or endocrine therapy.

Tumour or normal tissue materials are further processed for DNA extraction. For the validation screen matched normal and tumour tissues are extracted from two patients, each with standard macrodissection and microdissection technologies.

Identification screen: During radical prostatectomy, tissue samples from the peripheral zone of the prostate were taken with a 6 mm punch biopsy instrument immediately after surgical removal of the prostate from tumerous and non-tumerous areas as described before. The punches were immersed in RNAlater (Qiagen) and subsequently stored at −80° C. To confirm the presence of tumour, all punches were sectioned, and tumour cell content was determined in every 10th section. Only sections containing at least 70% tumour cells were included in the study. Normal prostate tissue samples were obtained from 53 patients who underwent radical prostatectomy for prostate cancer. Only sections containing only normal tissue material with epithelial cell content between 20 and 40% were included in the study. Simultaneous DNA and RNA isolation from the tumour and normal tissue sections was performed using the Allprep kit (Qiagen) according to the manufacturer's instructions.

Validation screen: In order to exclude a possible bias in the identification screen because i) normal and tumour samples were taken from different patients and ii) epithelial cells were not microdissected from the stroma background, the validation study was performed on two patients with matched normal and tumour samples where the effect of epithelial cell microdissection versus whole section analysis was compared. Ten tissue sections (4-μm) were taken from each tissue block for DNA isolation from non-microdissected tissues. For Laser Capture Microdissection (LCM, Zeiss, Germany) of epithelial cells, 16-μm tissue sections were mounted on special LCM slides and briefly stained with hematoxilin and eosin to facilitate localization of epithelial cells. Epithelial cells were collected by LCM from 10 tissue sections each. DNA was isolated using the DNA mini kit (Qiagen) according to the manufacturer's instructions.

Primary samples from prostate tissues after radical prostatectomies were obtained from the University Hospital Eppendorf (Hamburg).

Clinical data obtained for each sample includes: age of the patient, PSA values, Gleason score, TNM classifications, TMPRESS-ERG-fusion status.

Methylation profiling by MeDIP-Seq: SOLiD sequencing libraries are prepared following the SOLiD v3 fragment multiplex library preparation protocol (Life Technologies) with slight modifications. Libraries are used for a methylated DNA immunoprecipitation using an anti-5-methyl cytosine antibody (Eurogentec) followed by SOLiD 3+ barcoded sequencing.

In detail, 2.5 μg of genomic DNA were fragmented to 100 to 200 bp using the Covaris S2 system and end repaired with End Repair mix (Enzymatics) followed by a purification step (Qiagen DNA purification kit). Barcoded sequencing adapters were ligated followed by nick translation with DNA polymerase I (NEB, 10 U).

For the enrichment step of the methylated DNA immunoprecipitation (MeDIP) 5 μg of an anti-5-methyl cytosine antibody (Eurogentec) coupled to magnetic beads were used (coupling was performed by incubation overnight in 1×PBS+0.5% BSA). The libraries were incubated with the beads for 4 hours in IP Buffer (10 mM sodium phosphate buffer pH 7, 140 mM NaCl, 0.25% Triton X100). Beads were washed three times with IP buffer and DNA was eluted in elution buffer (50 mM Tris-HCl pH 7.5, 10 mM EDTA, 1% SDS) by incubation for 15 min at 65° C. After two hours of incubation with proteinase K, the DNA was phenol/chloroform extracted and ammonium acetate/ethanol precipitated. Enrichment controls were performed with real time PCRs targeting methylated as well as unmethylated regions. Libraries were amplified with multiplex_PCR_primers 1 having a sequence according to SEQ ID NO. 111 and multiplex_PCR_primers 2 with a sequence of SEQ ID NO. 112, size-selected and quantified using qPCRs with primers Quant_PCR_primer 1 with the sequence of SEQ ID NO. 113 and primers Quant_PCR_primer 2 with the sequence of SEQ ID NO. 114. Libraries were diluted to 100 pg/µl, requantified by qPCR and pooled (up to 8 libraries/pool). Libraries were then coupled to P1-beads in an emulsion PCR reaction following the manufacturer's protocol. Approximately 500 million enriched beads were deposited per slide and sequencing was performed on a SOLiD 3+ machine using barcode sequencing chemistry (5+35 bp) (Lifetech).

Alignment and peak detection: Reads are aligned to HG19 using Applied Biosystem's Bioscope Alignment module in seed and extend mode taking the first 25 bp of the reads as seeds allowing 2 mismatches and a mismatch penalty score of −2 for extension. Then the aligned reads are elongated to 200 bp in a strand-oriented manner. Redundant reads and reads with no CpGs in the elongated sequence are excluded from further analyses. Next, the HG19 reference genome is split into adjacent 500 bp bins and the amount of reads per bin is counted. Reads are assigned to a bin when their centre is located within the bin. For sample wise normalizations total read counts are related to the total read count of each sample (reads per million=rpm). For the identification of differentially methylated regions a Mann-Whitney-test is performed using the rpm-values of all tumour and all normal samples in each bin. Resulting p-values are corrected for multiple testing using the Benjamini-Hochberg-approach. A binomial distribution of the reads (null hypothesis) is assumed and thus a probability value for the mean tumour and mean normal read count in each bin to appear solely by chance is assigned.

Principal component analyses (PCA): Principal component analyses are performed with the prcomp-function in R using the rpm-values of all 104 samples. Additional information like tissue type and copy number variation (chr8 q-arm) is visualized by colours.

PAM (Prediction Analysis of Microarrays): This supervised algorithm performs sample classification by applying the nearest shrunken centroid method and cross-validation and is here used to obtain loci which discriminate normal and tumour samples (Tibshirani et al. Diagnosis of multiple cancer types by shrunken centroids of gene expression. Proc Natl Acad Sci USA 99, 6567-6572, 2002). A set of 8 loci is chosen, classifying the two subsets with no miss-classifications in 100-fold cross-validation.

Mass spectrometry analyses: For DNA methylation analyses, 1 µg DNA is bisulphite (BS)-converted to preserve methylation information, and this is subsequently amplified with specific primer pairs carrying a T7-promoter that are designed using the Epidesigner tool (www.epidesigner.com) with standard criteria (amplicon length: 400-600 bp). In vitro transcription is performed and the transcripts are cleaved and subsequently analysed using MALDI-TOF mass spectrometry on a MassARRAY Analyser 4 at the Sequenom facility in Hamburg.

Results

Genome-wide profiles of cytosine methylation in prostate cancer: We prepared genomic DNA from human primary tissues and enriched methylated regions using a methylated DNA immunoprecipitation (MeDIP) methodology in combination with next generation SOLiD sequencing (FIG. 1A). All tumours selected for this study were staged pT2a or greater, Gleason 6 or greater, and had PSA levels between 1.9 and 100 ng/ml. Of the tumours, 17 contained chromosomal rearrangements involving TMPRESS-ERG loci and nine showed amplifications on chromosome 8q.

We performed 15 full slide runs with 8 barcoded samples/slide on a SOLiD 3+ machine and obtained an average sequencing depth of 20 million uniquely mappable reads per sample (0.7 billion bases). To determine the success of our MeDIP approach we counted the number of extended 200 bp reads bearing different numbers of CpGs and compared it to the distribution of CpGs in the genome. We found a significant enrichment of reads with at least three CpGs, with a maximum enrichment of reads with approximately 10 CpGs. In addition, we determined the number of reads without any CpGs for each sample (5-15%). We assume that reads without CpG result from unspecific binding of DNA to the beads because differentiated cells contain only very small amounts of non CpG-cytosine-methylation methylation (Lister and Ecker, 2009).

We discarded all reads without any CpG from further analyses. We next divided the genome into 500 bp genomic intervals (bins) and counted the number of reads located within each bin. To test whether a bin is covered by chance rather than by an underlying methylation we assumed a binomial distribution of the read counts per bin (null hypothesis) and assigned a probability value to each bin. We identified 682,510 bins with significant read counts (p<0.05) in tumour or normal samples. On the average, 39% of all reads are located within the significant bins and were assumed to represent the underlying methylation patterns.

We tested each bin for association to prostate cancer using a Mann-Whitney-test and corrected for multiple testing using the Benjamini-Hochberg approach. We identified approximately 147,000 differentially methylated regions (false detection rate (FDR)<0.05), examples of which are visualized in FIG. 1B.

To validate our findings we used mass spectrometry-based analyses of bisulphite-converted DNA (Epityper) (see Radpour et al. High-throughput hacking of the methylation patterns in breast cancer by in vitro transcription and thymidine-specific cleavage mass array on MALDI-TOF silico-chip. Mol Cancer Res 6, 1702-1709, 2008), which, as an independent technology, yields methylation values for single cytosine residues. Altogether, we analyzed 83 regions in 14 samples. We observed a fairly uniform methylation rate of the CpGs within most of the target regions for all samples (FIG. 1C). To compare mass spectrometry data to the MeDIP sequencing data we adjusted the former by utilizing the number of CpGs in the underlying bin. This roughly takes into account that regions with more CpGs might have a higher enrichment in MeDIP experiments. An average Pearson's correlation coefficient of 0.73 was achieved, showing that MeDIP-Seq can be used for genome-wide screening purposes. We did not expect perfect correlation since bisulphite conversion experiments do not discriminate between 5-methyl-cytosine and 5-hydroxymethyl-cytosine, but MeDIP experiments enrich only for 5-methyl-cytosine.

Tumour-specific differential methylations: Among the 682,510 genomic intervals (bins) with significant read-count distributions, we found 85,406 bins with significant hypermethylations and 61,308 bins with significant hypomethylations in tumour samples (FDR<0.05). Interestingly, we found tumour associations to be stronger for hypermethylated than for hypomethylated bins (lower p-values).

Figure 2A:
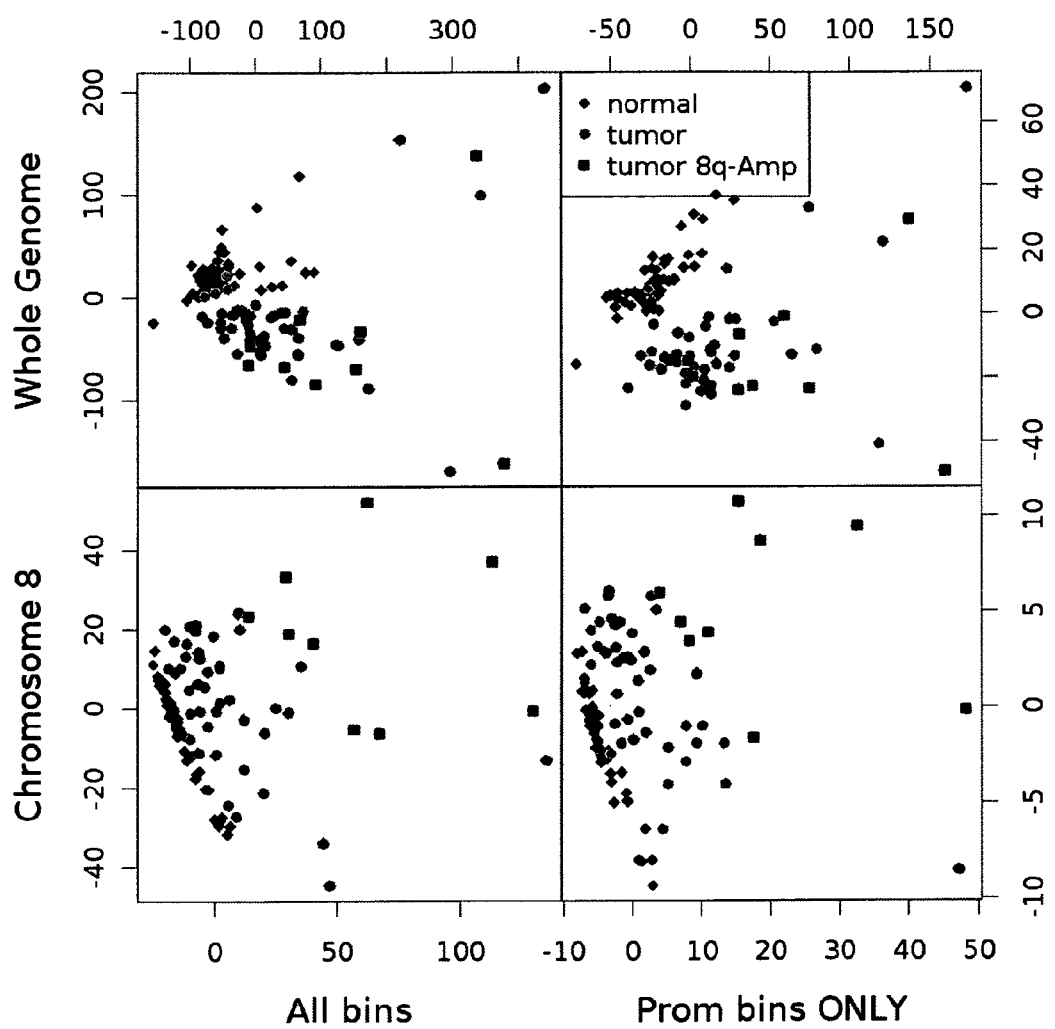

Differentiation between normal and tumour samples: To investigate whether it is possible to separate normal and tumour tissue samples using the MeDIP-Seq approach we performed principal component analyses (PCA) on methylation levels for the whole genome and on chromosome 8, a chromosome with frequent copy number variations in PC (FIG. 2A). We found a separation of tumour and normal samples for both data sets which could also be shown by calculating self organizing maps. The methylation patterns for normal samples were found to be more uniform since they are less scattered than the tumour samples. Interestingly, when we restricted the PCA to chromosome 8 we found samples with 8q amplifications separate from samples without, indicating an influence of copy number variations on methylation values.

Identification of biomarkers: One of the aims of our study was the identification of biomarkers for prostate cancer diagnostics based on the epigenetic cancer profiles. To extract one or a combination of a few regions out of our data set of 147,000 differentially methylated regions we used the 'nearest shrunken centroid' method (PAM).

Figure 2B:
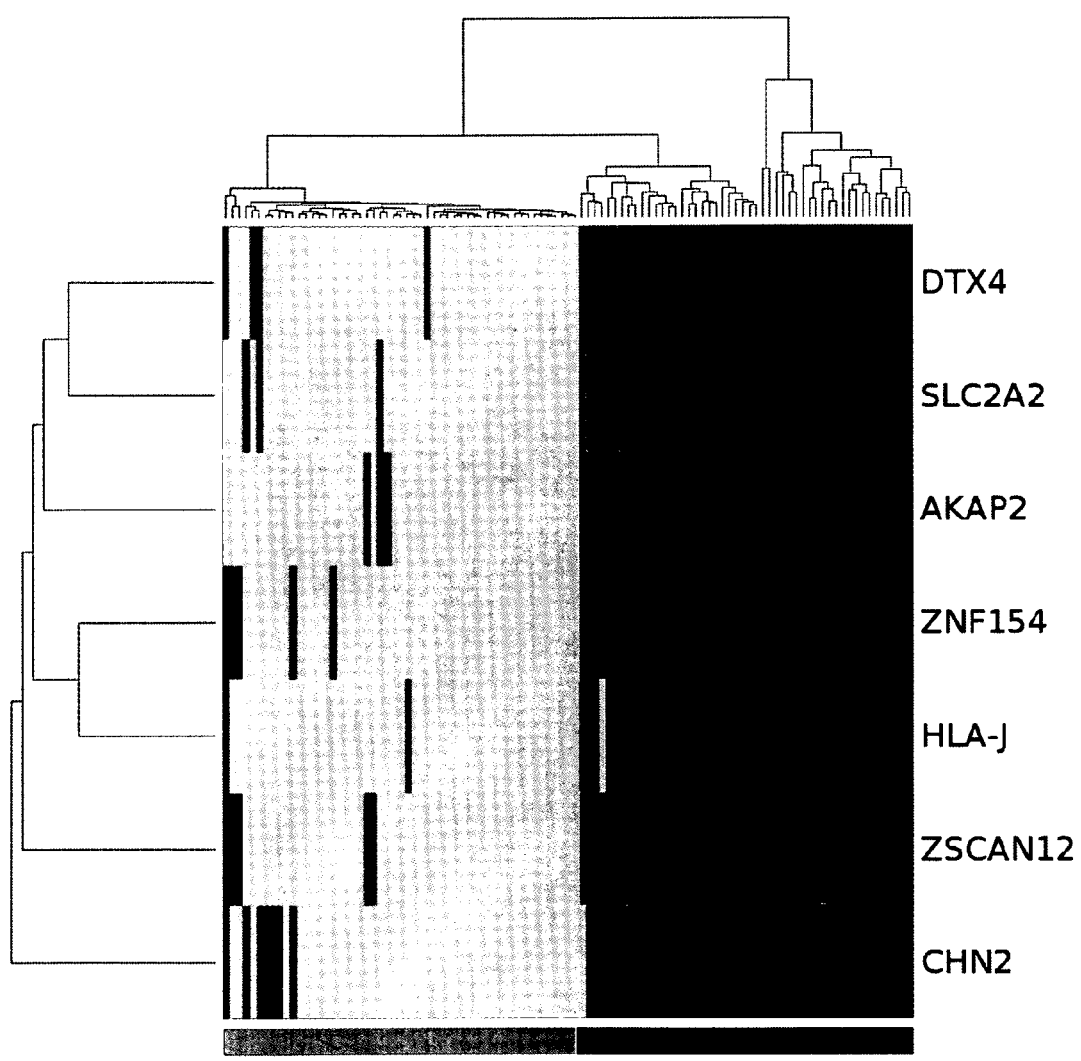

For the 'nearest shrunken centroid' method we followed the PAM (prediction analysis for microarrays) classification protocol (see Tibshirani et al. Diagnosis of multiple cancer types by shrunken centroids of gene expression. Proc Natl Acad Sci USA 99, 6567-6572, 2002). PAM was originally developed to analyse gene expression microarray data, but as we show here it is also applicable to other data where a large set of quantitative information has to be scaled down to the most significant classifiers. We identified seven features which allow a complete separation of tumour and normal samples in a self organizing map and in unsupervised clustering (FIG. 2B). These markers scored within the top 60 most significant promoter associated bins.

To reduce the marker set even further, we used the two most significantly differentially methylated regions for the classification analyses and were able to clearly separate the samples, albeit with lower discriminatory power than for the other marker sets. To evaluate our marker sets against a known classifier, we used differentially methylated bins within the GSTP1 promoter and found three samples incorrectly classified, showing that our marker sets have the potential to discriminate between benign and tumour tissues with a higher accuracy than GSTP1.

Since it is not feasible to use MeDIP-Seq with extensive statistical analyses for every tumour patient we also investigated the applicability of the bisulphite-based mass spectrometry (BS-MS) approach (Sequenom) as a potential technology for routine diagnostic usage. Similar to the validation experiments described earlier the regions selected covered a broad spectrum of CpG content with a peak of 20 to 35 CpGs. Using cluster analyses we were able to perfectly discriminate between tumour and normal samples based on the mass spectrometry data, either with all data points (FIG. 3B), or subsets of markers.

Differential methylations are specific for tumour cells: All experiments performed so far have used macrodissected preparations from tumour and benign tissue samples. To exclude the possibility that the observed differential methylations are due to an overrepresentation of epithelial or stromal cells within the tumour samples we also performed bisulphite analyses on micro- and macro-dissected samples of two additional patients: From each patient we used normal and tumour tissues, each after macrodissection and after laser-microdissection. Correlation analysis of methylation values comparing both dissection techniques reached values of 0.91 (FIG. 3), showing that our identified differential methylations are tumour-cell specific alterations. Comparing matched normal and tumour tissues from the same patients we identified clear differences between the sample types, proving that our methylation profiles are indeed tumour specific and are not due to inter-individual differences.

Figure 3A:
Figure 3B:
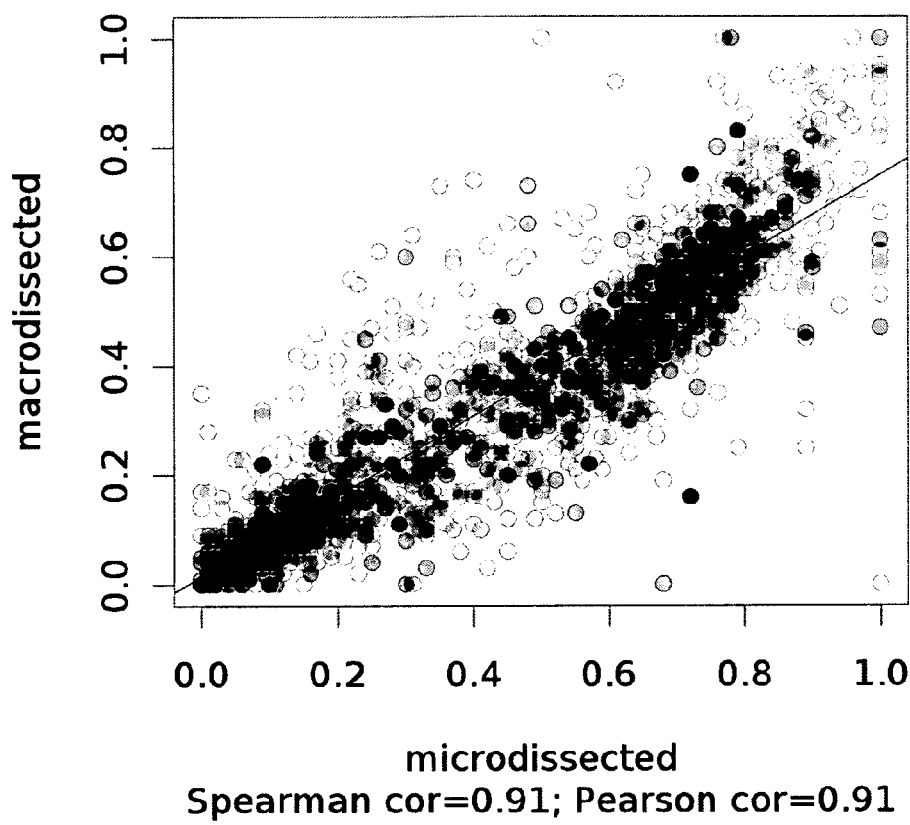
Figure 4:
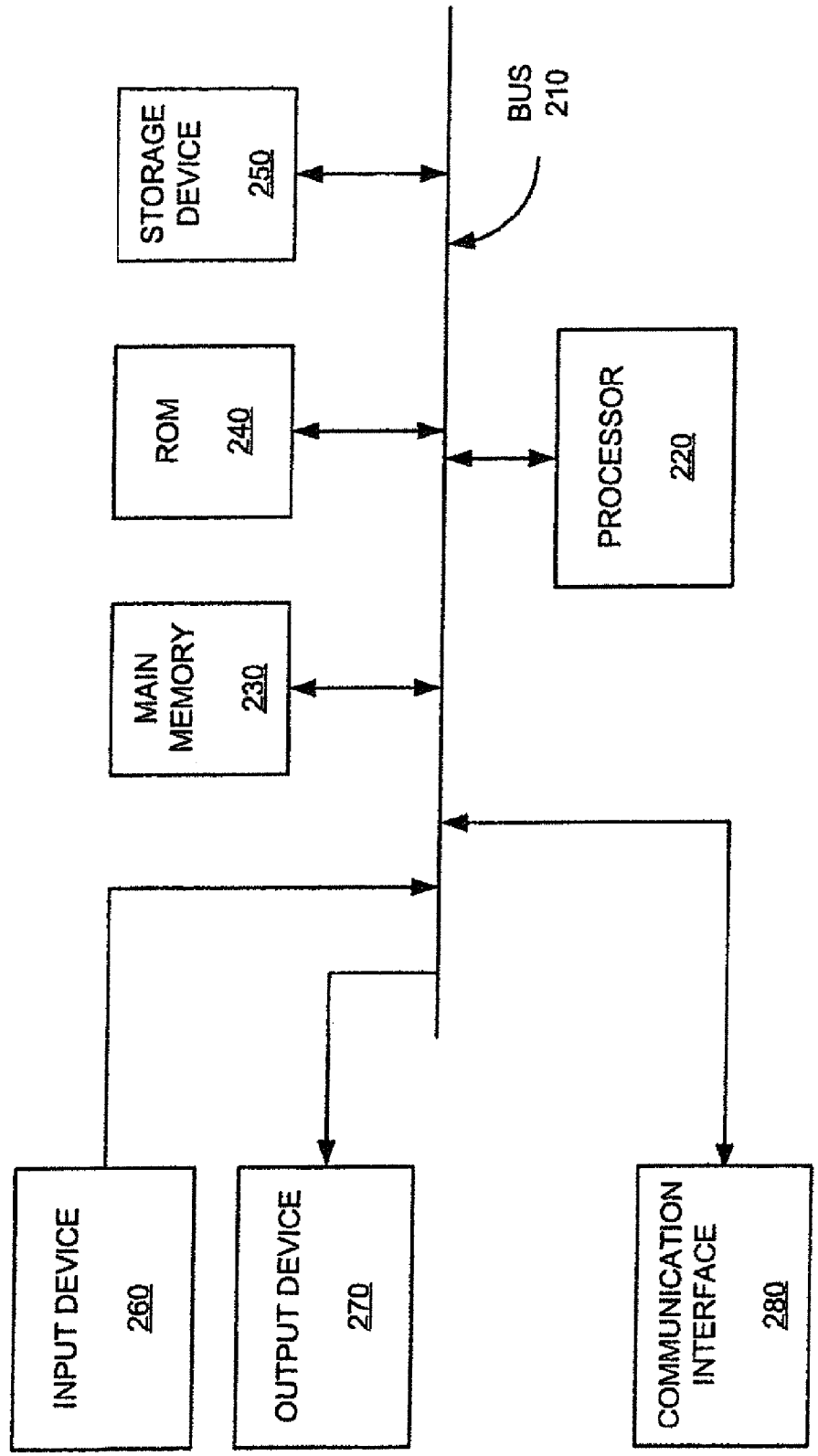
FIG. 4 is an exemplary diagram of a computing device comprising a client and/or server according to an implementation consistent with the principles of the invention.
Figure 5:
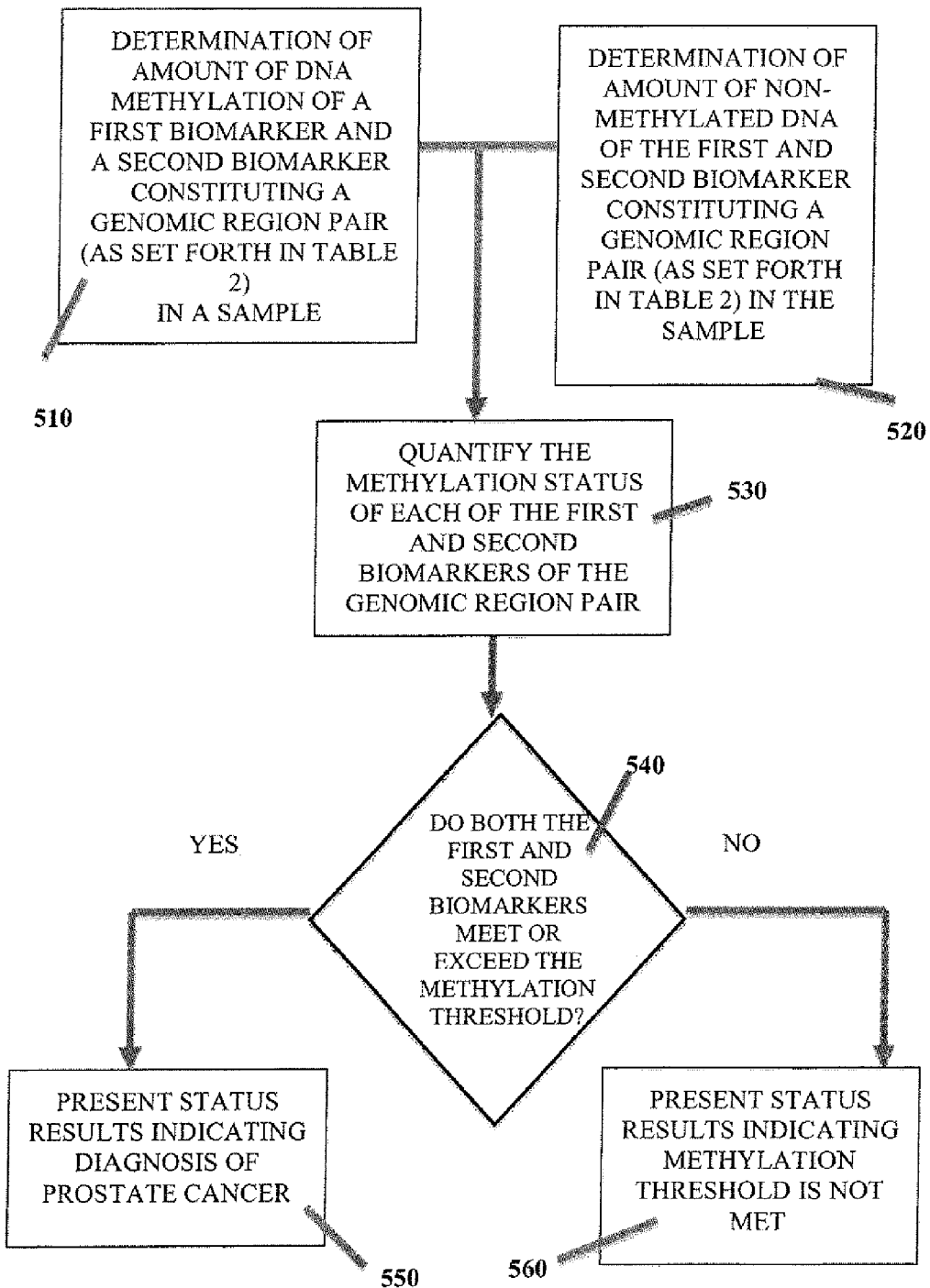
FIG. 5 is a flowchart of exemplary processing of methylation status for pairs of biomarkers present in biological samples according to an implementation consistent with the principles of the present invention.

Our study revealed approximately 147,000 differentially methylated regions in prostate cancer. Most of these differential methylations were also confirmed if neoplastic and non-neoplastic epithelium was microdissected. This suggests that these patterns are likely to be tumour cell-specific and may not result from connective tissue specific methylations (FIG. 3). Systematic genomic screening efforts have often focused primarily on gene-coding regions to identify "driver" mutations, but identified markedly less somatic mutations per megabase in prostate cancer as compared to many other tumour types. In contrast, high numbers of epigenetic alterations emphasize the relative importance of methylation changes for this tumour type.

This comprehensive analysis of cytosine methylation in a large set of normal and tumour prostate samples provides a unique catalogue of genes with differential methylation and may identify most significant marker regions dysregulated by methylation in prostate cancer development.

Earlier studies have only investigated the methylation status of several preselected gene regions in prostate cancer.

More than 30% of the differentially methylated regions hypermethylated in tumours belong to CpG-islands, CpG island shores and gene promoter regions.

Outside of gene regions we detected significant hypermethylations in evolutionary conserved regions and micro RNAs. Although 17% of the conserved regions with differential methylation were promoter regions, our data suggests that the non-promoter regions might carry an additional function for tumour formation as they might represent hot spots for long range transcriptional regulation mechanisms.

In contrast to hypermethylation of distinct positions hypomethylated regions result in less stringent p-values.

In addition, hypomethylations are less frequently found within specific regions such as promoters or conserved regions. In particular the correlation between hypermethylation and conserved regions, tumour suppressor genes and homeobox genes suggests that hypermethylation might be a directed process necessary in tumour evolution whereas hypomethylation is more unspecific. Most hypomethylation occurred in repetitive regions such as LINE1-elements and satellite DNA. Taking also non-uniquely mappable reads into account, the association of hypomethylations with satellite regions becomes even stronger.

We have used diverse machine-learning techniques and statistical approaches to identify signatures of differential methylation which correctly differentiate between tumour and normal samples based on our MeDIP-Seq results. Significantly, we found that a minimum of two genomic regions is sufficient to accurately discriminate between malignant and benign tissues (Table 1; Table 2). The extension with additional sites even increases the discriminatory potential of the marker set. The marker sets are independent of the technology used, since bisulphite-based approaches are similarly applicable. Based on our ability to clearly separate prostate cancer from benign prostate specimens by aid of only a few marker regions, we are now in the progress of extending our analyses to diverse body fluids—such as blood and urinary samples—with the goal of establishing the differentially methylated regions as biomarkers for the early detection of prostate cancer.

The invention claimed is:

1. A method of diagnosing and treating prostate cancer, comprising the steps of
   a. detecting in a sample of a subject the DNA methylation status of a genomic region pair by employing a method which includes contacting the sample with an oligonucleotide and performing an assay to detect the hypermethylation status of each of the genomic regions, wherein the genomic region pair is SEQ ID NO. 8 and SEQ ID NO. 86, and wherein at least one of these is hypermethylated in the sample,
   b. diagnosing the subject as prostate cancer positive; and
   c. treating the prostate cancer positive subject with radiation or prostatectomy.

2. A method according to claim 1, further comprising detecting the methylation states of genomic region pair is SEQ ID NO. 29 and SEQ ID NO. 86.

3. A method according to claim 1, wherein the methylation status of a further genomic region and/or a further biomarker is analyzed.

4. A method according to claim 1, wherein the methylation status is detected by non-methylation-specific PCR based methods, methylation-based methods or microarray-based methods.

5. A method according to claim 4, wherein the methylation status is analyzed by Epityper or Methylight assays.

6. A method of claim 1, wherein the methylation status is calculated as a ratio of the percentage of methylated DNA of the genomic region in the sample to the percentage of non-methylated DNA of the genomic region in the sample.

7. The method of claim 3, further comprising detecting in the sample the DNA methylation status of one or more additional genomic regions selected from the group consisting of SEQ ID NO: 1-7, 9-85, and 87-110.

* * * * *